United States Patent
Hook et al.

(10) Patent No.: US 8,580,974 B2
(45) Date of Patent: Nov. 12, 2013

(54) PROCESSES

(75) Inventors: David Hook, Rheinfelden (CH); Bernhard Riss, Huningue (FR); Daniel Kaufmann, Bättwil (CH); Matthias Napp, Lörrach (DE); Erhard Bappert, Basel (CH); Philippe Polleux, Riehen (CH); Jonathan Medlock, Cambridge (GB); Antonio Zanotti-Gerosa, Cambridge (GB)

(73) Assignee: Novartis AG, Basel (CH)

( * ) Notice: Subject to any disclaimer, the term of this patent is extended or adjusted under 35 U.S.C. 154(b) by 269 days.

(21) Appl. No.: 12/863,213

(22) PCT Filed: Jan. 16, 2009

(86) PCT No.: PCT/EP2009/050510
§ 371 (c)(1),
(2), (4) Date: Sep. 21, 2010

(87) PCT Pub. No.: WO2009/090251
PCT Pub. Date: Jul. 23, 2009

(65) Prior Publication Data
US 2011/0046397 A1    Feb. 24, 2011

(30) Foreign Application Priority Data
Jan. 17, 2008    (EP) .................................... 08150353

(51) Int. Cl.
*C07D 207/38*    (2006.01)
*C07D 207/26*    (2006.01)

(52) U.S. Cl.
USPC .......................................... 548/550; 548/551

(58) Field of Classification Search
USPC ................... 548/531, 550, 551, 518
See application file for complete search history.

(56) References Cited

U.S. PATENT DOCUMENTS

| | | | |
|---|---|---|---|
| 5,217,996 A | 6/1993 | Ksander | |
| 5,250,522 A | 10/1993 | De Lombaert | |
| 5,250,552 A | 10/1993 | Boschelli et al. | |
| 5,412,102 A | 5/1995 | Clark et al. | |
| 8,115,016 B2 | 2/2012 | Hook | |
| 2010/0113801 A1* | 5/2010 | Hook et al. | 548/406 |

FOREIGN PATENT DOCUMENTS

| | | |
|---|---|---|
| EP | 0 550 313 | 7/1993 |
| EP | 0 555 175 A | 8/1993 |
| EP | 0555175 A1 * | 8/1993 |
| FR | 2 688 503 | 3/1992 |
| WO | 2005/075462 | 8/2005 |

OTHER PUBLICATIONS

Blaser et al., "Selective Hydrogenation for Fine Chemicals: Recent Trends and New Developments", Adv. Synth. Catal., vol. 345, No. 1+2, pp. 103-151 (2003).
Katho T. et al: "Synthetic Studies on Quinocarcin and Its Related Compounds . . ." Tetrahedron, vol. 50, No. 21, 1994, pp. 6221-6238.
Baker S.R. et al: "4-Alkylidenyl glutamic acids, potent and selective gluR5 agonists" Bioorganic Medicinal Chemistry Letters, No. 10, 2000, pp. 1807-1810.
Dieterich P. et al: "Synthesis of (2S,3S_-[3-2H1]-4methyleneglutamic acid . . ." Organic and Biomolecular Chemistry, No. 4, 2006, pp. 1492-1496.
Hanessian S. et al: "The asymmetric synthesis of allyglycine and other unnatural . . ." Tetrahedron Letters, vol. 37, No. 30, 1996, pp. 5273-5276.

* cited by examiner

*Primary Examiner* — Joseph Kosack
*Assistant Examiner* — Matthew Coughlin
(74) *Attorney, Agent, or Firm* — Joseph Majka; Matthew Mulkeen

(57) ABSTRACT

The invention relates to a new process for producing NEP inhibitors or prodrugs thereof, in particular NEP inhibitors comprising a γ-amino-δ-biphenyl-α-methylalkanoic acid, or acid ester, backbone. In detail, the new processes, according to the present invention, are ultimately related to the synthesis of intermediates to prepare the above NEP inhibitors, namely compounds according to formula (1), or salt thereof, (1)

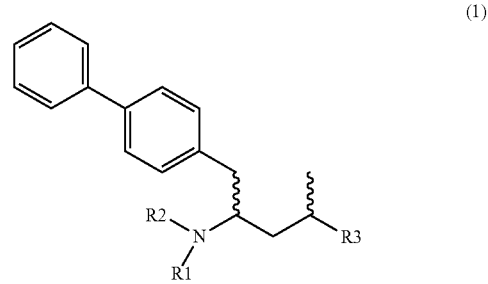

wherein R1 and R2 are, independently of each other, hydrogen or a nitrogen protecting group, and R3 is a carboxyl group or an ester group, preferably carboxyl group or alkyl ester.

8 Claims, 7 Drawing Sheets

Figure 1:    X-ray structure of N,N,N',N'-tetramethylformamidinium para-toluenesulfonate
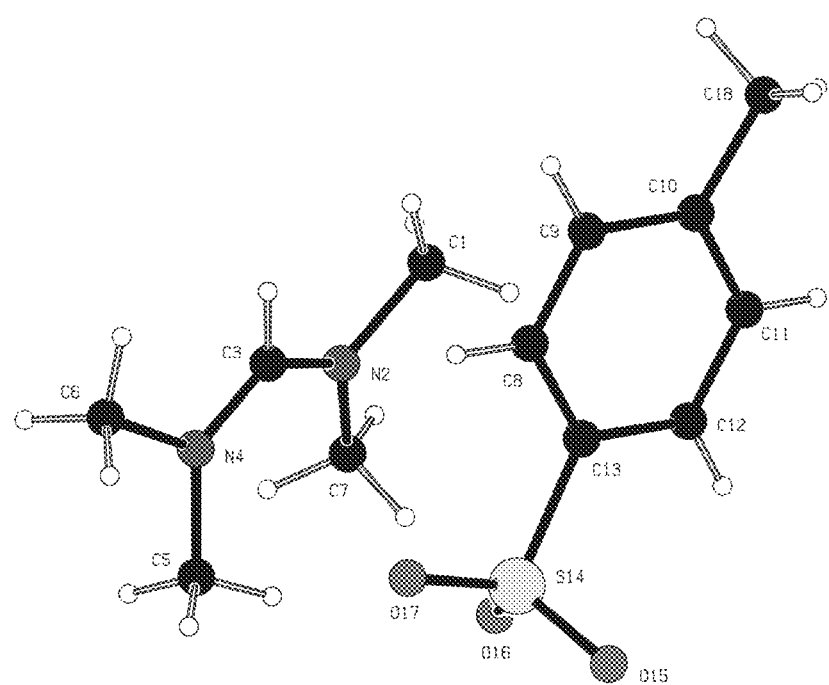

Figure 2: N,N,N'N'-Tetraethylformamidinium tetrafluoroborate
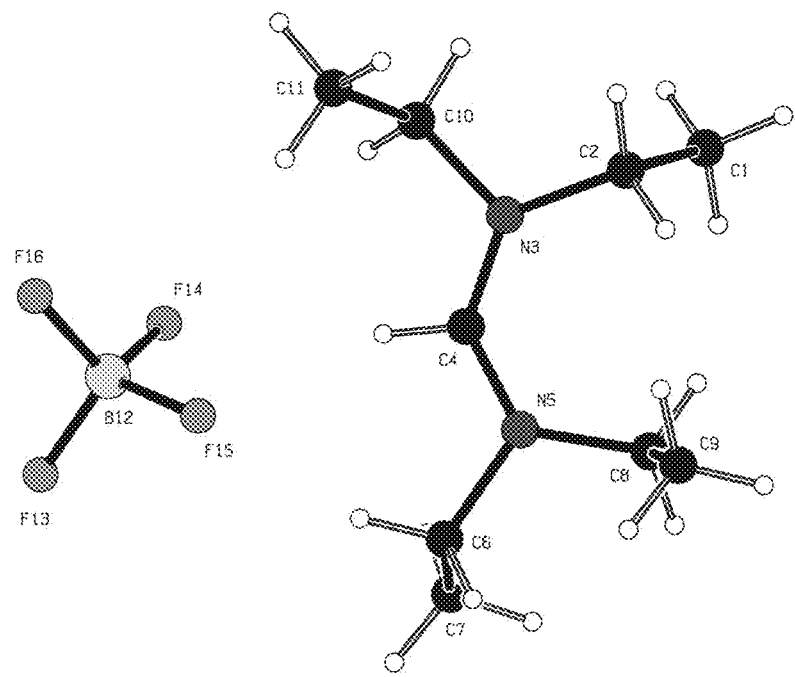

Figure 3: Diisopropyl(piperidin-1-ylmethylidene)ammonium hexafluorophosphate
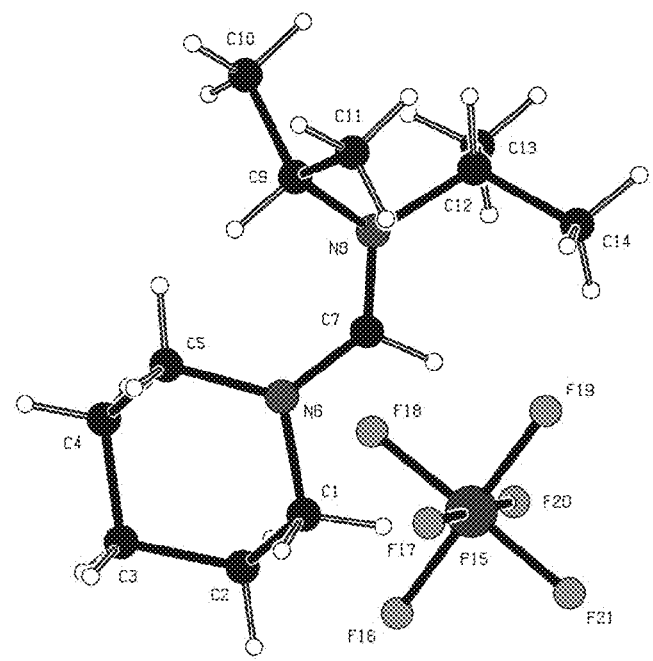

Figure 4: (R)-5-Biphenyl-4-ylmethyl-3-methylene-2-oxo-pyrrolidine-1-carboxylic acid *tert*-butyl ester (4-a, R1 = Boc)
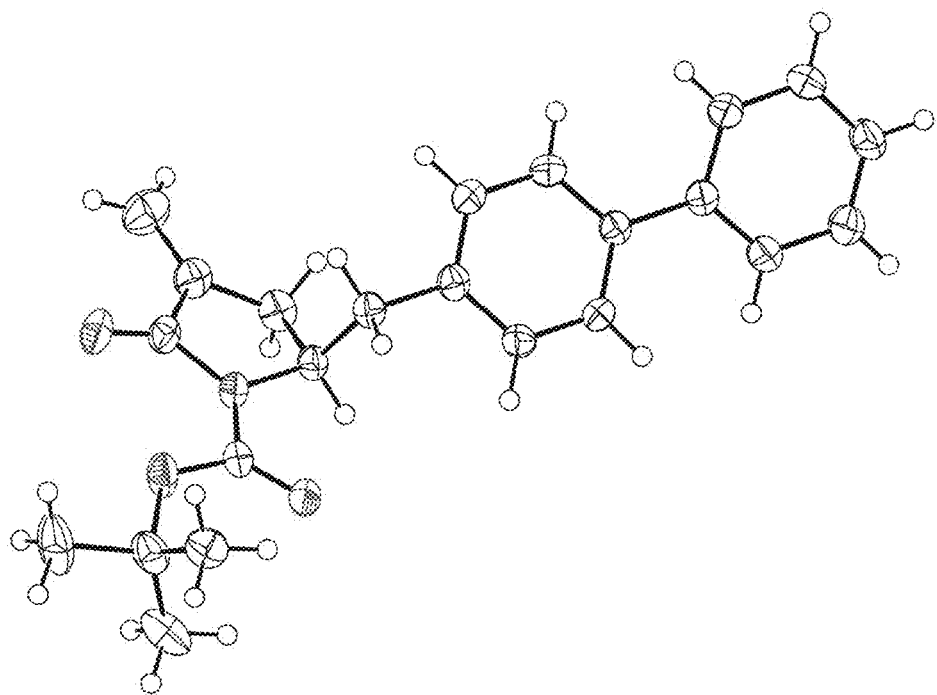

Figure 5a: (3R/S,5S)-5-Biphenyl-4-ylmethyl-3-dimethoxymethyl-2-oxo-pyrrolidine-1-carboxylic acid *tert*-butyl ester (16-a, R1 = Boc, R9 = Me, R9 = Me)
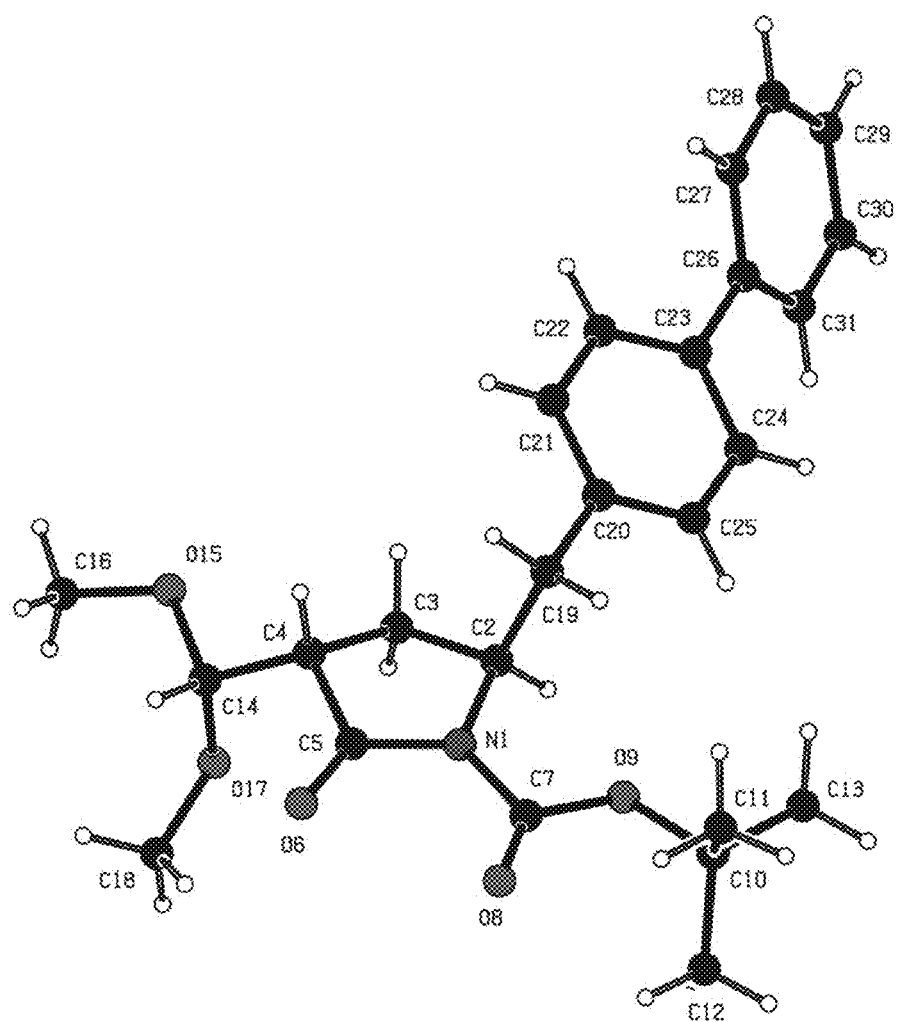

Figure 5b: (3R/S,5S)-5-Biphenyl-4-ylmethyl-3-dimethoxymethyl-2-oxo-pyrrolidine-1-carboxylic acid *tert*-butyl ester (16-a, R1 = Boc, R9 = Me, R9 = Me)
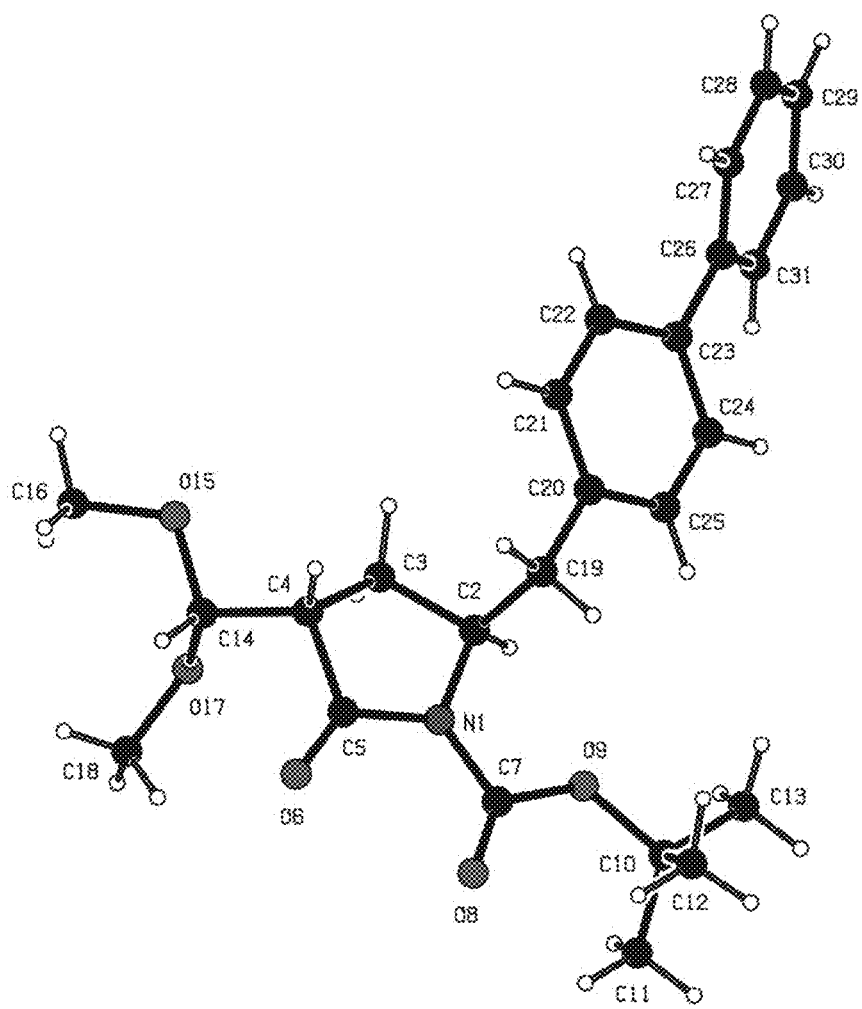

Figure 6: Potassium[(R)-5-biphenyl-4-ylmethyl-3-[1-dimethylaminometh-(E/Z)-ylidene]-2-oxo-pyrrolidine-1-carboxylic acid *tert*-butyl ester]hexafluorophosphate (7-a, R1 = Boc, R6 = Me, R7 = Me)
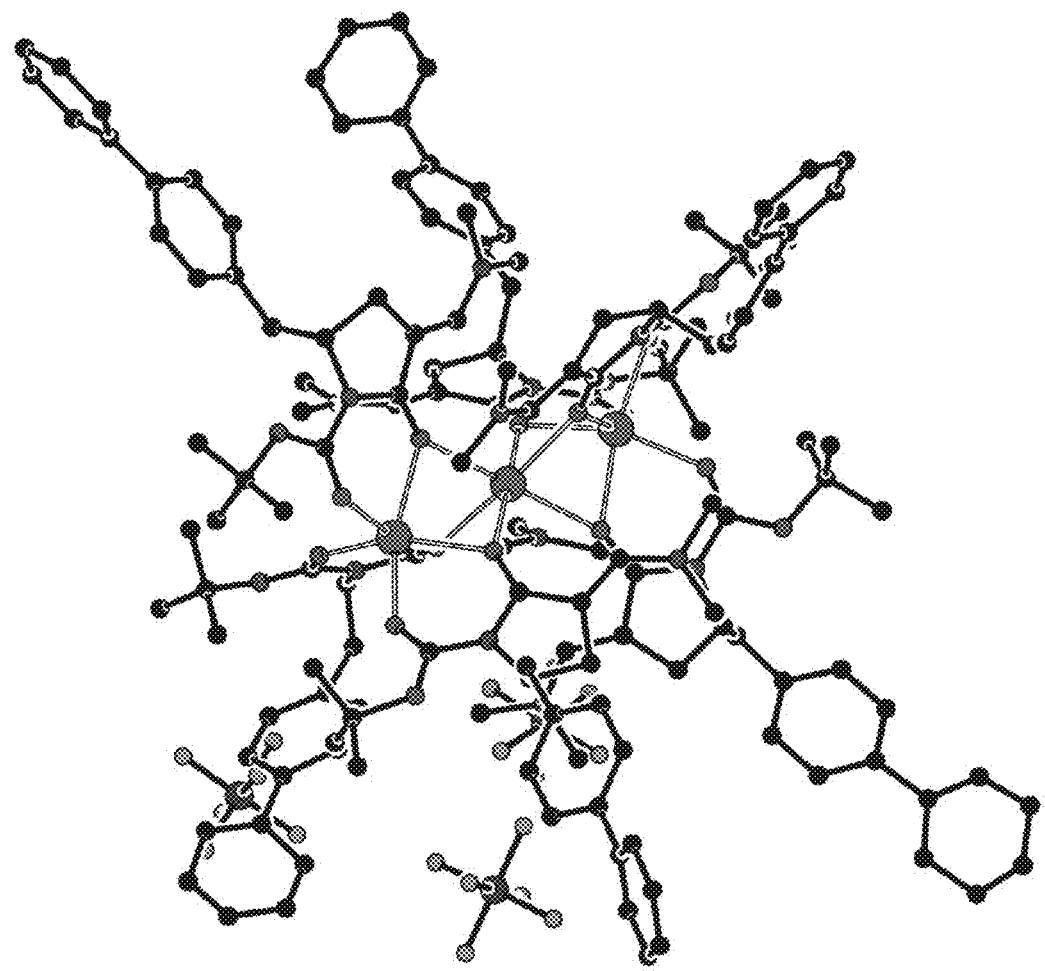

PROCESSES

This is a National Stage of International Application No. PCT/EP2009/050510 filed on Jan. 16, 2009, which in its entirety are herein incorporated by reference.

The invention relates to a new process for producing NEP inhibitors or prodrugs thereof, in particular NEP inhibitors comprising a γ-amino-δ-biphenyl-α-methylalkanoic acid, or acid ester, backbone.

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4.24.11), also responsible for e.g. the metabolic inactivation of enkephalins.

In the art biaryl substituted phosphonic acid derivatives are known which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Processes for preparing NEP-inhibitors are known. U.S. Pat. No. 5,217,996 describes biaryl substituted 4-amino-butyric acid amide derivatives which are useful as neutral endopeptidase (NEP) inhibitors, e.g. as inhibitors of the ANF-degrading enzyme in mammals. U.S. Pat. No. 5,217,996 discloses the preparation of N-(3-carboxyl-1-oxopropyl)-(4S)-(p-phenylphenylmethyl)-4-amino-(2R)-methyl butanoic acid ethyl ester. In the preparation of said compound N-t-butoxycarbonyl-(4R)-(p-phenylphenylmethyl)-4-amino-2-methyl-2-butenoic acid ethyl ester is hydrogenated in the presence of palladium on charcoal. A major drawback of said process is that such a hydrogenation step is not very selective and yields N-t-butoxycarbonyl-(4S)-(p-phenylphenylmethyl)-4-amino-2-methylbutanoic acid ethyl ester as a 80:20 mixture of diastereomers. Moreover, the process for preparing N-t-butoxycarbonyl-(4R)-(p-phenylphenylmethyl)-4-amino-(2)-methyl(2)-butenoic acid ethyl ester requires D-tyrosine as starting material, which is an unnatural amino acid and is not readily available.

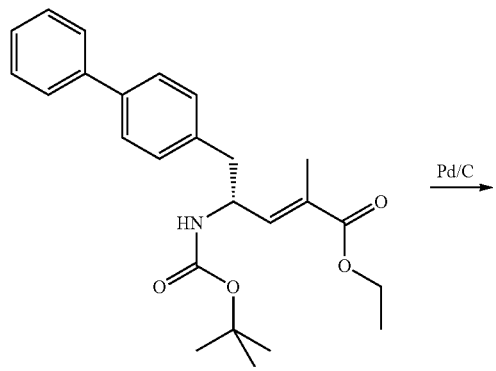

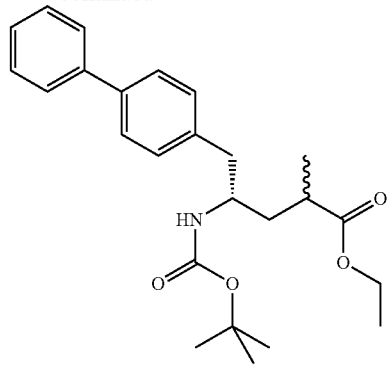

It was hence an object of the present invention to provide an alternative reaction route for preparing compound N-t-butoxycarbonyl(4S)-(p-phenylphenylmethyl)-4-amino-2-methylbutanoic acid ethyl ester, or salt thereof, preferably a reaction route which avoids the above-mentioned drawbacks of the prior art process.

It was a further object of the present invention to provide an alternative hydrogenation step in a process for producing NEP inhibitors or prodrugs thereof. In particular it was an object to provide an alternative process for producing compounds according to formula (1), or salt thereof,

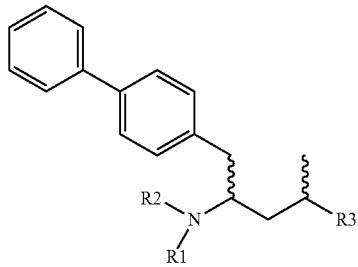

(1)

wherein R1 and R2 are, independently of each other, hydrogen or a nitrogen protecting group, and R3 is a carboxyl group or an ester group, preferably carboxyl group or alkyl ester. Compounds of formula (1) can be used as intermediates in the preparation of NEP inhibitors, or prodrugs thereof, in particular NEP inhibitors comprising a γ-amino-δ-biphenyl-α-methylalkanoic acid, or acid ester, backbone, preferably N-(3-carboxyl-1-oxopropyl)-(4S)-(p-phenylphenylmethyl)-4-amino-(2R)-methyl butanoic acid ethyl ester, for example, as described in the Journal of Medicinal Chemistry, 1995, 38, 1689.

It was a still further object to provide a process for producing compounds according to formulae (1-a) and (1-b), or salts thereof, wherein R1, R2 and R3 are defined as above, having a high diastereomeric ratio. Preferably, it was an object to provide a process for obtaining a diastereomeric ratio of compounds according to formula (1-a), or salts thereof, to compounds according to formula (1-b), or salts thereof, of at least 80:20, more preferably of at least 90:10, most preferably a ratio of (1-a) to (1-b) of at least 99:1. It was also an object to provide a process in which the compounds according to formula (1-b), or salts thereof, can be completely removed and compounds according to formula (1-a), or salts thereof, can be provided in pure form.

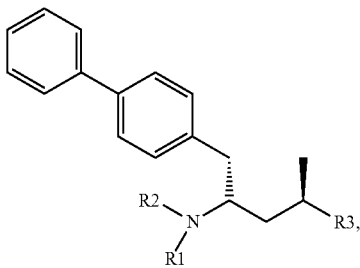

(1-a)

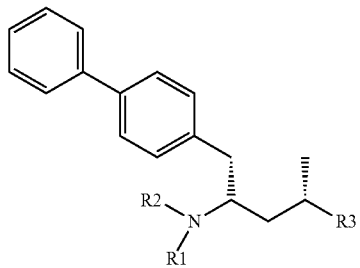

(1-b)

BRIEF DESCRIPTION OF THE SEVERAL VIEWS OF THE DRAWING(S)

FIG. 1 depicts the X-ray structure of N,N,N',N'-tetramethylformamidinium para-toluenesulfonate.

FIG. 2 depicts N,N,N'N'-Tetraethylformamidinium tetrafluoroborate.

FIG. 3 depicts Diisopropyl(piperidin-1-ylmethylidene) ammonium hexafluorophosphate.

FIG. 4 depicts (R)-5-Biphenyl-4-ylmethyl-3-methylene-2-oxo-pyrrolidine-1-carboxylic acid tert-butyl ester (4-a, R1=Boc).

FIG. 5 depicts (3R/S,5S)-5-Biphenyl-4-ylmethyl-3-dimethoxymethyl-2-oxo-pyrrolidine-1-carboxylic acid tert-butyl ester (16-a, R1=Boc, R9=Me, R9=Me).

FIG. 6 depicts (3R/S,5S)-5-Biphenyl-4-ylmethyl-3-dimethoxymethyl-2-oxo-pyrrolidine-1-carboxylic acid tert-butyl ester (16-a, R1=Boc, R9=Me, R9=Me).

FIG. 7 depicts Potassium[(R)-5-biphenyl-4-ylmethyl-3-[1-dimethylaminometh-(E/Z)-ylidene]-2-oxo-pyrrolidine-1-carboxylic acid tert-butyl ester]hexafluorophosphate (7-a, R1=Boc, R6=Me, R7=Me).

The new processes, according to the present invention, for producing compounds according to formula (1), or salt thereof, as defined herein, are summarized in Scheme 1.

Scheme 1

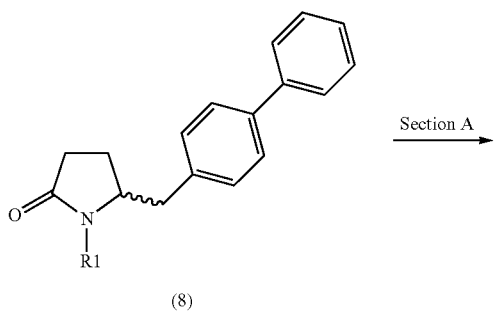

(8)

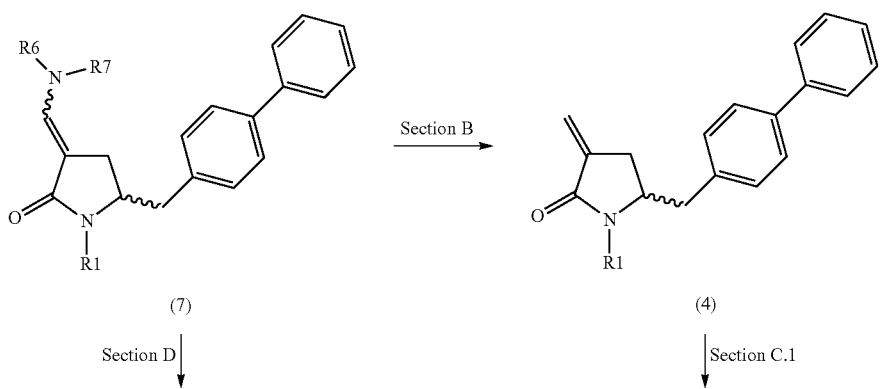

(7) (4)

Section D          Section C.1

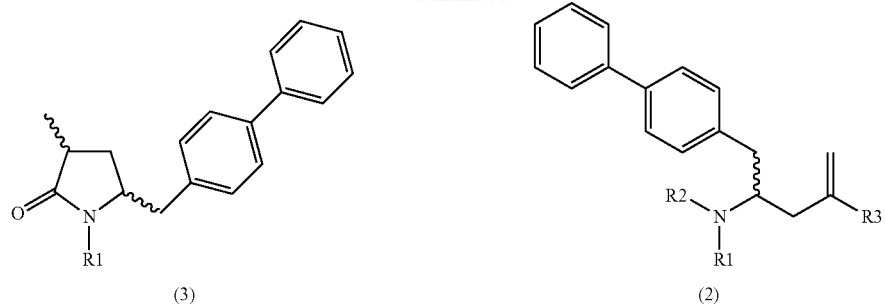

(3)    (2)

EP Application 07100451.9    Section C.2
or WO2008/083967

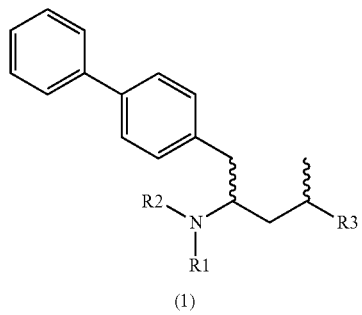

(1)

Namely, a compound of formula (8) is converted into a compound of formula (7), or salt thereof, wherein R1 is hydrogen or a nitrogen protecting group, according to a method described in Section A. Next, the compound of formula (7), or salt thereof, as described above, is converted into the compound of formula (1) or salt thereof, according to methods 1 or 2, wherein method 1 comprises a) any one of the methods in Section B to convert (7) into (4), b) any one of the methods in Section C to convert (4) into (2), and c) any one of the methods in Section C to convert (2) into (1);

method 2 comprises;

a) any one of the methods in Section D to convert (7) into (3), and b) conversion of the compound of formula (3) into (1), for example, as described in European patent application 07100451.9 or WO2008/083967.

As discussed below, Sections A, B, C and D as such are also preferred embodiments of the present invention.

SECTION A: PREPARATION OF A COMPOUND OF FORMULA (7)

In one aspect, the present invention relates to a process for preparing a compound of formula (7), or salt thereof,

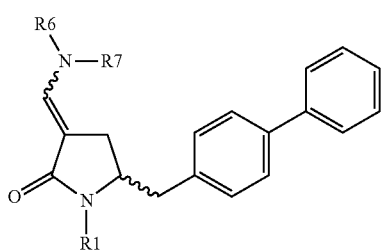

(7)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, said process comprising reacting a compound of formula (8), or salt thereof,

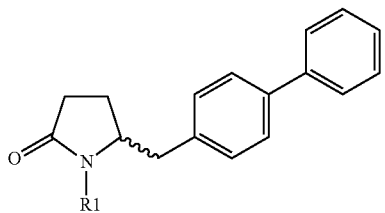

(8)

wherein R1 is hydrogen or a nitrogen protecting group, with an amine of formula (13), (14) or (15), or mixtures thereof,

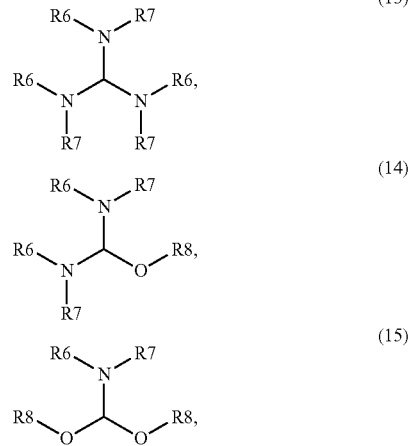

wherein each R6 and each R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, and each R8 is, independently, an alkyl group, an aryl group or an arylalkyl group to obtain the compound of formula (7).

The reaction to obtain the enamine of formula (7) can take place neat or in any inert solvent, preferably in an aprotic solvent such as halogenated hydrocarbons, such as methylene chloride; ethers, such as THF, dimethoxyethane, or dioxane; or aromatic solvents such as benzene, chlorobenzene, toluene, phenylethane or xylenes or mixtures thereof. Preferably the solvent is toluene or THF. Typically, the reaction can be conducted at 0° C. to reflux, preferably 0 to 200° C., more preferably 20 to 140° C., yet more preferably 40 to 100° C., most preferably 60 to 90° C.

Preferred examples of the amines of formulae (13), (14) and (15) include Bredereck's reagent {tert-butoxybis(dimethylamino)methane}, tert-butoxybis(diethylamino)methane, methoxybis(dimethylamino)methane, tert-pentoxy-bis(dimethylamino)methane, tris(dimethylamino)methane, tris(diethylamino)methane, and N,N-dimethylformamide dimethylacetal (DMFDMA), N,N-dimethylformamide diethylacetal, N,N-dimethylformamide diisopropylacetal, N,N-dimethylformamide di-tert-butylacetal, N,N-dimethylformamide di-tert-pentoxyacetal, or mixtures thereof.

In one embodiment the amine of formula (14) is preferably the Bredereck's reagent or tert-pentoxy-bis(dimethylamino) methane. In another embodiment, the amine of formula (13) is preferably tris(dimethylamino)methane. In still another embodiment, the amine of formula (15) is preferably N,N-dimethylformamide di-tert-butylacetal or N,N-dimethylformamide di-tert-pentoxyacetal. The amine of formulae (13), (14) or (15), or mixtures thereof, can be used in an amount of 1.0 to 10 equivalents, preferably 3 to 10 equivalents, more preferably 3 to 6 equivalents, such as 3 equivalents. Optionally, an alcohol may be present, preferably an alkyl alcohol such as 1-butanol, 2-butanol, tert-butanol or 2-methyl-2-butanol. Typically, the alcohol can be used in an amount of 1.0 to 10 equivalents, preferably 3 to 10 equivalents, more preferably 3 to 6 equivalents, such as 3 equivalents. In one embodiment, the alcohol can be used with (13) to make (14) and/or (15) in situ.

These amines can be purchased from suppliers, such as Aldrich, Fluka or Acros, or can be obtained according to methods known in the art, for example as described in Adv. Synth. Catal., 2004, 346, 1081; Encyclopedia of Reagents for Organic Synthesis, 2007, DOI: 10.1002/9780470842898.rb350.pub2; Tetrahedron Lett., 1983, 25, 285; Encyclopedia of Reagents for Organic Synthesis, 2007, DOI: 10.1002/047084289X.rt403; Synlett, 2006, 809; Recueil des travaux chimiques des Pays-Bas, 1969, 88, 289; J. Org. Chem., 1985, 50, 3573; J. Org. Chem., 1980, 45, 3986; Chem. Ber., 1968, 101, 1885; J. Chem. Soc., Perkin Trans. 2, 1985, 1669; Angew. Chem., Int. Ed., 1962, 1, 331; Chem. Ber., 1968, 101, 41; Chem. Ber., 1968, 101, 51; Liebigs Ann. Chem., 1972, 762, 62; Science of Synthesis, 2005, 22, 795; J. Am. Chem. Soc., 1961, 83, 2588 or in J. Org. Chem., 1962, 27, 3664, or according to methods in Section F of the present invention.

In one embodiment, the conversion of a compound of formula (8) into a compound of formula (7), as described above, takes place in the presence of a salt, for example an alkali metal salt (eg a salt of lithium, sodium or potassium), an alkaline earth metal salt (eg a salt of magnesium or calcium) or an ammonium salt, wherein the couterion is, for example, a halide, a carbonate, an amine, perchlorate, hexafluorophosphate or hexafluorosilicate. In particular, the salt is selected from lithium hexafluorophosphate ($LiPF_6$), sodium hexafluorophosphate ($NaPF_6$), potassium hexafluorophosphate ($KPF_6$), ammonium hexafluorophosphate ($NH_4PF_6$), lithium chloride (LiCl), lithium bromide (LiBr), sodium chloride (NaCl), potassium chloride (KCl), magnesium chloride ($MgCl_2$), potassium perchlorate ($KClO_4$), sodium hexafluorosilicate ($Na_2SiF_6$), lithium amide ($LiNH_2$) and lithium carbonate ($Li_2CO_3$). The salt may also be an ionic liquid, such as 1-butyl-3-methyl imidazolium tetrafluoroborate or 1-butyl-3-methyl imidazolium hexafluorophosphate. In one embodiment, the salt is lithium hexafluorophosphate, lithium chloride, magnesium chloride, or potassium hexafluorophosphate.

In another embodiment, the conversion of a compound of formula (8) into a compound of formula (7), as described above, takes place in the presence of a salt, as described above, and an amine. Typically, the amine is a secondary amine, such as a secondary amine of the formula HNR6R7 wherein R6 and R7 are independently as defined above for compounds of formula 13, 14 or 15. In particular, the amine is diphenylamine, diisopropylamine, dimethylamine or imidazole. Optionally, a base may be added to the amine of formula HNR6R7 to give a species of the formula M-NR6R7 wherein M is an alkali metal (eg lithium sodium, potassium) or an alkaline earth metal (eg magnesium, calcium) and R6 and R7 are independently as defined above. In particular, M is an alkali metal, such as lithium. In one embodiment, the base is LHMDS and the amine is diphenylamine.

In yet a further embodiment, the conversion of a compound of formula (8) into a compound of formula (7), as described above, takes place in the presence of a salt, as described above, and a crown ether. In particular, the salt is potassium hexafluorophosphate and the crown ether is 18-crown-6.

Typically, in the above embodiments, the salt may be used in a catalytic or in a stoichiometric amount with respect to the compound of formula (8). In particular, the salt may be used in an amount of, for example, 0.1 to 2 equivalents, in particular 0.5 to 2 equivalents, such as 1 to 2 equivalents.

In a preferred case, suitable reagents for preparing a compound of formula (7), or a salt thereof, from a compound of formula (8), or a salt thereof, involves reacting a compound of formula (7) with a compound prepared by mixing a compound of formula (18),

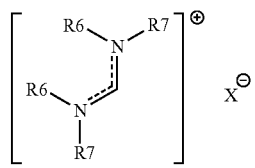

(18)

wherein R6 and R7 are, independently, defined as before, with an alcoholate of the formula M-OR8
wherein,
X is defined as an anion, for example, a halide (eg chloride, bromide, iodide), an anion of a sulphonic acid (eg trifluoromethanesulfonic acid, methanesulphonic acid, 4-toluenesulphonic acid), an anion of an alkylsulfate (eg methylsulfate), a tetrahalometalate, for example, a tetrachlorometalate (eg tetrachloromanganate, tetrachloroaluminate), hexafluorophosphate, hexafluoroantimonate, tetrafluoroborate, perchlorate, alkoxide, for example, R8O⁻ where R8 is defined as before (eg tert-butoxide, phenoxide), carboxylate, tribromide.

M is defined as an alkali metal (eg lithium, sodium, potassium, in particular sodium, potassium) or an alkaline earth metal (eg magnesium, calcium).

R8 is defined as before.

R8O is defined as an alkoxy group.

The reaction may be performed neat or in any inert solvent, as defined above.

In a preferred case, an alcoholate of the formula M-OR8 is added, optionally in a solvent for example an inert solvent such as tetrahydrofuran, methyltetrahydrofuran, toluene, alkanes (such as heptane, hexane), or mixtures thereof, to a compound according to formula (18), optionally in an inert solvent. M-OR8 is typically used in the range 0.5 to 1.5 equivalents, more preferably in the range 0.8 to 1.2 equivalents.

Typically the mixture is stirred, typically at 0° C. to reflux, preferably 0 to 120° C., more preferably 20 to 80° C.

The mixture is reacted with a compound according to formula (8), or a salt thereof, to provide a compound according to formula (7), or a salt thereof.

In a preferred case, the mixture can be used in an amount of 1.0 to 10 equivalents, preferably 3 to 10 equivalents, more preferably 3 to 6 equivalents, such as 3 equivalents. Typically, the equivalents used are relative to the compound according to formula (18). Typically, the reaction can be conducted at 0° C. to reflux, preferably 0 to 120° C., more preferably 20 to 80° C.

In one embodiment, the mixture of an alcoholate of the formula M-OR8 and a compound according to the formula (18), optionally in a solvent as defined above, which may be prepared as described above, is reacted with a compound according to formula (8). The mixture can be added to (8) in an amount of 1.0 to 10 equivalents, in particular 3 to 10 equivalents, such as 3 to 6 equivalents, in particular 3 equivalents. When the amount of alcoholate M-OR8 and a compound according to the formula (18) are not equimolar amounts, the equivalents of the mixture used in relation to (8) are relative to the amount of (18). Typically, the reaction involving the mixture of alcoholate of the formula M-OR8 and a compound according to the formula (18), optionally in a solvent as defined above, is conducted at 0° C. to reflux, in particular 0 to 120° C., such as 20 to 80° C.

Compound of the formula (7) can be optionally isolated as a residue by removal of volatile substances from the mixture. The distillate may contain an amine of formula (13), (14) or (15), or mixtures thereof. Where a solid is present after formation of a compound of the formula (7), this may be optionally removed, for example by filtration, prior to distillation. The solid may contain a compound of formula (18).

In a further preferred case, a compound according to formula (18), optionally in the presence of an alcoholate of formula R8O-M, may be treated with a salt of formula M1X', which partially or fully exchanges the anionic counterion (X) of compounds according to formula (18) by an anionic counterion (X'), wherein X' is defined as described above for X and M1 is an alkali metal (eg lithium, sodium or potassium), an alkaline earth metal (eg magnesium or calcium) or ammonium, in order to give compounds of the formula (18').

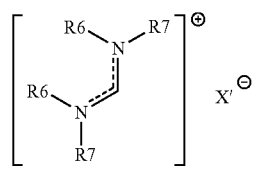

(18')

Suitable reagents for this exchange include alkali metal salts (such as lithium, sodium or potassium tetrafluoroborate or hexafluorophosphate, sodium methylsulfate, sodium perchlorate), alkaline earth metal salts (such as magnesium or calcium perchlorate), ammonium salts (such as ammonium tetrafluoroborate or hexafluorophosphate). Preferably hexafluorophosphate salts or tetrafluoroborate salts are used, more preferably ammonium hexafluorophosphate or ammonium tetrafluoroborate or sodium tetrafluoroborate is used. Most preferably hexafluorophosphate salts are used, preferably ammonium hexafluorophosphate. Relative to the anionic counterion (X), the anionic counterion (X') of suitable reagents may be used in catalytic or stoichiometric quantities.

The mixture obtained after such an exchange may be used as-is, such that the mixture contains both (18) and (18'), and optionally R8O-M. Alternatively, the anion of formula (X) may be removed from the mixture, for example by filtration, such that the mixture subsequently contains (18'), and optionally R8O-M.

Furthermore, compounds of formula (18) or (18') or mixtures thereof, are suitable reagents for the present invention. Compounds according to the formula (18') are, independently, defined according to compounds according to the formula (18).

As such, in a preferred case, a compound of formula (8) is converted into a compound according to formula (7) by reaction with a compound of formula (18) and an alcoholate of formula R8O-M, optionally in the presence of a compound of formula (18').

Furthermore, in a preferred case, a compound of formula (8) is converted into a compound according to formula (7) by reaction with a compound of formula (18) and an alcoholate of formula R8O-M, optionally in the presence of a compound of formula (18') and an amine of formula (13), (14) or (15), or mixtures thereof.

Optionally, a compound of formula (8) can be converted into a compound according to formula (7) by reaction with a compound of formula (18) and an alcoholate of formula R8O-M optionally in the presence of a compound of formula (18') and an amine of formula (13), (14) or (15), or mixtures thereof, in the presence of an amine, typically of the formula HNR6R7, where R6 and R7 are independently as defined above. In particular, the amine is diphenylamine, diisopropylamine, dimethylamine or imidazole. Optionally, a base may be added to the amine of formula HNR6R7 to give a species of formula M-NR6R7 where M is an alkali metal (eg lithium sodium, potassium) or an alkaline earth metal (eg magnesium, calcium) and R6 and R7 are independently as defined above. In particular, M is an alkali metal, such as lithium. In one embodiment, the base is LHMDS and the amine is diphenylamine.

Compounds of the formula (18) or (18') can be purchased from suppliers such as Aldrich and Fluka, or can be obtained according to methods known in the art, for example, as described in J. Chem. Soc., Perkin Trans. 1, 2001, 1586; J. Chem. Soc., Perkin Trans. 1, 1987, 845; Synthesis, 1977, 273; Science of Synthesis, 2005, 22, 221; Synthesis Communications, 1983, 785; Recueil des travaux chimiques des Pays-Bas, 1969, 88, 289; Chem. Res. Chinese U., 2005, 21, 177; Chem. Ber., 1993, 126, 1859; Synthetic Communications, 1998, 28, 1223; J. Org. Chem., 1965, 2464; J. Org. Chem., 1970, 35, 1542; Liebigs Ann. Chem., 1972, 762, 62; J. Am. Chem. Soc., 1961, 83, 2588; J. Org. Chem., 1962, 27, 3664 or J. Chem. Soc., 1949, 3319, or according to methods in Section F of the present invention.

Compounds of the formula R8O-M can be purchased from suppliers such as Aldrich, BASF, Chemetall GmbH, or can be obtained according to methods known to persons skilled in the art.

The following preferences apply:

For compounds of formula (18) or (18'), R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms. Most preferably, R6 is alkyl. Still more preferably R6 is methyl or ethyl and R7 is methyl or ethyl. X is preferably chloride, methylsulfate, tetrafluoroborate or hexafluorophosphate. Most preferably, X is chloride or hexafluorophosphate. In a preferred case, compounds of formula (18) or (18') are preferably N,N,N,N-tetramethylformamidinium or N,N,N,N-tetraethylformamidinium chloride, N,N,N,N-tetramethylformamidinium or N,N,N,N-tetraethylformamidinium hexafluorophosphate For compounds of the formula R8O-M, R8 is preferably alkyl, most preferably tert-butyl or amylate. M is preferably an alkali metal, most preferably sodium or potassium. Further preferred is when R8O-M is sodium tert-butoxide (NaOCMe$_3$) or potassium tert-butoxide (KOCMe$_3$) or sodium amylate (NaOCMe$_2$Et) or potassium amylate (KOCMe$_2$Et). Most preferred is when R8O-M is potassium tert-butoxide or sodium amylate.

SECTION B: PREPARATION OF A COMPOUND OF FORMULA (4)

The processes, according to the present invention, to convert of a compound of formula (7), as defined herein, into a compound of formula (4), as defined herein, are outlined in Scheme 2.

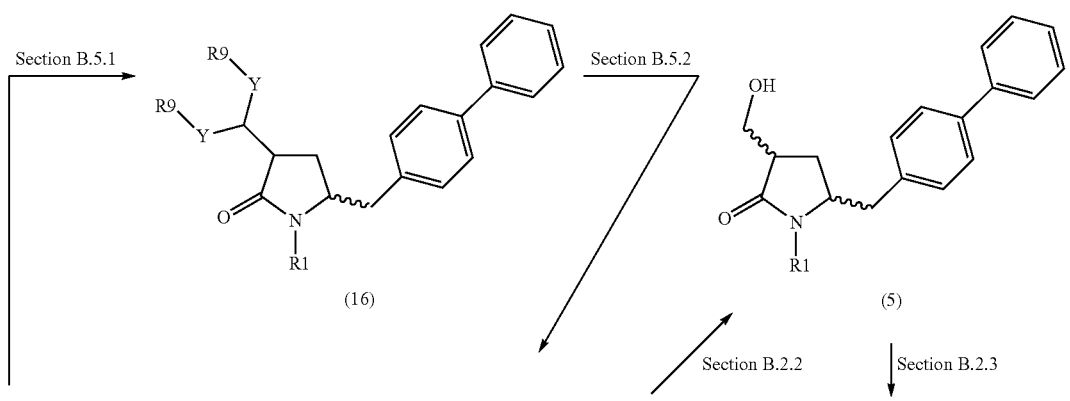

Scheme 2

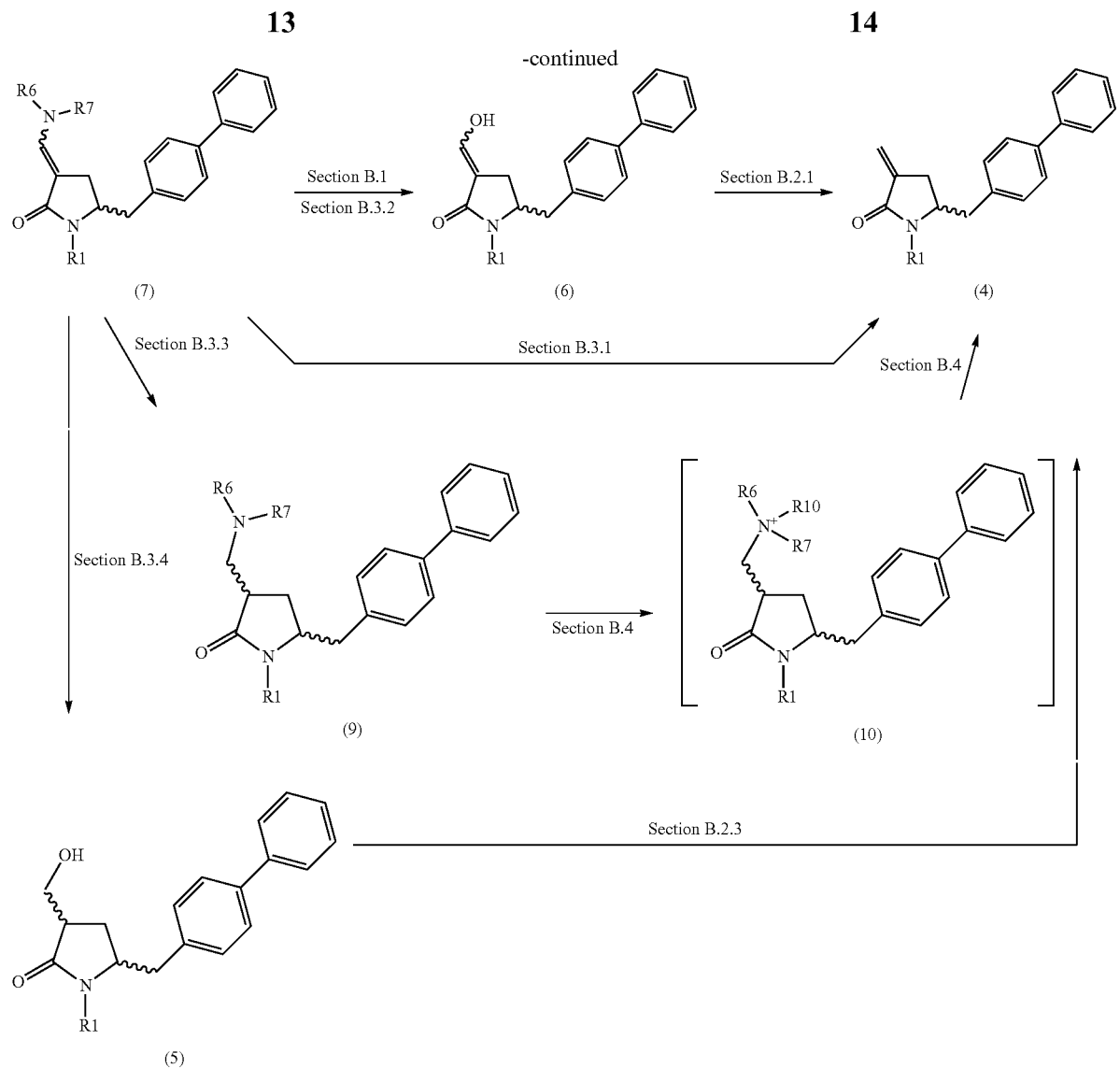

The present invention relates thus to the conversion of a compound of formula (7), as described herein, into a compound of formula (4), as described herein, according to any one of methods 1 to 9, wherein method 1 comprises
  a) any one of methods in Section B.1 to convert (7) into (6), and
  b) any one of methods in Section B.2.1 to convert (6) into (4);

method 2 comprises
  a) any one of methods in Section B.1 to convert (7) into (6),
  b) any one of methods in Section B.2.2 to convert (6) into (5), and
  c) any one of methods in Section B.2.3 to convert (5) into (4);

method 3 comprises any one of methods in Section B.3.1 to convert (7) into (4);

method 4 comprises
  a) any one of methods in Section B.3.2 to convert (7) into (6), and
  b) any one of methods in Section B.2.1 to convert (6) into (4);

method 5 comprises
  a) any one of methods in Section B.3.2 to convert (7) into (6),
  b) any one of methods in Sections B.2.2 to convert (6) into (5), and
  c) any one of methods in Section B.2.3 to convert (5) into (4);

method 6 comprises
  a) any one of methods in Section B.3.3 to convert (7) into (9),
  b) any one of methods in Section B.4 to convert (9) into (10), and
  c) any one of methods in Section B.4 to convert (10) into (4);

method 7 comprises
  a) any one of methods in Section B.3.4 to convert (7) into (5), and
  b) any one of methods in Section B.2.3 to convert (5) into (4);

method 8 comprises
  a) any one of methods in Section B.5.1 to convert (7) into (16),
  b) any one of methods in Section B.5.2 to convert (16) into (6), c) any one of methods in Section B.2.2 to convert (6) into (5), and
d) any one of methods in Section B.2.3 to convert (5) into (4);

method 9 comprises
a) any one of methods in Section B.5.1 to convert (7) into (16),
b) any one of methods in Section B.5.2 to convert (16) into (6), and
c) any one of methods in Section B.2.1 to convert (6) into (4);

preferably the conversion of a compound of formula (7), as described herein, into a compound of formula (4), as described herein, is according to methods 1, 4 or 6; in particular methods 1 or 4.

As discussed below, Sections B.1, B.2.1, B.2.2, B.2.3, B.3.1, B.3.2, B.3.3, B.3.4, B.4, B.5.1 and B.5.2 as such are also preferred embodiments of the present invention.

Section B.1:

In another aspect, the present invention relates to a process for preparing a compound of formula (6) or a tautomer thereof.

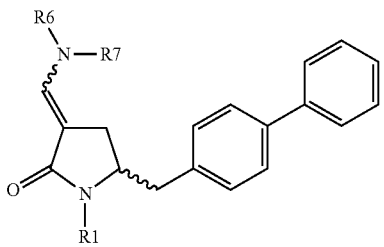

(7)

or salt thereof,
wherein R1 is hydrogen or a nitrogen protecting group,
comprising treating a compound of formula (7), or salt thereof,

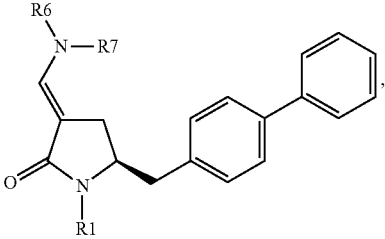

(7)

wherein R1 is hydrogen or a nitrogen protecting group and R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with an acid to obtain the compound of formula (6), preferably of the formula (6-a). In a preferred embodiment, the starting compound of formula (7), or salt thereof, is according to formula (7-a), or salt thereof,

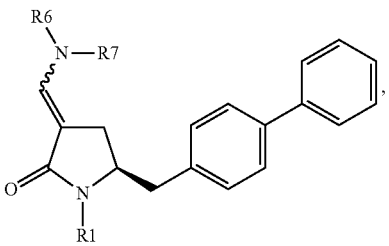

(7-a)

wherein R1 is hydrogen or a nitrogen protecting group and R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, more preferably the starting compound of formula (7), is according to formulae (7b) or (7c), or salts thereof, most preferably according to formula (7-b), or salt thereof,

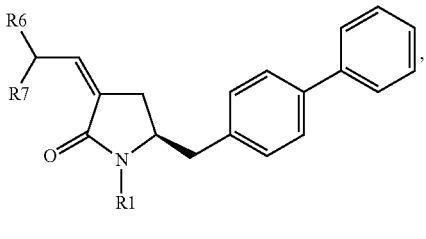

(7-b)

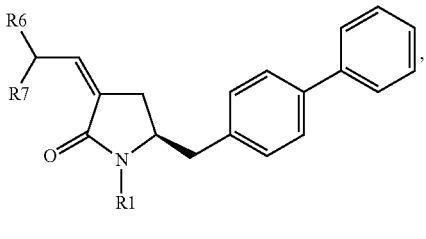

(7-c)

wherein R1 is hydrogen or a nitrogen protecting group and R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms.

The compound of formula (6), or salt thereof, preferably of formula (6-a), or a tautomer thereof, which is obtained according to the above process can be isolated or used as a solution in a subsequent transformation, for example conversion into the compound of formula (4), or salt thereof, as defined herein.

In a preferred embodiment, the present invention relates to a process for preparing a compound of formula (6-a), or a tautomer thereof

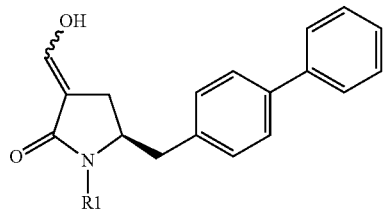
(6-a)

or salt thereof,
wherein R1 is hydrogen or a nitrogen protecting group, comprising treating a compound of formula (7-a), or salt thereof,

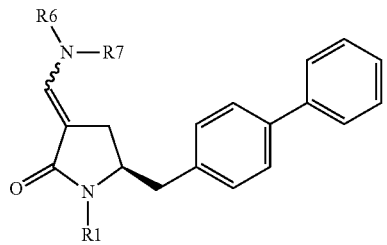
(7-a)

wherein R1 is hydrogen or a nitrogen protecting group and R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with an acid to obtain the compound of formula (6-a). In a preferred embodiment, the starting compound of formula (7-a), or salt thereof, is according to formula (7-b), as defined above.

Preferred examples of acid are aqueous mineral acids, such as hydrochloric acid, hydrobromic acid, sulphuric acid and phosphoric acid. Most preferred is aqueous sulfuric acid. Preferably, the amount of acid employed is such that the pH of the reaction mixture is of from 1 to 7, more preferably pH of from 2 to 5, most preferably pH of from 2 to 3. A solvent can be used, preferably one that is miscible or partly miscible in water, for example acetonitrile. Optionally, a phase transfer catalyst, such as tetra-n-butylammonium halide, for example tetra-n-butylammonium bromide, can be added. Typically the reaction can be conducted at −20 to 30° C., preferably −20 to 20° C., more preferably −10 to 10° C., most preferably 0 to 10° C.

Section B.2:
Section B.2.1:
In another aspect, the present invention relates to a process for preparing a compound of formula (4)

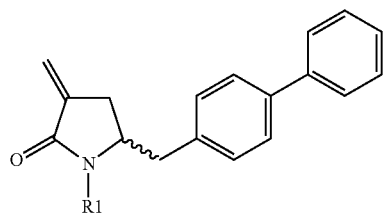
(4)

or salt thereof,
wherein R1 is hydrogen or a nitrogen protecting group, comprising treating a compound of formula (6), or salt or a tautomer thereof,

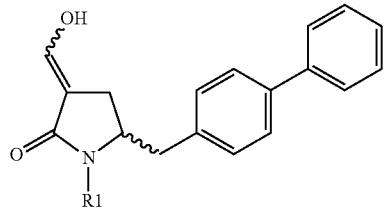
(6)

wherein R1 is hydrogen or a nitrogen protecting group, with a reducing agent, preferably in the form of an aldehyde, to obtain the compound of formula (4). In a preferred embodiment, the starting compound of formula (6), or salt thereof, is according to formula (6-a),

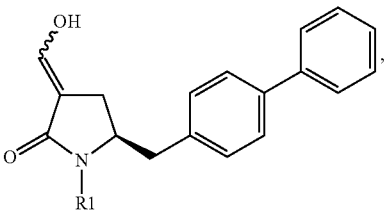
(6-a)

or salt thereof, wherein R1 is hydrogen or a nitrogen protecting group.

In a preferred embodiment, a compound of formula (6-a), or salt, or a tautomer thereof,

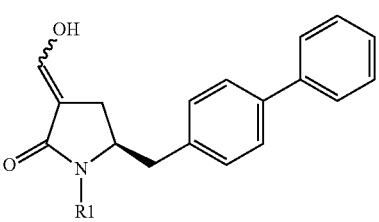
(6-a)

wherein R1 is hydrogen or a nitrogen protecting group, is treated with a reducing agent, preferably in the form of an aldehyde, to obtain a compound of formula (4-a), or salt thereof,

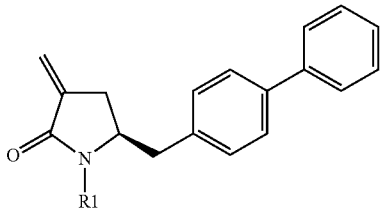

(4-a)

wherein R1 is hydrogen or a nitrogen protecting group.

The reducing agent is typically an aldehyde, more preferably a non-enolisable aldehyde, even more preferably an arylaldehyde, such as benzaldehyde, or a trihaloacetaldehyde, such as chloral, yet more preferably formaldehyde, such as monomeric formaldehyde (obtained by, e.g. 'cracking' paraformaldehyde), 1,3,5-trioxane, paraformaldehyde or an aqueous solution of formaldehyde (for example 37% in water).

Preferably, the reduction of the compound of formula (6), or salt thereof, preferably of the formula (6-a), or salt thereof, is carried out at pH of from 7, more preferably pH of from 7 to 14, most preferably pH of from 10 to 11. A base is used to maintain pH of from 7. Suitable bases are weak bases or strong bases or mixtures of thereof. Preferably, the base is an alkali metal carbonate, such as potassium carbonate, or as metal alkali hydroxide, such as sodium hydroxide. Most preferably the base is potassium carbonate. In a preferred embodiment, the reduction is performed as a biphasic mixture of water and an organic solvent, preferably in the presence of a phase transfer catalyst such as tetrabutylammonium hydroxide.

Section B.2.2:

In a particular embodiment, treatment of the compound of formula (6), or salt thereof, as defined above, with a reducing agent, preferably with hydrogen and a transition metal catalyst (eg a palladium catalyst) for example as described in Section B.3.3, leads to a compound of formula (5), or salt thereof,

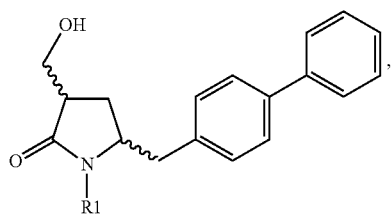

(5)

wherein R1 is hydrogen or a nitrogen protecting group, or leads to a mixture of the compounds of formulae (4) and (5).

In another particular embodiment, treatment of the compound of formula (6-a), or salt thereof, as defined above, with a reducing agent, preferably with hydrogen and a transition metal catalyst (eg a palladium catalyst) for example as described in Section B.3.3, leads to a compound of formula (5-a), or salt thereof,

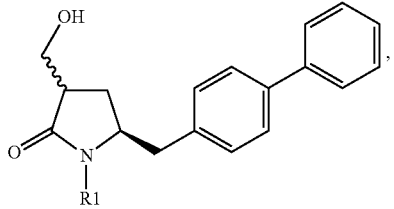

(5-a)

wherein R1 is hydrogen or a nitrogen protecting group, preferably of formula (5-b),

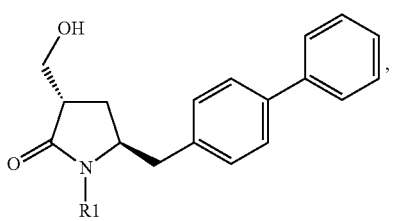

(5-b)

or leads to a mixture of the compounds of formulae (4-a) and (5-a), preferably a mixture of the compounds of formulae (4-a) and (5-b).

Section B.2.3:

Section B.2.3.1:

In a further aspect, the present invention relates to a process for preparing a compound of formula (4)

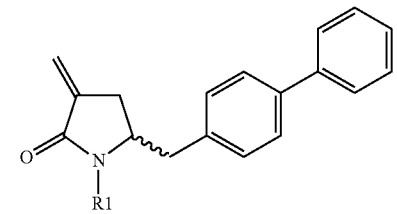

(4)

or salt thereof, wherein R1 is hydrogen or a nitrogen protecting group, said process comprising a) treating a compound of formula (5), or salt thereof,

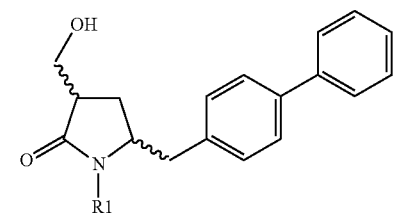

(5)

wherein R1 is hydrogen or a nitrogen protecting group,
with an OH-activating agent to obtain a compound of formula (11)

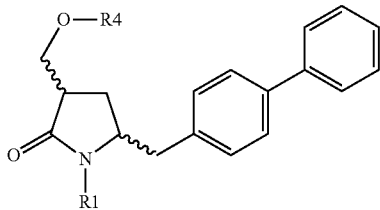

(11)

or salt thereof, wherein R1 is hydrogen or a nitrogen protecting group and R4 is an OH-activating group; and
b) reacting the compound of formula (11), or salt thereof, with a base to obtain the compound of formula (4).

Steps a) and b) as such are also an embodiment of the present invention.

In a preferred embodiment, the present invention relates to a process for preparing a compound of formula (4-a)

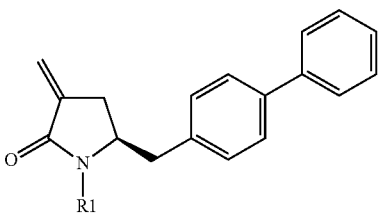

(4-a)

or salt thereof,
wherein R1 is hydrogen or a nitrogen protecting group,
said process comprising
a) treating a compound of formula (5-a), or salt thereof,

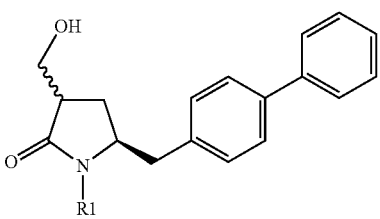

(5-a)

wherein R1 is hydrogen or a nitrogen protecting group,
with an OH-activating agent to obtain a compound of formula (11-a)

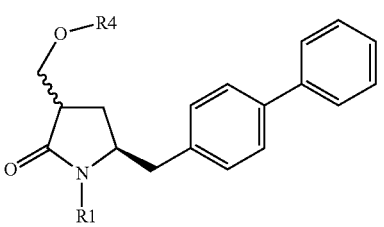

(11-a)

or salt thereof, wherein R1 is hydrogen or a nitrogen protecting group and R4 is an OH-activating group; and
b) reacting the compound of formula (11-a), or salt thereof, with a base to obtain the compound of formula (4-a).

Steps a) and b) as such are also a preferred embodiment of the present invention.

Section B.2.3.2:

In a preferred embodiment, the conversion of the OH-group of the compound of formula (5), or salt thereof, preferably of formula (5-a), into an OH-activated group occurs in the presence of the base. According to this preferred embodiment, the activation of the OH-group and the subsequent elimination of the OH-activated group occurs in situ to give the compound of formula (4), or salt thereof, preferably of formula (5-a); i.e. without isolation of the OH-activated compound of the formula (11), or salt thereof, preferably of formula (11-a).

In a more preferred embodiment, the present invention relates to a process for preparing a compound of formula (4-a)

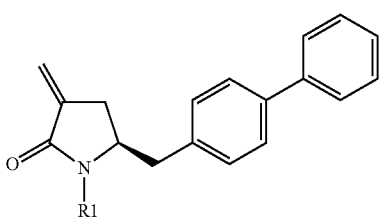

(4-a)

or salt thereof,
wherein R1 is hydrogen or a nitrogen protecting group,
comprising treating a compound of formula (5-a), or salt thereof,

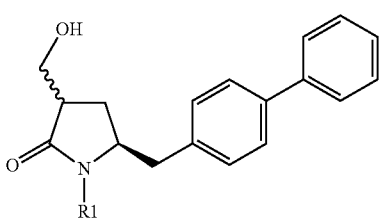

(5-a)

wherein R1 is hydrogen or a nitrogen protecting group,
with an OH-activating agent in the presence of a base to obtain the compound of formula (4-a).

In the above described methods (Sections B.2.3.1 and B.2.3.2), an OH-activating agent is any reagent which can convert a hydroxyl group into a leaving group. Examples of suitable OH-activating agents are sulphonating agents, such as methanesulfonyl- or toluenesulfonyl halides, for example methanesulfonylchloride or toluenesulfonylchloride. Preferred base is, for example, an amine, such as 1,8-diazabicyclo[5.4.0]undec-7-ene (DBU), 2,6-lutidine, diisopropylethylamine, a metal hydride, such as sodium or potassium hydride, or bases such as lithium, sodium or potassium bis (trimethylsilyl)amide and butyllithium.

The conversion of the compound of the formula (5), preferably of the formula (5-a), or salts thereof, into the compound of formula (4), preferably of the formula (4-a), or salts thereof, can also be performed, as described in methods above, on a mixture of compounds (4) and (5), preferably a mixture of compounds (4-a) and (5-a), or salts thereof, as shown in Scheme 3.

Scheme 3

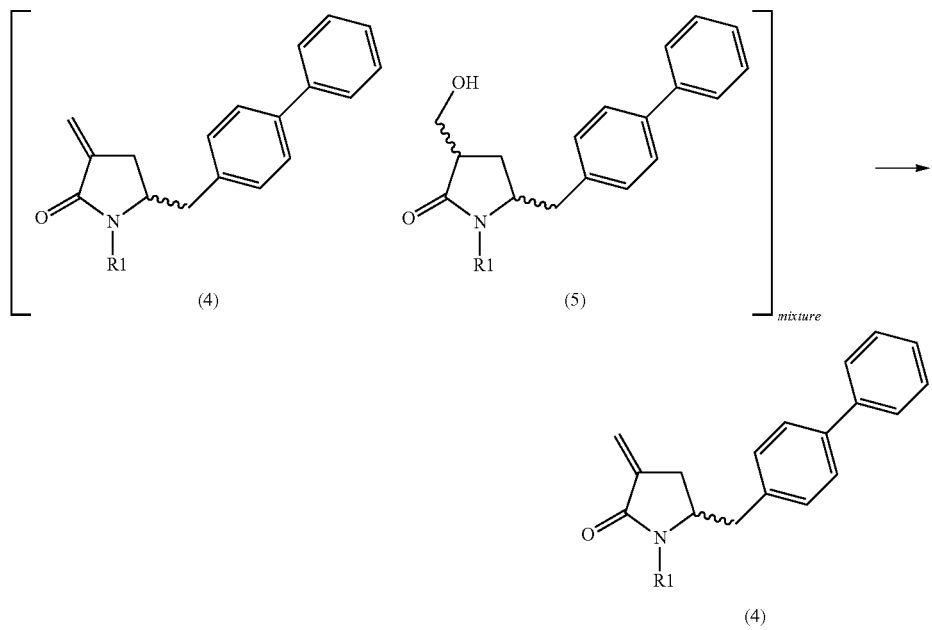

Section B.2.3.3:

In a further aspect, the present invention relates to a process for preparing a compound of formula (4)

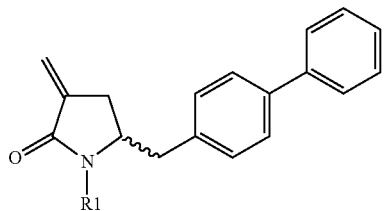

(4)

or salt thereof, wherein R1 is hydrogen or a nitrogen protecting group, said process comprising a) treating a compound of formula (5), or salt thereof,

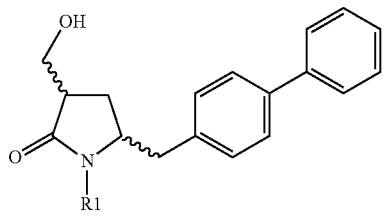

(5)

wherein R1 is hydrogen or a nitrogen protecting group, with an OH-activating agent to obtain a compound of formula (11)

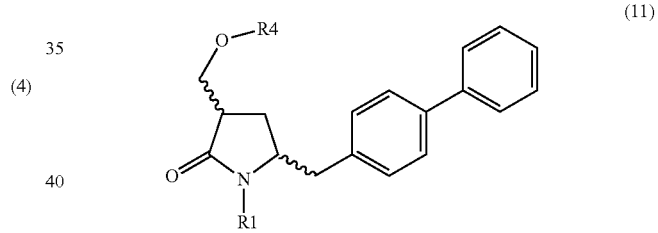

(11)

or salt thereof, wherein R1 is hydrogen or a nitrogen protecting group and R4 is an OH-activating group; and b) converting the compound of formula (11), or salt thereof, into a compound of formula (12)

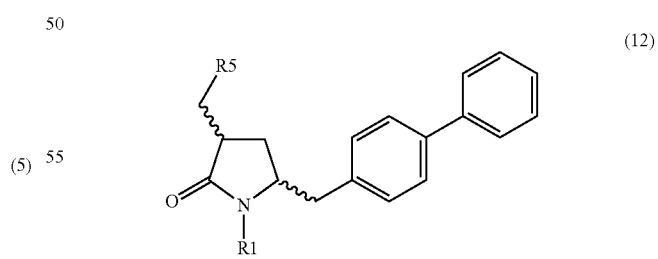

(12)

or a salt thereof, wherein R1 is hydrogen or a nitrogen protecting group and R5 is a leaving group; and c) reacting the compound of formula (12), or salt thereof, with a base to obtain the compound of formula (4)

In a preferred embodiment, the present invention relates to a process for preparing a compound of formula (4-a)

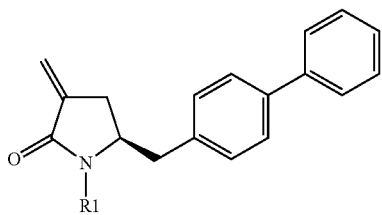

(4-a)

or salt thereof,
wherein R1 is hydrogen or a nitrogen protecting group,
said process comprising
a) treating a compound of formula (5-a), or salt thereof,

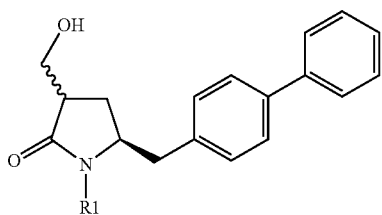

(5-a)

wherein R1 is hydrogen or a nitrogen protecting group,
with an OH-activating agent to obtain a compound of formula (11-a)

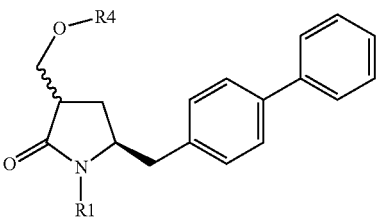

(11-a)

or salt thereof, wherein R1 is hydrogen or a nitrogen protecting group and R4 is an OH-activating group; and
b) converting the compound of formula (11-a), or salt thereof, into a compound of formula (12-a).

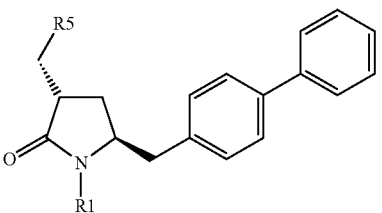

(12-a)

or a salt thereof, wherein R1 is hydrogen or a nitrogen protecting group and R5 is a leaving group; and
c) reacting the compound of formula (12-a), or salt thereof, with a base to obtain the compound of formula (4-a).

The conversion of the –OR4 group of the compound of formulae (11) or (11-a) into a leaving group is a well-known reaction to the person skilled in the art, for example as described in Richard C. Larock, "Comprehensive Organic Transformations: A Guide to Functional Group Preparations", Second Edition, Wiley-VCH Verlag GmbH, 2000, in particular as described in the relevant chapters thereof; for example it may be effected by the use of a metal halide, such as an alkali metal halide or an alkaline earth metal halide. In one embodiment the metal halide is, for example, sodium iodide.

Preferred leaving groups are halo, such as bromo or iodo.
Preferred examples of a base in step c) are amine bases, for example, triethylamine.

In one embodiment, the conversion of a compound according to formula (12), preferably of (12-a), into a compound according to formula (4), preferably of formula (4-a), is performed in the presence of a reagent which can change the identity of R1. In one embodiment, a compound according to the formula (12-a) wherein R1=H and R5=I is treated with a base (eg triethylamine) and the reagent di-tert-butyl dicarbonate to give a compound according to the formula (4-a) wherein R1=Boc.

Section B.2.3.4:

In a further aspect, the present invention relates to a process for preparing a compound of formula (4)

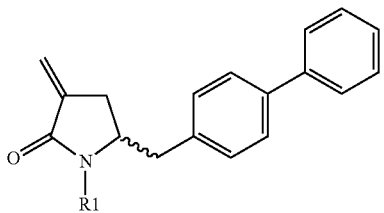

(4)

or salt thereof,
wherein R1 is hydrogen or a nitrogen protecting group,
said process comprising
a) converting a compound of formula (5), or salt thereof,

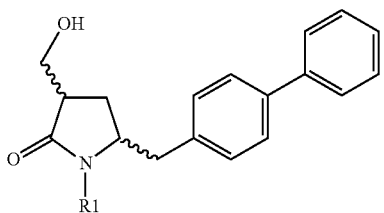

(5)

wherein R1 is hydrogen or a nitrogen protecting group,
into a compound of formula (12)

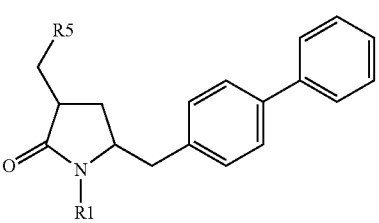

(12)

or salt thereof, wherein R1 is hydrogen or a nitrogen protecting group and R5 is a leaving group; and b) reacting the compound of formula (12), or salt thereof, with a base to obtain the compound of formula (4).

Steps a) as such is also an embodiment of the present invention.

In a preferred embodiment, the present invention relates to a process for preparing a compound of formula (4-a)

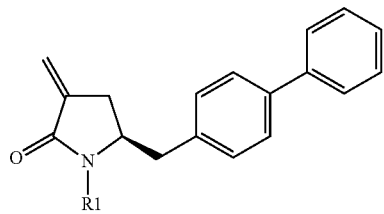
(4-a)

or salt thereof,
wherein R1 is hydrogen or a nitrogen protecting group,
said process comprising
a) converting a compound of formula (5-a), or salt thereof,

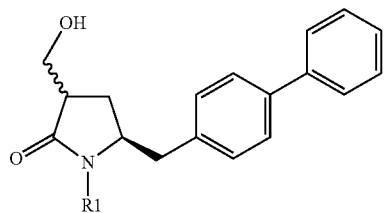
(5-a)

wherein R1 is hydrogen or a nitrogen protecting group, into a compound of formula (12-a)

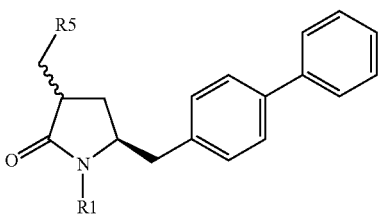
(12-a)

or salt thereof, wherein R1 is hydrogen or a nitrogen protecting group and R5 is a leaving group; and
b) reacting the compound of formula (12-a), or salt thereof, with a base to obtain the compound of formula (4-a).

The conversion of the hydroxyl group of the compound of formulae (5) or (5-a) into a leaving group is a well-known reaction to the person skilled in the art, for example as described in Richard C. Larock, "Comprehensive Organic Transformations: A Guide to Functional Group Preparations", Second Edition, Wiley-VCH Verlag GmbH, 2000, in particular as described in the relevant chapters thereof; for example it may be effected by the use of $PPh_3$ and $I_2$.

Section B.3:
Section B.3.1:
In another aspect, the present invention relates to a process for preparing a compound of formula (4)

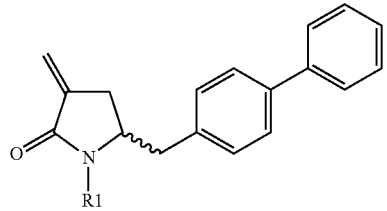
(4)

or salt thereof,
wherein R1 is hydrogen or a nitrogen protecting group,
comprising treating a compound of formula (7),

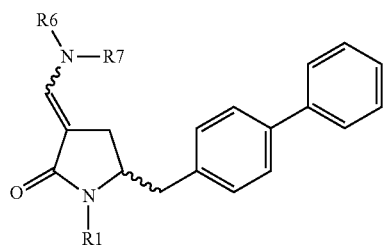
(7)

or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms,
with a reducing agent to obtain the compound of formula (4), preferably of the formula (4-a). In a preferred embodiment, the starting compound of formula (7), or salt thereof, is according to formula (7-a), or salt thereof, as defined above; more preferably the starting compound is according to formulae (7-b) or (7-c), or salts thereof, as defined above, most preferably the starting compound is according to formula (7-b), or salts thereof, as defined above.

In a preferred embodiment, the present invention relates to a process for preparing a compound of formula (4-a)

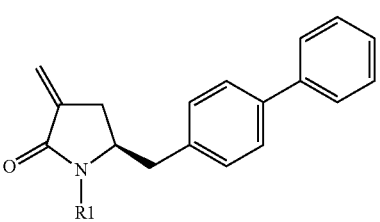
(4-a)

or salt thereof,
wherein R1 is hydrogen or a nitrogen protecting group,
comprising treating a compound of formula (7-a),

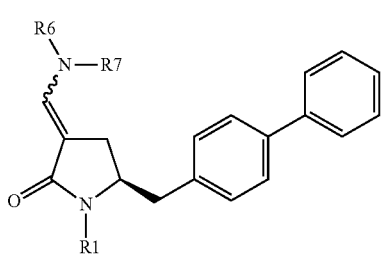

(7-a)

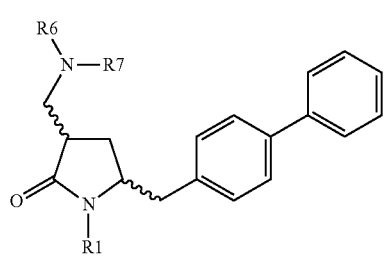

(9)

or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with a reducing agent to obtain the compound of formula (4-a). In a preferred embodiment, the starting compound of formula (7), or salt thereof, is according to formulae (7-b) or (7-c), or salts thereof, as defined above, preferably of formula (7-b).

Preferred reducing agents are hydrides, such as metal alkali borohydrides, for example sodium borohydride, lithium borohydride, potassium borohydride, calcium borohydride, sodium triacetoxyborohydride, tetramethylammonium borohydride or triacetoxyborohydride, and alkali metal hydrides, for example, lithium aluminium hydride, L-Selectride®, K-Selectride®, N-Selectride® or diisobutylaluminium hydride. Preferred reducing agents are sodium triacetoxyborohydride and diisobutylaluminium hydride; more preferably diisobutylaluminium hydride; most preferably diisobutylaluminium hydride in THF. Preferably, the reaction takes place in an ethereal solvent, such as THF, dimethoxyethane, or dioxane; preferably the solvent is THF. Typically the reaction can be conducted at −78 to 30° C., preferably −20 to 25° C., more preferably 15 to 25° C.

Section B.3.2:

In yet another embodiment, the treatment of the compound of formula (7), or salt thereof, as defined above, with a reducing agent, preferably with hydrogen and a transition metal catalyst (eg a palladium catalyst) for example as described in Section B.3.3, can lead to a compound of formula (6), or salt thereof, as defined above, or can lead to a mixture of the compounds of formulae (4) and (6).

In still another embodiment, treatment of the compound of formula (7-a), or salt thereof, as defined above, with a reducing agent leads to a compound of formula (6-a), or salt thereof, as defined above, or leads to a mixture of the compounds of formulae (4-a) and (6-a).

Section B.3.3:

In a further embodiment, the treatment of the compound of formula (7), or salt thereof, as defined above, with a reducing agent, preferably with hydrogen and a transition metal catalyst, can lead to a compound of formula (9), or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, or can lead to a mixture of the compounds of formulae (4) and (9).

In yet a further embodiment, the treatment of the compound of formula (7-a), or salt thereof, as defined above, with a reducing agent, preferably with hydrogen and a transition metal catalyst, leads to a compound of formula (9-a), or salt thereof,

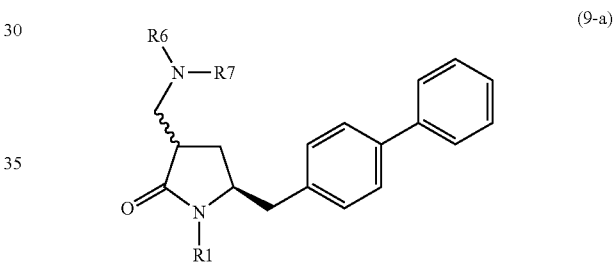

(9-a)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms. In one embodiment, the compound of formula (9-a), or salt thereof, is according to formula (9-b),

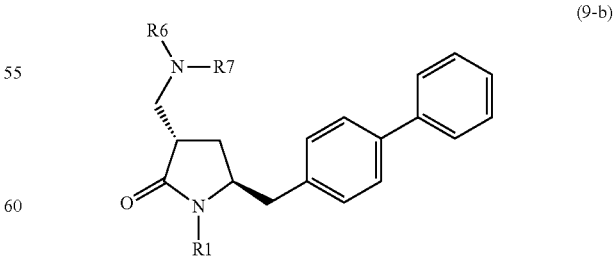

(9-b)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms. In another embodiment, the compound of formula (9-a), or salt thereof, is according to formula (9-c),

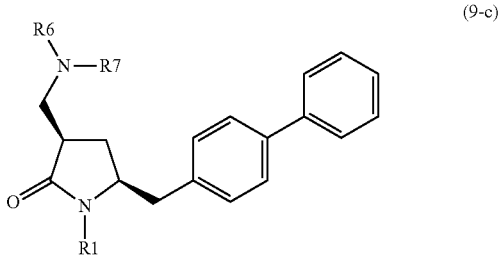

(9-c)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms.

In one embodiment, the reduction of the compound of formula (7), or salt thereof, preferably of formula (7-a), takes place with hydrogen in the presence of a transition metal catalyst, wherein the transition metal is selected from group 9 or 10 of the periodic table. Therefore, the transition metal catalyst comprises, for example, Cobalt (Co), Rhodium (Rh), Iridium (Ir), Nickel (Ni), Palladium (Pd) and/or Platinum (Pt). The reduction may occur under hetero- or homogeneous hydrogenation conditions, preferably under heterogeneous hydrogenation conditions. In particular, the transition metal is selected from Pt, Pd, or Ir; wherein the transition metal may optionally be poisoned by, for example, sulfur or lead. Examples of poisoned transition metals are Pd(S), Pd(Pb) or Pt(S). In particular, the transition metal catalyst comprises a transition metal on a solid support. The loading of the transition metal on the solid support is, for example, of from 1% to 10% w/w. Solid supports are, for example, carbon, metal oxides (e.g. aluminium oxide, zirconium oxide, titanium oxide or silicon dioxide/aluminium oxide), sulfates (e.g. barium sulfate) or carbonates (e.g. calcium carbonate and barium carbonate). In one embodiment, the transition metal catalyst may contain water, for example, of from 0 mass % to 61 mass % content of water.

In one embodiment, the hydrogenation takes place in the presence of a base, such as amine bases (e.g. triethylamine) or alkali metal bases (e.g. cesium carbonate or potassium carbonate).

In particular, the transition metal is palladium and the solid support is, for example, carbon, metal oxides (e.g. aluminium oxide, zirconium oxide, titanium oxide or silicon dioxide/aluminium oxide), carbonates (e.g. calcium carbonate and barium carbonate) or sulfates (e.g. barium sulfate).

In one embodiment, the transition metal catalyst is a Pd catalyst selected from the group consisting of palladium on carbon, such as 1% Pd/C (e.g. 1% Pd/C type 39), 3% Pd/C (e.g. 3% Pd/C type 39), 5% Pd/C (e.g. 5% Pd/C A401102-5, 5% Pd/C A401102, 5% Pd/C A109047, 5% Pd/C A405028, 5% Pd/C A405032, 5% Pd/C A405038, 5% Pd/C A503023, 5% Pd/C A503032, 5% Pd/C A503038, 5% Pd/C A102023, 5% Pd/C A102038, 5% Pd/C type 374, 5% Pd/C type 398, 5% Pd/C type 37, 5% Pd/C type 87L, 5% Pd/C type 487, 5% Pd/C type 39, 5% Pd/C type 394, 5% Pd/C type 487 (powder), 5% Pd/C type 472 (powder), 5% Pd/C type 87L (powder), 5% Pd/C Type 5R394, 5% Pd/C Type 5R338 or 5% Pd(S)/C [e.g. 5% Pd(S)/C A103038]), or 10% Pd/C (e.g. 10% Pd/C type 374, 10% Pd/C type 394, 10% Pd/C type 87L or 10% Pd/C type 37); of palladium on aluminium oxide, such as 5% Pd/Al$_2$O$_3$ (e.g. 5% Pd/Al$_2$O$_3$ A302084-5 or 5% Pd/Al$_2$O$_3$ A302011); of palladium on calcium carbonate, such as 5% Pd/CaCO$_3$ (e.g. 5% Pd/CaCO$_3$ A303060 or 5% Pd/CaCO$_3$ type 405) or 5% Pd(Pb)/CaCO$_3$ (e.g. 5% Pd(Pb)/CaCO$_3$ A 305060); of palladium on titanium oxide, such as 5% Pd/TiO$_2$ (e.g. 5% Pd/TiO$_2$ C6944); of palladium on barium sulfate, such as 5% Pd/BaSO$_4$ (e.g. 5% Pd/BaSO$_4$ A 308053); of palladium on zirconium oxide, such as 5% Pd/ZrO$_2$ (e.g 5% Pd/ZrO$_2$ C7140); and of palladium on silicon dioxide/aluminium oxide, such as 5% Pd/SiO$_2$/Al$_2$O$_3$ (e.g. 5% Pd/SiO$_2$/Al$_2$O$_3$ C7078 or 5% Pd/SiO$_2$/Al$_2$O$_3$ C7079); which are commercially available, for example from Johnson Matthey.

In another embodiment, the transition metal catalyst is a Pt catalyst such as platinum on carbon, for example 5% Pt/C (e.g. 5% Pt/C B103032, 5% Pt/C B103018, 5% Pt/C B103014, 5% Pt/C B104032, 5% Pt/C B 501032, 5% Pt/C B109032 or 5% Pt/C B501018) or 5% Pt(S)/C (e.g 5% Pt(S)/C B106032); which are commercially available, for example from Johnson Matthey.

In another embodiment, the transition metal catalyst is an Ir catalyst such as iridium on carbon, for example 5% Ir/C (e.g. 5% Ir/C C-7750) or on calcium carbonate, for example 5% Ir/CaCO$_3$ (e.g. 5% Ir/CaCO$_3$ type 30); which are commercially available, for example from Johnson Matthey.

The amount of transition metal catalyst to substrate, typically employed in the process, may be in the range of from 1 to 75 wt %, preferably of from 10 to 50 wt %, more preferably of from 20 to 50 wt %.

Solvents generally known in the art can be used. Preferred solvents are, for example, alcohol solvents (e.g. methanol, ethanol or isopropanol), ether solvents (e.g. tetrahydrofuran, methyltetrahydrofuran or tetrahydrofuran/water), aromatic solvents (e.g. toluene) or ester solvents (e.g. ethyl acetate or isopropyl acetate). In one embodiment the solvent is ethanol or tetrahydrofuran. The amount of solvent employed may be such that the concentration of substrate is in a the range of from 0.01 to 1 M, such as 0.05 M, in particular of from 0.1 to 0.5 M or of from 0.1 to 0.3 M.

The hydrogenation usually is carried out at a temperature of from 20° C. to 100° C., in particular of from 25° C. to 75° C., such as; of from 30° C. to 75° C., of from 45° C. to 75° C., of from 25° C. to 65° C. or of from 25° C. to 55° C. The applied hydrogen pressure usually ranges of from 1 bar to 40 bar, such as of from 3 bar to 30 bar, in particular; of from 5 bar to 30 bar, of from 3 bar to 20 bar or of from 3 bar to 10 bar.

In the above hydrogenation reaction the stereochemistry might be of importance. Thus, it is a further object to provide a process for producing compounds according to formulae (9-b) and (9-c), or salts thereof, as defined above, wherein the molar ratio of compounds according to formula (9-b), or salts thereof, to compounds according to formula (9-c), or salts thereof, is at least 50 to 50, in particular at least 60 to 40, such as at least 71 to 29, in particular at least 82 to 18. In particular, this objective can be achieved by using a transition metal catalyst such as a Pd or Pt catalyst; for example: palladium on carbon, such as 5% Pd/C (e.g. 5% Pd/C A401102-5, 5% Pd/C A401102, 5% Pd/C A109047, 5% Pd/C A503038, 5% Pd/C A405028, 5% Pd/C A405038, 5% Pd/C A503023, 5% Pd/C A102023, 5% Pd/C type 37, 5% Pd/C type 39, 5% Pd/C type 394, 5% Pd/C type 87L), 5% Pd(S)/C [e.g. 5% Pd(S)/C A103038], 5% Pd/C Type 5R394 or 5% Pd/C Type 5R338), 10% Pd/C (e.g. 10% Pd/C type 394 or 10% Pd/C type 37), 1% Pd/C (e.g. 1% Pd/C type 39) or 3% Pd/C (e.g. 3% Pd/C type 39); palladium on barium sulfate, such as 5% Pd/BaSO$_4$ (e.g. 5% Pd/BaSO$_4$ A 308053); palladium on aluminium oxide, such as 5% Pd/Al$_2$O$_3$ (e.g. 5% Pd/Al$_2$O$_3$ A302084-5); palladium on calcium carbonate, such as 5% Pd/CaCO$_3$ (e.g 5% Pd/CaCO$_3$ A303060); palladium on zirconium oxide, such as 5% Pd/ZrO$_2$ (e.g 5% Pd/ZrO$_2$ C7140); or platinum on carbon, for example 5% Pt/C (e.g. 5% Pt/C B103032, 5% Pt/C B103018, 5% Pt/C B103014, 5% Pt/C B104032, 5% Pt/C B 501032, 5% Pt/C B109032 or 5% Pt/C B501018) or 5% Pt(S)/C (e.g 5% Pt(S)/C B106032); which are commercially available, for example from Johnson Matthey.

Thus it is a further object to provide a process for producing compounds according to formulae (9-b) and (9-c), or salts thereof, as defined above, wherein the molar ratio of compounds according to formula (9-c), or salts thereof, to compounds according to formula (9-b), or salts thereof, is at least 50 to 50, in particular at least 67 to 33. In particular, this objective can be achieved by using a transition metal catalyst such as a Pd or Pt catalyst; for example: palladium on carbon, such as 5% Pd/C (e.g. 5% Pd/C A401102-5, 5% Pd/C A401102, 5% Pd/C A109047, 5% Pd/C A405028, 5% Pd/C A405032, 5% Pd/C A405038, 5% Pd/C A503023, 5% Pd/C A503032, 5% Pd/C A102023, 5% Pd/C A102038, 5% Pd/C type 374, 5% Pd/C type 398, 5% Pd/C type 87L or 5% Pd/C type 487), 10% Pd/C (e.g. 10% Pd/C type 87L) or 5% Pd(S)/C [e.g. 5% Pd(S)/C A103038]; palladium on aluminium oxide, such as 5% Pd/Al$_2$O$_3$ (e.g. 5% Pd/Al$_2$O$_3$ A302084-5 or 5% Pd/Al$_2$O$_3$ A302011); palladium on calcium carbonate, such as 5% Pd/CaCO$_3$ (e.g 5% Pd/CaCO$_3$ type 405) or 5% Pd(Pb)/CaCO$_3$ (e.g. 5% Pd(Pb)/CaCO$_3$ A 305060); palladium on titanium oxide, such as 5% Pd/TiO$_2$ (e.g. 5% Pd/TiO$_2$ C6944); palladium on silicon dioxide/aluminium oxide, such as 5% Pd/SiO$_2$/Al$_2$O$_3$ (e.g. 5% Pd/SiO$_2$/Al$_2$O$_3$ C7078 or 5% Pd/SiO$_2$/Al$_2$O$_3$ C7079); or platinum on carbon, for example 5% Pt/C (e.g. 5% Pt/C B501018); which are commercially available, for example from Johnson Matthey.

Section B.3.4:

In one embodiment, the treatment of the compound of formula (7), or salt thereof, as defined above, with a reducing agent, preferably with a hydride reducing agent for example as described in Section B.3.1 or as described in J. Chem. Soc., Perkin Trans 1, 1996, (11), 1131, can lead to a compound of formula (5), or salt thereof,

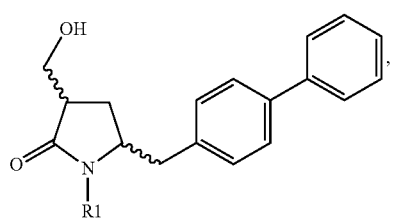

(5)

wherein R1 is hydrogen or a nitrogen protecting group,
or can lead to a mixture of the compounds of formulae (4) and (5).

In another embodiment, treatment of the compound of formula (7-a), or salt thereof, as defined above, with a reducing agent leads to a compound of formula (5-a), or salt thereof, as defined above, preferably of formula (5-b), or salt thereof, or leads to a mixture of the compounds of formulae (4-a) and (5-a), preferably a mixture of the compounds of formulae (4-a) and (5-b).

Section B.3.5:

In another embodiment, the treatment of the compound of formula (7), or salt thereof, as defined above, with a reducing agent, for example, as defined in Section B.3.1 to B.3.4, can lead to a mixture of compounds of formulae (5) and (6), or salts thereof, a mixture of compounds of formulae (5) and (9), or salts thereof, a mixture of compounds of formulae (6) and (9), or salts thereof, or a mixture of compounds of formulae (5), (6) and (9), or salts thereof; wherein each mixture may further comprise the compound of formula (4), or salt thereof, as defined above. In a preferred embodiment, the treatment of the compound of formula (7-a), or salt thereof, as defined above, with a reducing agent can lead to a mixture of compounds of formulae (5-a) and (6-a), or salts thereof, a mixture of compounds of formulae (5-a) and (9-a), or salts thereof, a mixture of compounds of formulae (6-a) and (9-a), or salts thereof, or a mixture of compounds of formulae (5-a), (6-a) and (9-a), or salts thereof; wherein each mixture may further comprise the compound of formula (4-a), or salt thereof, as defined above.

Section B.4:

In another aspect, the present invention relates to a process for preparing a compound of formula (4), or salt thereof,

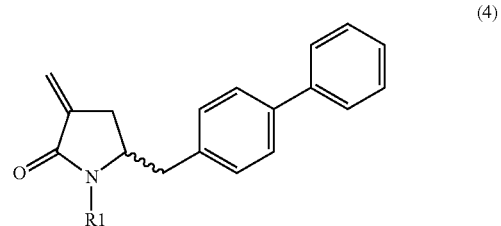

(4)

wherein R1 is hydrogen or a nitrogen protecting group,
said process comprising reacting a compound of formula (9), or salt thereof,

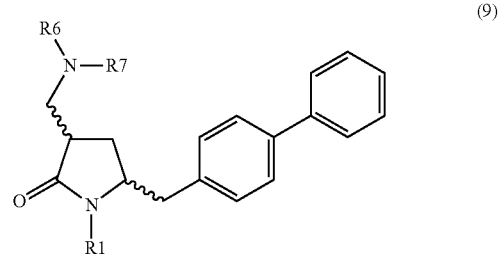

(9)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms,
with a quaternisation agent and a base to obtain the compound of formula (4).

In a preferred embodiment, the present invention relates to a process for preparing a compound of formula (4-a), or salt thereof,

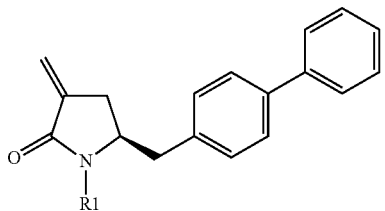

(4-a)

wherein R1 is hydrogen or a nitrogen protecting group, said process comprising reacting a compound of formula (9-a), or salt thereof,

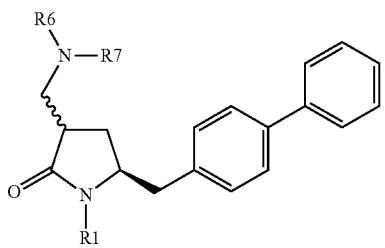

(9-a)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with a quaternisation agent and a base to obtain the compound of formula (4).

In another aspect, the present invention relates to a process for preparing a compound of formula (4), or salt thereof,

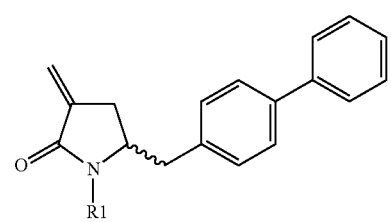

(4)

wherein R1 is hydrogen or a nitrogen protecting group, said process comprising a) reacting a compound of formula (9), or salt thereof,

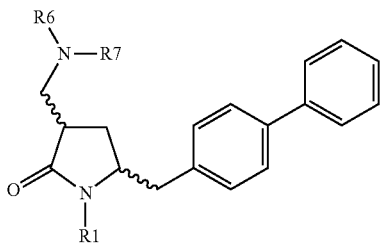

(9)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with a quaternisation agent to obtain a compound of formula (10), or salt thereof,

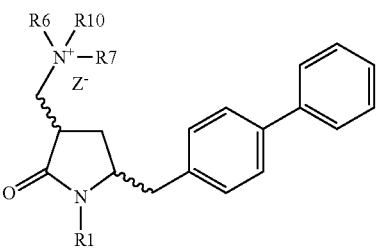

(10)

wherein R1 is hydrogen or a nitrogen protecting group, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, $Z^-$ is a halide (eg iodide, bromide, chloride), an alkyl sulphate (eg methyl sulphate) or a sulfonyl ester (eg triflate) and R10 is hydrogen, alkyl or aryl; and b) reacting the compound of formula (10), or salt thereof, with a base to obtain the compound of formula (4).

In a preferred embodiment, the present invention relates to a process for preparing a compound of formula (4-a), or salt thereof,

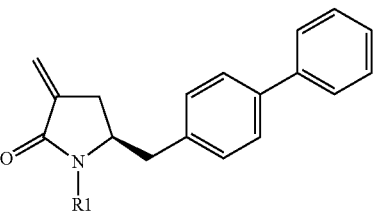

(4-a)

wherein R1 is hydrogen or a nitrogen protecting group,
said process comprising
a) reacting a compound of formula (9-a), or salt thereof,

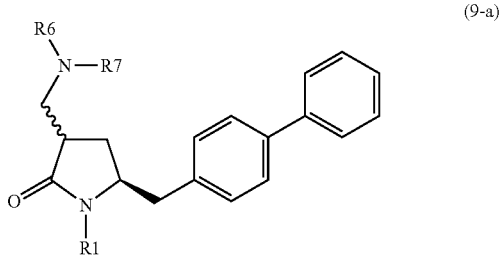

(9-a)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms,
with a quaternisation agent to obtain a compound of formula (10-a), or salt thereof,

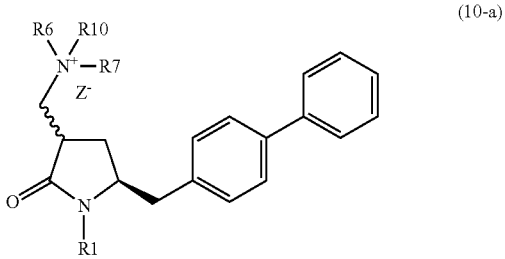

(10-a)

wherein R1 is hydrogen or a nitrogen protecting group, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, $Z^-$ is a halide (eg iodide, bromide, chloride), an alkyl sulphate (eg methyl sulphate) or a sulfonyl ester (eg triflate) and R10 is hydrogen, alkyl or aryl; and
b) reacting the compound of formula (10-a), or salt thereof, with a base to obtain the compound of formula (4-a).

Steps a) and b) as such are also preferred embodiments of the present invention.

The term quaternisation agent relates to any agent which is able to convert a tertiary amine into a quaternary amine, for example, an alkyl halide (such as methyl iodide, methyl bromide, methyl chloride, ethyl chloride, ethyl bromide or ethyl iodide), a dialkylsulfate (such as dimethylsulfate), a sulfonate (such as 4-methylsulfonyltoluene and methyl triflate) or a compound of the formula $(R10)_3O^+Z^-$ wherein R10 is alkyl (such as methyl or ethyl), and $Z^-$ is tetrafluoroborate or hexafluorophosphate. More preferably, the alkylating reagent is methyl iodide or dimethylsulfate.

Preferred bases in step b) are, for example, amines such as triethylamine, pyridine, 1,8-diazabicyclo[5.4.0]undec-7-ene (DBU). Also preferred is an ionic base, such a metal alkali carbonate (for example sodium carbonate, potassium carbonate and cesium carbonate), a metal alkali hydride (for example NaH), a metal alkali hydrogen carbonate (for example $NaHCO_3$). More preferably the base is $NaHCO_3$.

The reaction to convert the compound of formula (9) to a compound of formula (4) is preferably 'step-wise' in the sense that (9) is quaternised and then treated with a base.

Section B.5:
Section B.5.1

In another aspect, the present invention relates to a process for preparing a compound of formula (16)

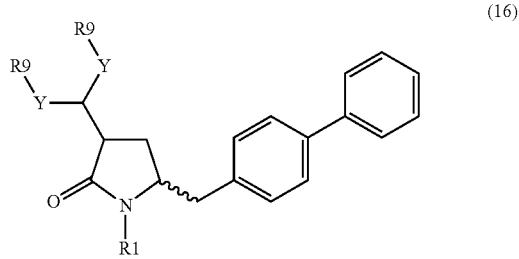

(16)

or salt thereof,
wherein R1 is hydrogen or a nitrogen protecting group, Y is oxygen and each R9, is, independently, alkyl, aryl, arylalkyl (eg benzyl) or acetyl or both R9 form together a 4 to 7, preferably a 5 to 6 membered acetal ring,
comprising treating a compound of formula (7),

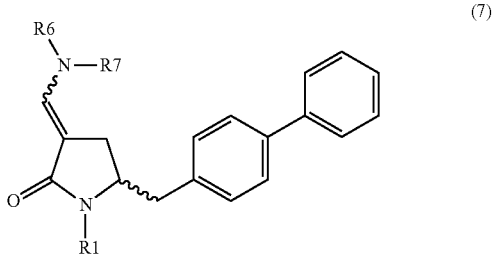

(7)

or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms,
with an acetal forming agent to obtain the compound of formula (16).

In a preferred embodiment, the present invention relates to a process for preparing a compound of formula (16-a),

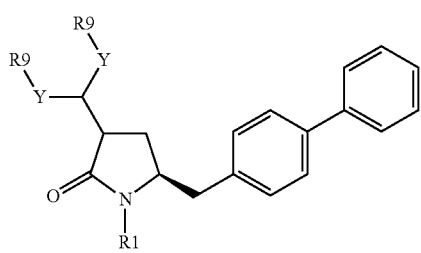

(16-a)

or salt thereof, wherein R1 is hydrogen or a nitrogen protecting group, Y is oxygen and each R9, is, independently, alkyl, aryl, arylalkyl (eg benzyl) or acetyl or both R9 form together a 4 to 7, preferably a 5 to 6 membered acetal ring, said process comprising treating a compound of formula (7-a),

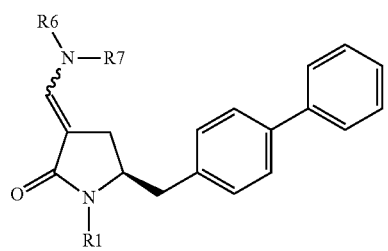

(7-a)

or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with an acetal forming agent to obtain the compound of formula (16-a). In a preferred embodiment, the starting compound of formula (7-a), or salt thereof, is according to formulae (7b) or (7c), or salts thereof, as defined above, preferably of formula (7-b).

Preferred "acetal forming" agents are alcohols (eg methanol, ethanol, isopropanol), a diol (eg ethylene glycol, 1,3-propanediol) or a trialkyl orthoformate (eg dimethyl orthoformate). Usually the reaction is performed in the presence of an acid, for example a Brønsted acid (such as hydrochloric acid, sulphuric acid) or a sulfonic acid (such as 4-toluenesulfonic acid). Resin-bound acids such as Amberlyst-15® are also suitable acids. Conditions whereby an acid is generated in situ (eg acetyl chloride) are also appropriate. Preferably, the acid is used in catalytic quantities. Preferably a mineral acid is used, such as hydrochloric acid, preferably in the presence of an alcohol, preferably methanol or ethanol are used. Further examples of preferred "acetal forming" reagents are described, e.g. in relevant chapters of standard reference works such as P. G. M. Wuts and T. W. Greene, "Greene's Protective Groups in Organic Synthesis', Fourth Edition, Wiley, New Jersey, 2007.

In another aspect, the present invention relates to a process for preparing a compound of formula (16)

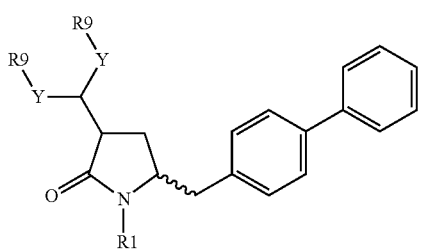

(16)

or salt thereof, wherein R1 is hydrogen or a nitrogen protecting group, Y is sulfur and each R9, is, independently, alkyl, aryl, arylalkyl (eg benzyl) or acetyl or both R9 form together a 4 to 7, preferably a 5 to 6 membered thioacetal ring, comprising treating a compound of formula (7),

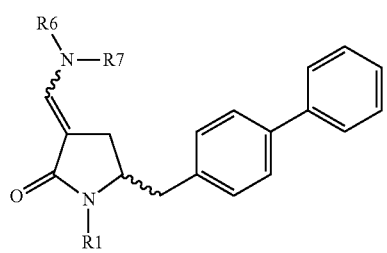

(7)

or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with a thioacetal forming agent to obtain the compound of formula (16).

In a preferred embodiment, the present invention relates to a process for preparing a compound of formula (16-a),

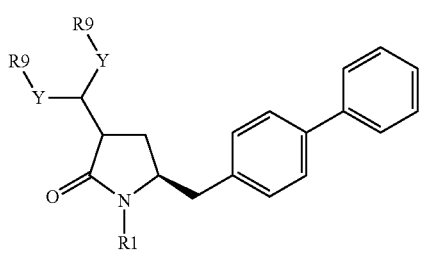

(16-a)

or salt thereof, wherein R1 is hydrogen or a nitrogen protecting group, Y is sulfur and each R9, is, independently, alkyl, aryl, arylalkyl (eg benzyl) or acetyl or both R9 form together a 4 to 7, preferably a 5 to 6 membered thioacetal ring, said process comprising treating a compound of formula (7-a),

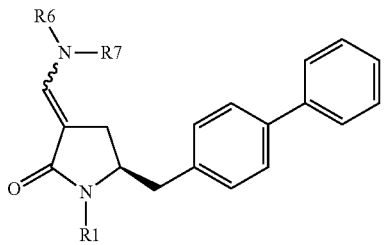

(7-a)

or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, with a thioacetal forming agent to obtain the compound of formula (16-a). In a preferred embodiment, the starting compound of formula (7-a), or salt thereof, is according to formulae (7b) or (7c), or salts thereof, as defined above, preferably of formula (7-b).

Preferred "thioacetal forming" agents are thiols (eg methanethiol, ethanethiol, thiophenol) or a dithiol (eg 1,2-ethanedithiol, 1,3-propanedithiol). Usually the reaction is performed in the presence of an acid, for example, a Brønsted acid (such as hydrochloric acid), a Lewis acid (such as borontrifluoride or titanium tetrachloride) or a solid-supported acid (such as Amberlyst-15®). Conditions whereby the acid is generated in situ (eg dimethylsulfide-bromine complex) are also suitable. Preferably the acid is used in catalytic quantities. Further examples of preferred "thioacetal forming" reagents are described, e.g. in relevant chapters of standard reference works such as P. G. M. Wuts and T. W. Greene, "Greene's Protective Groups in Organic Synthesis', Fourth Edition, Wiley, New Jersey, 2007.

Section B.5.2:

In another aspect, the present invention relates to a process for preparing a compound of formula (6), or a tautomer thereof,

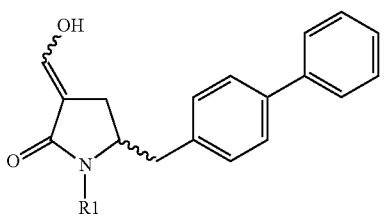

(6)

or salt thereof, wherein R1 is hydrogen or a nitrogen protecting group, said process comprising removal of the acetal functionality in a compound of formula (16), or salt thereof,

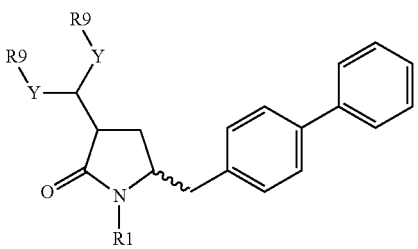

(16)

wherein R1 is hydrogen or a nitrogen protecting group, Y is oxygen and each R9, is, independently, alkyl, aryl, arylalkyl (eg benzyl) or acetyl or both R9 form together a 4 to 7, preferably a 5 to 6 membered acetal ring,
to obtain the compound of formula (6).

In another aspect, the present invention relates to a process for preparing a compound of formula (6-a), or a tautomer thereof

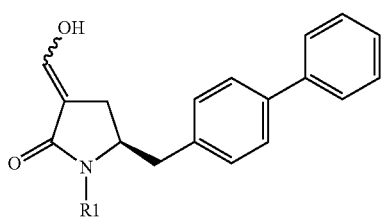

(6-a)

or salt thereof, wherein R1 is hydrogen or a nitrogen protecting group,
said process comprising removal of the acetal functionality in a compound of formula (16-a), or salt thereof,

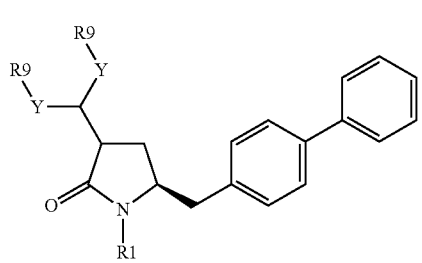

(16-a)

wherein R1 is hydrogen or a nitrogen protecting group, Y is oxygen and each R9, is, independently, alkyl, aryl, arylalkyl (eg benzyl) or acetyl or both R9 form together a 4 to 7, preferably a 5 to 6 membered acetal ring,
to obtain the compound of formula (6-a).

Suitable conditions for the removal of the acetal functionality include hydrolysis, e.g. the use of an acid in the presence of water. Suitable acids include Brønsted acids (such as hydrochloric acid, acetic acid, trifluoroaceteic acid, oxalic acid), Lewis acids (such as iron trichloride), sulphonic acids (such as 4-toluenesulphonic acid) or conditions that generate an acid in situ (eg iodine), as defined above. Other conditions include hydrogenation (eg Pd/C) [for e.g. arylalkyl, such as when R9 is arylakyl] or a base (such as sodium hydroxide or potassium carbonate [for e.g. diacetylacetals, such as when R9 is an acetyl group, for example an alkylacetyl group [R9=—C(=O)alkyl] such as methylacetyl [R9=—C(=O) CH₃]. Further examples of preferred agents for the removal of acetal functionalities are described, e.g. in relevant chapters of standard reference works such as P. G. M. Wuts and T. W. Greene, "Greene's Protective Groups in Organic Synthesis', Fourth Edition, Wiley, New Jersey, 2007.

In another aspect, the present invention relates to a process for preparing a compound of formula (6), or a tautomer thereof,

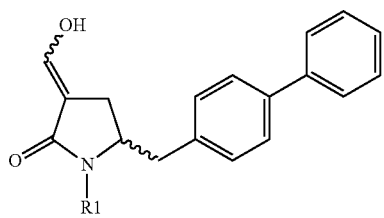

(6)

or salt thereof, wherein R1 is hydrogen or a nitrogen protecting group, said process comprising removal of the thioacetal functionality in a compound of formula (16), or salt thereof,

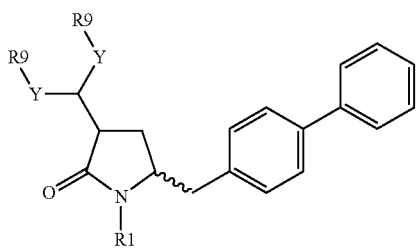

(16)

wherein R1 is hydrogen or a nitrogen protecting group, Y is sulfur and each R9, is, independently, alkyl, aryl, arylalkyl (eg benzyl) or acetyl or both R9 form together a 4 to 7, preferably a 5 to 6 membered thioacetal ring, to obtain the compound of formula (6).

In another aspect, the present invention relates to a process for preparing a compound of formula (6-a), or a tautomer thereof,

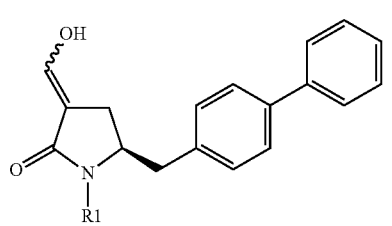

(6-a)

or salt thereof, wherein R1 is hydrogen or a nitrogen protecting group, said process comprising removal of the thioacetal functionality in a compound of formula (16-a), or salt thereof,

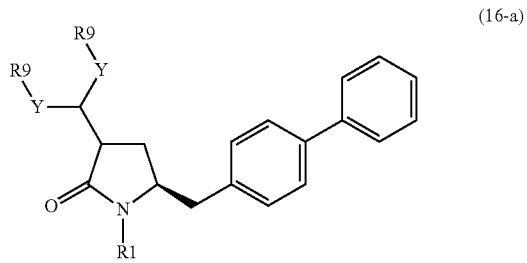

(16-a)

wherein R1 is hydrogen or a nitrogen protecting group, Y is sulfur and each R9, is, independently, alkyl, aryl, arylalkyl (eg benzyl) or acetyl or both R9 form together a 4 to 7, preferably a 5 to 6 membered acetal ring, to obtain the compound of formula (6-a).

This removal of the thioacetal functionality takes place preferably by treatment with a Lewis acid or by oxidation. Lewis acids (such as silver perchlorate, iron trichloride) or oxidising agents {such as iodine, 2,3-dichloro-5,6-dicyano-p-benzoquinone (DDQ), peroxides, [bis(trifluoroacetoxy)iodo]benzene or alkylating agents (such as methyl iodide in the presence of water) or mercury(II) salts (such as mercury dichloride, mercury perchlorate, mercury oxide)}. Further examples of preferred agents for removing thioacetal functionalities are described, e.g. in relevant chapters of standard reference works such as P. G. M. Wuts and T. W. Greene, "Greene's Protective Groups in Organic Synthesis', Fourth Edition, Wiley, New Jersey, 2007.

SECTION C: CONVERSION OF A COMPOUND OF FORMULA (7) INTO A COMPOUND OF FORMULA (1) VIA A COMPOUND OF FORMULA (2)

The processes, according to the present invention, to convert of a compound of formula (7), as defined herein, into a compound of formula (1), as defined herein, are outlined in Scheme 4.

Scheme 4

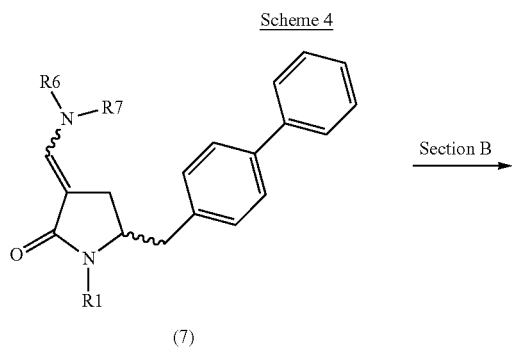

(7)

-continued

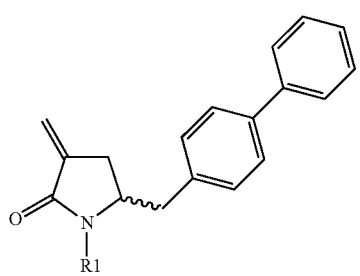

(4)

Section C.1 →

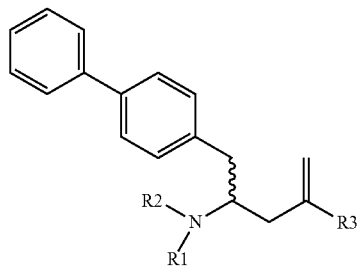

(2)

or salt thereof,
wherein R1 and R2 are, independently of each other, hydrogen or a nitrogen protecting group, and R3 is a carboxyl group or an ester group, comprising reacting a compound of formula (4)

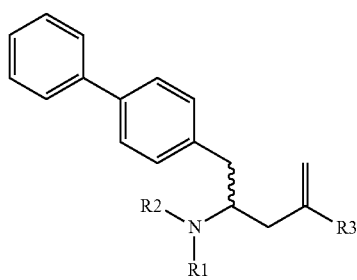

(2)

↓ Section C.2

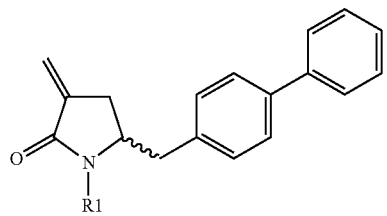

(4)

or salt thereof,
wherein R1 is hydrogen or a nitrogen protecting group, with a lactam ring opening agent to obtain the compound of formula (2).

In a preferred embodiment, a compound of formula (4-a)

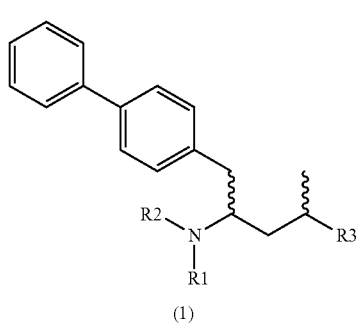

(1)

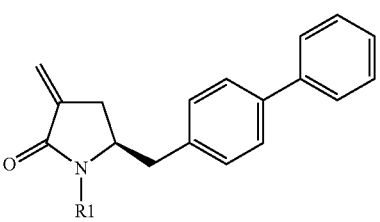

(4-a)

or salt thereof,
wherein R1 is hydrogen or a nitrogen protecting group, is treated with a lactam ring opening agent to obtain a compound according to formula (2-a), Thus, in another aspect the present invention relates to a process to convert a compound of formula (7), as described herein, into a compound of formula (1), as described herein, said method comprising:

a) any one of methods in Section B to convert (7) into (4), b) any one of methods in Section C.1 to convert (4) into (2), and c) any one of methods in Section C.2 to convert (2) into (1).

As discussed below, Sections C.1 and C.2 as such are also preferred embodiments of the present invention.

Section C.1: Ring Opening of a Compound of Formula (4)

In another aspect, the present invention relates to a process for preparing a compound according to formula (2),

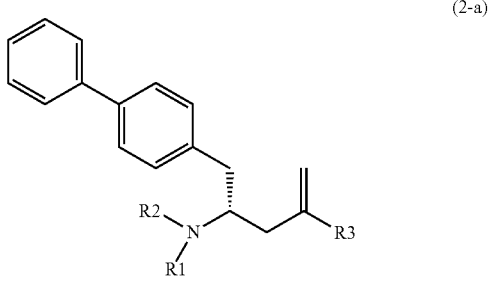

(2-a)

or salt thereof, wherein R1 and R2 are, independently of each other, hydrogen or a nitrogen protecting group, and R3 is a carboxyl group or an ester group.

Examples of lactam ring opening agents are: nucleophilic bases such as alkali metal hydroxides (for example sodium hydroxide or lithium hydroxide), neutral compounds such as hydrogenperoxides (such as lithium hydrogenperoxide) and acids. Acids are, for example, Lewis or Brønsted acids, mineral acids such as sulphuric, perchloric and hydrochloric acid, sulphonic acids such as para-toluenesulphonic acid or polymer-bound acids such as Amberlyst®. Preferably, hydrochloric acid is used as a lactam ring opening agent. Preferably acids are used in the presence of water or an alcohol (such as methanol or ethanol). The lactam ring opening agent can be used catalytically or stoichiometrically. Preferably, the lactam ring opening agent is used in an amount from 1 to 10 equivalents.

Section C.2: Reduction of a Compound of Formula (2)

The subject-matter of the present invention relates to a process for preparing a compound according to formula (1),

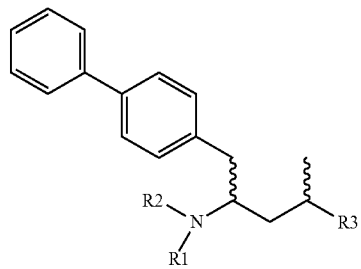

(1)

or salt thereof, wherein R1 and R2 are, independently of each other, hydrogen or a nitrogen protecting group, and R3 is a carboxyl group or an ester group, comprising reducing a compound according to formula (2),

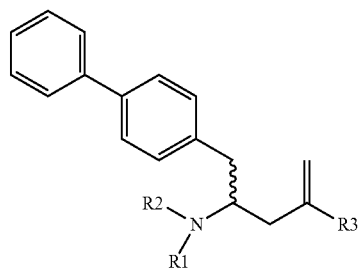

(2)

or salt thereof, wherein R1 and R2 are, independently of each other, hydrogen or a nitrogen protecting group, and R3 is a carboxyl group or an ester group, to obtain the compound of formula (1). In particular, R3 is a carboxyl group, ethyl ester or methyl ester.

Preferably, a compound according to formula (2-a), or salt thereof,

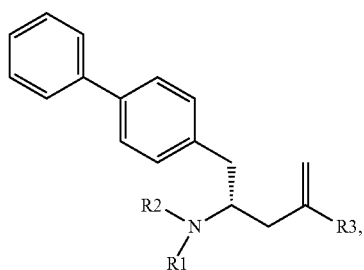

(2-a)

wherein R1, R2 and R2 are defined as above, is used as starting compound. If the compound (2-a), or salt thereof, is used as starting compound, compounds according to formula (1-a)

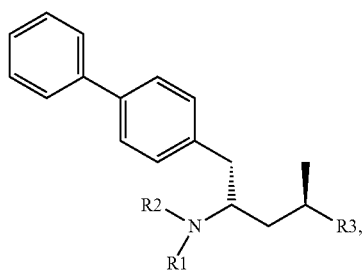

(1-a)

and formula (1-b),

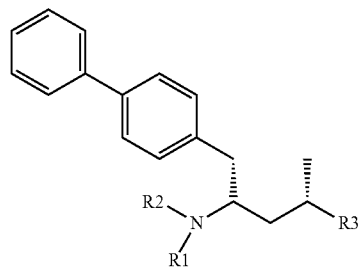

(1-b)

or salts thereof, wherein R1, R2 and R3 are defined as above, can be obtained. In a preferred embodiment R1=Boc and/or R2=H. In another preferred embodiment, R3=$CO_2H$, or $CO_2Et$, or $CO_2^-$ (carboxylate). Most preferably R3=$CO_2H$.

In particular, the group R3 of the compounds of formula (1) or (2), preferably of formula (1-a) or (2-a), is $CO_2H$, $CO_2Et$ or $CO_2Me$.

In one embodiment, the salts of the compounds according to formula (1-a) or (1-b) are generated (e.g. R3=$CO_2^-$) under the conditions employed in accordance with the present invention. The salts can then be optionally hydrolysed to give the free acid. Preferred salts are those of alkali metals (Li, Na, K) or amines (eg diisopropylethylamine, triethylamine).

In a preferred embodiment, the reduction of the compound of formula (2), or salt thereof, preferably of formula (2-a), takes place with hydrogen in the presence of a transition metal catalyst, preferably in the presence of a transition metal catalyst comprising an organometallic complex and a chiral ligand. The reduction may occur under hetereo- or homogeneous hydrogenation conditions, preferably under homogeneous hydrogenation conditions. In one embodiment, the hetereo- or homogeneous hydrogenation takes place in the presence of a base, such as amine bases (e.g. triethylamine, iPr₂EtN or 1,4-diazabicyclo[2.2.2]octane) or alkali metal bases (e.g. LiOH, NaOH or KOH). In one embodiment, the heterogeneous hydrogenation takes place in the presence of an alkali metal, in particular in an alcohol solvent (e.g. iPrOH, EtOH, MeOH); for example KOH in ethanol. In a further embodiment, the hydrogenation, in particular the homogeneous hydrogenation, takes place in the presence of an acid such as methanesulfonic acid or tetrafluoroboric acid.

Generally, the heterogeneous hydrogenation is carried out in the presence of a transition metal catalyst, wherein the transition metal is selected from group 9 or 10 of the periodic table. Therefore, the transition metal catalyst comprises, for example, Cobalt (Co), Rhodium (Rh), Iridium (Ir), Nickel (Ni), Palladium (Pd) and/or Platinum (Pt). In particular, the transition metal catalyst is Pt, Pd, or Rh on a solid support, such as carbon. In one embodiment the transition metal catalyst is Pd on carbon.

The heterogeneous hydrogenation is usually performed in a solvent, such as ether solvents (eg THF), ester solvents (eg isopropyl acetate) or alcohol solvents (eg isopropanol, ethanol or methanol); in particular isopropyl acetate and ethanol.

Generally, the homogeneous hydrogenation is carried out in the presence of a transition metal catalyst, wherein the transition metal is selected from group 7, 8 or 9 of the periodic table. Therefore, the transition metal catalyst comprises, for example, the transition metal Manganese (Mn), Rhenium (Re), Iron (Fe), Ruthenium (Ru), Osmium (Os), Cobalt (Co), Rhodium (Rh) and/or Iridium (Ir).

In a preferred embodiment, the transition metal catalyst comprises an organometallic complex and a chiral ligand.

The organometallic complex comprises a transition metal selected from group 7, 8 or 9 of the periodic table, for example the transition metal rhodium, iridium or ruthenium in particular rhodium or ruthenium. An organometallic complex comprising rhodium is particularly suitable.

The organometallic complexes can comprise a single transition metal atom. In preferred embodiments the complexes can comprise two or more transition metal atoms, optionally comprising a metal-metal bond. In a preferred embodiment two metal atoms are bridged via two halides. Generally, the organometallic complex, comprises one or more transition metal atoms and suitable achiral ligands.

Suitable achiral ligands for the organometallic complex generally are σ-donor ligands, σ-donor/π-acceptor ligands or σ,π-donor/π-acceptor ligands. Examples for suitable achiral ligands are among others carbon monoxide, halides (e.g. Cl, I or Br), phosphines [e.g. tricyclohexylphosphine (PCy₃)], alkenyls (e.g. cod, nbd, 2-metallyl), alkynyls, aryls (e.g. pyridine, benzene, p-cymene), carbonyls (e.g. acac, trifluoroacetate or dimethylformamide) and mixtures thereof.

Examples of preferred achiral ligands for the organometallic complex are: norbornadiene (nbd), cyclooctadiene (cod), pyridine (pyr), cymene, in particular p-cymene, and iodide.

Examples for organometallic complexes are: a ruthenium organometallic complex, such as [RuI₂(p-cymene)]₂, [Ru(cod)(2-metallyl)₂] or [Ru(cod)(OOCCF₃)₂]; a rhodium organometallic complex, such as [Rh(nbd)₂BF₄] or [Rh(cod)₂]BF₄; or an iridium organometallic complex such as [(Cy₃P)Ir(pyr)]Cl, [Ir(cod)₂]BArF or [Ir(cod)₂Cl]₂; in particular [Ru(cod)(2-metallyl)₂], [Ru(cod)(OOCCF₃)₂] or [RuI₂(p-cymene)]₂; in particular [Rh(NBD)₂]BF₄, [Ru(COD)(OOCCF₃)₂] or [RuCl₂(p-cymene)₂].

In one embodiment the organometallic complex is [Rh(nbd)₂]BF₄{=Bis(norbornadiene)rhodium(I)tetrafluoroborate}.

In another embodiment, the organometallic complex is [RuI₂(p-cymene)]₂ (=Diiodo(p-cymene)ruthenium(II) dimer):

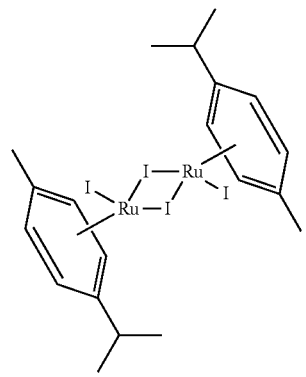

Generally, the term "chiral ligand" comprises any ligand that is suitable to build chiral organometallic complexes and that comprises a chiral centre. The transition metal catalyst comprises an organometallic complex and a chiral ligand. The chiral ligand comprises, for example, a chiral phosphine and/or a chiral ferrocene. In particular, the chiral ferrocene comprises a Cp (cyclopentadienyl) moiety which is substituted with a chiral group, such as a chiral amine, a chiral phosphine or a chiral alkyl, for example as illustrated herein.

In a first embodiment, the reduction of the compound of formula (2-a), or salt thereof, provides a composition comprising the compounds according to formulae (1-a) and (1-b), or salts thereof, wherein the molar ratio of compounds according to formula (1-a), or salts thereof, to compounds according to formula (1-b), or salts thereof, is at least 55 to 45, preferably at least 80 to 20, more preferably at least 96 to 4, most preferably at least 99 to 1.

In one embodiment, the transition metal catalyst comprises an organometallic complex and a chiral ligand such as a Fenphos ligand, a Josiphos ligand, a Mandyphos ligand, a Walphos ligand, a Taniaphos ligand, a Phospholane ligand, an Atropisomer ligand, a BoPhoz ligand, a QUINAPHOS ligand or mixtures thereof; in particular the chiral ligand is selected from the group consisting of Fenphos ligand, Josiphos ligand, Mandyphos ligand, Walphos ligand, Taniaphos ligand, Phospholane ligand, Atropisomer ligand or mixtures thereof.

Josiphos ligands, Walphos ligands, Taniaphos ligands, Mandyphos ligands, Fenphos ligands, Phospholane ligands, Atropisomer ligands and BoPhoz ligands are of the formulae:

Josiphos:

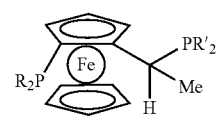

Walphos:

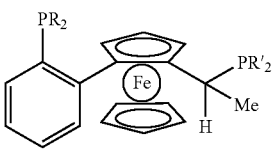

Taniaphos:

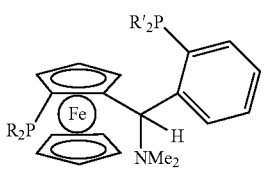

Mandyphos:

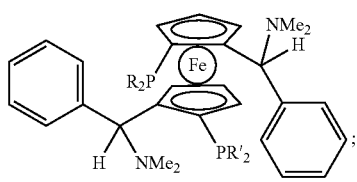

Fenphos:

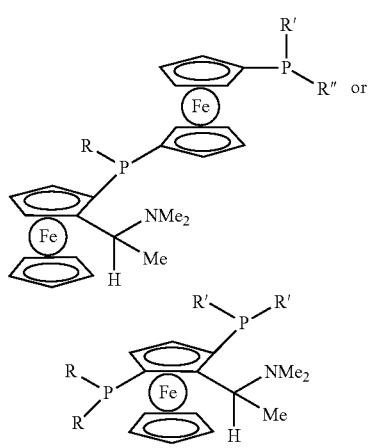

Atropisomer:

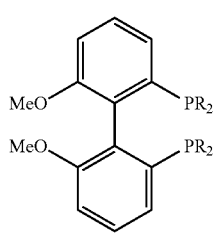

Phospholane:

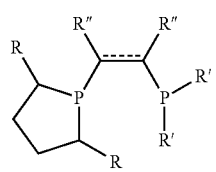

wherein R, R' and R" are, for example, as described in WO2006/003196, EP-B1-612758, WO2006/017045, WO2006/117369, WO2007/116081, WO2006/075166, WO2008/101868, WO2006/117369, WO2004/099226, EP0967015, WO2004099226, EP0967015, Chem. Eur. J., 2002, 8, 843, WO2005/108409, WO2005/056568, EP1582527, U.S. Pat. No. 5,171,892, J. Am. Chem. Soc., 1991, 113, 8518, WO9315091, EP398132, EP646590, WO9521151, EP612758, EP564406, WO2002/002578, Chem. Rev., 2003, 103 (8), 3029 and references cited therein and in particular as shown in examples herein.

BoPhoz:

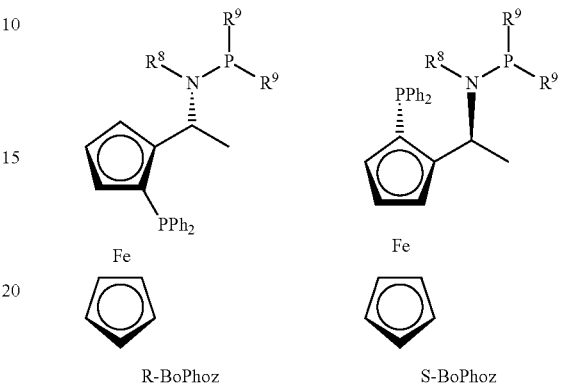

wherein R8 and R9 are, for example, as described in: Boaz, N. W.; Debenham, S. D.; Mackenzie, E. B.; Large, S. E. *Org. Lett.* 2002, 4, 2421; Boaz, N. W.; Debenham, S. D.; Large, S. E.; Moore, M. K. *Tetrahedron: Asymmetry* 2003, 14, 3575; Jia, X.; Li, X.; Lam, W. S.; Kok, S. H. L.; Xu, L.; Lu, G.; Yeung, C.-H.; Chan, A. S. C. *Tetrahedron: Asymmetry* 2004, 15, 2273 and Boaz, N. W.; Large, S. E.; Ponasik, J. A., Jr.; Moore, M. K.; Barnette, T.; Nottingham, W. D. *Org. Process Res. Dev.* 2005, 9, 472; Chem: Rev., 2003, 103 (8), 3029. In particular R8 and R9 are:

$R^8$=Me, $R^9$=Ph (=MeBoPhoz);
$R^8$=Me, $R^9$=p-fluorophenyl (=p-fluorophenyl-MeBoPhoz);
$R^8$=Me, $R^9$=3,5-difluorophenyl (=3,5-$F_2C_6H_3$-MeBoPhoz);
$R^8$=Bn, $R^9$=3,5-difluorophenyl (=3,5-$F_2C_6H_3$-BnBoPhoz);
$R^8$=Me, $R^9$=(R)-binol {=(R)-BINOL-MeBoPhoz};
$R^8$=Me, $R^9$=(S)-binol {=(S)-BINOL-MeBoPhoz};
$R^8$=Me, $R^9$=p-$CF_3$-phenyl (=p-$CF_3$-phenyl-MeBoPhoz);
$R^8$=Bn, $R^9$=Ph (=Bn-BoPhoz);
$R^8$=Me, $R^9$=cyclohexyl (=Cy-MeBoPhoz);
$R^8$=Me, $R^9$=p-fluorophenyl (=p-F-MeBoPhoz);
$R^8$=(S)-phenethyl, $R^9$=Ph {(S)-phenethyl-BoPhoz};
$R^8$=(R)-phenethyl, $R^9$=Ph {(S)-phenethyl-BoPhoz};
$R^8$=(S)-phenethyl, $R^9$=Me {(S)-phenethyl-MeBoPhoz}; and
$R^8$=(R)-phenethyl, $R^9$=Me {(R)-phenethyl-MeBoPhoz};
wherein BINOL means 2,2'-dihydroxy-1,1'-dinaphthyl.
(R)—N-Methyl-N-diphenylphosphino-1-[(S)-2-diphenylphosphino)ferrocenyl]ethylamine (=(R)MeBoPhoz)
(S)—N-Methyl-N-diphenylphosphino-1-[(R)-2-(diphenylphosphino)ferrocenyl]ethylamine (=(S)MeBoPhoz)
1-(R)—N-Di(3,5-difluorophenyl)phosphine-N-benzyl-1-[(S)-diphenylphosphino]ferrocenyl]ethylamine=(R)-3,5-$F_2C_6H_3$-BnBoPhoz
1(R)—N-Dicyclohexylphosphine-N-methyl-1-[(S)-diphenylphosphino]ferrocenyl]ethylamine=(R)-Cy-MeBoPhoz
1-(R)—N-Diphenylphosphino-N—[(R)-1-phenylethyl]-1-[(S)-2-diphenylphosphino]ferrocenylethylamine=(R)-Phenethyl-(R)-BoPhoz 1-(R)—N-Diphenylphosphino-N—[(R)-1-phenylethyl]-1-[(R)-2-diphenylphosphino]ferrocenylethylamine=(R)-Phenethyl-(S)-BoPhoz 1-(R)—N-Di(4-fluorophenyl)phosphine-N-methyl-1-[(S)-diphenylphosphino]ferrocenyl]ethylamine=(R)-4-F—C6H4-MeBoPhoz 1-(R)—N-Di[(R)-1-phenylethyl]-N-methyl-1-[(S)-diphenylphosphino]ferrocenyl]ethylamine=(R)-Phenethyl-(R)-MeBoPhoz 1-(R)—N—[(R)-2,2'-Dihydroxy-1,1'-dinaphthyl]-N-methyl-1-[(S)-diphenylphosphino]ferrocenyl]ethylamine=(R)-BINOL-(R)-MeBoPhoz 1-(R)—N—[(S)-2,2'-Dihydroxy-1,1'-dinaphthyl]-N-methyl-1-[(S)-diphenylphosphino]ferrocenyl]ethylamine=(S)-BINOL-(R)-MeBoPhoz 1-(R)—N-Di(4-fluorophenyl)phosphine-N-methyl-1-[(S)-diphenylphosphino]ferrocenyl]ethylamine=(R)-p-F-MeBoPhoz QuinaPhos ligands are of the formula:

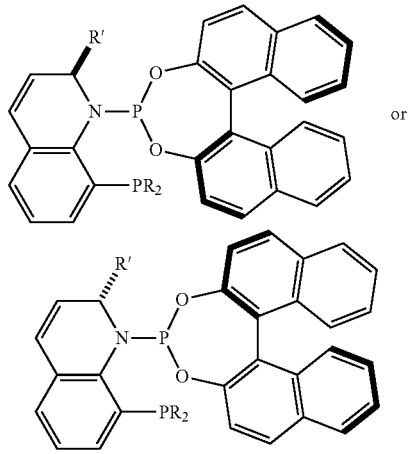

wherein R and R' are, for example, as described in G. Franciò, F. Faraone, W. Leitner, Angew. Chem. Int. Ed., 39, 1428 (2000), 39, 1428; Chem. Rev., 2003, 103 (8), 3029, for example R is Ph and R' is naphthyl. In particular, suitable QuinaPhos ligands are, for example, $(R_a,S_c)$-1Np-QUINAPHOS or $(S_a,R_c)$-1Np-QUINAPHOS.

Examples of suitable chiral ligands are:
Examples of Mandyphos Ligands:

SL-M002-1:

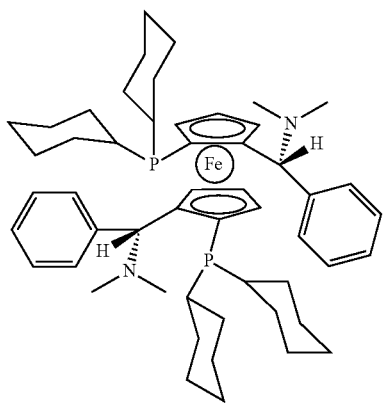

SL-M003-1:

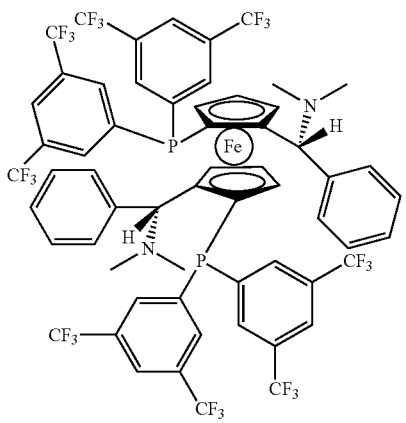

SL-M010-1:

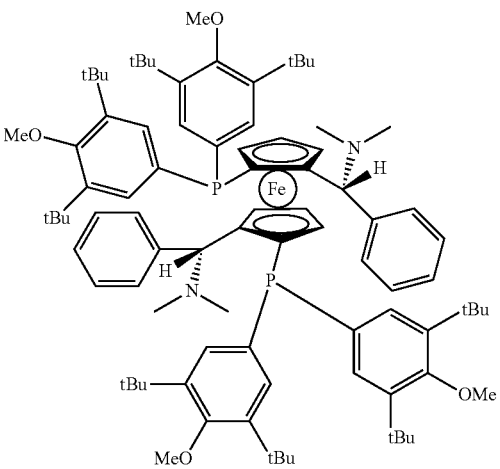

SL-M009-1:

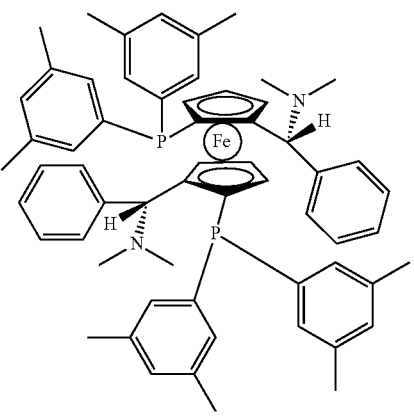

SL-M012-1:

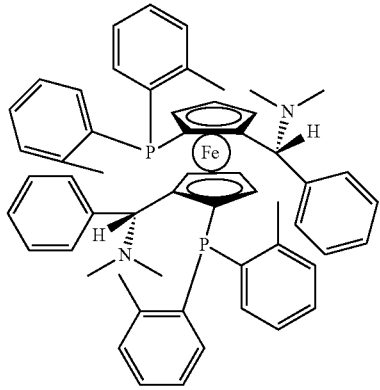

SL-M004-2:

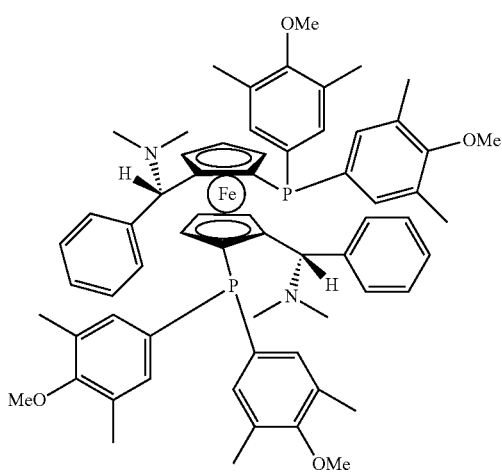

SL-M001-1:

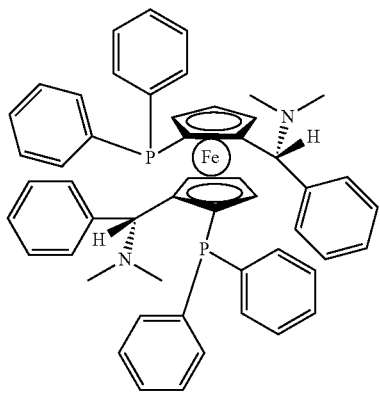

SL-M004-1:

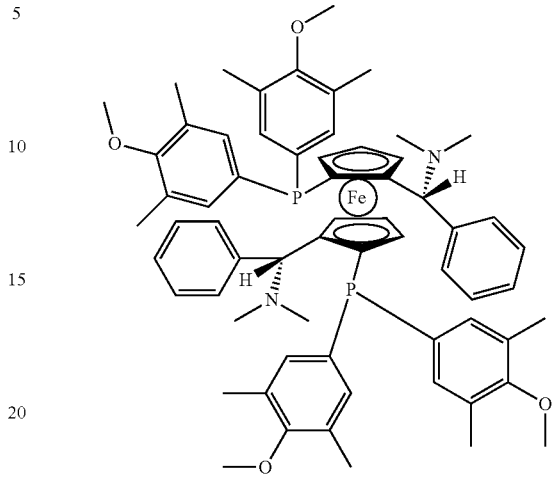

(αR,αR)-2,2'-Bis(α-N,N-dimethylaminophenylmethyl)-(S,S)-1,1'-bis(diphenylphosphino)ferrocene (=Mandyphos SL-M001-1)

(αR,αR)-2,2'-bis(α-N,N-dimethylaminophenylmethyl)-(S,S)-1,1'-bis(dicyclohexylphosphino)ferrocene (=Mandyphos SL-M002-1)

(αR,αR)-2,2'-Bis(α-N,N-dimethylaminophenylmethyl)-(S,S)-1,1'-bis-[di(bis-(3,5-trifluoromethyl)phenyl)-phosphino]ferrocene (=Mandyphos SL-M003-1)

(αR,αR)-2,2'-Bis(α-N,N-dimethylaminophenylmethyl)-(S,S)-1,1'-bis[di(3,5-dimethyl-4-methoxyphenyl)phosphino]ferrocene (=Mandyphos SL-M004-1)

(αS,αS)-2,2'-Bis(α-N,N-dimethylaminophenylmethyl)-(R,R)-1,1'-bis[di(3,5-dimethyl-4-methoxyphenyl)phosphino]ferrocene (=Mandyphos SL-M004-2)

(αR,αR)-2,2'-Bis(α-N,N-dimethylaminophenylmethyl)-(S,S)-1,1'-bis[di(3,5-dimethylphenyl)phosphino]ferrocene (=Mandyphos SL-M009-1)

(1R,1'R)-1,1'-Bis[bis(3,5-tert-butyl-4-methoxyphenyl)phosphino]-2,2'-bis[(R)-(dimethylamino)phenylmethyl]ferrocene (=Mandyphos SL-M010-1)

(αR,αR)-2,2'-Bis(α-N,N-dimethylaminophenylmethyl)-(S,S)-1,1'-bis[di-(2-methylphenyl)phosphino]-ferrocene (=Mandyphos SL-M012-1)

Examples of Josiphos Ligands:

SL-J002-1:

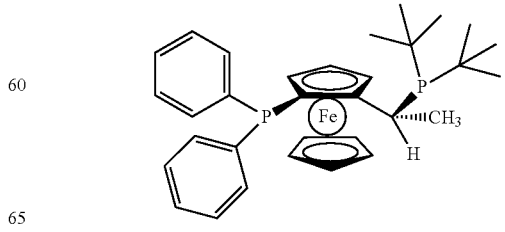

SL-J003-1:
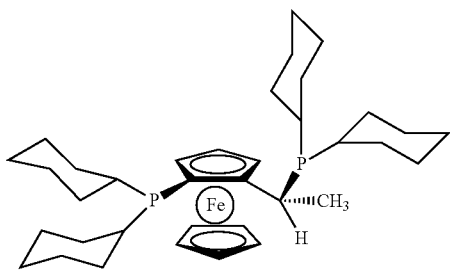
SL-J006-1:
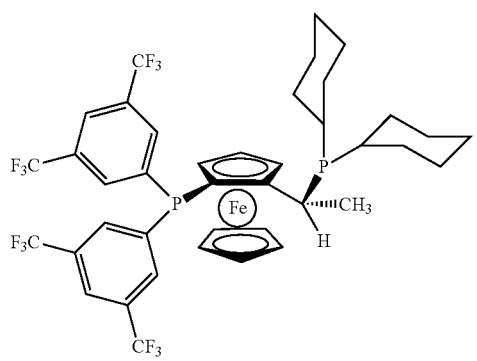
SL-J006-2:
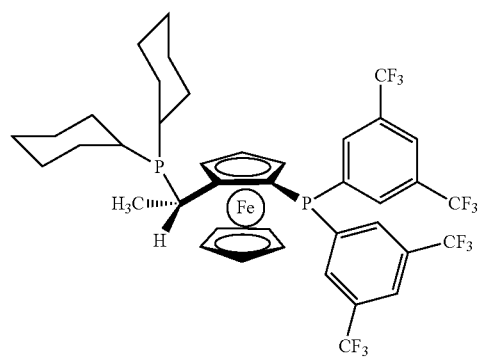
SL-J009-1:
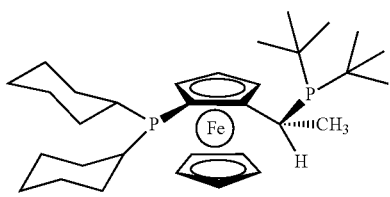
SL-J011-1:
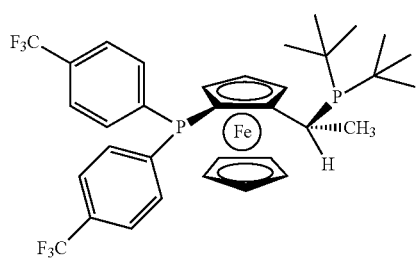
SL-J013-1:
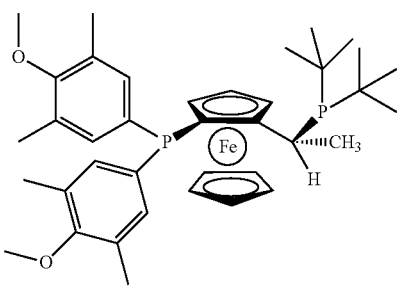
SL-J302-1:
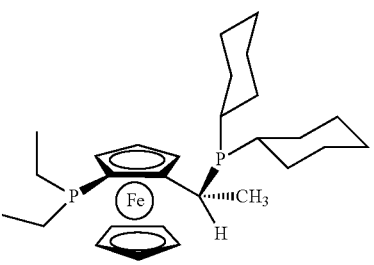
SL-J501-1:
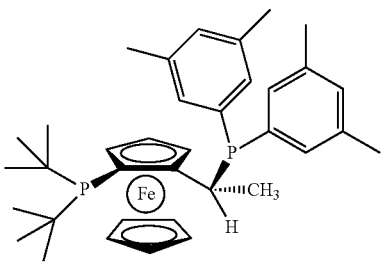
SL-J505-1:
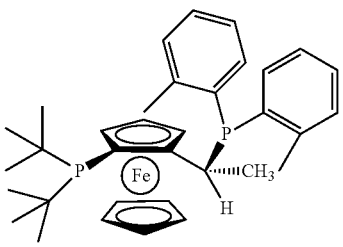
SL-J008-1:
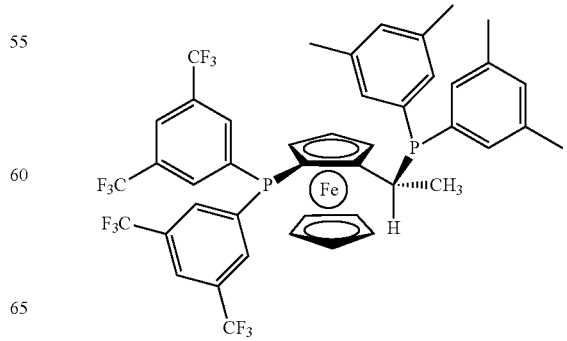

SL-J211-1:
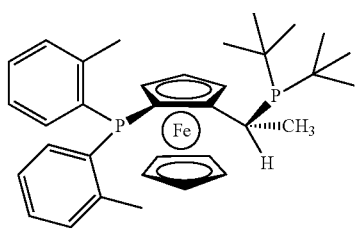
SL-J005-2:
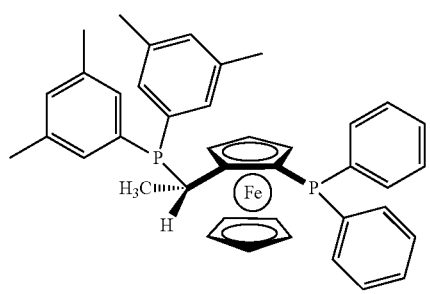
SL-J412-1:
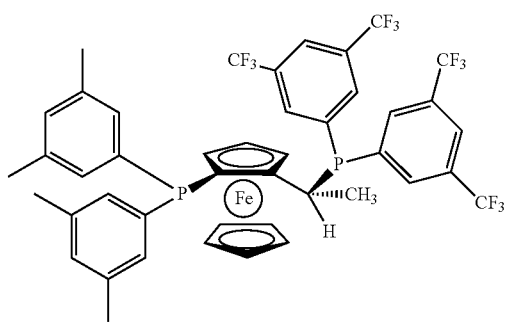
SL-J013-1:
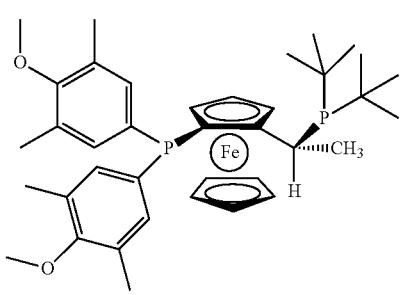
SL-J301-1:
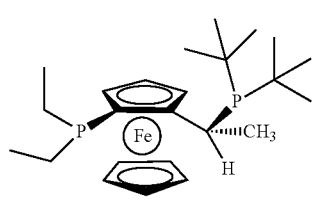
SL-J504-1:
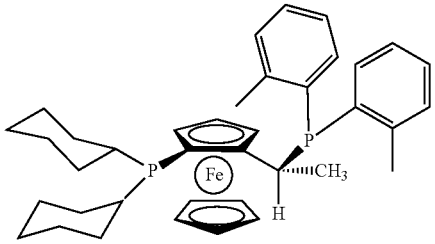
SL-J403-1
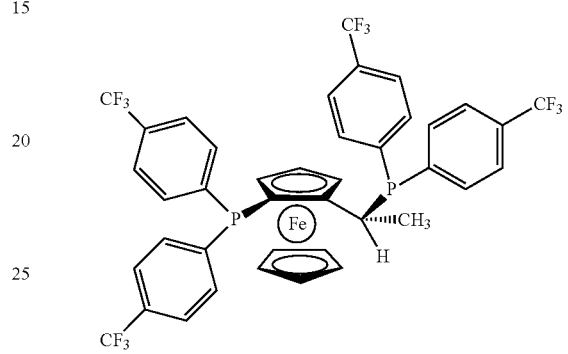
SL-J408-1:
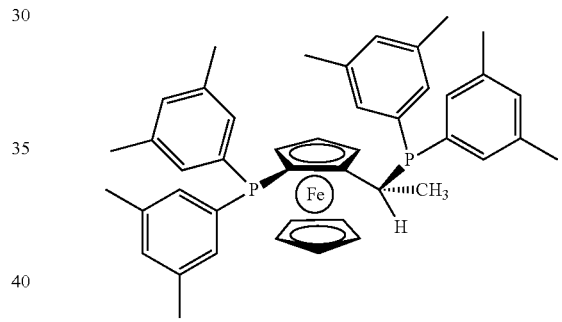
SL-J430-1:
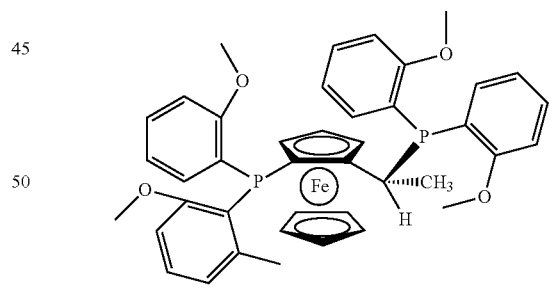
SL-J505-2:
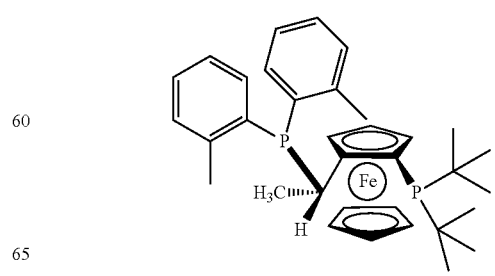

-continued

SL-J431-1:

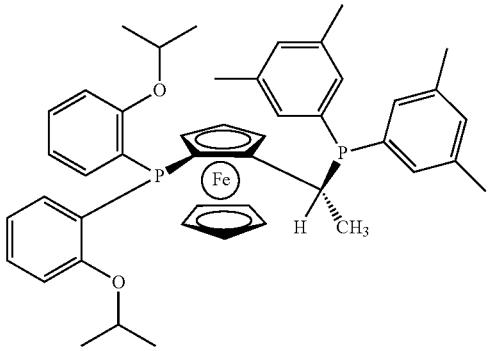

SL-J506-1:

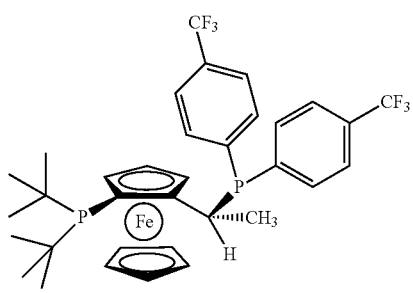

SL-J503-1:

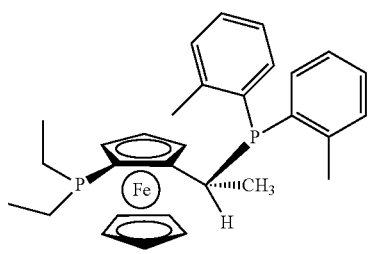

SL-J504-2:

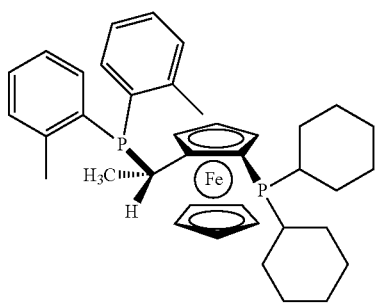

SL-J005-1:

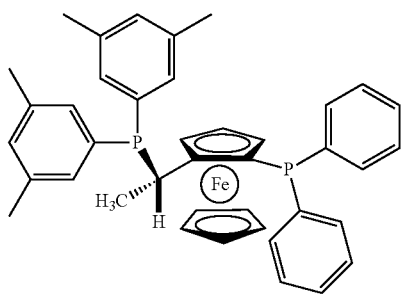

(R)-1-[(S)-2-Diphenylphosphino)ferrocenyl]ethyldi-tert-butylphosphine (=Josiphos SL-J002-1)

(R)-1-[(S)-2-Dicyclohexylphosphino)ferrocenyl]ethyldicyclohexylphosphine (=Josiphos SL-J003-1)

(R)-1-[(S)-2-(Diphenylphosphino)ferrocenyl]ethyldi(3,5-xylyl)phosphine (=Josiphos SL-J005-1)

(S)-1-[(R)-2-(Diphenylphosphino)ferrocenyl]ethyldi(3,5-xylyl)phosphine (=Josiphos SL-J005-2)

(R)-1-[(S)-2-Di-(3,5-bis(trifluoromethyl)phenyl)-phosphino)ferrocenyl]ethyldicyclohexylphosphine (=Josiphos SL-J006-1)

(S)-1-[(S)-2-Di-(3,5-bis(trifluoromethyl)phenyl)-phosphino)ferrocenyl]ethyldicyclohexylphosphine (=Josiphos SL-J006-2)

(R)-1-[(S)-2-Di-(3,5-bis(trifluoromethyl)phenyl)-phosphino)ferrocenyl]ethyldi(3,5-dimethylphenyl)phosphine (=Josiphos SL-J008-1)

(R)-1-[(S)-2-Dicyclohexylphosphino)ferrocenyl]ethyldi-tert-butylphosphine (=Josiphos SL-J009-1)

(R)-1-[(S)-2-Di(4-trifluoromethylphenyl)phosphino)ferrocenyl]ethyldi-tert.-butylphosphine (=Josiphos SL-J011-1)

(R)-1-[(S$_P$)-2-[Bis(4-methoxy-3,5-dimethylphenyl)phosphino]ferrocenyl}ethyldi-tert-butylphosphine (=Josiphos SL-J013-1)

(R)-1-[(S)-2-bis(2-methylphenyl)phosphino)ferrocenyl]ethyl di(tert-butyl)-phosphine (=Josiphos SL-J211-1)

(R)-1-[(S)-2-diethylphosphino)ferrocenyl]ethyl di(tert-butyl)-phosphine (=Josiphos SL-J301-1)

(R)-1-[(S)-2-Di-ethylphosphino)ferrocenyl]ethyldi-(2-methylphenyl)phosphine (=Josiphos SL-J302-1)

(R)-1-[(S)-2-bis(4-trifluoromethylphenyl)phosphino)ferrocenyl]ethyl bis(4-trifluoromethyl)-phosphine (=Josiphos SL-J403-1)

(R)-1-[(S)-2-bis(3,5-dimethylphenyl)phosphino)ferrocenyl]ethyl bis(3,5-dimethylphenyl)-phosphine (=Josiphos SL-J408-1)

(R)-1-[(S)-2-bis(3,5-dimethylphenyl)phosphino)ferrocenyl]ethyl bis[bis-(3,5-trifluoro-methyl)phenyl]-phosphine (=Josiphos SL-J412-1)

(R)-1-[(S)-2-bis(2-methoxyphenyl)phosphino)ferrocenyl]ethyl bis(2-methoxyphenyl)-phosphine (=Josiphos SL-J430-1)

(R)-1-[(S)-2-bis(2-isopropoxyphenyl)phosphino)ferrocenyl]ethyl bis(3,5-dimethylphenyl)-phosphine (=Josiphos SL-J431-1)

(R)-1-[(S)-2-di(tert-butyl)phosphino)ferrocenyl]ethyl bis(3,5-dimethylphenyl)-phosphine (=Josiphos SL-J501-1)

(R)-1-[(S)-2-diethylphosphino)ferrocenyl]ethyl bis(2-methylphenyl)-phosphine (=Josiphos SL-J503-1)

(R)-1-[(S)-2-cyclohexylphosphino)ferrocenyl]ethyl bis(2-methylphenyl)-phosphine (=Josiphos SL-J504-1)

(S)-1-[(R)-2-cyclohexylphosphino)ferrocenyl]ethyl bis(2-methylphenyl)-phosphine (=Josiphos SL-J504-2)

(R)-1-[(S)-2-Di-tert.-butylphosphino)ferrocenyl]ethyldicyclohexylphosphine (=Josiphos SL-J505-1)

(S)-1-[(R)-2-di(tert-butyl)phosphino)ferrocenyl]ethyl bis(2-methylphenyl)-phosphine (=Josiphos SL-J505-2)

(R)-1-[(S)-2-di(tert-butyl)phosphino)ferrocenyl]ethyl bis(4-trifluoromethyl)-phosphine (=Josiphos SL-J506-1)

Examples of Walphos Ligands:
SL-W008-1:
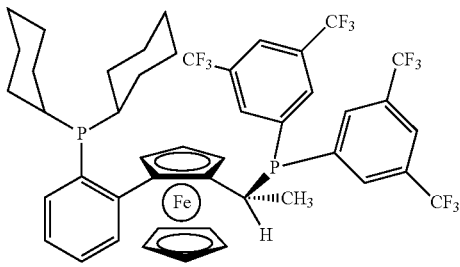
SL-W001-1:
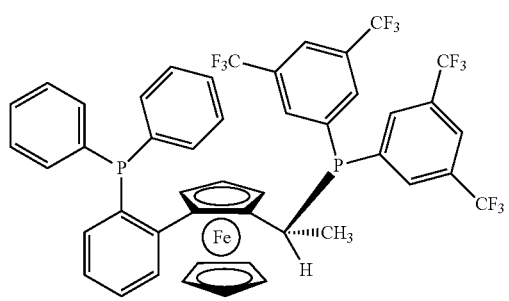
SL-W001-2:
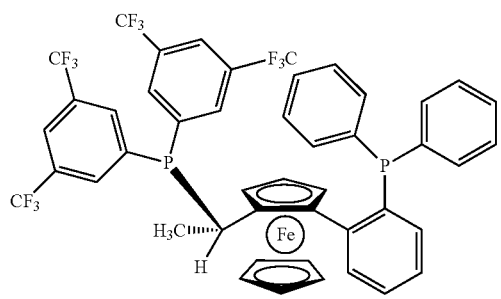
SL-W003-1:
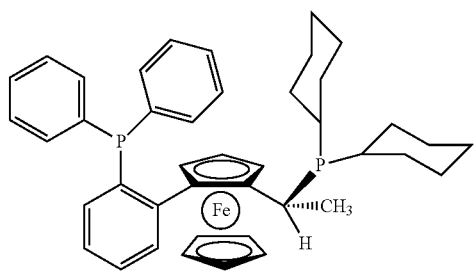
SL-W005-1:
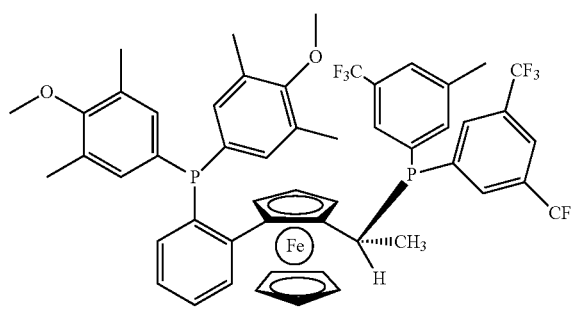
SL-W006-1:
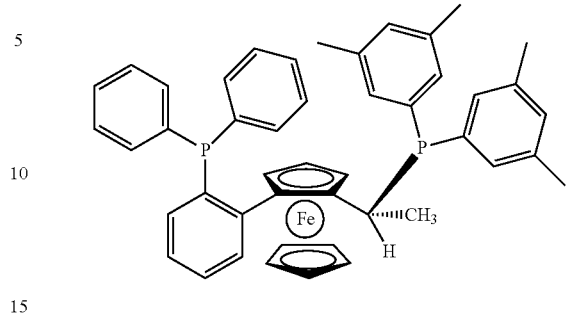
SL-W009-1:
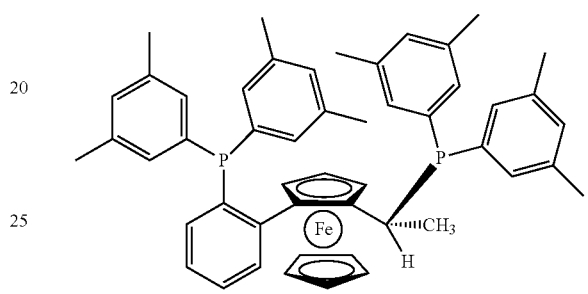
SL-W012-1:
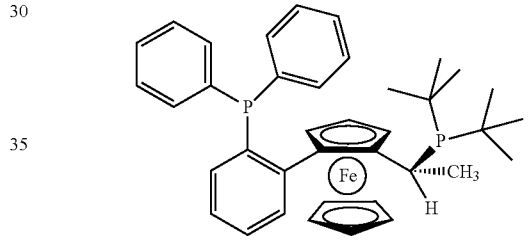
SL-W021-1:
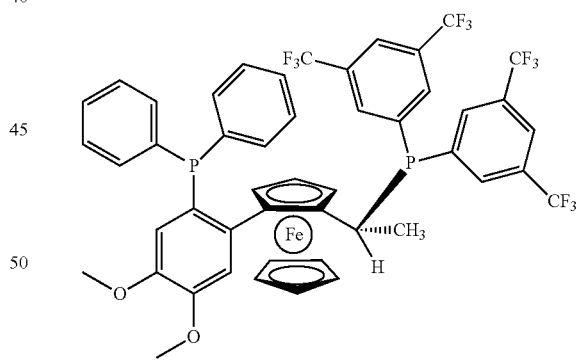
SL-W024-1:
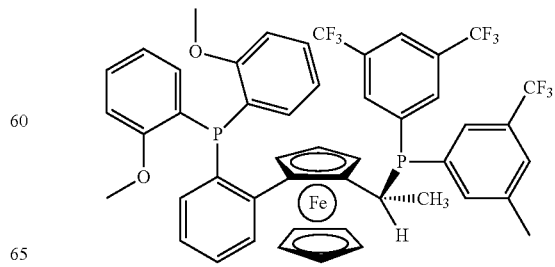

-continued

SL-W008-2:

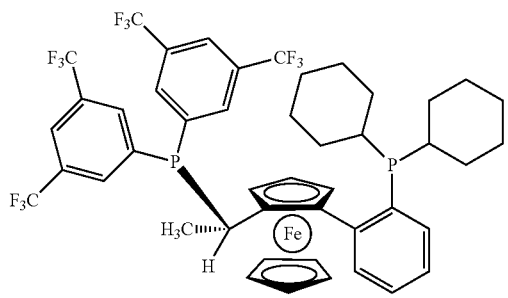

(R)-1-[(R)-2-(2.-Diphenylphosphinophenyl)ferrocenyl]eth-yldi(bis-3,5-trifluoromethylphenyl)phosphine (=Walphos SL-W001-1)

(S)-1-[(S)-2-(2.-Diphenylphosphinophenyl)ferrocenyl]eth-yldi(bis-3,5-trifluoromethylphenyl)phosphine (=Walphos SL-W001-2)

(R)-1-[(R)-2-(2'-Diphenylphosphinophenyl)ferrocenyl]eth-yldicyclohexylphosphine (=Walphos SL-W003-1)

(R)-1-[(R)-2-{2'-Di(3,5-dimethyl-4-methoxyphenyl)-phosphinophenyl}ferrocenyl]ethyldi(bis-3,5-trifluoromethylphenyl)phosphine (=Walphos SL-W005-1)

(R)-1-[(R)-2-(2'-Diphenylphosphinophenyl)ferrocenyl]eth-yldi(3,5-xylyl)phosphine (=Walphos SL-W006-1)

(R)-1-[(R)-2-(2'-Dicyclohexylphosphinophenyl)ferrocenyl]ethyldi(bis-(3,5-trifluoromethyl)-phenyl)-phosphine (=Walphos SL-W008-1)

(S)-1-[(S)-2-(2'-Dicyclohexylphosphinophenyl)ferrocenyl]ethyldi(bis-(3,5-trifluoromethyl)-phenyl)-phosphine (=Walphos SL-W008-2)

(R)-1-[(R)-2-(2.-Di-(3,5-xylyl) phosphinophenyl)-ferrocenyl]ethyldi(3,5-xylyl)phosphine (=Walphos SL-W009-1)

(R)-1-[(R)-2-(2'-(Diphenylphosphinophenyl)ferrocenyl]ethyl di(tert-butyl)-phosphine (=Walphos SL-W012-1)

(R)-1-{(R)-2-[4',5'-dimethoxy-2'-(Diphenylphosphino)phenyl]ferrocenyl}ethyl di(bis-(3,5-trifluoromethyl)phenyl)-phosphine (=Walphos SL-W021-1)

(R)-1-{(R)-2-[2'-bis(2-methoxyphenyl)phosphinophenyl]ferrocenyl}ethyl di(bis-(3,5-trifluoro-methyl)phenyl)-phosphine (=Walphos SL-W024-1)

Examples of Fenphos Ligands:

SL-F131-1:

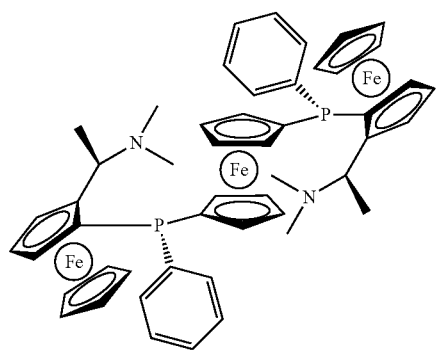

SL-F132-1

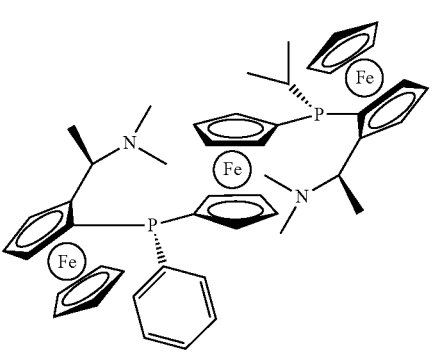

SL-F133-1:

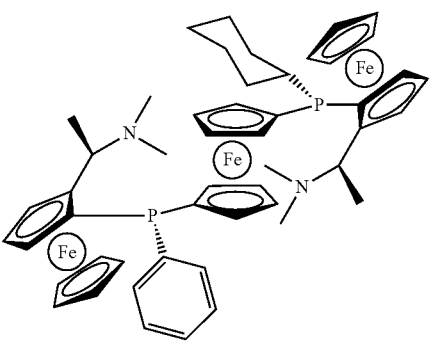

SL-F134-1:

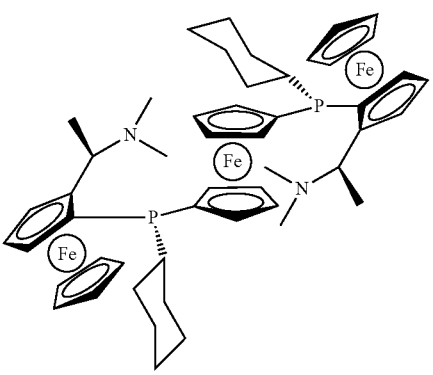

SL-F135-1:

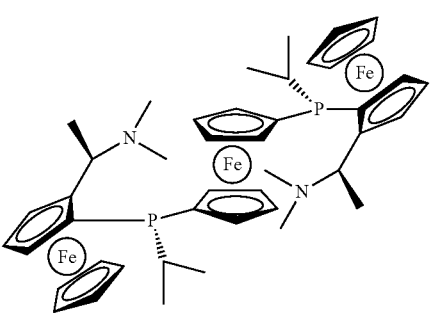

-continued

SL-F356-1:

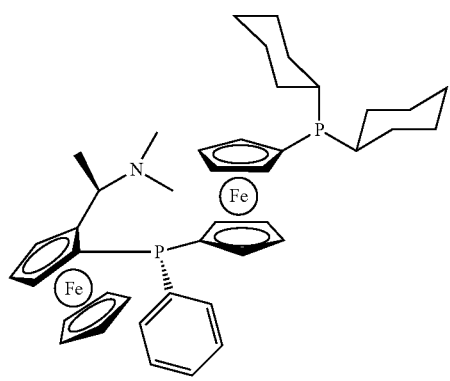

SL-F355-1:

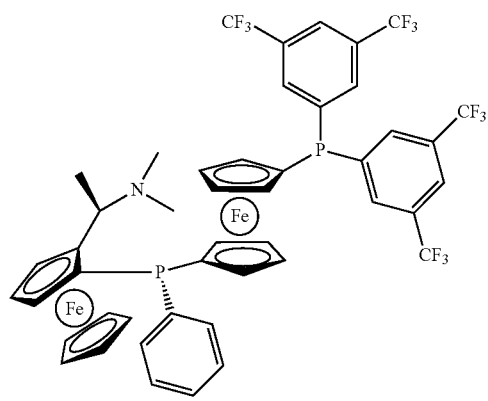

SL-F365-1:

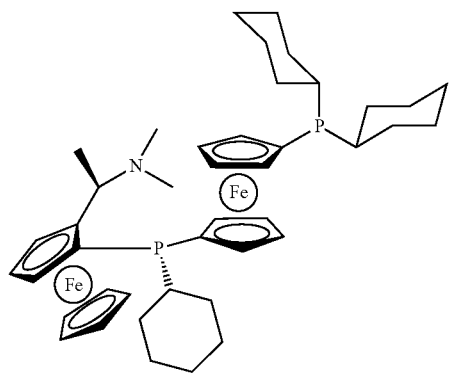

SL-F055-1:

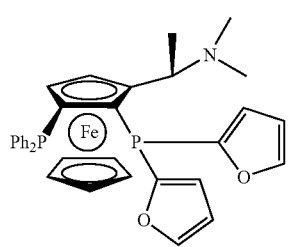

-continued

SL-F056-1:

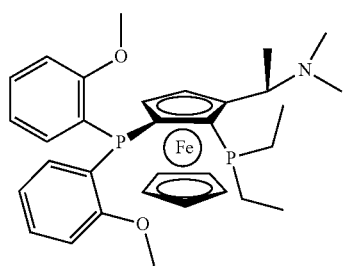

SL-F061-1:

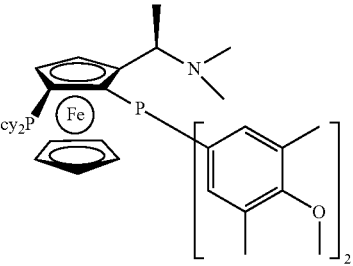

SL-F062-1:

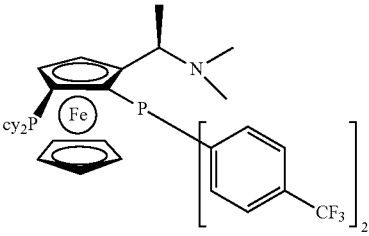

(R)—(S)-1-(Dimethylamino-eth-1-yl)-2-difurylphosphino-3-diphenylphosphino-ferrocene (=Fenphos SL-F055-1)

(R)—(S)-1-(Dimethylamino-eth-1-yl)-2-diethylphosphino-3-bis(2-Methoxyphenyl)-phosphino-ferrocene (=Fenphos SL-F056-1)

(R)—(S)-1-(Dimethylamino-eth-1-yl)-2-bis(3,5-dimethyl-4-methoxyphenyl)phosphino-3-dicyclohexylphosphino-ferrocene (=Fenphos SL-F061-1)

(R)—(S)-1-(Dimethylamino-eth-1-yl)-2-bis(4-trifluoromethylphenyl)phosphino-3-dicyclohexylphosphino-ferrocene (=Fenphos SL-F062-1)

(Rc)-(Sp)-(Se)-1,1'-Bis[2-(1-N,N-Dimethylaminoethyl)-1-ferrocenyl]phenylphosphino ferrocene (=Fenphos SL-F131-1)

(Rc)-(Sp)-(Se)-1-{[2-(1-N,N-Dimethylaminoethyl)-1-ferrocenyl]phenylphosphino}-2-{[2-(1-N,N-Dimethylaminoethyl)-1-ferrocenyl]isopropylphosphino}ferrocene (=Fenphos SL-F132-1)

(Rc)-(Sp)-(Se)-1-{[2-(1-N,N-Dimethylaminoethyl)-1-ferrocenyl]phenyl phosphino}-2-{[2-(1-N,N-Dimethylaminoethyl)-1-ferrocenyl]cyclohexylphosphino}ferrocene (=Fenphos SL-F133-1)

(Rc)-(Sp)-(Se)-1,1'-Bis[2-(1-N,N-Dimethylaminoethyl)-1-ferrocenyl]cyclohexyl phosphino ferrocene (=Fenphos SL-F134-1)

(Rc)-(Sp)-(Se)-1,1'-Bis[2-(1-N,N-Dimethylaminoethyl)-1-ferrocenyl]isopropyl phosphino ferrocene (=Fenphos SL-F135-1)

(Rc)-(Sp)-(Se)-1-{[2-(1-N,N-Dimethylaminoethyl)-1-ferrocenyl]phenylphosphino}-1'{di[bis-(3,5-trifluoromethyl)phenyl]-phosphino}ferrocene (=Fenphos SL-F355-1)

(Rc)-(Sp)-(Se)-1-{[2-(1-N,N-Dimethylaminoethyl)-1-ferrocenyl]phenylphosphino}-1'-(dicyclohexylphosphino) ferrocene (=Fenphos SL-F356-1)

(Rc)-(Sp)-(Se)-1-{[2-(1-N,N-Dimethylaminoethyl)-1-ferrocenyl]cyclohexylphosphino}-1'-(dicyclohexylphosphino) ferrocene (=Fenphos SL-F365-1)

Examples of Atropisomer Ligands:

SL-A116-2:

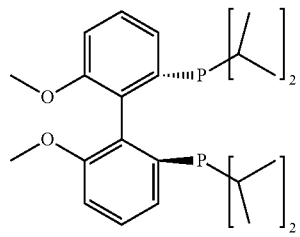

SL-A101-1:

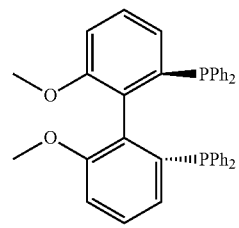

SL-A109-2:

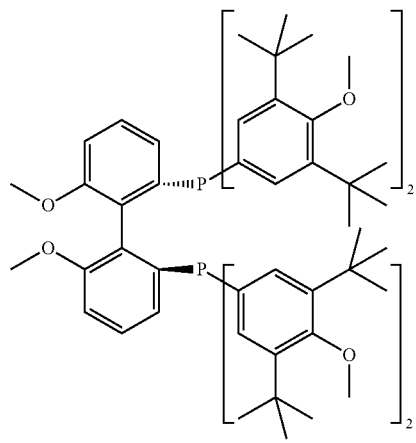

SL-A118-1:

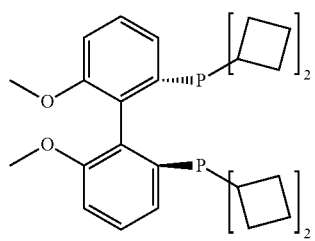

(R)-(+)-(6,6i-Dimethoxybiphenyl-2,2'-diyl)-bis(diphenylphosphine) (=Atropisomer SL-A101-1)

(S)-(6,6'-Dimethoxybiphenyl-2,2'-diyl)-bis[bis(3,5-di-tert-butyl-4-methoxyphenyl)phosphine) (=Atropisomer SL-A109-2)

(S)-(6,6'-Dimethoxybiphenyl-2,2'-diyl)bis(diisopropylphosphine) (=Atropisomer SL-A116-2)

(R)-(6,6'-Dimethoxybiphenyl-2,2'-diyl)bis(dicycylobutylphosphine) (=Atropisomer SL-A118-1)

Examples of Taniaphos Ligands:

SL-T001-1:

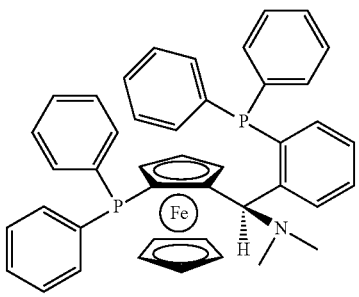

SL-T021-1:

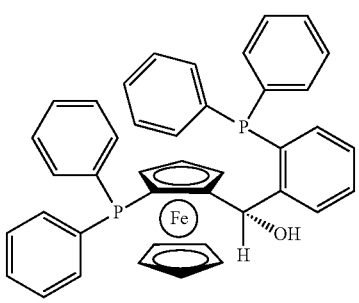

SL-T003-1:

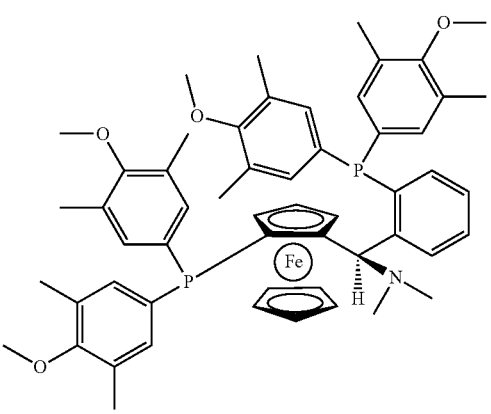

SL-T001-2:

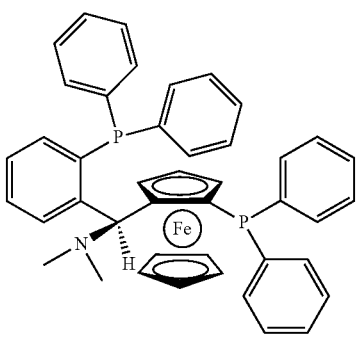

(1S)-Diphenylphosphino-2-[(R)-α-(N,N-dimethylamino)-o-diphenylphosphinophenyl)-methyl]ferrocene (=Taniaphos SL-T001-1)

(1R)-Diphenylphosphino-2-[(S)-α-(N,N-dimethylamino)-o-diphenylphosphinophenyl)-methyl]ferrocene (=Taniaphos SL-T001-2)

(R)-1-bis(4-methoxy-3,5-dimethylphenyl)phosphino-2-{(R)-(dimethylamino)$_{42}$-(bis(4-methoxy-3,5-dimethylphenyl)phosphino)phenyl]methy}ferrocene (=Taniaphos SL-T003-1)

(S)-1-diphenylphosphino-2-[(S)-hydroxy-[2-(diphenylphosphino)phenyl]methyl]ferrocene (=Taniaphos SL-T021-2)

Examples of Phospholane Ligands:

SL-P051-1:

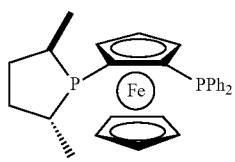

SL-P005-1:

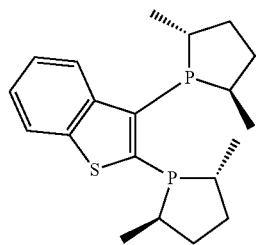

SL-P102-1:

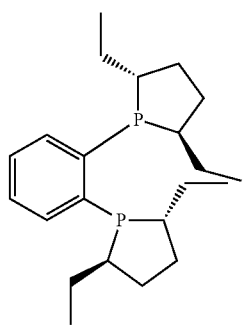

SL-P104-2:

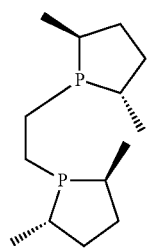

2-[(2',5'R)-2',5'-dimethylphospholano]-1-[(R)-diphenylphosphino]ferrocene (=Phospholane SL-P051-1)

1,2-Bis[(2S,5S)-2,5-dimethylphospholano]ethane (=Phospholane SL-P104-2)

1,2-Bis[(2R,5R)-2,5-diethylphospholano]benzene (=Phospholane SL-P102-1)

(R,R,R,R)-2,3-Bis(2,5-dimethyl-phospholanyl)benzo[b]thiophene (=Phospholane SL-P005-1)

Examples for Further Suitable Chiral Ligands are:

(S)-C4-TunaPhos:

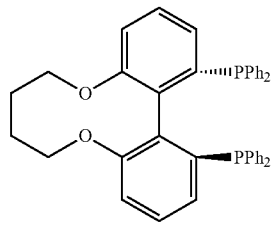

SL-A001-1:

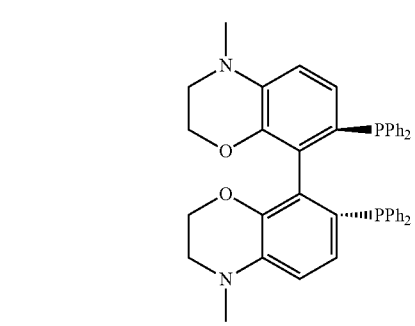

(R)-(+)-BINAP:

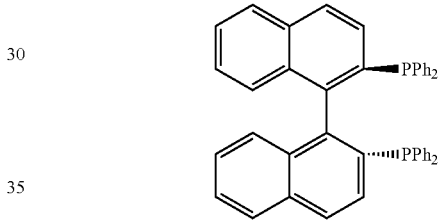

SL-M036-2:

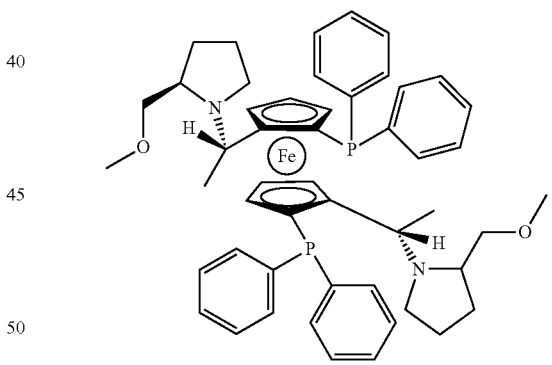

SL-M040-2:

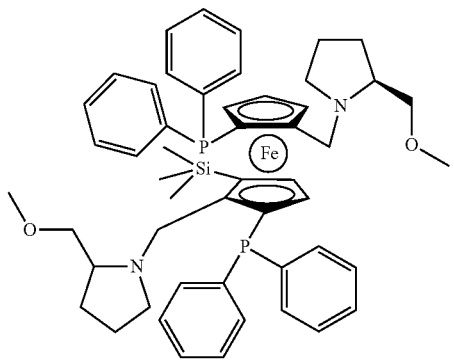

SL-M041-2:

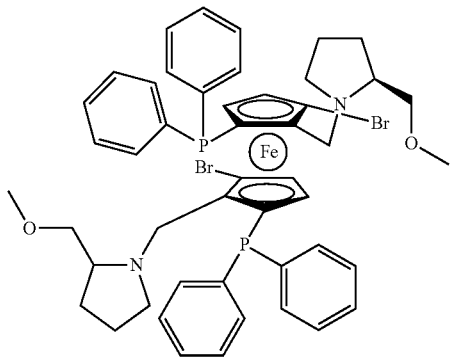

SL-A132-2:

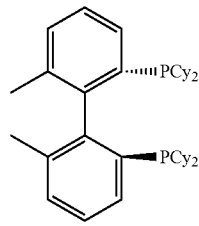

(S)-(6,6'-Dimethylbiphenyl-2,2'-diyl)bis(dicyclohexylphosphine) (=Atropisomer SL-A132-2).

A further suitable ligand is a BDPP ligand as define herein below, in particular (S,S)-BDPP.

The preparation of ligand (S)—C4-TunaPhos is described in J. Org. Chem., 2000, 65, 6223 (Example 4). Ligand (R)-(+)-BINAP can be purchased from commercial sources such as Aldrich. BoPhoz and QUINAPHOS ligands are commercially available from Johnson Matthey plc (London, United Kingdom). All other above-mentioned ligands (Mandyphos, Josiphos, Walphos, etc.) are commercially available from Solvias AG (Basel, Switzerland).

In particular, suitable chiral ligands are, for example:
SL-M004-1, SL-M004-2, SL-M002-1, SL-M003-1, SL-M009-1, SL-M0010-1, SL-M012-1, SL-J005-1, SL-J505-1, SL-J005-2, SL-J008-1, SL-J009-1, SL-J013-1, SL-J211-1, SL-J301-1, SL-J403-1, SL-J408-1, SL-J412-1, SL-J430-1, SL-J431-1, SL-J501-1, SL-J503-1, SL-J504-1, SL-J505-2, SL-J506-1, SL-F131-1, SL-F132-1, SL-F133-1, SL-F134-1, SL-F135-1, SL-F355-1, SL-F356-1, SL-F365-1, SL-T001-1, SL-T001-2, SL-T003-1, SL-T021-2, (S,S')-BDPP, (R)-MeBoPhoz, (S)-MeBoPhoz, (R)-3,5-F$_2$C$_6$H$_3$-Bn-BoPhoz, (R)-Cy-MeBoPhoz, (R)-Phenethyl-(R)-BoPhoz, (R)-Phenethyl-(S)-BoPhoz, SL-W001-1, SL-W005-1, SL-W009-1, SL-W012-1, SL-W024-1, SL-W008-1, SL-A101-1, SL-A109-1, SL-A109-2, SL-A118-1, SL-A116-2, SL-A132-2, SL-P102-1, SL-P005-1, SL-P104-2, (R$_a$,S$_c$)1Np-QUINAPHOS} and/or (S$_a$,R$_c$)1Np-QUINAPHOS}, Particularly suitable chiral ligands are, for example:
(R)-Cy-MeBoPhoz; (R)-Phenethyl-(S)-BoPhoz; SL-A101-1; SL-A109-2; SL-A116-2; SL-A118-1; SL-A132-2; SL-F131-1; SL-F132-1; SL-F133-1; SL-F134-1; SL-F135-1; SL-F355-1; SL-F356-1; SL-F365-1; SL-J005-2; SL-J505-1; SL-J008-1; SL-J013-1; SL-J301-1; SL-J403-1; SL-J408-1; SL-J430-1; SL-J431-1; SL-J501-1; SL-J504-1; SL-J504-2; SL-J505-2; SL-J506-1; SL-M002-1; SL-M003-1; SL-M004-1; SL-M009-1; SL-M010-1; SL-P051-1; SL-T001-1; SL-T001-2; SL-T003-1; SL-T021-2; (S,S)-BDPP; SL-W001-1; SL-W005-1; SL-W008-1; SL-W008-2; SL-W009-1; SL-W012-1; SL-W021-1; and/or SL-W024-1.

Further particularly suitable ligands are, for example:
SL-A101-1; SL-F131-1; SL-F132-1; SL-F356-1; SL-J505-1; SL-J008-1; SL-J504-2; SL-J505-2; SL-M010-1; SL-P051-1; (S,S)-BDPP; SL-W001-1; SL-W005-1; SL-W008-1; SL-W009-1; SL-W012-1; SL-W021-1

Suitable combinations of organometallic complex and chiral ligand are, for example:
rhodium organometallic complex and a Fenphos, Walphos, Josiphos or a Phospholane ligand; in particular [Rh(nbd)$_2$]BF$_4$ and a Fenphos, Walphos, Josiphos or a PhanePhos ligand; such as Rh(nbd)$_2$]BF$_4$ and SL-W005-1, SL-W008-1, SL-F356-1, SL-J008-1, SL-P051-1, SL-W009-1, SL-W001-1, SL-W012-1, SL-W021-1, SL-J505-2 or SL-J504-2; in particular, Rh(nbd)$_2$]BF$_4$ and SL-W008-1, SL-J008-1, SL-P051-1, SL-J505-2 or SL-J504-2;

ruthenium organometallic complex and an Atropisomer, Mandyphos or a Fenphos ligand; in particular [RuI$_2$(p-cymene)]$_2$, [Ru(cod)(2-metallyl)$_2$] or [Ru(cod)(OOCCF$_3$)$_2$] and an Atropisomer, Mandyphos, BDPP, Josiphos or a Fenphos ligand; such as [RuI$_2$(p-cymene)]$_2$, [Ru(cod)(2-metallyl)$_2$] or [Ru(cod)(OOCCF$_3$)$_2$] and SL-A101-1, SL-M010-1, (S,S)-BDPP, SL-J505-1, SL-F131-1, SL-F132-1 or SL-F134-1; or iridium organometallic complex and a Fenphos, Walphos or Josiphos ligand; in particular [Ir(cod)Cl]$_2$ and a Fenphos, Walphos or Josiphos ligand; such as [Ir(cod)Cl]$_2$ and SL-F356-1, SL-W024-1 or SL-J504-1.

When using these combinations, the reduction of the compound of formula (2-a), or salt thereof, provides a composition comprising the compounds according to formulae (1-a) and (1-b), or salts thereof, wherein the molar ratio of compounds according to formula (1-a), or salts thereof, to compounds according to formula (1-b), or salts thereof, is at least 55 to 45, preferably at least 80 to 20, more preferably at least 96 to 4, most preferably at least 99 to 1.

In a second embodiment, the reduction of the compound of formula (2-a), or salt thereof, provides a composition comprising the compounds according to formulae (1-a) and (1-b), or salts thereof, wherein the molar ratio of compounds according to formula (1-b), or salts thereof, to compounds according to formula (1-a), or salts thereof, is at least 55 to 45, preferably at least 80 to 20, more preferably at least 91 to 9.

In one embodiment, the transition metal catalyst comprises an organometallic complex and a chiral ligand such as a Fenphos ligand, a Josiphos ligand, a Mandyphos ligand, a Walphos ligand, a Taniaphos ligand, a Phospholane, an Atropisomer ligand, a BoPhoz ligand, a QUINAPHOS ligand or mixtures thereof; in particular the chiral ligand is selected from the group consisting of Josiphos ligand, Mandyphos ligand, Walphos ligand, Taniaphos ligand, Atropisomer ligand, QUINAPHOS ligand or mixtures thereof.

Suitable chiral ligands are, for example:
SL-A132-2, SL-W008-2, SL-A109-2, SL-A109-2, SL-T021-2, SL-T003-1, SL-M003-1, SL-A101-1, SL-J002-1, SL-J504-1, SL-T001-1, SL-J501-1, SL-W008-1, SL-J301-1, SL-F356-1, SL-M004-2, SL-M012-1, SL-J013-1, SL-J211-1, SL-W009-1, SL-J412-1, SL-W012-1, SL-J009-1, SL-J503-1, SL-J506-1, SL-J431-1, SL-J430-1 or (R$_a$,S$_c$)1Np-QUINAPHOS; in particular SL-W008-2, SL-J504-1, SL-W009-1, SL-J412-1, SL-J503-1

Combinations of organometallic complex and chiral ligand are for example:
rhodium organometallic complex and an Atropisomer, Walphos, Taniaphos, Josiphos, Mandyphos or Quinaphos ligand; such as [Rh(nbd)$_2$]BF$_4$ or [Rh(cod) 2]BF4 and an Atropisomer, Walphos, Taniaphos, Josiphos, Mandyphos or a Quinaphos ligand; in particular [Rh(nbd)$_2$]BF$_4$ and SL-W008-2, SL-J504-1, SL-W009-1, SL-J41201 or SL-J503-1;

ruthenium organometallic complex and an Atropisomer, Taniaphos, Mandyphos, Walphos, Josiphos or Fenphos ligand; such as [RuI$_2$(p-cymene)]$_2$, [Ru(cod)(2-metallyl)$_2$], [RuI$_2$(p-cymene)]$_2$ or [Ru(cod)(OOCCF$_3$)$_2$] and an Atropisomer, Taniaphos, Mandyphos, Walphos, Josiphos or Fenphos ligand. Even more preferably, [RuI$_2$(p-cymene)]$_2$, [Ru(cod)(2-metallyl)$_2$], [RuI$_2$(p-cymene)]$_2$ or [Ru(cod)(OOCCF$_3$)$_2$] and SL-A109-2, SL-T021-2, SL-M003-1, SL-W008-1, SL-J301-1, SL-F356-1, SL-M004-2, SL-M012-1, SL-J002-1, SL-J013-1, SL-J211 or SL-J503-1; or iridium organometallic complex and a Walphos or Josiphos ligand; in particular [Ir(cod)Cl]$_2$ and a Walphos or Josiphos ligand; such as [Ir(cod)Cl]$_2$ and SL-W009-1, SL-W012-1 or SL-J009-1.

When using these combinations, the reduction of the compound of formula (2-a), or salt thereof, provides a composition comprising the compounds according to formulae (1-a) and (1-b), or salts thereof, wherein the molar ratio of compounds according to formula (1-b), or salts thereof, to compounds according to formula (1-a), or salts thereof, is at least 55 to 45, preferably at least 80 to 20, more preferably at least 91 to 9.

In a third embodiment, the reduction of the compound of formula (2-a), or salt thereof, provides a composition comprising the compounds according to formulae (1-a) and (1-b), or salts thereof, wherein the molar ratio of compounds according to formula (1-a), or salts thereof, to compounds according to formula (1-b), or salts thereof, is at least 55 to 45, preferably at least 80 to 20, more preferably at least 97 to 3, most preferably at least 99 to 1.

In one embodiment, the transition metal catalyst comprises a transition metal selected from the group 8 or 9, such as rhodium, ruthenium or iridium and a chiral ligand selected from the group consisting of BoPhoz ligand, BINAP ligand, BINOL ligand, a Phospholane ligand, PhanePhos ligand, P-Phos ligand, QuinaPhos ligand, ProPhos ligand, BDPP ligand, DIOP ligand, DIPAMP ligand, DuanPhos ligand, Nor Phos ligand, BINAM ligand, CatAsium ligand, SimplePHOX ligand, PHOX ligand, ChiraPhos ligand, Ferrotane ligand, BPE ligand, TangPhos ligand, JafaPhos ligand, DuPhos ligand, Binaphane ligand and mixtures thereof.

BoPhoz ligands are of the formula described above, in particular (R)-4-F—C$_6$H$_4$-MeBoPhoz, (R)-BINOL-(R)-MeBoPhoz, (R)-MeBoPhoz, (R)-p-F-MeBoPhoz, (R)-Phenethyl-(R)-MeBoPhoz, (S)-BINOL-(R)-MeBoPhoz or (S)-MeBoPhoz.

QUINAPHOS ligands are of the formula described above, in particular (R$_a$,S$_c$)-1Np-QUINAPHOS or (S$_a$,R$_c$)-1Np-QUINAPHOS.

(S)-2-(1-Naphthyl)-8-diphenylphosphino-1-(R)-3,5-dioxa-4-phosphacyclohepta[2,1-a;3,4-a]dinaphthalen-4-yl)-1,2-dihydroquinoline=(R$_a$,S$_c$)-1Np-QUINAPHOS (R)-2-(1-Naphthyl)-8-diphenylphosphino-1-(S)-3,5-dioxa-4-phosphacyclohepta[2,1-a;3,4-a']dinaphthalen-4-yl)-1,2-dihydroquinoline=(S$_a$,R$_c$)-1Np-QUINAPHOS BINAP ligands are of the formula:

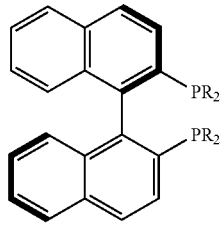
(R)-BINAP

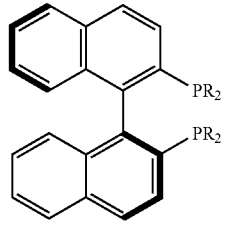
(S)-BINAP wherein R is, for example, as described in R. Noyori, H. Takaya, Acc. Chem. Res., 23 345 (1990), for example R is phenyl (=BINAP) or tolyl (=Tol-BINAP). In particular, suitable BINAP ligands are (R)-BINAP, (R)-Tol-BINAP, (S)-BINAP or (S)-Tol-BINAP.

(R)-2,2'-Bis(di-p-tolylphosphino)-1,1'-binapthalene=(R)-Tol-BINAP (S)-2,2'-Bis(di-p-tolylphosphino)-1,1'-binapthalene=(S)-Tol-BINAP (R)-2,2'-Bis(diphenylphosphino)-1,1'-binapthalene=(R)-BINAP (S)-2,2'-Bis(diphenylphosphino)-1,1'-binapthalene=(S)-BINAP BINOL ligands are of the formula:

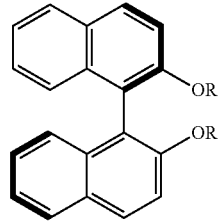
(R)-BINOL

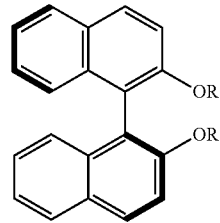
(S)-BINOL wherein R is, for example, as described in Noyori, R.; Tomino, I.; Tanimoto, Y.; Nishizawa, M. J. Am. Chem. Soc, 106, 6709 (1984); Noyori, R.; Tomino, I.; Yamada, M.; Nishizawa, M. J. Am. Chem. Soc., 106, 6717 (1984), for example is phenyl (=BINOL). In particular, suitable BINOL ligands are, for example, (R)-BINOL or (S)-BINOL.

PhanePhos ligands are of the formula:

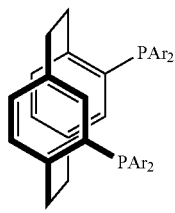

wherein Ar is, for example, as described in K. Rossen, P. J. Pye, R. A. Reamer, N. N. Tsou, R. P. Volante, P. J. Reider J. Am. Chem. Soc. 119, 6207 (1997), for example Ar is Ph (=PhanePhos), 4-Me-$C_6H_4$ (=Tol-PhanePhos), 4-MeO—$C_6H_4$ (An-PhanePhos), 3,5-$Me_2$-$C_6H_3$ (=Xyl-Phanephos) or 3,5-$Me_2$-4-MeO—$C_6H_2$ (=MeO-Xyl-Phanephos). In particular, suitable PhanePhos ligands are, for example, (R)-PhanePhos, (R)-Xyl-PhanePhos, (S)-Xyl-PhanePhos, (S)-PhanePhos, (R)-An-PhanePhos, (R)-MeO-Xyl-PhanePhos or (R)-Tol-PhanePhos.

(R)-4,12-Bis(diphenylphosphino)[2.2]-paracyclopentane=(R)-PhanePhos (S)-4,12-Bis(diphenylphosphino)[2.2]-paracyclopentane=(S)-PhanePhos (R)-4,12-Bis(di(3,5-xylyl)phosphino)[2.2]-paracyclopentane=(R)-Xyl-PhanePhos (S)-4,12-Bis(di(3,5-xylyl)phosphino)[2.2]-paracyclopentane=(S)-Xyl-PhanePhos (R)-4,12-Bis(di(p-tolyll)phosphino)-[2.2]-paracyclopentane=(R)-Tol-PhanePhos (R)-4,12-Bis(di(p-methoxyphenyl)phosphino)-[2.2]-paracyclopentane=(R)-An-PhanePhos (R)-4,12-Bis(di(p-methoxy-3,5-dimethylphenyl)phosphino)-[2.2]-paracyclopentane=(R)-MeO-Xyl-PhanePhos P-Phos ligands are of the formula:

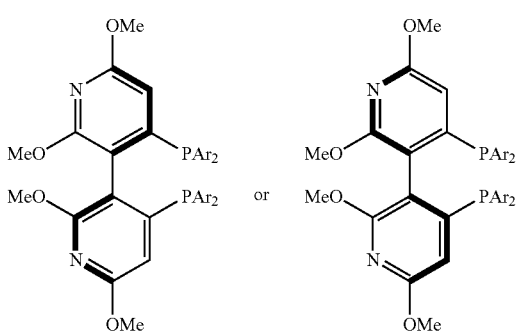

wherein Ar is, for example, as described in C.-C. Pai, C.-W. Lin, C.-C. Lin, C.-C. Chen, A. S. C. Chan, W. T. Wong, J. Am. Chem. Soc. 122, 11513 (2000), for example Ar is Ph (=P-Phos), 4-Me-$C_6H_4$ (=Tol-P-Phos), 4-MeO—$C_6H_4$ (An-P-Phos), 3,5-$Me_2$-$C_6H_3$ (=Xyl-P-Phos) or 3,5-$Me_2$-4-MeO-$C_6H_2$ (=MeO-Xyl-P-Phos). In particular, suitable P-Phos ligands are, for example, (R)—P-Phos, (R)-Xyl-P-Phos, (S)—P-Phos or (S)-Xyl-P-Phos.

(R)-2,2',6,6'-Tetramethoxy-4,4'-bis(diphenylphosphino)-3,3'-bipyridine=(R)—P-Phos (S)-2,2',6,6'-Tetramethoxy-4,4'-bis(diphenylphosphino)-3,3'-bipyridine=(S)—P-Phos (R)-2,2',6,6'-Tetramethoxy-4,4'-bis(di(3,5-xylyl)phosphino)-3,3'-bipyridine=(R)-Xyl-P-Phos (S)-2,2',6,6'-Tetramethoxy-4,4'-bis(di(3,5-xylyl)phosphino)-3,3'-bipyridine=(S)-Xyl-P-Phos ProPhos ligands are of the formula:

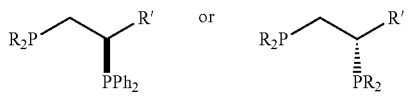

wherein R and R' are, for example, as described in Fryzuk, M. D.; Bosnich, B. J. Am. Chem. Soc., 100, 5491 (1978), for example R' is Me and R is Ph. In particular, a suitable ProPhos ligands is, for example, (R)-ProPhos.

(R)-1,2-Bis(diphenylphosphino)propane=(R)-ProPhos

BDPP ligands are of the formula:

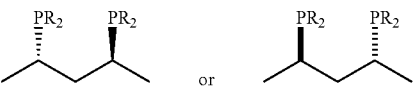

wherein R is, for example, as described in Bakos, J.; Toth, I.; Marko', L. J. Org. Chem., 46, 5427 (1981), for example R is Ph. In particular, suitable BDPP ligands are, for example, (R,R)-BDPP or (S,S)-BDPP.

(2R,4R)-2,4-Bis(diphenylphosphino)pentane=(R,R)-BDPP (2S,4S)-2,4-Bis(diphenylphosphino)pentane=(S,S)-BDPP DIOP ligands are of the formula:

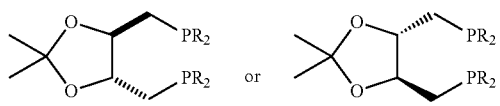

wherein R is, for example, as described in Kagan, H. B.; Dang, T. P. Chem. Commun. 1971, 481; Kagan, H. B.; Dang, T. P. J. Am. Chem. Soc., 94, 6429 (1972), for example R is Ph. In particular, suitable DIOP ligands are, for example, (S,S)-DIOP or (R,R)-DIOP.

(4R,5R)-4,5-Bis(diphenylphosphino-methyl)-2,2-dimethyl-1,3-dioxolane=(R,R)-DIOP (4S,5S)-4,5-Bis(diphenylphosphino-methyl)-2,2-dimethyl-1,3-dioxolane=(S,S)-DIOP DIPAMP ligands are of the formula:

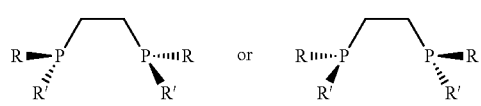

wherein R and R' are, for example, as described in Knowles, W. S. Acc. Chem. Res. 16, 106 (1983), for example R is Ph and R' is Anisyl. In particular, a suitable DIPAMP ligand is, for example, (R,R)-DIPAMP.

(R,R)-1,2-Ethanediylbis[(2-methoxyphenyl)phenylphosphine]=(R,R)-DIPAMP

DuanPhos ligands are of the formula:

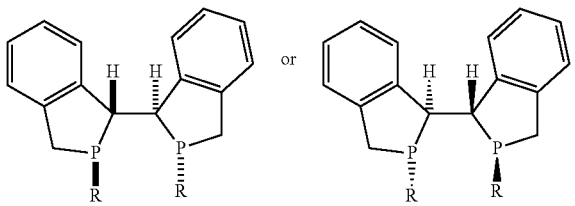

wherein R is, for example, as described in PCT/US02/35788, for example R is tert-butyl. In particular, a suitable DuanPhos ligand is, for example, (R,R)-DuanPhos.

(1R,1R,2S,2'S)-2,2'-Di-tert-butyl-2,3,2',3'-tetrahydro-1H, 1'H-(1,1')biisophosphindolyl=(R,R)-DuanPhos NorPhos ligands are of the formula:

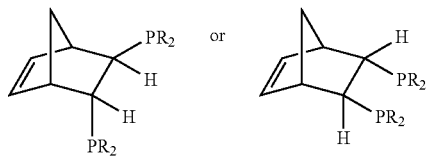

wherein R is, for example, as described in Brunner, H.; Pieronczyk, W.; Schoenhammer, B.; Streng, K.; Bernal, I.; Korp, J. Chem. Ber. 114, 1137 (1981), for example R is Ph. In particular, suitable Nor Phos ligands are, for example, (R,R)-NorPhos or (S,S)-NorPhos.

(2R,3R)-2,3-Bis(diphenylphosphino)bicyclo[2.2.1]hept-5-ene=(R,R)-NorPhos (2S,3S)-2,3-Bis(diphenylphosphino)bicyclo[2.2.1]hept-5-ene=(S,S)-NorPhos BINAM ligands are of the formula:

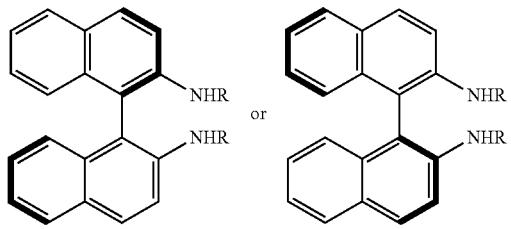

wherein R is, for example, as described in F.-Y. Zhang, C.-C. Pai, A. S. C. Chan J. Am. Chem. Soc. 120, 5808 (1998), for example R is PR'$_2$, wherein R' for example is Ph. In particular, suitable BINAM ligands are, for example, (R)-BINAM-P or (S)-BINAM-P.

(R)—N,N'-Bis(diphenylphosphino)-1,1'-binaphthyl-2,2'-diamine=(R)-BINAM-P (S)—N,N'-Bis(diphenylphosphino)-1,1'-binaphthyl-2,2'-diamine=(S)-BINAM-P CatASium ligands are of the formula:

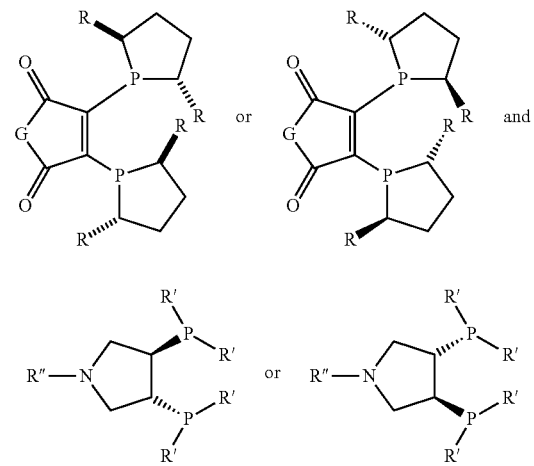

wherein R, R' and R" are, for example, as described in Holz, J.; Monsees, A.; Jiao, H.; You, J.; Komarov, I. V.; Fischer, C.; Drauz, K.; Börner, A. J. Org. Chem., 68, 1701-1707 (2003); Holz, J.; Zayas, O.; Jiao, H.; Baumann, W.; Spannenberg, A.; Monsees, A.; Riermeier, T. H.; Almena, J.; Kadyrov, R.; Boörner, A. Chem. Eur. J, 12, 5001-5013 (2006), for example, R is Me, R' is Ph, R" is benzyl and G is O, NMe, N(Me)N (Me). In particular, suitable CatAsium ligands are, for example, (R)-CatASium M, (S)-CatASium M, (R)-CatASium MN, (S)-CatASium MN, (R)-CatASium D or (R)-CatASium MNN.

N-Benzyl-(3R,4R)-bis(diphenylphosphino)pyrrolidine=(R)-CatASium D 2,3-Bis[(2R,5R)-2,5-dimethylphospholano]maleic anhydride=(R)-CatASium M 2,3-Bis[(2R,5R)-2,5-dimethylphospholano]-N-methylmaleimide=(R)-CatASium MN 4,5-Bis[(2R,5R)-2,5-dimethylphospholano]-1,2-dihydro-1, 2-dimethyl-3,6-pyridazinedione=(R)-CatASium MNN 2,3-Bis[(2S,5S)-2,5-dimethylphospholano]maleic anhydride=(S)-CatASium M 2,3-Bis[(2S,5S)-2,5-dimethylphospholano]-N-methylmaleimide=(S)-CatASium MN SimplePHOX ligands are of the formula:

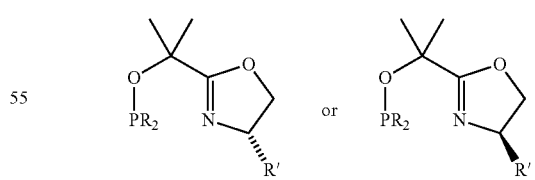

wherein R and R' are, for example, as described in S. Smidt, F. Menges, A. Pfaltz, Org. Lett. 6, 2023 (2004), for example R is Cyclohexyl and R' is tert-butyl. In particular, a suitable SimplePHOX ligand is, for example, (S)-Cy-tBu-SimplePHOX.

(S)-4-tert-butyl-2-(2-(dicyclohexylphosphinooxy)propan-2-yl)-4,5-dihydrooxazole=(S)-Cy-tBu-SimplePHOX PHOX ligands are of the formula:

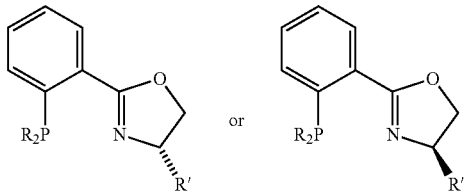

wherein R and R' are, for example, as described in A. Lightfoot, P. Schnider, A. Pfaltz, Angew. Chem. In. Ed., 37, 2897 (1998), for example R is Ph and R' is iPr. In particular, a suitable PHOX ligand is, for example (S)-iPr-PHOX.

(S)-4-tert-Butyl-2-[2-(diphenylphosphino)phenyl]-2-oxazoline=(S)-iPr-PHOX

ChiraPhos ligands are of the formula:

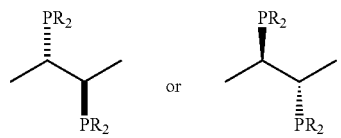

wherein R is, for example, as described in Fryzuk, M. B.; Bosnich, B. J. Am. Chem. Soc, 99, 6262 (1977); Fryzuk, M. B.; Bosnich, B. J. Am. Chem. Soc, 101, 3043 (1979), for example R is Ph. In particular, a suitable ChiraPhos ligand is, for example, (S,S)-ChiraPhos.

(2S,3S)-(−)-Bis(diphenylphosphino)butane=(S,S)-Chiraphos

Ferrotane ligands are of the formula:

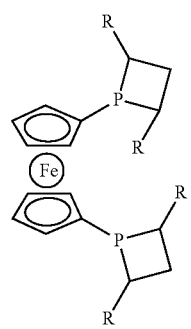

wherein R is, for example, as described in Berens, U.; Burk, M. J.; Gerlach, A.; Hems, W. Angew. Chem., Int. Ed. Engl. 2000, 39, 1981 (2000)., for example R is methyl or ethyl, preferably ethyl. In particular, a suitable ferrotane ligand is, for example, (S,S)-Et-Ferrotane.

1,1'-Bis[(2S,4S)-2,4-diethylphosphotano)ferrocene=(S,S)-Et-Ferrotane

BPE ligands are of the formula:

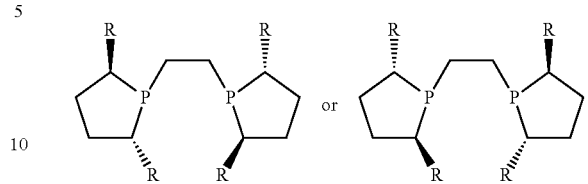

wherein R is, for example, as described in Burk, M. J. Acc. Chem. Res, 33, 363 (2000), for example R is Me or Ph In particular, suitable BPE ligands are, for example, (S,S)-Me-BPE or (S,S)-Ph-BPE.

,2-Bis[(2S,5S)-2,5-dimethylphospholano]ethane=(S,S)-Me-BPE

,2-Bis[(2S,5S)-2,5-diphenylphospholano]ethane=(S,S)-Ph-BPE

TangPhos ligands are of the formula:

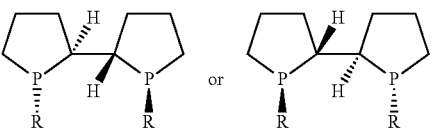

wherein R is, for example, as described in Tang, W.; Zhang, X. Angew. Chem., Int. Ed. Engl, 41, 1612 (2002), for example R is tert-butyl. In particular, a suitable TangPhos ligand is, for example, (S,S,R,R)-TangPhos.

(1S,1S',2R,2R')-1,1'-Di-tert-butyl-(2,2)-diphospholane=(S,S,R,R)-TangPhos

JafaPhos ligands are of the formula:

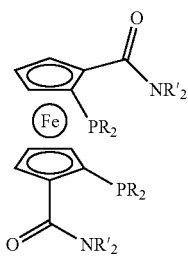

wherein R and R' are, for example, as described in Jendralla, H.; Paulus, E. Synlett (E. J. Corey Special Issue) 1997, 471., for example R is Ph and R' is isopropyl. In particular, a suitable JafaPhos ligand is, for example, (R)-JafaPhos.

[(R)-1,1'-Bis(diphenylphosphino)-2,2'-bis(N,N-diisopropylamido)ferrocene]=(R)-JafaPhos DuPhos ligands are of the formula:

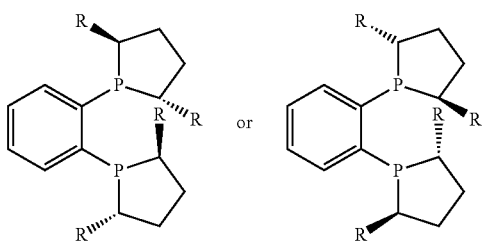

wherein R is, for example, as described in Burk, M. J. Acc. Chem. Res, 33, 363 (2000), for example R is Me. In particular, a suitable DuPhos ligand is, for example, (R)-MeDuPhos.
1,2-Bis[(2R,5R)-2,5-dimethylphospholano]benzene=(R)-MeDuPhos Binaphane ligands are of formula:

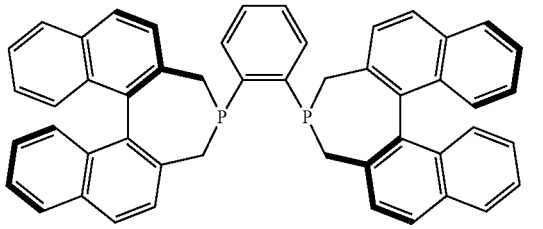

or

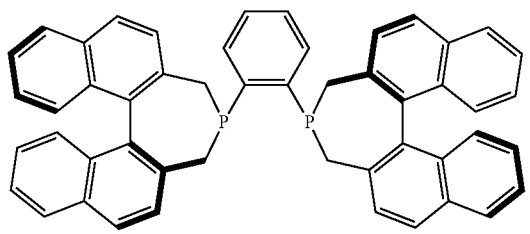

for example as described in Xiao D, Zhang Z, Zhang X., Org. Lett. 1999 Nov. 18; 1(10):1679. In particular, a suitable Binaphane ligand is, for example, (R)-Binaphane.
(R,R)-1,2-Bis[(R)-4,5-dihydro-3H-binaphtho(1,2-c:2',1'-e) phosphepino]benzene=(R)-Binaphane Further suitable chiral ligands and chiral groups are given, for example, in Tang, W and Zhang, X, Chem. Rev., 2003, 103 (8), 3029 and references cited therein.

The ligands above-mentioned are commercially available from Johnson Matthey plc (London, United Kingdom) and/or from Solvias AG (Basel, Switzerland).

In one embodiment, the transition metal catalyst comprises, for example:

the transition metal rhodium and a chiral ligand such as a P-Phos, a PhanePhos, a Phospholane, a BoPhoz, a DIOP, a BINAP, a CatAsium, a TangPhos, a JafaPhos, a DuPhos, a BPE, a Ferrotane, a BINAM, a DuanPhos, a Nor Phos, a BDPP, a ProPhos, a DIPAMP, a ChiraPhos ligand or a Binaphane ligand. For example, the transition metal catalyst comprises the transition metal rhodium and a chiral ligand such as SL-P104-2, SL-P102-1, SL-P005-1, (R)—P-Phos, (S)—P-Phos, (S)-PhanePhos, (R)-PhanePhos, (R)-An-PhanePhos, (R)-MeO-Xyl-PhanePhos, (R)-Xyl-PhanePhos, (R)-Tol-PhanePhos, (S)-MeBoPhoz, (S,S)-DIOP, (R,R)-DIOP, (S)-BINAP, (S)-Tol-BINAP, (R)-CatASium M, (S)-CatASium M, (R)-CatASium MN, (S)-CatASium MN, (R)-CatASium D, (R)-CatASium MNN, (S,S,R,R)-TangPhos, (R)-JafaPhos, (R)-MeDuPhos, (S,S)-Me-BPE, (S,S)-Ph-BPE, (S,S)-Et-Ferrotane, (S)-BINAM-P, (R)-BINAM-P, (R,R)-DuanPhos, (R,R)-NorPhos, (S,S)-NorPhos, (R,R)-BDPP, (S,S)-BDPP, (R)-Pro-Phos, (R,R)-DIPAMP, (S,S)-ChiraPhos or (R)-Binaphane. Particularly suitable transition metal catalyst are for example: [Rh(COD)(SL-P104-2)]O$_3$SCF$_3$, [Rh(COD)(SL-P102-1)]BF$_4$, [Rh(COD)(SL-P005-1)]BF$_4$, [Rh(COD)(SL-P102-1)]O$_3$SCF$_3$, [(R)—P-Phos Rh(COD)]BF$_4$, [(S)—P-Phos Rh(COD)]BF$_4$, [(R)-PhanePhos Rh(COD)]BF$_4$, [(S)-PhanePhos Rh(COD)]BF$_4$, [(R)-Xyl-PhanePhos Rh(COD)]BF$_4$, [(S)-MeBoPhoz Rh(COD)]BF$_4$, [(S,S)-DIOP Rh(COD)]BF$_4$, [(S)-BINAP Rh(COD)]BF$_4$, [(R)-CatASium M Rh(COD)]BF$_4$, [(S)-CatASium M Rh(COD)]BF$_4$, [(R)-CatASium MN Rh(COD)]BF$_4$, [(S)-CatASium MN Rh(COD)]BF$_4$, [(R)-CatASium D Rh(COD)]BF$_4$, [(S,S,R,R)-TangPhos Rh(COD)]BF$_4$, [(R)-JafaPhos Rh(COD)]BF$_4$, [(R)-MeDuPhos Rh(COD)]BF$_4$, [(S,S)-Me-BPE Rh(COD)]BF$_4$, [(S,S)-Ph-BPE Rh(COD)]BF$_4$, [(S,S)-Et-Ferrotane Rh(COD)]BF$_4$, [(R)-An-PhanePhos Rh(COD)]BF$_4$, [(R)-CatASium MNN Rh(COD)]BF$_4$, [(S)-Tol-BINAP Rh(COD)]BF$_4$, [(S)-BINAM-P Rh(COD)]BF$_4$, [(R)-BINAM-P Rh(COD)]BF$_4$, [(R,R)-DuanPhos Rh(COD)]BF$_4$, [(R)-Binaphane Rh(COD)]BF$_4$, [(R,R)-NorPhos Rh(COD)]BF$_4$, [(S,S)-NorPhos Rh(COD)]BF$_4$, [(R,R)-BDPP Rh(COD)]BF$_4$, [(S,S)-BDPP Rh(COD)]BF$_4$, [(R,R)-DIOP Rh(COD)]BF$_4$, [(R)-ProPhos Rh(COD)]BF$_4$, [(R,R)-DIPAMP Rh(COD)]BF$_4$, [(S,S)-ChiraPhos Rh(COD)]BF$_4$, [(R)-MeO-Xyl-PhanePhos Rh(COD)]BF$_4$ or [(R)-Tol-PhanePhos Rh(COD)]BF$_4$; in particular [Rh(COD)(SL-P102-1)]BF$_4$, [Rh(COD)(SL-P005-1)]BF$_4$, [Rh(COD)(SL-P102-1)]O$_3$SCF$_3$, [(R)-PhanePhos Rh(COD)]BF$_4$, [(R) Xyl-PhanePhos Rh(COD)]BF$_4$, [(S,S)-DIOP Rh(COD)]BF$_4$, [(S)-BINAP Rh(COD)]BF$_4$, [(R)-CatASium M Rh(COD)]BF$_4$, [(R)-CatASium MN Rh(COD)]BF$_4$, [(S)-CatASium MN Rh(COD)]BF$_4$, [(S,S,R,R)-TangPhos Rh(COD)]BF$_4$, [(S,S)-Me-BPE Rh(COD)]BF$_4$, [(S,S)-Ph-BPE Rh(COD)]BF$_4$, [(R)-An-PhanePhos Rh(COD)]BF$_4$, [(R)-CatASium MNN Rh(COD)]BF$_4$, [(S)Tol-BINAP Rh(COD)]BF$_4$, [(S)-BINAM-P Rh(COD)]BF$_4$, [(R,R)-DuanPhos Rh(COD)]BF$_4$, [(R)-Binaphane Rh(COD)]BF$_4$, [(S,S)-NorPhos Rh(COD)]BF$_4$, [(R,R)-BDPP Rh(COD)]BF$_4$, [(S,S)-BDPP Rh(COD)]BF$_4$, [(R,R)-DIOP Rh(COD)]BF$_4$, [(R)-ProPhos Rh(COD)]BF$_4$, [(R,R)-DIPAMP Rh(COD)]BF$_4$, [(S,S)-ChiraPhos Rh(COD)]BF$_4$, [(R)-MeO-Xyl-PhanePhos Rh(COD)]BF$_4$ or [(R)-Tol-PhanePhos Rh(COD)]BF$_4$; such as [Rh(COD)(SL-P102-1)]BF$_4$, [Rh(COD)(SL-P005-1)]BF$_4$, [(R)PhanePhos Rh(COD)]BF$_4$, [(R)Xyl-PhanePhos Rh(COD)]BF$_4$, [(R)CatASium M Rh(COD)]BF$_4$, [(R)CatASium MN Rh(COD)]BF$_4$, [(S,S,R,R)TangPhos Rh(COD)]BF$_4$, [(S,S)Ph-BPE Rh(COD)]BF$_4$, [(R)An-PhanePhos Rh(COD)]BF$_4$, [(R,R)DuanPhos Rh(COD)]BF$_4$, [(S,S) Nor Phos Rh(COD)]BF$_4$ or [(R)MeO-Xyl-PhanePhos Rh(COD)]BF$_4$;

the transition metal ruthenium and a chiral ligand such as a BoPhoz, a BINAP, a BINOL, a PhanePhos, a P-Phos or a QUINAPHOS ligand. For example, the transition metal catalyst comprises the transition metal ruthenium and a chiral ligand such as (R)-4-F—C$_6$H$_4$-MeBoPhoz, (R)-BINAP, (R)-BINOL-(R)-MeBoPhoz, (R)-MeBoPhoz, (R)-p-F-MeBoPhoz, (R)-PhanePhos, (R)-Phenethyl-(R)-MeBoPhoz, (R)—P-Phos, (R)-Tol-BINAP, (R)-Xyl-PhanePhos, (R)-Xyl-P-Phos, (R$_a$,S$_c$)1Np-QUINAPHOS, (S)-BINAP, (S)-BINOL-(R)-MeBoPhoz, (S)—P-Phos, (S)-Xyl-PhanePhos, (S)-Xyl-P-Phos or (Sa,Rc)1Np-QUINAPHOS. Particularly suitable transition metal catalyst are for example: [(R)-4-F—C$_6$H$_4$-MeBoPhoz Ru(benzene)Cl]Cl, [(R)-BINAP RuCl(benzene)]Cl, [(R)-BINOL-(R)-MeBoPhoz Ru(benzene)Cl]Cl, [(R)-MeBoPhoz RuCl(Benzene)]Cl, [(R)-p-F-MeBoPhoz RuCl(Benzene)]Cl, [(R)-PhanePhos RuCl$_2$(dmf)$_2$], [(R)-Phenethyl-(R)-MeBoPhoz Ru(benzene)Cl]Cl, [(R)—P-Phos RuCl(benzene)]Cl, [(R)-Tol-BINAP RuCl(benzene)]Cl, [(R)-Xyl-PhanePhos RuCl$_2$(dmf)$_2$], [(R)-Xyl-P-Phos RuCl$_2$(dmf)$_2$], [(R$_a$,S$_c$)1Np-QUINAPHOS RuCl$_2$(dmf)$_2$], [(S)-BINAP RuCl(benzene)]Cl, [(S)-BINOL-(R)-MeBoPhoz Ru(benzene)Cl]Cl, [(S)—P-Phos RuCl(benzene)]Cl, [(S)-Xyl-PhanePhos RuCl$_2$(dmf)$_2$], [(S)-Xyl-P-Phos RuCl$_2$(dmf)$_2$], [(S$_a$,R$_c$)1Np-QUINAPHOS RuCl$_2$(dmf)$_2$], [(R)—P-Phos Ru(acac)$_2$], [(R)-Xyl-P-Phos Ru(acac)$_2$] or [(R)-Xyl-P-Phos RuCl(benzene)]Cl; in particular, [(R)-4-F—C$_6$H$_4$-MeBoPhoz Ru(benzene)Cl]Cl, [(R)-BINAP RuCl(benzene)]Cl, [(R)-MeBoPhoz RuCl(Benzene)]Cl, [(R)-p-F-MeBoPhoz RuCl(Benzene)]Cl, [(R)-PhanePhos RuCl$_2$(dmf)$_2$], [(R)-Phenethyl-(R)-MeBoPhoz Ru(benzene)Cl]Cl, [(R)—P-Phos RuCl(benzene)]Cl, [(R)-Tol-BINAP RuCl(benzene)]Cl, [(R)-Xyl-P-Phos RuCl$_2$(dmf)$_2$], [(S)-BINAP RuCl(benzene)]Cl, [(S)-BINOL-(R)-MeBoPhoz Ru(benzene)Cl]Cl, [(S)—P-Phos RuCl(benzene)]Cl, [(S)-Xyl-PhanePhos RuCl$_2$(dmf)$_2$], [(Sa,Rc)1Np-QUINAPHOS RuCl$_2$(dmf)$_2$], [(R)—P-Phos Ru(acac)$_2$], [(R)-Xyl-P-Phos Ru(acac)$_2$] or [(R)-Xyl-P-Phos RuCl(benzene)]Cl; or the transition metal iridium and a chiral ligand such as a P-Phos, a BoPhoz, a SimplePHOX or a PHOX ligand. For example, the transition metal catalyst comprises the transition metal iridium and a chiral ligand such as (S)—P-Phos, (S)-Xyl-P-Phos, (S)-MeBoPhoz, (R)-MeBoPhoz, (S)-Cy-tBu-SimplePHOX or (S)-iPr-PHOX. Particularly suitable transition metal catalyst are for example: [(S)—P-Phos Ir(COD)]Cl, [(S)-Xyl-P-Phos Ir(COD)]Cl, [(S)-MeBoPhoz Ir(COD)]Cl, [(R)-MeBoPhoz Ir(COD)]Cl, [(S)-Cy-tBu-simplePHOX Ir(COD)]BArF or [(S)-iPr-PHOX Ir(COD)]BArF.

When using these combinations, the reduction of the compound of formula (2-a), or salt thereof, provides a composition comprising the compounds according to formulae (1-a) and (1-b), or salts thereof, wherein the molar ratio of compounds according to formula (1-a), or salts thereof, to compounds according to formula (1-b), or salts thereof, is at least 55 to 45, preferably at least 80 to 20, more preferably at least 97 to 3, most preferably at least 99 to 1.

In a fourth embodiment, the reduction of the compound of formula (2-a), or salt thereof, provides a composition comprising the compounds according to formulae (1-a) and (1-b), or salts thereof, wherein the molar ratio of compounds according to formula (1-b), or salts thereof, to compounds according to formula (1-a), or salts thereof, is at least 55 to 45, preferably at least 70 to 30, more preferably at least 76 to 24.

In one embodiment, the transition metal catalyst comprises, for example:

the transition metal rhodium and a chiral ligand such as a PhanePhos, a BoPhoz, a JafaPhos, a CatASium, a BINAM or a Nor Phos ligand. For example, the transition metal catalyst comprises the transition metal rhodium and a chiral ligand such as (S)-PhanePhos, (S)-MeBoPhoz, (R)-JafaPhos, (S)-CatASium M, (R)-BINAM-P or (R,R)-Norphos. Particularly suitable transition metal catalyst are for example: [(S)-PhanePhos Rh(COD)]BF$_4$, [(S)-MeBoPhoz Rh(COD)]BF$_4$, [(R)-JafaPhos Rh(COD)]BF$_4$, [(S)-CatASium M Rh(COD)]BF$_4$, [(R)-BINAM-P Rh(COD)]BF$_4$ or [(R,R)-NorPhos Rh(COD)]BF$_4$;

the transition metal ruthenium and a chiral ligand such as a PhanePhos, a P-Phos, a BINOL, a QUINAPHOS, a BoPhoz or a BINAP ligand. For example, the transition metal catalyst comprises the transition metal ruthenium and a chiral ligand such as (S)-Xyl-PhanePhos, (S)-Xyl-P-Phos, (R)-BINOL-(R)-MeBoPhoz, (R$_a$,S$_c$)1Np-QUINAPHOS or (R)-Tol-BINAP. Particularly suitable transition metal catalyst are for example [(S)Xyl-PhanePhos RuCl$_2$(dmf)$_2$], [(S)Xyl-P-Phos RuCl$_2$(dmf)$_2$], [(R)BINOL-(R)-MeBoPhoz Ru(benzene)Cl]Cl, [(R$_a$,S$_c$)1Np-QUINAPHOS RuCl$_2$(dmf)$_2$] or [(R)Tol-BINAP RuCl(benzene)]Cl; or the transition metal iridium and a chiral ligand such as a P-Phos or BoPhoz ligand, for example (S)-Xyl-P-Phos or (S)-MeBoPhoz. Particularly suitable transition metal catalyst are for example [(S)-Xyl-P-Phos Ir(COD)]Cl or [(S)-MeBoPhoz Ir(COD)]Cl.

When using these combinations, the reduction of the compound of formula (2-a), or salt thereof, provides a composition comprising the compounds according to formulae (1-a) and (1-b), or salts thereof, wherein the molar ratio of compounds according to formula (1-b), or salts thereof, to compounds according to formula (1-a), or salts thereof, is at least 55 to 45, preferably at least 70 to 30, more preferably at least 76 to 24.

In a further preferred embodiment, the reduction of the compound of formula (2-a), or salt thereof, provides a composition comprising the compounds according to formulae (1-a) and (1-b), or salts thereof, wherein the molar ratio of compounds according to formula (1-a), or salts thereof, to compounds according to formula (1-b), or salts thereof, is at least 88 to 12, preferably at least 90 to 10, more preferably at least 99 to 1.

SECTION D: CONVERSION OF A COMPOUND OF FORMULA (7) INTO A COMPOUND OF FORMULA (1) VIA A COMPOUND OF FORMULA (3)

The methods, according to the present invention, to convert a compound formula (7), as described herein, into a compound of formula (3), as described herein, are summarized in Scheme 5.

Scheme 5

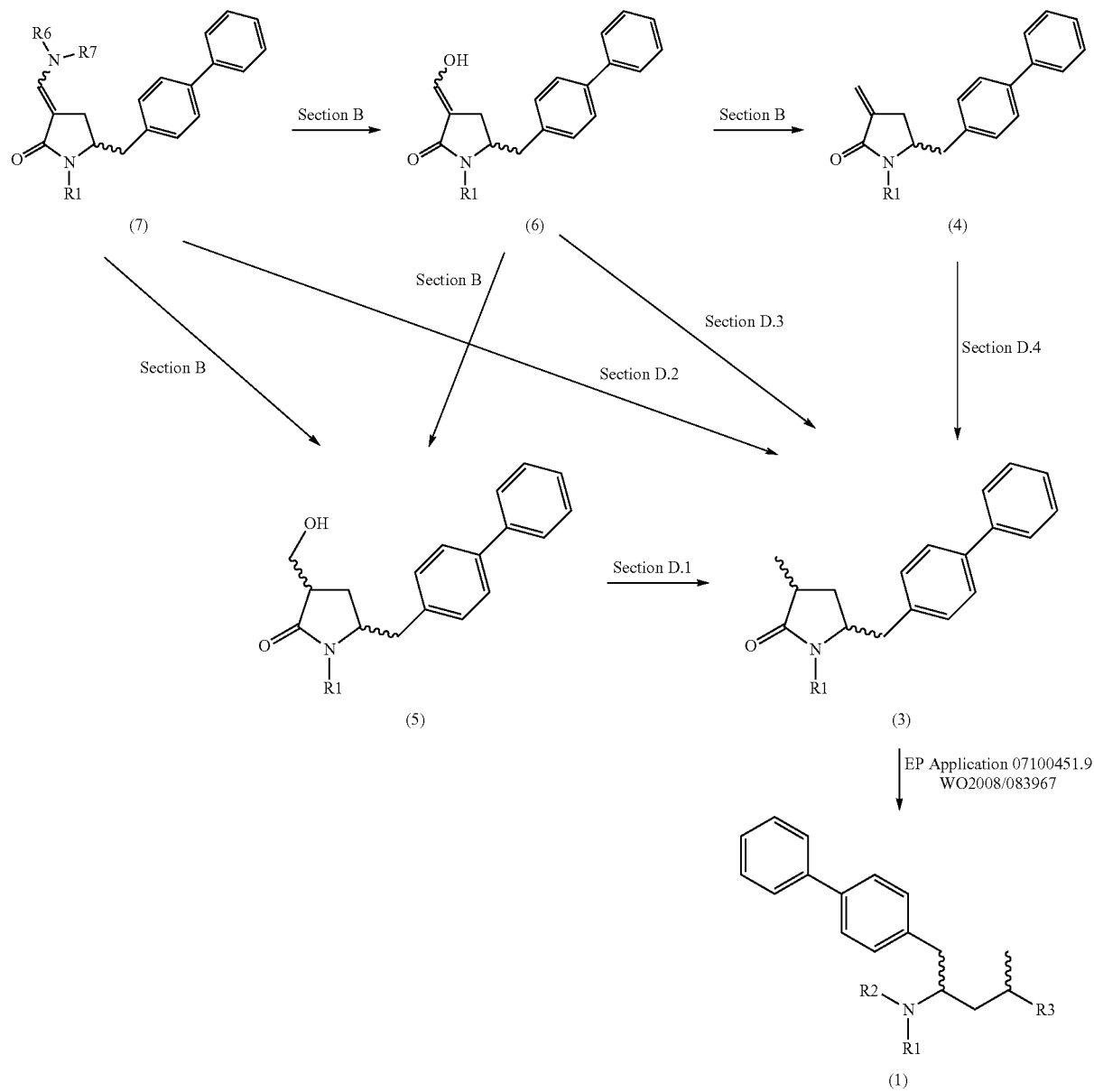

Thus, in another aspect the present invention relates to the conversion of a compound of formula (7), as described herein, into a compound of formula (3), as described herein, according to any one of methods 1 to 5, wherein
method 1 comprises
  a) any one of methods in Section B to convert (7) into (5), and
  b) any one of methods in Section D.1 to convert (5) into (3);
method 2 comprises any one of methods in Section D.2 to convert (7) into (3);
method 3 comprises
  a) any one of methods in Section B to convert (7) into (6),
  b) any one of methods in Section B to convert (6) into (5), and
  c) any one of methods in Section D.1 to convert (5) into (3);
method 4 comprises
  a) any one of methods in Section B to convert (7) into (6), and
  b) any one of methods in Section D.3 to convert (6) into (3);
method 5 comprises
  a) any one of methods in Section B to convert (7) into (6),
  b) any one of methods in Section B to convert (6) into (4), and
  c) any one of methods in Section D.4 to convert (4) into (3);
in particular according to methods 1, 2, 4 or 5; particularly according to method 5.

As discussed below, Sections D.1, D.2, D.3 and D.4 as such are also preferred embodiments of the present invention.

Section D.1: Conversion of a Compound of Formula (5) into a Compound of Formula (3)

In a further aspect, the present invention relates to a process for preparing a compound of formula (3)

(3)

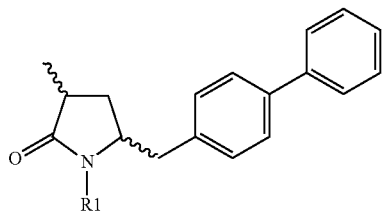

or salt thereof,
wherein R1 is hydrogen or a nitrogen protecting group, said process comprising
a) converting a compound of formula (5), or salt thereof, (5)

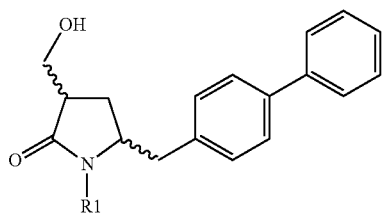

wherein R1 is hydrogen or a nitrogen protecting group, into a compound of formula (12)

(12)

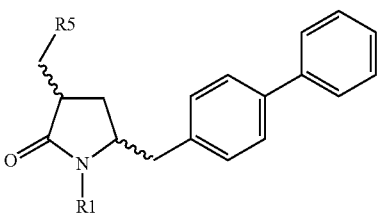

or salt thereof, wherein R1 is hydrogen or a nitrogen protecting group and R5 is a leaving group; and
b) reacting the compound of formula (12), or salt thereof, with a reducing agent to obtain the compound of formula (3).

Steps a) and b) as such are also an embodiment of the present invention.

In a preferred embodiment, the present invention relates to a process for preparing a compound of formula (3-a)

(3-a)

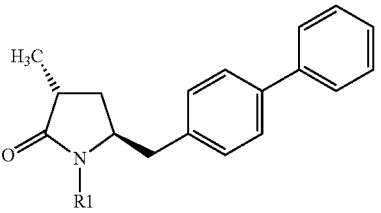

or salt thereof,
wherein R1 is hydrogen or a nitrogen protecting group, said process comprising
a) converting a compound of formula (5-b), or salt thereof, (5-b)

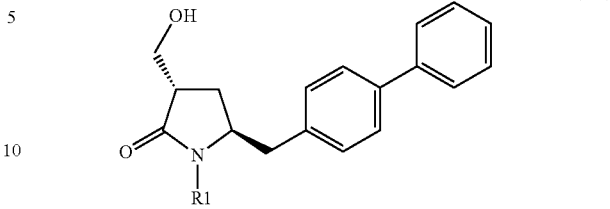

wherein R1 is hydrogen or a nitrogen protecting group, into a compound of formula (12-b)

(12-b)

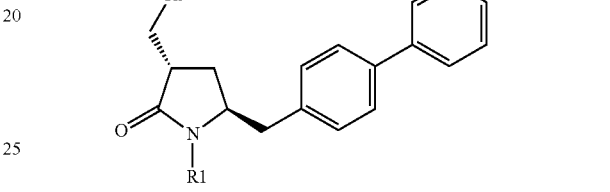

or salt thereof, wherein R1 is hydrogen or a nitrogen protecting group and R5 is a leaving group; and
b) reacting the compound of formula (12-b), or salt thereof, with a reducing agent to obtain the compound of formula (3).

Typical reducing agents are well known in the art and can be taken e.g. from relevant chapters of standard reference works such as P. G. M. Wuts and T. W. Greene, "Greene's Protective Groups in Organic Synthesis', Fourth Edition, Wiley, New Jersey, 2007 and include:

hydrides (eg lithium aluminium hydride, sodium borohydride, sodium cyanoborohydride), metals (eg zinc, tin dichloride, tributyltin hydride, lithium), hydrogenation (eg hydrogen and a hydrogenation catalyst such as Pd/C, for example as described in Section B.3.3) [especially when R5=halide], hydrides (eg lithium aluminium hydride, sodium borohydride, diisobutyl aluminium hydride) or tributyltin hydride-sodium iodide. [especially when R5=sulphonate]

In general, these methods work for both halides and suphonates

Steps a) and b) as such are also a preferred embodiment of the present invention.

The conversion of a OH-group into a leaving group and the subsequent treatment with a reducing agent are well-known reactions to the person skilled in the art, for example as described in Richard C. Larock, "Comprehensive Organic Transformations: A Guide to Functional Group Preparations", Second Edition, Wiley-VCH Verlag GmbH, 2000, in particular as described in the relevant chapters thereof. Preferred leaving groups are halo, such as bromo or iodo, or a sulphonate group, such as tosylate, mesylate or triflate. Preferred reducing agents are, for example, hydrides (LiAlH$_4$, NaBH$_4$) and hydrogen in the presence of a hydrogenation catalysts (eg Pd/C) [see Section B.3.3 above].

Section D.2: Conversion of a Compound of Formula (7) into a Compound of Formula (3)

In a further aspect, the present invention relates to a process for preparing a compound of formula (3)

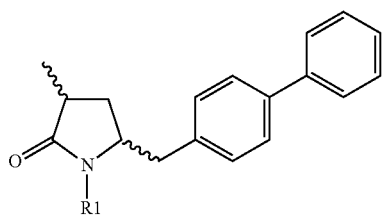
(3)

or salt thereof,
wherein R1 is hydrogen or a nitrogen protecting group, said process comprising treating a compound of formula (7),

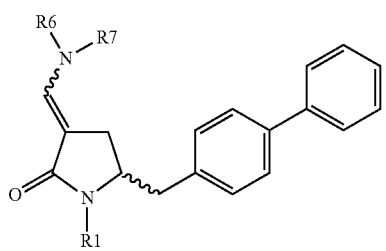
(7)

or salt thereof, wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms,
with a reducing agent to obtain the compound of formula (3), or salt thereof, wherein R1 is hydrogen or a nitrogen protecting group, preferably of formulae (3-a) or (3-b), more preferably of formula (3-a),

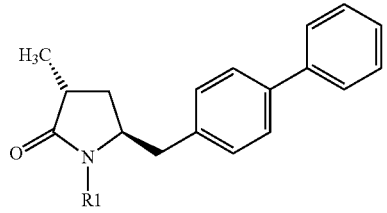
(3-a)

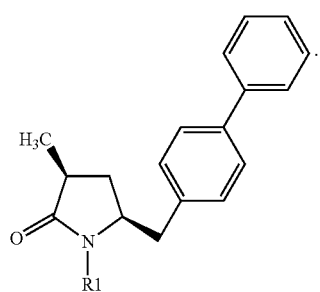
(3-b)

In a preferred embodiment, the starting compound of formula (7), or salt thereof, is according to formula (7-a), or salt thereof, as defined above; more preferably the starting compound is according to formulae (7b) or (7c), or salts thereof, as defined above.

Preferred reducing agents are, for example, hydrogen in the presence of a heterogeneous hydrogenation catalysts, for example, palladium or platinum on a solid support, for example, on carbon, alumina, barium carbonate or calcium carbonate, in particular on carbon, alumina or barium carbonate. Preferably, palladium on carbon (Pd/C) or palladium on calcium carbonate (Pd/CaCO$_3$) which is poisoned with lead (known in the art as Lindlar catalyst) is used, in particular palladium on carbon (Pd/C).

In a preferred embodiment, the reduction of the compound of formula (7-a), or salt thereof, provides a composition comprising the compounds according to formulae (3-a) and (3-b), or salts thereof, wherein the molar ratio of compounds according to formula (3-a), or salts thereof, to compounds according to formula (3-b), or salts thereof, is at least 88 to 12, preferably at least 90 to 10, more preferably at least 99 to 1.

Section D.3: Conversion of a Compound of Formula (6) into a Compound of Formula (3)

In a further aspect, the present invention relates to a process for preparing a compound of formula (3)

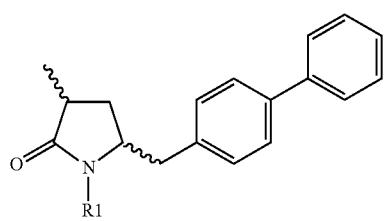
(3)

or salt thereof,
wherein R1 is hydrogen or a nitrogen protecting group, said process comprising treating a compound of formula (6),

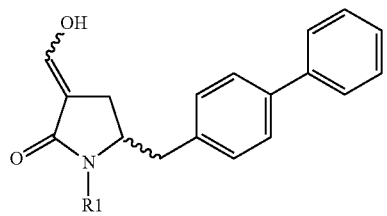
(6)

or salt thereof, wherein R1 is hydrogen or a nitrogen protecting group,
with a reducing agent, for example as described in Section B.3.3, to obtain the compound of formula (3), or salt thereof, wherein R1 is hydrogen or a nitrogen protecting group, preferably of formulae (3-a) or (3-b), as defined herein, more preferably of formula (3-a), as defined herein.

In a preferred embodiment, the starting compound of formula (6), or salt thereof, is according to formula (6-a), or salt thereof, as defined herein.

In a preferred embodiment, the reduction of the compound of formula (6-a), or salt thereof, provides a composition comprising the compounds according to formulae (3-a) and (3-b), or salts thereof, wherein the molar ratio of compounds according to formula (3-a), or salts thereof, to compounds according to formula (3-b), or salts thereof, is at least 88 to 12, preferably at least 90 to 10, more preferably at least 99 to 1.

Section D.4: Reduction of a Compound of Formula (4)

In a further aspect, the present invention relates to a process for preparing a compound according to formula (3),

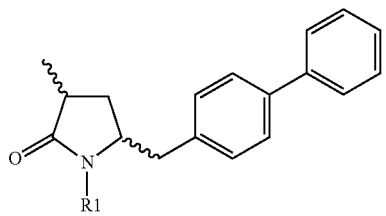

(3)

or salt thereof,
wherein R1 is hydrogen or a nitrogen protecting group, comprising reducing a compound according to formula (4),

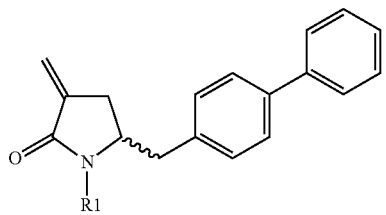

(4)

or salt thereof,
wherein R1 is hydrogen or a nitrogen protecting group, to obtain the compound of formula (3).

Preferably, a compound according to formula (4-a), or salt thereof,

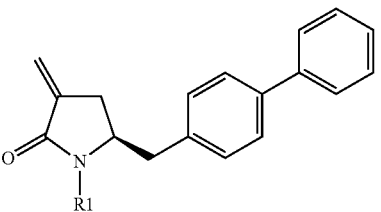

(4-a)

wherein R1 is hydrogen or a nitrogen protecting group, is used as starting compound. If the compound (4-a), or salt thereof, is used as starting compound, compounds according to formula (3-a) and formula (3-b), as defined herein, can be obtained.

Preferably R1 is BOC.

In a preferred embodiment, the reduction of the compound of formula (4), or salt thereof, takes place with hydrogen in the presence of a transition metal catalyst, preferably in the presence of a transition metal catalyst and a chiral ligand. The reduction may occur under hetereo- or homogeneous hydrogenation conditions, preferably under homogeneous hydrogenation conditions.

In one embodiment, the reduction of the compound of formula (4), or salt thereof, takes place under heterogeneous hydrogenation conditions.

Generally, the heterogeneous hydrogenation is carried out in the presence of a transition metal catalyst, wherein the transition metal is selected from group 9 or 10 of the periodic table. Therefore, the transition metal catalyst comprises, for example, Cobalt (Co), Rhodium (Rh), Iridium (Ir), Nickel (Ni), Palladium (Pd) and/or Platinum (Pt). In particular, the transition metal catalyst is Pt, Pd, or Rh, preferably on a solid support, such as carbon. In one embodiment the transition metal catalyst is Pt on carbon (Pt/C) or Pd on carbon (Pd/C).

The heterogeneous hydrogenation of the compound of formula (4), or salt thereof, provides a composition comprising the compounds according to formulae (3-a and (3-b), or salts thereof, wherein the molar ratio of compounds according to formula (3-b, or salts thereof, to compounds according to formula (3-a), or salts thereof, is of from at least 67 to 33, preferably of from at least 85 to 15.

The heterogeneous hydrogenation is usually performed in a solvent, such as ether solvents (eg THF), ester solvents (eg isopropyl acetate) or alcohol solvents (eg isopropanol, ethanol or methanol); in particular an alcohol or ester solvent, such ethanol or isopropyl acetate. In one embodiment, Pd/C is used with ethanol or isopropyl acetate as solvent. In another embodiment, Pt/C is used with isopropyl acetate as solvent.

Generally, the homogeneous hydrogenation is carried out in the presence of a transition metal catalyst, wherein the transition metal is selected from group 8 or 9 of the periodic table. Therefore, the transition metal catalyst comprises, for example, the transition metal Iron (Fe), Ruthenium (Ru), Osmium (Os), Cobalt (Co), Rhodium (Rh) and/or Iridium (Ir).

In a preferred embodiment, the transition metal catalyst comprises an organometallic complex and optionally a chiral ligand.

The organometallic complex comprises a transition metal selected from group 8 or 9 of the periodic table, for example the transition metal rhodium, iridium or ruthenium in particular rhodium or ruthenium. The organometallic complexes can comprise a single transition metal atom. In preferred embodiments the complexes can comprise two or more transition metal atoms, optionally comprising a metal-metal bond. In a preferred embodiment two metal atoms are bridged via two halides. Generally, the organometallic complex, comprises one or more transition metal atoms and suitable achiral ligands.

Suitable achiral ligands for the organometallic complex generally are σ-donor ligands, σ-donor/π-acceptor ligands or σ,π-donor/π-acceptor ligands. Examples for suitable achiral ligands are among others carbon monoxide, halides (e.g. Cl, I or Br), phosphines [e.g. tricyclohexylphosphine (PCy$_3$)], alkenyls (e.g. cod, nbd, 2-metallyl), alkynyls, aryls (e.g. pyridine, benzene, p-cymene), carbonyls (e.g. acac, trifluoroacetate or dimethylformamide) and mixtures thereof.

Examples of preferred achiral ligands for the organometallic complex are: norbornadiene (nbd), cyclooctadiene (cod), pyridine (pyr), cymene, in particular p-cymene, and iodide.

Examples for organometallic complexes are: a ruthenium organometallic complex, such as [RuI$_2$(p-cymene)]$_2$, [Ru(cod)(2-metallyl)$_2$] or [Ru(cod)(OOCCF$_3$)$_2$]; a rhodium organometallic complex, such as [Rh(nbd)$_2$BF$_4$] or [Rh(cod)$_2$]BF$_4$; or an iridium organometallic complex such as [(Cy$_3$P)Ir(pyr)]Cl or [Ir(cod)$_2$Cl]$_2$; in particular [Ru(cod)(2-metallyl)$_2$], [Ru(cod)(OOCCF$_3$)$_2$] or [RuI$_2$(p-cymene)]$_2$; in particular [Rh(NBD)$_2$]BF$_4$, [Ru(COD)(OOCCF$_3$)$_2$] or [RuCl$_2$(p-cymene)$_2$].

The transition metal catalyst comprises an organometallic complex and a chiral ligand. The chiral ligand comprises, for example, a chiral phosphine and/or a chiral ferrocene. In particular, the chiral ferrocene comprises a Cp-ligand which is substituted with a chiral group, such as a chiral amine, a chiral phosphine or a chiral alkyl, for example as illustrated herein.

Suitable chiral ligands are, for example, an Atropisomer ligand (e.g. SL-A101-2), a Fenphos ligand (e.g. SL-F115-1), a Mandyphos ligand (e.g. SL-M004-2), a Walphos ligand (e.g. SL-W008-1), a Josiphos ligand (e.g SL-J504-1 or SL-J002-2) or mixtures thereof. Atropisomer ligands, Fenphos ligands, Mandyphos ligands, Walphos ligands and Josiphos ligands are of the formulae described in Section C.2.

Suitable combinations of organometallic complex and chiral ligand are, for example:
- rhodium organometallic complex and a Fenphos or Walphos ligand; in particular [Rh(nbd)$_2$]BF$_4$ and SL-F115-1 or SL-W008-1; or
- ruthenium organometallic complex and an Atropisomer a Mandyphos or a Josiphos ligand; in particular [RuI$_2$(p-cymene)]$_2$ or [Ru(COD)(OOCCF$_3$)$_2$] and SL-A101-2, SL-M004-2, SL-J504-1 or SL-J002-2.

In one embodiment, the reduction of the compound of formula (4-a), or salt thereof, provides a composition comprising the compounds according to formulae (3-a) and (3-b), or salts thereof, wherein the molar ratio of compounds according to formula (3-a), or salts thereof, to compounds according to formula (3-b), or salts thereof, is at least 88 to 12, preferably at least 90 to 10, more preferably at least 99 to 1.

In another embodiment, the reduction of the compound of formula (4-a), or salt thereof, provides a composition comprising the compounds according to formulae (3-a) and (3-b), or salts thereof, wherein the molar ratio of compounds according to formula (3-a), or salts thereof, to compounds according to formula (3-b), or salts thereof, is at least 53 to 47, preferably at least 71 to 29, more preferably at least 82 to 18.

Alternative combinations of organometallic complex and chiral ligand are, for example:
- rhodium organometallic complex and a Fenphos or Walphos ligand; in particular [Rh(nbd)$_2$]BF$_4$ and SL-W008-1.

In another embodiment, the reduction of the compound of formula (4-a), or salt thereof, provides a composition comprising the compounds according to formulae (3-a) and (3-b), or salts thereof, wherein the molar ratio of compounds according to formula (3-b), or salts thereof, to compounds according to formula (3-a), or salts thereof, is at least 73 to 27.

SECTION E

In the processes shown above several novel and inventive compounds are involved. Consequently, further subjects of the present invention are the compounds shown below.

A compound according to formula (2),

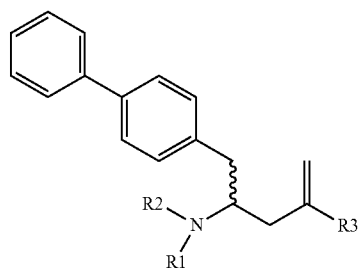

(2)

or salt thereof, wherein R1 and R2 are, independently of each other, hydrogen or a nitrogen protecting group, and R3 is a carboxyl group or an ester group, preferably having a configuration according to formula (2-a),

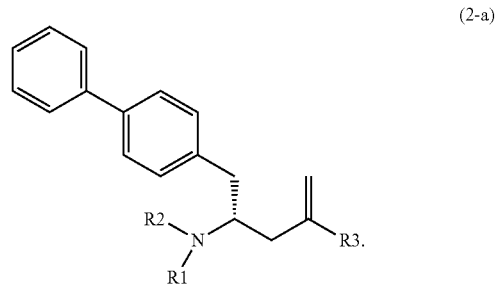

(2-a)

In a preferred embodiment of formulae (2) or (2-a), R1 is BOC and/or R2 is H.

In a preferred embodiment of formulae (2) or (2-a), R3 is CO$_2$H.

A compound of formula (4)

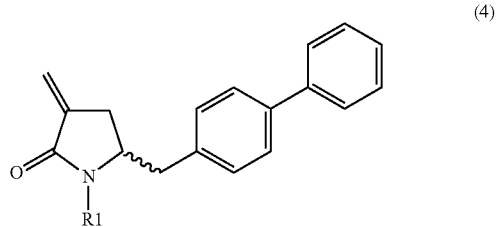

(4)

or salt thereof,
wherein R1 is hydrogen or a nitrogen protecting group, preferably having a configuration according to formula (4-a),

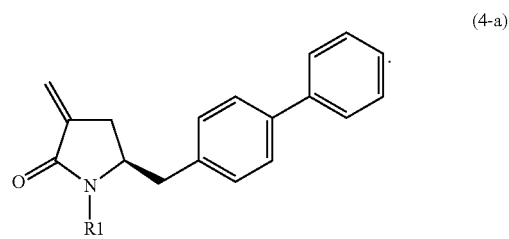

(4-a)

In a preferred embodiment of formulae (4) or (4-a), R1 is BOC or Piv.

A compound of formula (5), or salt thereof,

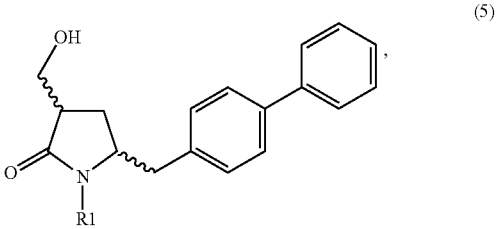

(5)

wherein R1 is hydrogen or a nitrogen protecting group, preferably of formulae (5-a), (5-b) or (5-c), more preferably (5-b),

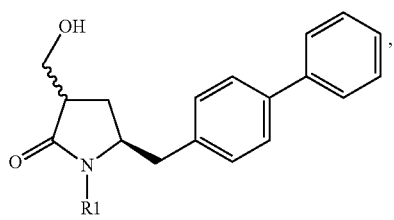
(5-a)

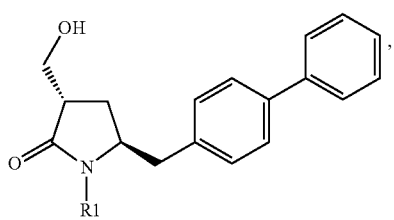
(5-b)

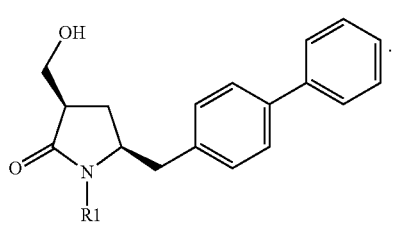
(5-c)

In a preferred embodiment of formulae (5), (5-a), (5-b) or (5-c), R1 is BOC.

A compound of formula (6), or a tautomer thereof,

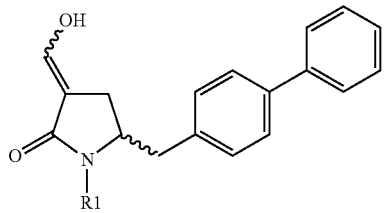
(6)

or salt thereof,
wherein R1 is hydrogen or a nitrogen protecting group, preferably having a configuration according to formula (6-a),

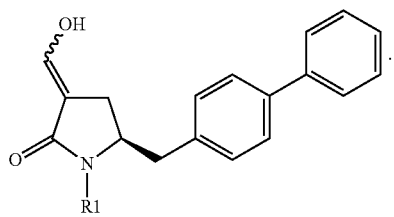
(6-a)

In a preferred embodiment of formulae (6) or (6-a), R1 is BOC or Piv.

A compound of formula (7), or salt thereof,

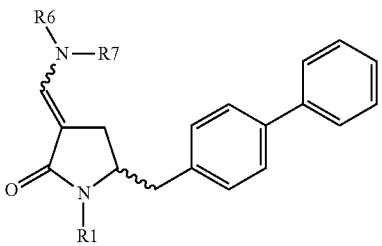
(7)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, preferably having a configuration according to formula (7-a), (7-b) or (7-c), more preferably (7-b),

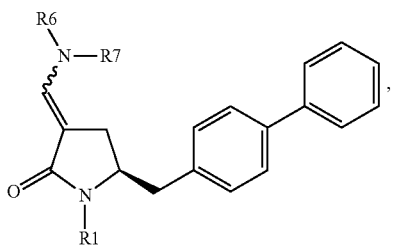
(7-a)

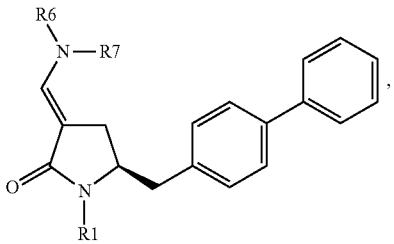
(7-b)

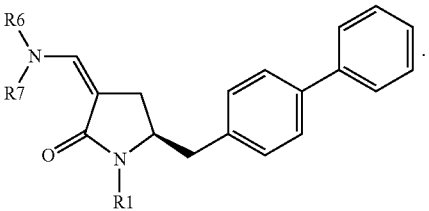
(7-c)

In a preferred embodiment of formulae (7), (7-a) or (7-b), R1 is BOC or Piv.

In a preferred embodiment of formulae (7), (7-a) or (7-b), R6 is Methyl or Ethyl and/or R7 is Methyl or Ethyl.

A compound of formula (9-a), or salt thereof,

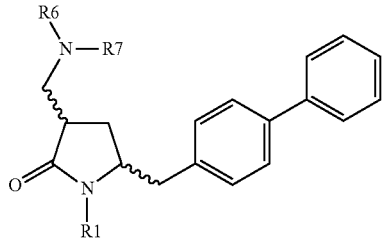
(9)

wherein R1 is hydrogen or a nitrogen protecting group and, R6 and R7 are, independently, an alkyl group or together are an alkylene group, preferably having a configuration according to formula (9-a) (9-b) or (9-c), more preferably (9-b),

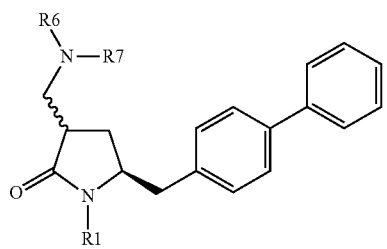
(9-a)

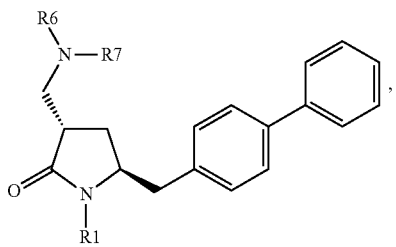
(9-b)

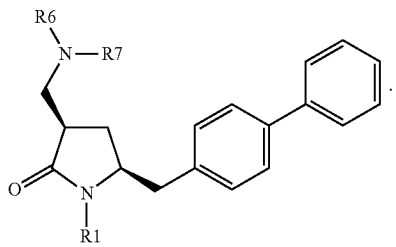
(9-c)

In a preferred embodiment of formulae (9), (9-a), (9-b) or (9-c), R1 is Boc.

In a preferred embodiment of formulae (9), (9-a), (9-b) or (9-c), R6 is Methyl and R7 is Methyl.

A compound of formula (10), or salt thereof,

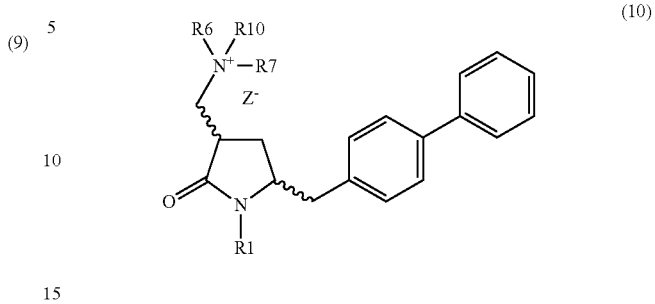
(10)

wherein R1 is hydrogen or a nitrogen protecting group, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such a nitrogen, oxygen or sulphur, whereby the cycle contains 3 to 8, such as 4 to 7 ring atoms, $Z^-$ is a halide (eg iodide, bromide, chloride), an alkyl sulphate (eg methyl sulphate) or a sulfonyl ester (eg triflate) and R10 is hydrogen, alkyl or aryl; preferably having a configuration according to formula (10-a), (10-b) or (10-c), more preferably (10-b),

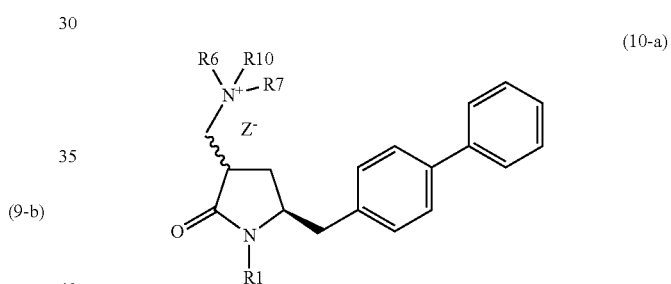
(10-a)

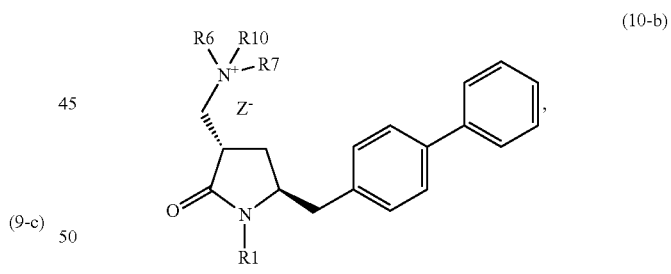
(10-b)

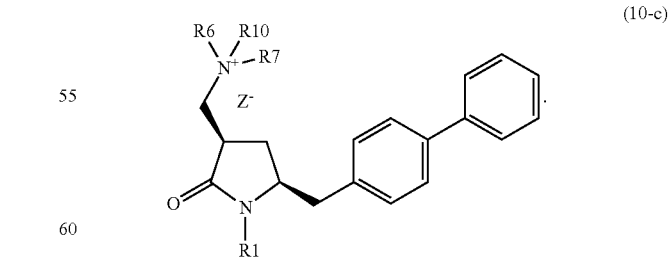
(10-c)

In a preferred embodiment of formulae (10), (10-a), (10-b) or (10-c), R1 is Boc.

In a preferred embodiment of formulae (10), (10-a), (10-b) or (10-c), R6 is Methyl, R7 is Methyl and/or R10 is Methyl.

A compound of formula (11)

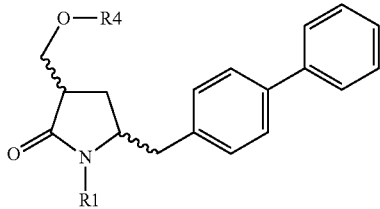
(11)

or salt thereof, wherein R1 is hydrogen or a nitrogen protecting group and R4 is an OH-activating group, preferably having a configuration according to formula (11-a), (11-b) or (11-c), more preferably (11-b),

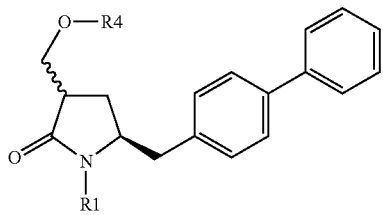
(11-a)

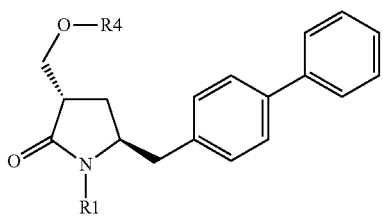
(11-b)

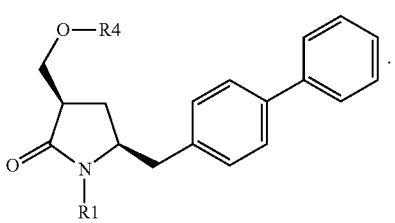
(11-c)

In a preferred embodiment of formulae (11), (11-a), (11-b) or (11-c), R1 is Boc.
In a preferred embodiment of formulae (11), (11-a), (11-b) or (11-c), R4 is mesylate.

A compound of formula (12)

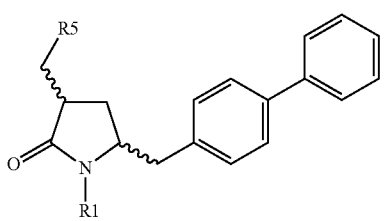
(12)

or salt thereof, wherein R1 is hydrogen or a nitrogen protecting group and R5 is a leaving group; preferably of formulae (12-a), (12-b) or (12-c), more preferably (12-b),

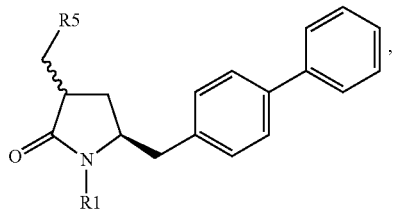
(12-a)

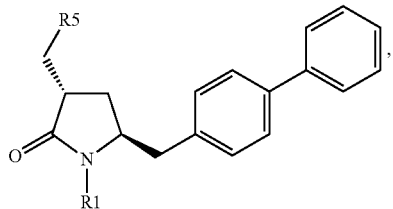
(12-b)

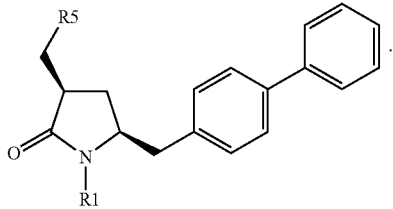
(12-c)

In a preferred embodiment of formulae (12), (12-a), (12-b) or (12-c), R1 is Boc.
In a preferred embodiment of formulae (12), (12-a), (12-b) or (12-c), R5 is a halide, preferably bromide or iodide.

A compound of formula (16)

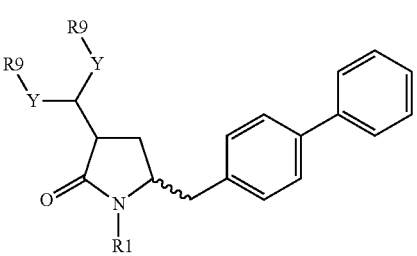
(16)

or salt thereof,
wherein R1 is hydrogen or a nitrogen protecting group, Y is O or S and each R9, is, independently, alkyl, aryl, arylalkyl or acetyl.
preferably having a configuration according to formula (16-a),

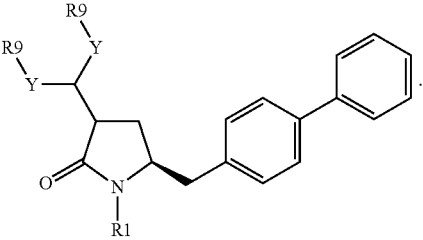
(16-a)

In a preferred embodiment of formulae (16) or (16-a), R1 is Boc.

In a preferred embodiment of formulae (16) or (16-a), R9 is methyl or ethyl.

In a preferred embodiment of formulae (16) or (16-a), Y is oxygen.

GENERAL TERMS

The general definitions used above and below, unless defined differently, have the following meanings:

The term "ester group" comprises any ester of a carboxyl group generally known in the art; for example groups —COOR, wherein R is selected from the group consisting of: $C_{1-6}$alkyl, such as methyl, ethyl or t-butyl, $C_{1-6}$alkoxy$C_{1-6}$alkyl, heterocyclyl, such as tetrahydrofuranyl, $C_{6-10}$aryloxy$C_{1-6}$alkyl, such as benzyloxymethyl (BOM), silyl, such as trimethylsilyl, t-butyldimethylsilyl and t-butyldiphenylsilyl, cinnamyl, allyl, $C_{1-6}$alkyl which is mono-, di- or trisubstituted by halogen, silyl, cyano or $C_{1-6}$aryl, wherein the aryl ring is unsubstituted or substituted by one, two or three, residues selected from the group consisting of $C_{1-7}$alkyl, $C_{1-7}$alkoxy, halogen, nitro, cyano and $CF_3$; or $C_{1-2}$alkyl substituted by 9-fluorenyl. In a preferred embodiment, the "ester group" is —COOR, wherein R is a $C_{1-6}$alkyl residue. In particular, R is methyl or ethyl.

The term "nitrogen protecting group" comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis', Fourth Edition, Wiley, New Jersey, 2007, in "The Peptides"; Volume 3 (editors: E. Gross and J. Meienhofer), Academic Press, London and New York 1981, and in "*Methoden der organischen Chemie*" (Methods of Organic Chemistry), Houben Weyl, 4th edition, Volume 15/I, Georg Thieme Verlag, Stuttgart 1974.

Preferred nitrogen protecting groups generally comprise: $C_1$-$C_6$-alkyl, preferably $C_1$-$C_4$-alkyl, more preferably $C_1$-$C_2$-alkyl, most preferably $C_1$-alkyl which is mono-, di- or tri- substituted by trialkylsilyl$C_1$-$C_7$alkoxy (eg. trimethylsilyethoxy) aryl, preferably phenyl, or an heterocyclic group, preferably pyrrolidinyl, wherein the aryl ring or the heterocyclic group is unsubstituted or substituted by one or more, e.g. two or three, residues, e.g. selected from the group consisting of $C_1$-$C_7$alkyl, hydroxy, $C_1$-$C_7$-alkoxy, $C_2$-$C_8$-alkanoyl-oxy, halogen, nitro, cyano, and $CF_3$; aryl-C1-C2-alkoxycarbonyl (preferably phenyl-C1-C2-alkoxycarbonyl eg. benzyloxycarbonyl); $C_{1-10}$alkenyloxycarbonyl; $C_{1-6}$alkylcarbonyl (eg. acetyl or pivaloyl); $C_{6-10}$arylcarbonyl; $C_{1-6}$alkoxycarbonyl (eg. t-butoxycarbonyl); $C_{6-10}$aryl$C_{1-6}$alkoxycarbonyl; allyl or cinnamyl; sulfonyl or sulfenyl; succinimidyl group, silyl, e.g. triarylsilyl or trialkylsilyl (eg. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonyl (Adoc), allyl, allyloxycarbonyl, trimethylsilyl, tert.-butyl-dimethylsilyl, triethylsilyl (TES), triisopropylsilyl, trimethylsilyethoxymethyl (SEM), t-butoxycarbonyl (BOC), t-butyl, 1-methyl-1,1-dimethylbenzyl, (phenyl)methylbenzene, pyrridinyl and pivaloyl. Most preferred nitrogen protecting groups are acetyl, benzyl, benzyloxycarbonyl (Cbz), triethylsilyl (TES), trimethylsilyethoxymethyl (SEM), t-butoxycarbonyl (BOC), pyrrolidinylmethyl and pivaloyl.

Examples of more preferred nitrogen protecting groups are pivaloyl, pyrrolidinylmethyl, t-butoxycarbonyl, benzyl and silyl groups, particularly silyl groups according to the formula SiR11R12R13, wherein R11, R12 and R13 are, independently of each other, alkyl or aryl. Preferred examples for R11, R12 and R13 are methyl, ethyl, isopropyl, t-butyl and phenyl.

Particularly preferred as nitrogen protecting groups are pivaloyl and t-butoxycarbonyl (BOC).

Alkyl is defined as a radical or part of a radical is a straight or branch (one or, if desired and possible, more times) carbon chain, and is especially $C_1$-$C_7$alkyl, preferably $C_1$-$C_4$-alkyl.

The term "$C_1$-$C_7$-" defines a moiety with up to and including maximally 7, especially up to and including maximally 4, carbon atoms, said moiety being branched (one or more times) or straight-chained and bound via a terminal or a non-terminal carbon Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy is, for example, $C_1$-$C_7$alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred.

Alkanoyl is, for example, $C_2$-$C_8$-alkanoyl and is, for example, acetyl [—C(=O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$alkyl and is in particular halo-$C_1$-$C_4$alkyl, such as trifluoromethyl, 1,1,2-trifluoro-2-chloroethyl or chloromethyl. Preferred halo-$C_1$-$C_7$alkyl is trifluoromethyl.

Alkenyl may be linear or branched alkyl containing a double bond and comprising preferably 2 to 12 C atoms, 2 to 10 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$alkyl and is especially $C_2$-$C_7$alkylene or $C_2$-$C_7$-alkylene and, optionally, can be interrupted by one or more, e.g. up to three, O, NR14 or S, wherein R14 is alkyl, each of which can be unsubstituted or substituted, by one or more substituents independently selected from for example, $C_1$-$C_7$alkyl, $C_1$-$C_7$alkoxy-$C_1$-$C_7$alkyl or $C_1$-$C_7$alkoxy.

Alkenylene is a bivalent radical derived from $C_{2-7}$alkenyl and can be interrupted by, one or more, e.g. up to three, O, NR14 or S, wherein R14 is alkyl, and is unsubstituted or substituted by one or more, e.g. up to three, substitutents preferably independently selected from the substitutents mentioned above for alkylene.

Aryl being a radical or part of a radical is, for example $C_{6-10}$aryl, and is, preferably a mono- or polycyclic, especially monocyclic, bicyclic or tricyclic aryl moiety with 6 to 10 carbon atoms, preferably phenyl, and which can be unsubstituted or substituted, by one or more substituents independently selected from for example, $C_1$-$C_7$alkyl, $C_1$-$C_7$-alkoxy-$C_1$-$C_7$-alkyl or $C_1$-$C_7$-alkoxy.

The term arylalkyl refers to aryl-$C_1$-$C_7$-alkyl, wherein aryl is as defined herein and is for example benzyl.

The term carboxyl refers to —$CO_2H$.

Aryloxy refers to a Aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms independently selected from nitrogen, oxygen, sulfur, S(═O)— or S—(═O)$_2$, and is unsubstituted or substituted by one or more, e.g. up to three, substitutents preferably independently selected from the Preferred substituents are selected from the group consisting of halo, $C_1$-$C_7$alkyl, $C_1$-$C_7$alkoxy, halo-$C_1$-$C_7$-alkoxy, such as trifluoromethoxy and $C_1$-$C_7$alkoxy-$C_1$-$C_7$alkoxy. When the heterocyclyl is an aromatic ring system, it is also referred to as heteroaryl.

Acetyl is —C(═O)$C_1$-$C_7$alkyl, preferably —C(═O)Me.

Silyl is —SiRR'R", wherein R, R' and R" are independently of each other $C_{1-7}$alkyl, aryl or phenyl-$C_{1-4}$alkyl.

Sulfonyl is (unsubstituted or substituted) $C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$alkyl, halo-$C_1$-$C_7$-alkyloxy- and $C_1$-$C_7$-alkyloxy. Especially preferred is $C_1$-$C_7$alkylsulfonyl, such as methylsulfonyl, and (phenyl- or naphthyl)-$C_1$-$C_7$-alkylsulfonyl, such as phenylmethanesulfonyl.

Sulfenyl is (unsubstituted or substituted) $C_{6-10}$aryl-$C_1$-$C_7$-alkylsulfenyl or (unsubstituted or substituted) $C_{6-10}$arylsulfenyl, wherein if more than one substituent is present, e.g. one to four substitutents, the substituents are selected independently from nitro, halo, halo-$C_1$-$C_7$alkyl and $C_1$-$C_7$alkyloxy.

A "heterogeneous" catalyst as used herein refers to a catalyst supported on a carrier, typically although not necessarily a substrate comprised of an inorganic material, for example, a porous material such as carbon, silicon and/or aluminum oxide. In one embodiment, the heterogeneous catalyst is a hydrogenation catalyst, in particular those described in Section D.4.

A "homogeneous" catalyst as used herein refers to a catalyst that is not supported on a carrier. In one embodiment, the homogeneous catalyst is a hydrogenation catalyst, in particular those described in Section D.4.

The term "transition metal catalyst" refers to an organometallic catalyst, an organometallic complex or an organometallic complex and a chiral ligand. Transition metal catalysts are in particular those described in Sections C.1, B 3.3 and D.4.

The term "organometallic complex" refers to complexes derived from a transition metal and one or more (for example up to four) achiral (non chiral) ligands; for example, ruthenium organometallic complexes, such as [RuI$_2$(p-cymene)]$_2$, [Ru(cod)(2-metallyl)$_2$] or [Ru(cod)(OOCCF$_3$)$_2$]; rhodium organometallic complexes, such as [Rh(nbd)$_2$BF$_4$] or [Rh(cod)$_2$]BF$_4$; or an iridium organometallic complexes, such as [(Cy$_3$P)Ir(Pyr)]Cl or [Ir(cod)$_2$Cl]$_2$.

The term "organometallic catalyst" refers to a catalysts derived from a transition metal and one or more (for example up to four) chiral ligands.

The term "ligand" means any compound, achiral or chiral, that can form a complex with a transition metal. Chiral and achiral ligands are in particular those described in Section C.1

The term "catalyst" means any substance that affects the rate of a chemical reaction by lowering the activation energy for the chemical reaction.

The term "powder" means a catalyst with a water contain of from 0 to 30 mass %.

The term "substrate to catalyst ratio" (S/C) refers to the molar ratio of starting compounds, or salts thereof, to "transition metal catalyst".

The term "chiral" refers to molecules which have the property of non-superimposability on their mirror image partner, while the term "achiral" refers to molecules which are superimposable on their mirror image partner.

The term "tautomer" refers in particular to the enol tautomer of the pyrrolidin-2-one moiety of the compounds of the present invention. Additionally, the term "tautomer" also refers in particular to the aldehyde tautomer of compounds of the present invention, e.g. compounds of the formula (6), where such compounds can exists in either an enol or aldehyde form, or mixtures thereof.

In the formulae of the present application the term "〰〰" on a C-sp$^3$ represents a covalent bond, wherein the stereochemistry of the bond is not defined. This means that the term "〰〰" on a C-sp$^3$ comprises an (S) configuration as well as an (R) configuration of the respective chiral centre. Furthermore, mixtures are also encompassed, e.g., mixtures of enantiomers, such as racemates, are encompassed by the present invention.

In the formulae of the present application the term "〰〰" on a C-sp$^2$ represents a covalent bond, wherein the stereochemistry or the geometry of the bond is not defined. This means that the term "〰〰" on a C-sp$^2$ comprises a cis (Z) configuration as well as a trans (E) configuration of the respective double bond. Furthermore, mixtures are also encompassed, e.g., mixtures of double bond isomers are encompassed by the present invention.

The compounds of the present invention can possess one or more asymmetric centers. The preferred absolute configurations are as indicated herein specifically.

In the formulae of the present application the term "⋰" on a C-sp$^3$ indicates the absolute stereochemistry, either (R) or (S).

In the formulae of the present application the term "⋰" on a C-sp$^3$ indicates the absolute stereochemistry, either (R) or (S).

In the formulae of the present application, the term " ═══ " indicates a Csp$^3$-Csp$^3$ bond or a Csp$^2$-Csp$^2$ bond.

Salts are especially pharmaceutically acceptable salts or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Any of the lactams according to the present invention, or salts thereof, wherein R1 is hydrogen can be converted into a corresponding protected lactam, or salt thereof, wherein R1 is a nitrogen protecting group, as defined above, according to standard methods of organic chemistry known in the art, in particular reference is made to conventional nitrogen protecting group methods described in J. F. W. McOmie, "Protective Groups in Organic Chemistry", Plenum Press, London and New York 1973, in P. G. M. Wuts and T. W. Greene, "Greene's Protective Groups in Organic Synthesis', Fourth Edition, Wiley, New Jersey, 2007 and in Richard C. Larock, "Comprehensive Organic Transformations: A Guide to Functional Group Preparations", Second Edition, Wiley-VCH Verlag GmbH, 2000, in particular, in the relevant chapters thereof.

Analogously, any of the lactams according to the present invention, or salt thereof, wherein R1 is a nitrogen protecting group, can be converted into the corresponding lactam, or salt thereof, wherein R1 is a hydrogen, according to standard methods of organic chemistry known in the art, in particular reference is made to conventional nitrogen protecting group methods described in the books mentioned above, in particular, in the relevant sections.

SECTION F: EXAMPLES

The following Examples serve to illustrate the invention without limiting the scope thereof, while they on the other hand represent preferred embodiments of the reaction steps, intermediates and/or the process of the present invention.

ABBREVIATIONS $\delta$ chemical shift
$\mu$l microliter
Ac acetyl
acac acetylacetone
An anisyl (4-methoxyphenyl)
BArF tetrakis[3,5-bis(trifluoromethyl)phenyl]boron
BINOL 2,2'-dihydroxy-1,1'-dinaphthyl
Bn benzyl
Boc tert-butoxycarbonyl
$BOC_2O$ di-tert-butyl carbonate
COD=cod cyclooctadiene
Cp cyclopentadienyl
Cy cyclohexyl
DABCO 1,4-diazobicyclo[2.2.2]octane
de diastereomeric excess
dr diastereomeric ratio
DMAP 4-(dimethylamino)pyridine
DMF=dmf N,N-dimethylformamide
DMPU 1,3-dimethyl-3,4,5,6-tetrahydro-2(1H)-pyrimidinone
DMSO dimethylsulfoxide
ee enantiomeric excess
ES electrospray
ESI electrospray ionisation
Et ethyl
EtOAc ethyl acetate
EtOH ethanol
h hour(s)
HNMR proton nuclear magnetic resonance
HPLC high performance liquid chromatography
iPr isopropyl
iPrOAc isopropyl acetate
iPrOH isopropanol
IR infra red
L liter
LC-MS liquid chromatography-mass spectrometry
LHMDS lithium bis(trimethylsilyl)amide
M molarity
m/e mass-to-charge ratio
Me methyl
2-MeTHF=Me-THF 2-Methyltetrahydrofuran
MeOH methanol
mg milligram
min minute(s)
ml milliliter
mmol(s) millimole(s)
mol(s) mole(s)
MS mass spectrometry
nm nanometer
NMR nuclear magnetic resonance
NDB=nbd norbornadiene
Np naphthyl
Pd/C palladium on carbon
Ph phenyl
Piv pivaloyl
Piv-Cl pivaloyl chloride
ppm parts per million
Pt/C platinum on carbon pyr pyridine Rh/C rhodium on carbon RT=rt room temperature tBu tertiary-butyl TFA trifluoroacetic acid THF tetrahydrofuran TLC thin layer chromatography TMG 1,1,3,3-tetramethylguanidine Tol toluene $t_R$ retention time Xyl xylene In quoting NMR data, the following abbreviations may be used: s, singlet; d, doublet; t, triplet; q, quartet; quint., quintet; m, multiplet.

Example 1

N,N,N',N'-Tetramethylformamidinium methylsulfate (18, R6=Me, R7=Me)

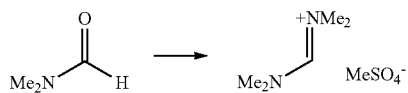

A mixture of N,N-dimethylformamide (7.31 g) and dimethylsulfate (12.60 g) are heated to 60° C. for 4 h. Then dimethylamine in THF (100 ml, 2 M solution) and toluene (15 ml) are added and the resulting mixture is stirred at reflux for 1 h. The reaction mixture is cooled to room temperature and the phases are separated. The lower layer is washed three times with anhydrous tert-butyl methyl ether to give N,N,N',N'-tetramethylformamidinium methylsulfate (18, R6=Me, R7=Me). $^1$H NMR($C_6D_6$), 7.95 (1H), 3.70 (3H), 3.32 (6H), 3.29 (6H).

Example 2

N,N,N',N'-Tetramethylformamidinium para-toluenesulfonate (18, R6=Me, R7=Me)

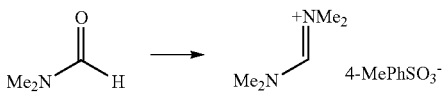

A mixture of p-toluenesulfonyl chloride (20.0 g) and dimethylformamide (38.3 g) is allowed to stand for 2 h at room temperature. The mixture is then stirred at 120° C. for 2 h. The mixture is then cooled to room temperature and the precipitates are removed by filtration. The mother liquor is diluted with acetone and the mixture cooled to 0° C. Filtration affords N,N,N',N'-tetramethylformamidinium para-toluenesulfonate (18, R6=Me, R7=Me) as white crystals. $^1$H NMR ($D_2O$), 7.65-7.60 (2H), 7.39 (1H), 7.30-7.25 (2H), 3.14 (6H), 3.05 (6H), 2.31 (3H).

The X-ray Structure of the obtained crystals is shown in FIG. 1.

Crystal Data [Recorded at 100(2) K]

| | |
|---|---|
| Empirical formula | $C_{12}H_{20}N_2O_3S$ |
| Formula weight | 272.36 |
| Crystal system | Monoclinic |
| Space group | Cc |
| Cell parameters | a = 7.998(2) Å |
| | b = 14.331(2) Å |
| | c = 11.953(2) Å |
| | $\alpha = 90°$ |
| | $\beta = 103.615(4)°$ |
| | $\gamma = 90°$ |
| Volume of unit cell | 1331.5(4) Å$^3$ |
| Z* | 4 |
| Calculated density | 1.359 mg m$^{-3}$ |

*(number of asymmetric units in the unit cell)

Example 3

N,N,N',N'-Tetramethylformamidinium hexafluorophosphate (18, R6=Me, R7=Me)

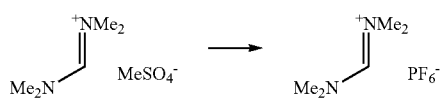

N,N,N',N'-tetramethylformamidinium methylsulfate (3 g) is added to water (25 ml) and the resulting mixture is cooled to 0° C. This mixture is then added to a cooled solution of ammonium hexafluorophosphate (4.6 g) in water (25 ml). The so formed precipitate is then collected by filtration. The precipitate is washed with cold water (2×10 ml) and then with diethyl ether (10 ml). Drying in vacuo gives N,N,N',N'-tetramethylformamidinium hexafluorophosphate (18, R6=Me, R7=Me) as a white solid. $^1$H NMR (DMSO-d6), 7.90 (1H), 3.26 (6H), 3.14 (6H).

Example 4

N,N,N',N'-Tetraethylformadinium methylsulfate (18, R6=Et, R7=Et)

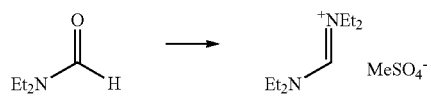

A mixture of N,N-diethylformamide (30 g) and dimethylsulfate (37.5 g) are heated to 50° C. for 4 h. Then a mixture of diethylamine (32.6 g) and toluene (20 ml) are added and the resulting mixture is stirred at reflux for 1 h. The reaction mixture is cooled to room temperature and the phases are separated. The lower layer is washed ten times with diethyl ether to give N,N,N',N'-tetraethylformamidinium methylsulfate (18, R6=Et, R7=Et). 1H NMR (DMSO-d6), 7.26 (1H), 3.51 (8H), 3.42 (3H), 1.24 (12H) ppm.

Example 5

N,N,N'N'-Tetraethylformamidinium tetrafluoroborate (18, R6=Et, R7=Et)

N,N,N',N'-Tetraethylformamidinium methylsulfate (4 g) is added to water (25 ml) and the resulting mixture is cooled to 0° C. This mixture is then added to a cooled solution of ammonium tetrafluoroborate (3.15 g) in water (25 ml). The mixture is then extracted with dichloromethane. Removal of the dichloromethane gives N,N,N'N'-tetraethylformamidinium tetrafluoroborate (18, R6=Et, R7=Et) as a white solid. 1H NMR (DMSO-d6), 7.80 (1H), 3.70-3.40 (8H), 1.40-1.33 (12H).

The X-ray Structure of the obtained crystals is shown in FIG. 2.

Crystal Data [Recorded at 100(2) K]

| | |
|---|---|
| Empirical formula | $C_9H_{21}BF_4N_2$ |
| Formula weight | 244.09 |
| Crystal system | Monoclinic |
| Space group | P21/c |
| Cell parameters | a = 9.738(2) Å |
| | b = 8.580(2) Å |
| | c = 15.519(2) Å |
| | α = 90° |
| | β = 100.840(6)° |
| | γ = 90° |
| Volume of unit cell | 1273.5(4) Å$^3$ |
| Z* | 4 |
| Calculated density | 1.273 mg m$^{-3}$ |

*(number of asymmetric units in the unit cell)

Example 6

N,N,N',N'-Tetraethylformamidinium hexafluorophosphate (18, R6=Et, R7=Et)

N,N,N',N'-Tetraethylformamidinium methylsulfate (4 g) is added to water (25 ml) and the resulting mixture is cooled to 0° C. This mixture is then added to a cooled solution of ammonium hexafluorophosphate (4.9 g) in water (25 ml). The formed precipitate is collected by filtration. The precipitate is then washed with cold water (2×10 ml) and then with diethyl ether (10 ml). Drying in vacuo gives N,N,N',N'-tetraethylformamidinium hexafluorophosphate (18, R6=Et, R7=Et) as a yellow solid. 1H NMR (DMSO-d6), 7.92 (1H), 3.85-3.54 (8H), 1.45-1.38 (12H).

Example 7

1-Pyrrolidin-1-ylmethylene-pyrrolidinium methylsulfate (18, R6/R7=Pyrrolidinyl)

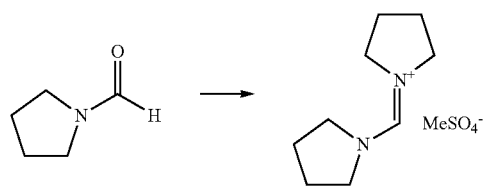 [SMILES: "MeSO4-" ; O=CN1CCCC1 ; C(N1CCCC1)=[N+]1CCCC1]

A mixture of N-formylpyrrolidine (100 g) and dimethylsulfate (126 g) are heated to 80° C. for 4 h. Then a mixture of pyrrolidine (71 g) and toluene (100 ml) are added and the resulting mixture is stirred at reflux for 1 h. The reaction mixture is cooled to room temperature and the phases are separated. The lower layer is concentrated in vacuo and triturated with diethyl ester. The precipitate is collected by filtration and recrystallised using ethyl acetate to give 1-pyrrolidin-1-ylmethylene-pyrrolidinium methylsulfate (18, R6/R7=Pyrrolidinyl). 1H NMR (DMSO-d6), 8.28 (1H), 3.90-3.85 (4H), 3.68-3.62 (4H), 3.38 (3H), 1.99-1.90 (4H), 1.86-1.77 (4H).

Example 8

1-Pyrrolidin-1-ylmethylene-pyrrolidinium hexafluorophosphate (18, R6/R7=Pyrrolidinyl)

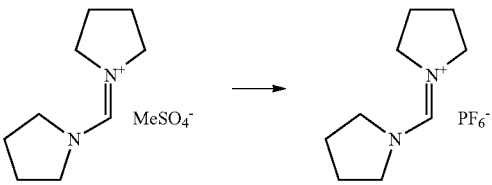

1-pyrrolidin-1-ylmethylene-pyrrolidinium methylsulfate (5 g) is added to water (25 ml) and the resulting mixture is cooled to 0° C. This mixture is then added to a cooled solution of ammonium hexafluorophosphate (6.2 g) in water (25 ml). The formed precipitate is collected by filtration. The precipitate is washed with cold water (2×10 ml) and then with diethyl ether (10 ml). Drying in vacuo gives 1-pyrrolidin-1-ylmethylene-pyrrolidinium hexafluorophosphate (18, R6/R7=Pyrrolidinyl) as a white solid. m.p. 229-231° C. 1H NMR (DMSO-d6), 8.25 (1H), 3.91-3.83 (4H), 3.67-3.60 (4H), 1.99-1.90 (4H), 1.86-1.77 (4H).

Example 9

N,N,N',N'-Tetraisopropylformamidinium chloride
(18, R6=iPr, R7=iPr)

A mixture of phosphorus oxychloride (10.58 g) and diethyl ether (50 ml) is stirred at 0° C. for 10 min. Diisopropylformamide (8.91 g) in diethyl ether (20 ml) is then added drop-wise over a period of 10 min. The resulting mixture is then stirred at room temperature for 30 min. The formed precipitate is allowed to settle and the supernatant removed. Dichloromethane (60 mL) is then added to the mixture. Diisopropylamine (6.98 g) in dichloromethane (20 ml) is then added drop-wise at 0° C. over 10 min. The mixture is then warmed at room temperature and stirred for a further 1.5 h. Diethyl ether (30 ml) is added and the resulting precipitate is removed by filtration. The mother liquor is concentrated in vacuo. Acetone (30 ml) is added and the mixture filtered. The mother liquor is then concentrated in vacuo and subsequently is crystallised with diethyl ether (30 ml) to give N,N,N',N'-tetraisopropylformamidinium chloride (18, R6=iPr, R7=iPr). 1H NMR (DMSO-d6), 7.49 (1H), 4.15-3.95 (4H), 1.33 (12H), 1.31 (12H).

Example 10

N,N,N',N'-Tetraisopropylformamidinium hexafluorophosphate (18, R6=iPr, R7=iPr)

A mixture of N,N-diisopropyllformamide (10 g) in anhydrous dichloromethane (40 mL) is added to a solution of phosphorus oxychloride (11.8 g) in dichloromethane (100 ml) at −78° C. The resulting mixture is stirred for 30 min at −78° C. The reaction mixture is then warmed to room temperature and stirred for a further 2 h. The mixture is then cooled to 0° C. To this mixture, a solution of diisopropylamine (10.9 ml) and triethylamine (10.7 ml) in dichloromethane (50 ml) is added dropwise over a period of 30 min. The reaction mixture is then allowed to warm slowly to room temperature and stirred for a further 2 h. The mixture is then concentrated in vacuo. Water (25 ml) is added and the resulting mixture is cooled to 0° C. This mixture is then added to a cooled solution of ammonium hexafluorophosphate (14.9 g) in water (25 ml). The formed precipitate is collected by filtration. The precipitate is washed with cold water (2×10 ml) and then with diethyl ether (10 ml). The material is dried in vacuo and then recrystallised from acetone to give N,N,N',N'-tetraisopropylformamidinium hexafluorophosphate (18, R6=iPr, R7=iPr) as a colourless solid. 1H NMR (DMSO-d6), 7.48 (1H), 4.15-4.00 (4H), 1.36-1.29 (24H).

Example 11

N,N,N',N'-Tetraisopropylformamidinium tetrafluoroborate (18, R6=iPr, R7=iPr)

A mixture of N,N-diisopropyllformamide (10 g) in anhydrous dichloromethane (40 ml) is added to a solution of phosphorus oxychloride (11.9 g) in dichloromethane (100 ml) at −78° C. The reaction mixture is then warmed to room temperature and stirred for 2 h. The mixture is then cooled to 0° C. To this mixture, a solution of diisopropylamine (7.8 g) and triethylamine (10.8 ml) in dichloromethane (50 ml) is added dropwise over a period of 30 min. The reaction mixture is then allowed to warm slowly to room temperature and stirred for a further 2 h. The reaction mixture is washed with aqueous sodium hydroxide (20 ml, 2 M) and saturated sodium tetrafluoroborate (13.2 g) and extracted with dichloromethane. The organic layer is dried (MgSO₄) and then concentrated in vacuo. The residue is taken up in acetone. Addition of a mixture of diethyl ether and pentane (4:1, 20.5 ml) followed by filtration gives N,N,N',N'-tetraisopropylformamidinium tetrafluoroborate (18, R6=iPr, R7=iPr). 1H NMR (DMSO-d6), 7.48 (1H), 4.15-3.95 (4H), 1.35-1.30 (24H).

Example 12

Diisopropyl(piperidin-1-ylmethylidene)ammonium hexafluorophosphate (18, R6=iPr, R7=Piperidinyl)

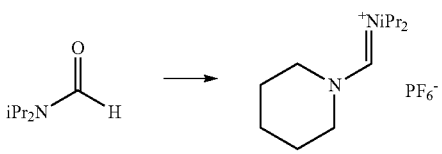

A mixture of N,N-diisopropyllformamide (5 g) in anhydrous dichloromethane (40 mL) is added to a solution of phosphorus oxychloride (5.9 g) in dichloromethane (100 ml) at −78° C. The resulting mixture is stirred for 30 min at −78° C. The reaction mixture is then warmed to room temperature and stirred for a further 2 h. The mixture is then cooled to 0° C. To this mixture, a solution of piperidine (3.3 g) and triethylamine (3.92 g) in dichloromethane (50 ml) is added dropwise over a period of 30 min. The reaction mixture is then allowed to warm slowly to room temperature and stirred for a further 2 h. The mixture is then concentrated in vacuo. Water (25 ml) is then added and the resulting mixture is cooled to 0° C. This mixture is then added to a cooled solution of ammonium hexafluorophosphate (6.3 g) in water (25 ml). The precipitate is collected by filtration. The precipitate is washed with cold water (2×10 ml) and then with diethyl ether (10 ml). The material is dried in vacuo and then recrystallised from acetone to give diisopropyl(piperidin-1-ylmethylidene)ammonium hexafluorophosphate (18, R6=iPr, R7=Piperidinyl) as a colourless solid. m.p. 239-240° C. 1H NMR (DMSO-d6), 7.83 (1H), 4.30-3.80 (2H), 3.64-3.59 (4H), 1.63-1.71 (6H), 1.30-1.24 (12H).

The X-ray Structure of the obtained crystals is shown in FIG. 3.

Crystal Data [Recorded at 100(2) K]

| Empirical formula | $C_{12}H_{25}F_6N_2P$ |
|---|---|
| Formula weight | 342.31 |
| Crystal system | Orthorhombic |
| Space group | P212121 |
| Cell parameters | a = 9.315(2) Å |
| | b = 12.051(2) Å |
| | c = 14.134(2) Å |
| | α = 90° |
| | β = 90° |
| | γ = 90° |
| Volume of unit cell | 1586.6(5) Å$^3$ |
| Z* | 4 |
| Calculated density | 1.433 mg m$^{-3}$ |

*(number of asymmetric units in the unit cell)

Example 13

Tris(morpholino)methane (13, R6/R7=morpholino)

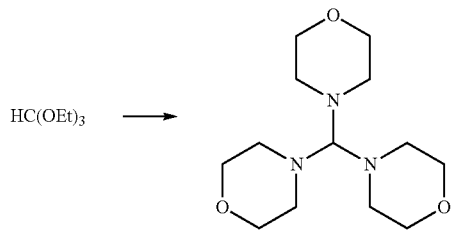 [SMILES: C1CN(C(N2CCOCC2)N2CCOCC2)CCO1 ; "HC(OEt)3"]

A mixture of triethylorthoformate (62.2 g), morpholine (54.5 g) and glacial acetic acid (1.26 g) is stirred at 180° C. for 5 h. During this time, the ethanol formed is continuously removed by distillation. The reaction mixture is left to cool to room temperature overnight. The resulting precipitate is filtered and washed with heptane. The solid is re-crystallised using toluene to give tris(morpholino)methane, 13 (R6/R7=morpholine). 1H NMR (CDCl$_3$), 3.66-3.60 (12H), 3.26 (1H), 2.80-2.70 (12H).

Example 14

Tris(dimethylamino)methane (13, R6=Me, R7=Me), Tert-Butoxy-bis(dimethylamino)methane (14, R6=Me, R7=Me, R8=tBu) and N,N-Dimethylformamide di-tert-butyl acetal (15, R6=Me, R7=Me, R8=tBu)

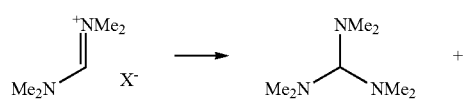

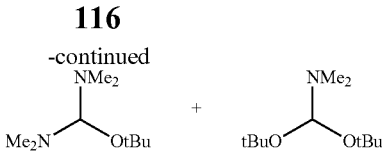

Method 1

N,N,N',N'-tetramethylformadinium methyl sufate (5 g) (prepared according to Example 1, X=MeSO$_4$) is added to a solution of potassium tert-butoxide in THF (23.6 ml, 1 M). The mixture is then stirred for 1 h at 60° C. The reaction mixture is then filtered under argon. The mother liquor is then concentrated in vacuo to afford a residue (1.60 g) containing 13, 14 and 15 (R6=Me, R7=Me, R8=tBu). 1H NMR (C$_6$D$_6$): 1.08, 1.16, 1.24, 2.29, 2.33, 3.02, 4.06, 5.00. Relative amounts of 13 (R6=Me; R7=Me), 14 (R6=Me, R7=Me, R8=tBu), 15 (R6=Me, R7=Me, R8=Me) are determined by integration of signals at 3.02, 4.06 and 5.00 ppm, respectively.

Method 2

N,N,N',N'-tetramethylformadinium para-toluenesulfonate (500 mg) (prepared according to Example 2, X=4-MePhSO$_3$) is added to a solution of potassium tert-butoxide in THF (1.8 ml, 1 M). The mixture is then stirred for 1 h at 50° C. The reaction mixture is then filtered under argon. The mother liquor is then concentrated in vacuo to afford a residue containing 13, 14 and 15 (R6=Me, R7=Me, R8=tBu).

Method 3

N,N,N',N'-tetramethylformadinium hexafluorophosphate (500 mg) (prepared according to Example 3, X=PF$_6$) is added to a solution of potassium tert-butoxide in THF (2 ml, 1 M). The mixture is then stirred for 1 h at 50° C. The reaction mixture is then filtered under argon. The mother liquor is then concentrated in vacuo to afford a residue containing 13, 14 and 15 (R6=Me, R7=Me, R8=tBu).

Example 15

Tris(diethylamino)methane (13, R6=Et, R7=Et), Tert-Butoxy-bis(diethylamino)methane (14, R6=Et, R7=Et, R8=tBu) and N,N-Diethylformamide di-tert-butyl acetal (15, R6=Et, R7=Et, R8=tBu)

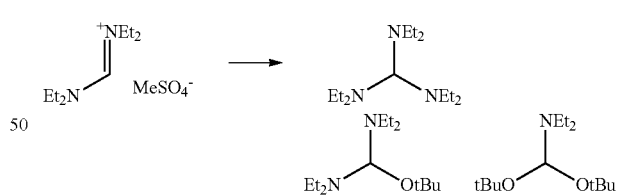

Method 1

N,N,N',N'-tetraethylformadinium methyl sulfate (5 g) (prepared according to Example 4, X=MeSO$_4$) is added to a solution potassium tert-butoxide in THF (18.7 ml, 1 M). The resulting mixture is then stirred for 1 h at 60° C. The reaction mixture is filtered under argon and the mother liquor is then concentrated in vacuo to afford a residue (1.31 g) containing 13, 14 and 15 (R6=Et, R7=Et, R8=tBu). 1H NMR (C$_6$D$_6$): 0.55-0.59, 0.81-0.85, 0.98-1.06, 1.19, 1.24, 2.46-2.52, 2.64-2.80, 3.04-3.09, 3.80, 4.56, 5.18. Relative amounts of 13 (R6=Et; R7=Et), 14 (R6=Et, R7=Et, R8=tBu), 15 (R6=Et, R7=Et, R8=tBu) are determined by integration of signals at 3.80, 4.56 and 5.18 ppm, respectively.

Method 2

N,N,N',N'-tetraethylformadinium tetrafluoroborate (500 mg) (prepared according to Example 5, X=BF$_4$) is added to a solution of potassium tert-butoxide in THF (2.05 ml, 1 M). The mixture is then stirred for 1 h at 50° C. The reaction mixture is then filtered under argon. The mother liquor is then concentrated in vacuo to afford a residue containing 13, 14 and 15 (R6=Et, R7=Et, R8=tBu).

Method 3

N,N,N',N'-tetraethylformadinium hexafluorophosphate (500 mg) (prepared according to Example 6, X=PF$_6$) is added to a solution of potassium tert-butoxide in THF (1.66 ml, 1 M) The mixture is then stirred for 1 h at 50° C. The reaction mixture is then filtered under argon. The mother liquor is then concentrated in vacuo to afford a residue containing 13, 14 and 15 (R6=Et, R7=Et, R8=tBu).

Example 16-1

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me)

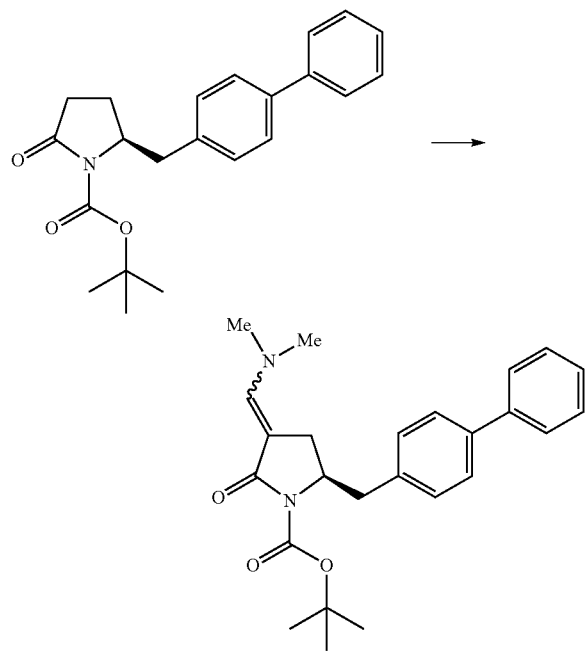

Method 1

A mixture of 1 g (S)-2-Biphenyl-4-ylmethyl-5-oxo-pyrrolidine-1-carboxylic acid tert-butyl ester (8-a, R1=Boc) and 0.7 ml tris(dimethylamine)methane (13, R6=Me, R7=Me) (Aldrich, #221058) in toluene (5 ml) are heated for 16 h at 115° C. The mixture is concentrated in vacuo to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 2

To 1 g (S)-2-Biphenyl-4-ylmethyl-5-oxo-pyrrolidine-1-carboxylic acid tert-butyl ester (8-a, R1=Boc) in solution in 5 ml toluene are added 3 g of tris(dimethylamino)methane (13, R6=Me, R7=Me) (Aldrich, #221058) and 1 ml tert-butanol. The mixture is stirred at 80° C. for 24 h to yield after concentration to dryness nearly pure (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 3

To a mixture of 200 mg (S)-2-Biphenyl-4-ylmethyl-5-oxo-pyrrolidine-1-carboxylic acid tert-butyl ester (8-a, R1=Boc) and 0.49 ml tris(dimethylamino)methane (13, R6=Me, R7=Me) (Aldrich, #221058), tert-butanol (0.21 ml) is added. The mixture is stirred at 80° C. for 24 h to yield after concentration to dryness (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 4

To a mixture of 200 mg (S)-2-Biphenyl-4-ylmethyl-5-oxo-pyrrolidine-1-carboxylic acid tert-butyl ester (8-a, R1=Boc) and 0.49 ml tris(dimethylamino)methane (13, R6=Me, R7=Me) (Aldrich, #221058), isobutyl alcohol (0.21 ml) is added. The mixture is stirred at 80° C. for 24 h to yield after concentration to dryness (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 5

To a mixture of 200 mg (S)-2-Biphenyl-4-ylmethyl-5-oxo-pyrrolidine-1-carboxylic acid tert-butyl ester (8-a, R1=Boc) and 0.49 ml tris(dimethylamino)methane (13, R6=Me, R7=Me) (Aldrich, #221058), isopropyl alcohol (0.17 ml) is added. The mixture is stirred at 80° C. for 24 h to yield after concentration to dryness (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 6

To a mixture of 200 mg (S)-2-Biphenyl-4-ylmethyl-5-oxo-pyrrolidine-1-carboxylic acid tert-butyl ester (8-a, R1=Boc) and 0.49 ml tris(dimethylamino)methane (13, R6=Me, R7=Me) (Aldrich, #221058), dimethoxyethane (0.2 ml) is added. The mixture is stirred at 80° C. for 24 h to yield after concentration to dryness (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 7

Tert-butanol (0.67 g) is added to 1.65 g tris(dimethylamino)methane (13, R6=Me, R7=Me) (Aldrich, #221058) and the resulting mixture is stirred for 1 h at 80° C. (S)-2-Biphenyl-4-ylmethyl-5-oxo-pyrrolidine-1-carboxylic acid tert-butyl ester (8-a, R1=Boc) (1.00 g) is added and the resulting mixture heated at 80° C. for 8 h. The reaction mixture is cooled to room temperature and concentrated in vacuo. Azeotropic distillation using toluene affords (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 8

1 g of (S)-2-Biphenyl-4-ylmethyl-5-oxo-pyrrolidine-1-carboxylic acid tert-butyl ester (8-a, R1=Boc) is added to 10 g of a mixture containing 13, 14 and 15 (R6=Me, R7=Me, R8=CMe$_2$Et) (prepared according to Example 36, Method 1) and heated to 80° C. After 2 hours, the reaction is shown to be complete and is concentrated under vacuum to yield (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 9

N,N,N',N'-tetramethylformamidinium methylsulfate (302 mg) (prepared according to Example 1) is added to a 1 M solution of potassium-tert-butoxide in THF (1.14 ml). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (100 mg) is then added and the mixture stirred at 60° C. for 3 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 10

N,N,N',N'-tetramethylformamidinium para-toluenesulfonate (1.93 g) (prepared according to Example 2) is added to a 1 M solution of potassium-tert-butoxide in THF (5.69 ml). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (500 mg) is then added and the mixture stirred at 60° C. for 10 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 11

N,N,N',N'-Tetramethylformamidinium hexafluorophosphate (1.75 g) (prepared according to Example 3) is added to a 1 M solution of potassium-tert-butoxide in THF (5.69 ml). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (500 mg) is then added and the mixture stirred at 60° C. for 1 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 12

10 g (S)-2-Biphenyl-4-ylmethyl-5-oxo-pyrrolidine-1-carboxylic acid tert-butyl ester (8-a, R1=Boc) in 75 ml 1,2-dimethoxyethane. 17.8 ml tert-butoxy-bis(dimethylamino)methane (14, R6=Me, R7=Me, R8=tBu) (Fluka #20425) is added and the mixture stirred overnight at 75° C. The mixture is concentrated in vacuo to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 13

A mixture of (S)-2-biphenyl-4-ylmethyl-5-oxo-pyrrolidine-1-carboxylic acid tert-butyl ester (8-a, R1=Boc) (1 g) and a mixture containing 13, 14 and 15 (R6=Me, R7=Me, R8=tBu) (prepared according to Example 14, Method 1) are heated at 80° C. for 4 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 14

Mixture of 10 g (S)-2-biphenyl-4-ylmethyl-5-oxo-pyrrolidine-1-carboxylic acid tert-butyl ester (8-a, R1=Boc) and 52 g tert-butoxy-bis(dimethylamino)methane (14, R6=Me, R7=Me, R8=tBu) is heated at 80° C. for 4 hours. The mixture is concentrated in vacuo to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 15

A mixture of 2 g (S)-2-Biphenyl-4-ylmethyl-5-oxo-pyrrolidine-1-carboxylic acid tert-butyl ester (8-a, R1=Boc) and 8.7 ml methoxy-bis(dimethylamine)methane (14, R6=Me, R7=Me, R8=Me) (Fluka #64875) is heated at 80° C. for 40 hours. The mixture is then concentrated in vacuo. The residue is dissolved in isopropyl acetate and passed through Kieselgel. The filtrate is concentrated to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 16

A mixture of 1 g (S)-2-Biphenyl-4-ylmethyl-5-oxo-pyrrolidine-1-carboxylic acid tert-butyl ester (8-a, R1=Boc) and 1.2 ml N,N-dimethylformamide diisopropyl acetal (15, R6=Me, R7=Me, R8=iPr) (Aldrich #178535) are heated at 105° C. overnight. A further portion of N,N-dimethylformamide diisopropyl acetal (15, R6=Me, R7=Me, R8=iPr) is added and the mixture is stirred for 2 days at 105° C. The mixture is then concentrated to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 17

To 0.2 g (S)-2-Biphenyl-4-ylmethyl-5-oxo-pyrrolidine-1-carboxylic acid tert-butyl ester (8-a, R1=Boc) in solution in 0.7 ml tetrahydrofuran are added 0.4 g of tris(dimethylamino)methane (13, R6=Me, R7=Me) (Aldrich, #221058) and 0.17 ml tert-butanol. The mixture is stirred at 80° C. for 8 h to yield after concentration to dryness to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 18

A mixture of 1 g (S)-2-biphenyl-4-ylmethyl-5-oxo-pyrrolidine-1-carboxylic acid tert-butyl ester (8-a, R1=Boc) and 3.4 ml N,N-dimethylformamide di-tert-butyl acetal (15, R6=Me, R7=Me, R8=tBu) (Aldrich #358800) are heated at 50° C. overnight. The mixture is then concentrated to give (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 19

7 g of (S)-2-Biphenyl-4-ylmethyl-5-oxo-pyrrolidine-1-carboxylic acid tert-butyl ester (8-a, R1=Boc) is added to 5.6 g of a mixture containing 13, 14 and 15 (R6=Me, R7=Me, R8=CMe$_2$Et) (prepared according to Example 36, Method 2) and heated to 85° C. The resulting mixture is stirred at this temperature for 48 h. The mixture is then concentrated in vacuo to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.

Method 20

7 g of (S)-2-Biphenyl-4-ylmethyl-5-oxo-pyrrolidine-1-carboxylic acid tert-butyl ester (8-a, R1=Boc) is added to 7.5 g of a mixture containing 13, 14 and 15 (R6=Me, R7=Me, R8=CMe$_2$Et) (prepared according to Example 36, Method 2) and heated to 85° C. The resulting mixture is stirred at this temperature for 48 h. The mixture is then concentrated in vacuo to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.
Method 21

7 g of (S)-2-Biphenyl-4-ylmethyl-5-oxo-pyrrolidine-1-carboxylic acid tert-butyl ester (8-a, R1=Boc) is added to 11.3 g of a mixture containing 13, 14 and 15 (R6=Me, R7=Me, R8=CMe₂Et) (prepared according to Example 36, Method 2) and heated to 85° C. The resulting mixture is stirred at this temperature for 24 h. The mixture is then concentrated in vacuo to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.
Method 22

7 g of (S)-2-Biphenyl-4-ylmethyl-5-oxo-pyrrolidine-1-carboxylic acid tert-butyl ester (8-a, R1=Boc) is added to 18.8 g of a mixture containing 13, 14 and 15 (R6=Me, R7=Me, R8=CMe₂Et) (prepared according to Example 36, Method 2) and heated to 85° C. The resulting mixture is stirred at this temperature for 24 h. The mixture is then concentrated in vacuo to give (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.
Method 23

N,N,N',N'-Tetramethylformamidinium hexafluorophosphate (350 mg) (prepared according to Example 3) is added to a 1 M solution of potassium-tert-butoxide in THF (1.1 ml). The resulting mixture is then stirred for 1 h at room temperature. (S)-2-Biphenyl-4-ylmethyl-5-oxo-pyrrolidine-1-carboxylic acid tert-butyl ester (8-a, R1=Boc) (100 mg) is then added and the mixture is heated to 55° C. The mixture is then stirred at this temperature for 3 h. The mixture is then cooled to room temperature and diluted by addition of 5 ml isopropyl acetate. The mixture is then filtered through silica and concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.
Method 24

N,N,N',N'-tetramethylformamidinium methylsulfate (302 mg) (prepared according to Example 1) is added to a 1 M solution of potassium-tert-butoxide in THF (1.1 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (302 mg) is then added and the mixture is then stirred overnight. The mixture is then concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.
Method 25

N,N,N',N'-tetramethylformamidinium para-toluenesulfonate (1.9 g) (prepared according to Example 2) is added to a 1 M solution of potassium-tert-butoxide in THF (5.7 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (500 mg) is then added and the mixture is then stirred overnight. The mixture is then concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.
Method 26

N,N,N',N'-tetramethylformamidinium hexafluorophosphate (1.75 g) (prepared according to Example 3) is added to a 1 M solution of potassium-tert-butoxide in THF (5.7 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (500 mg) is then added and the mixture is then stirred overnight. The mixture is then concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) as determined by hplc.
HPLC Method (Example 16-1, Methods 1-26)

Column: X-BRIDGE C18; 150×3.0 mm; 3.5 μm. Mobile Phase A (0.1% NH₃ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min⁻¹. Wavelength: 210 or 254 nm. Temperature 60±2° C.
Retention Times:
8-a (R1=Boc): 10.4 min
7-a (R1=Boc; R6=Me; R7=Me): 11.0 min Example 16-2

Work-up/Purification of (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me)

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) can be used directly from the reaction or can be purified, as required. This optional purification step can be performed to remove solvents, reagents, and/or products generated from said reagents, for example.
Method 1

Solution of 7-a (R1=Boc; R6=Me; R7=Me) (0.2 g in 2 ml isopropyl acetate) prepared according to Example 16-1, Method 14. Activated charcoal (ca 50 mg) is added and the mixture stirred at room temperature for 1 h. The mixture is filtered and concentrated in vacuo to give 7-a (R1=Boc; R6=Me; R7=Me) as determined by hplc. Spectroscopic data as for Example 16-2, Method 7.
Method 2

Solution of 7-a (R1=Boc; R6=Me; R7=Me) (0.2 g in 2 ml isopropyl acetate) prepared according to Example 16-1, Method 14. Activated charcoal (ca 50 mg) is added and the mixture stirred at reflux for 1 h. The mixture is filtered and concentrated in vacuo to give 7-a (R1=Boc; R6=Me; R7=Me) as determined by hplc. Spectroscopic data as for Example 16-2, Method 7.
Method 3

Solution of 7-a (R1=Boc; R6=Me; R7=Me) (0.2 g in 2 ml isopropyl acetate) prepared according to Example 16-1, Method 14. The mixture is passed through a pad of Celite. The filtrate is then concentrated in vacuo to give 7-a (R1=Boc; R6=Me; R7=Me) as determined by hplc. Spectroscopic data as for Example 16-2, Method 7.
Method 4

Solution of 7-a (R1=Boc; R6=Me; R7=Me) (0.2 g in 2 ml isopropyl acetate) prepared according to Example 16-1, Method 14. The mixture is passed through a pad of Kieselgel. The filtrate is then concentrated in vacuo to give 7-a (R1=Boc; R6=Me; R7=Me) as determined by hplc. Spectroscopic data reported as for Example 16-2, Method 7.

Method 5

11 g of 7-a (R1=Boc; R6=Me; R7=Me) prepared according to Example 16-1, Method 14 is dissolved in 15 ml isopropyl acetate. The mixture is passed through a pad of Kieselgel and washed with isopropyl acetate (5×20 ml). The filtrate is concentrated in vacuo to give 7-a (R1=Boc; R6=Me; R7=Me) as determined by hplc. Spectroscopic data as for Example 16-2, Method 7.

Method 6

9 g of 7-a (R1=Boc; R6=Me; R7=Me) prepared according to Example 16-2, Method 5 is added toluene (50 ml). The solvent is then removed in vacuo. Further portions of toluene (3×50 ml) are added and the solvent successively removed in vacuo to give 7-a (R1=Boc; R6=Me; R7=Me) as determined by hplc. Spectroscopic data as for Example 16-2, Method 7.

Method 7

9 g of 7-a (R1=Boc; R6=Me; R7=Me) prepared according to Example 16-2, Method 6 is added heptane (15 ml). Solvent is removed in vacuo. Ethyl acetate (5 ml) and the mixture is heated to 50° C. Heptane (10 ml) is added. The mixture is then cooled to room temperature then concentrated in vacuo to give 7-a (R1=Boc; R6=Me; R7=Me). Spectroscopic data for 7-b (R1=Boc; R6=Me; R7=Me): $R_f$ 0.49 (ethylacetate). $\delta_H$ (400 MHz; DMSO) 1.48 (9H), 2.63 (2H), 2.79 (1H), 2.93 (6H), 3.06 (1H), 4.19 (1H), 6.96 (1H), 7.32 (3H), 7.44 (2H), 7.63 (4H); m/z (ES+) 407.1 ([MH+, 71%), 351 (100), 307 (41).

HPLC Method (Example 16-2, Methods 1-7)

Column: X-BRIDGE C18; 150×3.0 mm; 3.5 μm. Mobile Phase A (0.1% NH$_3$ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min$^{-1}$. Wavelength: 210 or 254 nm. Temperature 60±2° C.

Retention Times:

8-a (R1=Boc): 10.4 min 7-a (R1=Boc; R6=Me; R7=Me): 11.0 min

Example 17

(R)-5-Biphenyl-4-ylmethyl-3-[1-diethylaminometh-(E/Z)-ylidene]-2-oxo-pyrrolidine-1-carboxylic acid tert-butyl ester (7-a, R1=Boc, R6=Et, R7=Et)

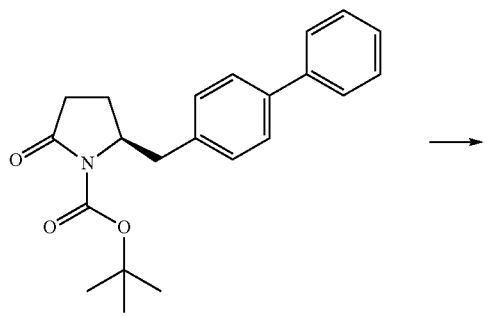

→

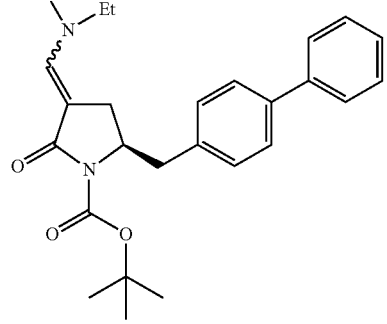

Method 1

A mixture of (S)-2-biphenyl-4-ylmethyl-5-oxo-pyrrolidine-1-carboxylic acid tert-butyl ester (8-a, R1=Boc) (1.41 g) tert-butoxy-bis(diethylamino)methane (14, R6=Et, R7=Et, R8=tBu) (3.76 g, prepared according to Example 15) is heated at 80° C. for 1 h. The mixture is then diluted with 10 ml isopropyl acetate and filtered through silica. The filtrate is then concentrated in vacuo and azeotroped successively with xylene (3×10 ml), toluene (3×10 ml), isopropyl acetate (3×10 ml) and diethyl ether (3×10 ml). Material is dried in vacuo to afford 1.54 g of (R)-5-biphenyl-4-ylmethyl-3-[1-diethylaminometh-(E/Z)-ylidene]-2-oxo-pyrrolidine-1-carboxylic acid tert-butyl ester (7-a, R1=Boc, R6=Et, R7=Et). $R_f$ 0.41 (ethyl acetate). $\delta_H$ (400 MHz, $C_6D_6$) 0.59 (6H), 1.63 (9H), 2.37 (2H), 2.44 (4H), 2.59 (1H), 3.50 (1H), 4.46 (1H), 7.10-7.29 (6H), 7.42-7.45 (4H).

Method 2

N,N,N',N'-tetraethylformamidinium methylsulfate (1.91 g, prepared according to Example 4) is added to a 1 M solution of potassium-tert-butoxide in THF (5.69 ml). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (500 mg) is then added and the mixture stirred at 60° C. for 1 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-diethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Method 3

N,N,N',N'-tetraethylformamidinium tetrafluoroborate (347 mg, prepared according to Example 5) is added to a 1 M solution of potassium-tert-butoxide in THF (1.14 ml). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (100 mg) is then added and the mixture stirred at 60° C. for 1 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-diethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Method 4

N,N,N',N'-Tetraethylformamidinium hexafluorophosphate (430 mg, prepared according to Example 6) is added to a 1 M solution of potassium-tert-butoxide in THF (1.14 ml). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (100 mg) is then added and the mixture stirred at 60° C. for 1 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-diethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Method 5

N,N,N',N'-Tetraethylformamidinium hexafluorophosphate (430 mg) (prepared according to Example 6) is added to a 1 M solution of potassium-tert-butoxide in THF (1.1 ml). The resulting mixture is then stirred for 1 h at room temperature. (S)-2-Biphenyl-4-ylmethyl-5-oxo-pyrrolidine-1-carboxylic acid tert-butyl ester (8-a, R1=Boc) (100 mg) is then added and the mixture is heated to 55° C. The mixture is then stirred at this temperature for 3 h. The mixture is then cooled to room temperature and diluted by addition of 5 ml isopropyl acetate. The mixture is then filtered through silica and concentrated in vacuo to afford (R)-5-biphenyl-4-ylmethyl-3-[1-diethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Method 6

N,N,N',N'-tetraethylformamidinium methylsulfate (1.9 g) (prepared according to Example 4) is added to a 1 M solution of potassium-tert-butoxide in THF (5.7 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (500 mg) is then added and the mixture is then stirred overnight. The mixture is then concentrated in vacuo to afford (R)-5-biphenyl-4-ylmethyl-3-[1-diethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Method 7

N,N,N',N'-tetraethylformamidinium hexafluorophosphate (430 mg) (prepared according to Example 6) is added to a 1 M solution of potassium-tert-butoxide in THF (1.1 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (100 mg) is then added and the mixture is then stirred overnight. The mixture is then concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Method 8

N,N,N',N'-tetraethylformamidinium tetrafluoroborate (347 mg) (prepared according to Example 5) is added to a 1 M solution of potassium-tert-butoxide in THF (1.1 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (100 mg) is then added and the mixture is then stirred overnight. The mixture is then concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Method 9

N,N,N',N'-tetraethylformamidinium tetrafluoroborate (347 mg) (prepared according to Example 5) is added to a 1 M solution of potassium-tert-butoxide in THF (1.1 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (100 mg) and ammonium hexafluorophosphate (ca 1 mg) are then added and the mixture is then stirred overnight. The mixture is then concentrated in vacuo to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Et, R7=Et). Spectroscopic data as for Example 17, Method 1.

Example 18

(R)-5-Biphenyl-4-ylmethyl-3-[1-pyrrolidin-1-yl-meth-(E/Z)-ylidene]-2-oxo-pyrrolidine-1-carboxylic acid tert-butyl ester (7-a, R1=Boc, R6/R7=Pyrrolidinyl)

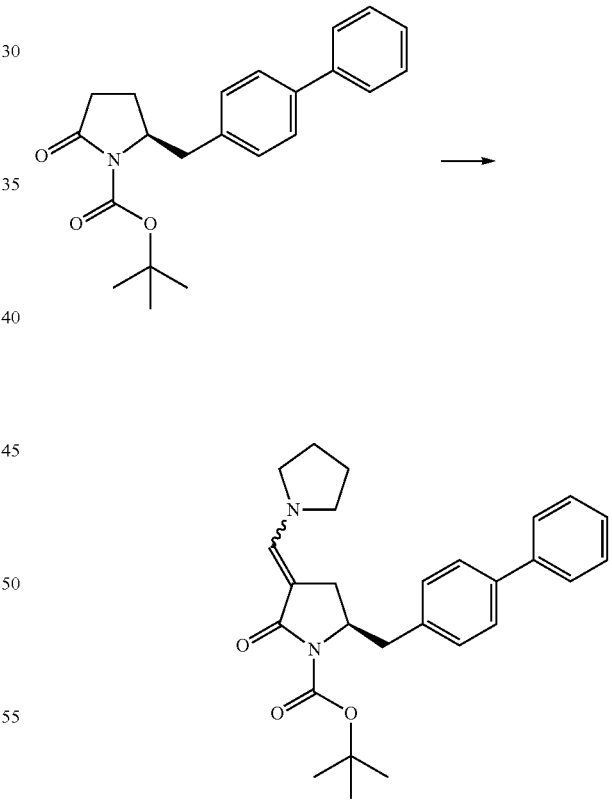

Method 1

A mixture of 1-pyrrolidin-1-ylmethylenepyrrolidinium methylsulfate (18.5 g, prepared according to Example 7) and potassium tert-butoxide (6.3 g) in toluene (40 ml) are stirred for 1 h. (S)-2-Biphenyl-4-ylmethyl-5-oxo-pyrrolidine-1-carboxylic acid tert-butyl ester (8-a, R1=Boc) (5 g) is added and the mixture heated to 80° C. After 1.5 h, the mixture is cooled to room temperature, diluted with isopropyl acetate and filtered through silica to give (7-a, R1=Boc, R6/R7=Pyrrolidinyl). Purification by chromatography (isopropyl acetate) gives (R)-5-biphenyl-4-ylmethyl-3-[1-pyrrolidin-1-yl-meth-(E/Z)-ylidene]-2-oxo-pyrrolidine-1-carboxylic acid tert-butyl ester (7-a, R1=Boc, R6/R7=Pyrrolidinyl). $R_f$ 0.32 (ethyl acetate). $\delta_H$ (400 MHz, DMSO) 1.50 (9H), 1.80 (4H), 2.62 (1H), 2.71 (1H), 2.82 (1H), 3.06 (1H), 3.46 (4H), 4.19 (1H), 7.19 (1H), 7.34 (2H), 7.36 (1H), 7.46 (2H), 7.62 (2H), 7.65 (2H). m/z (ES+) 433 ([MH]$^+$, 100%), 377 (64), 333 (36).

Method 2

A mixture of 1-pyrrolidin-1-ylmethylene-pyrrolidinium hexafluorophosphate (424 mg, prepared according to Example 8) and potassium tert-butoxide (1 M in THF, 1.1 ml) are stirred for 1 h at 50° C. (S)-2-Biphenyl-4-ylmethyl-5-oxo-pyrrolidine-1-carboxylic acid tert-butyl ester (8-a, R1=Boc) (0.1 g) is added and the mixture heated to 60° C. After 1.5 h, the mixture is cooled to room temperature, diluted with isopropyl acetate and filtered through silica to give (R)-5-biphenyl-4-ylmethyl-3-[1-pyrrolidin-1-yl-meth-(E/Z)-ylidene]-2-oxo-pyrrolidine-1-carboxylic acid tert-butyl ester (7-a, R1=Boc, R6/R7=Pyrrolidinyl). Spectroscopic data as for Example 18, Method 1.

Method 3

A mixture of 1-pyrrolidin-1-ylmethylenepyrrolidinium methylsulfate (380 mg, prepared according to Example 7) and sodium tert-butoxide (0.1 ml) in toluene are stirred overnight. (S)-2-Biphenyl-4-ylmethyl-5-oxo-pyrrolidine-1-carboxylic acid tert-butyl ester (8-a, R1=Boc) (100 mg) is added and the mixture heated to 80° C. After 4 h, the mixture is cooled to room temperature and concentrated in vacuo to give (7-a, R1=Boc, R6/R7=Pyrrolidinyl). Spectroscopic data as for Example 18, Method 1.

Method 4

1-Pyrrolidin-1-ylmethylene-pyrrolidinium hexafluorophosphate (424 mg) (prepared according to Example 8) is added to a 1 M solution of potassium-tert-butoxide in THF (1.1 ml). The resulting mixture is then stirred for 1 h at room temperature. (S)-2-Biphenyl-4-ylmethyl-5-oxo-pyrrolidine-1-carboxylic acid tert-butyl ester (8-a, R1=Boc) (100 mg) is then added and the mixture is heated to 55° C. The mixture is then stirred at this temperature for 3 h. The mixture is then cooled to room temperature and diluted by addition of 5 ml isopropyl acetate. The mixture is then filtered through silica and concentrated in vacuo to afford (R)-5-biphenyl-4-ylmethyl-3-[1-pyrrolidin-1-yl-meth-(E/Z)-ylidene]-2-oxo-pyrrolidine-1-carboxylic acid tert-butyl ester (7-a, R1=Boc, R6/R7=Pyrrolidinyl). Spectroscopic data as for Example 18, Method 1.

Method 5

1-Pyrrolidin-1-ylmethylene-pyrrolidinium hexafluorophosphate (424 mg) (prepared according to Example 8) is added to a 1 M solution of potassium-tert-butoxide in THF (1.1 ml). The resulting mixture is then stirred for 1 h at 50° C. The mixture is then cooled to room temperature. (S)-2-Biphenyl-4-ylmethyl-5-oxo-pyrrolidine-1-carboxylic acid tert-butyl ester (8-a, R1=Boc) (100 mg) is then added and the mixture is then stirred overnight. The mixture is then concentrated in vacuo to afford ((R)-5-biphenyl-4-ylmethyl-3-[1-pyrrolidin-1-yl-meth-(E/Z)-ylidene]-2-oxo-pyrrolidine-1-carboxylic acid tert-butyl ester (7-a, R1=Boc, R6/R7=Pyrrolidinyl). Spectroscopic data as for Example 18, Method 1.

Example 19

(R)-5-Biphenyl-4-ylmethyl-3-[1-diisopropylamino-meth-(E)-ylidene]-2-oxo-pyrrolidine-1-carboxylic acid tert-butyl ester (7-a, R1=Boc, R6=iPr, R7=iPr)

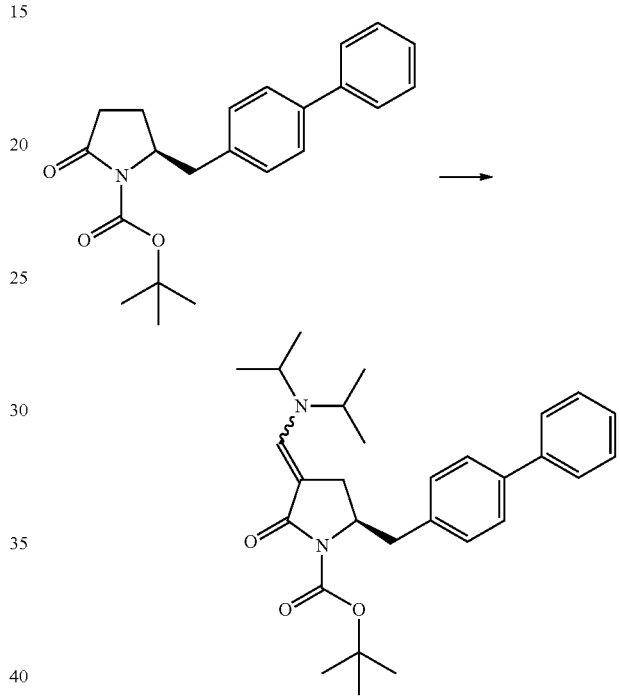

Method 1

A 1 M solution of potassium tert-butoxide in THF (11.7 ml) is added to diisopropyl(piperidin-1-ylmethylidene)ammonium hexafluorophosphate (5 g, prepared according to Example 12). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (1 g) is then added to the reaction and the resulting mixture is stirred for 1 h at room temperature. The mixture is diluted with isopropyl acetate and filtered through silica. The residue is concentrated in vacuo then purified by column chromatography (ethyl acetate) to give (R)-5-biphenyl-4-ylmethyl-3-[1-diisopropylamino-meth-(E)-ylidene]-2-oxo-pyrrolidine-1-carboxylic acid tert-butyl ester (7-a, R1=Boc, R6=iPr, R7=iPr). $R_f$ 0.55 (ethyl acetate). 1H NMR (DMSO-d6), 7.65-7.62 (2H), 7.61-7.58 (2H), 7.47-7.42 (2H), 7.37-7.31 (1H), 7.29-7.25 (2H), 7.01 (1H), 4.28-4.20 (1H), 3.84-3.70 (2H), 3.07-3.01 (1H), 2.82-2.73 (1H), 2.71-2.63 (1H) 2.49-2.44 (1H), 1.49 (9H), 1.13-1.08 (12H).

Method 2

N,N,N',N'-tetraisopropylformamidinium tetrafluoroborate (2.13 g, prepared according to Example 11) is added to a 1 M solution of potassium-tert-butoxide in THF (5.69 ml). The resulting mixture is then stirred for 1 h at 50° C. (S)-2-Biphenyl-4-ylmethyl-5-oxo-pyrrolidine-1-carboxylic acid tert-butyl ester (8-a, R1=Boc) (500 mg) is then added and the mixture stirred at 60° C. for 1 h. The mixture is then cooled to room temperature and diluted by addition of 10 ml isopropyl acetate. The mixture is then filtered through silica and concentrated in vacuo to afford (R)-5-biphenyl-4-ylmethyl-3-[1-diisopropylamino-meth-(E)-ylidene]-2-oxo-pyrrolidine-1-carboxylic acid tert-butyl ester (7-a, R1=Boc, R6=iPr, R7=iPr). Spectroscopic data as for Example 19, Method 1.

Example 20

(R)-5-Biphenyl-4-ylmethyl-3-[1-dimethylamino-meth-(E/Z)-ylidene]-1-(2,2-dimethylpropionyl)pyrrolidin-2-one (7-a, R1=Piv, R6=Me, R7=Me)

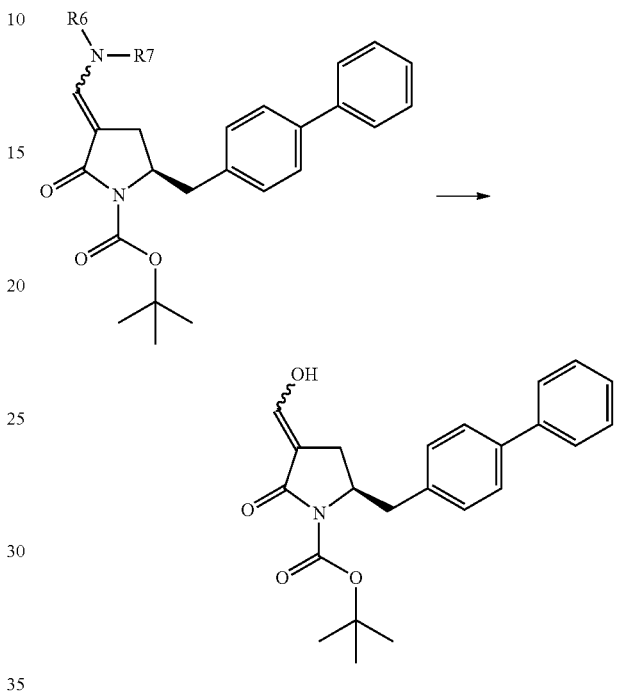

A mixture of (S)-5-Biphenyl-4-ylmethyl-1-(2,2-dimethyl-propionyl)-pyrrolidin-2-one (8-a, R1=Piv) (1.0 g, 3 mmol) and tert-butoxy-bis(dimethylamino)methane (14, R6=Me, R7=Me, R8=tBu) (Fluka #20425) (5.5 g) are stirred at 80° C. for 17 h. The mixture is then cooled to room temperature and concentrated in vacuo. The residue is then dissolved in isopropyl acetate and filtered through Kieselgel. The filtrate is concentrated in vacuo to give (R)-5-biphenyl-4-ylmethyl-3-[1-dimethylamino-meth-(E/Z)-ylidene]-1-(2,2-dimethylpropionyl)pyrrolidin-2-one (7-a, R1=Piv, R6=Me, R7=Me). $\delta_H$ (400 MHz; DMSO) 1.31 (9H), 2.57 (1H), 2.70 (1H), 2.81 (1H) 2.98 (6H), 3.00 (1H), 4.40 (1H), 7.06 (1H), 7.33 (3H), 7.45 (2H), 7.60 (2H), 7.65 (2H). m/z (ES+) 391 ([MH]+, 100%).

Example 21

(R)-5-Biphenyl-4-ylmethyl-3-[1-hydroxymeth-(E/Z)-ylidene]-2-oxo-pyrrolidine-1-carboxylic acid tert-butyl ester (6-a, R1=Boc)

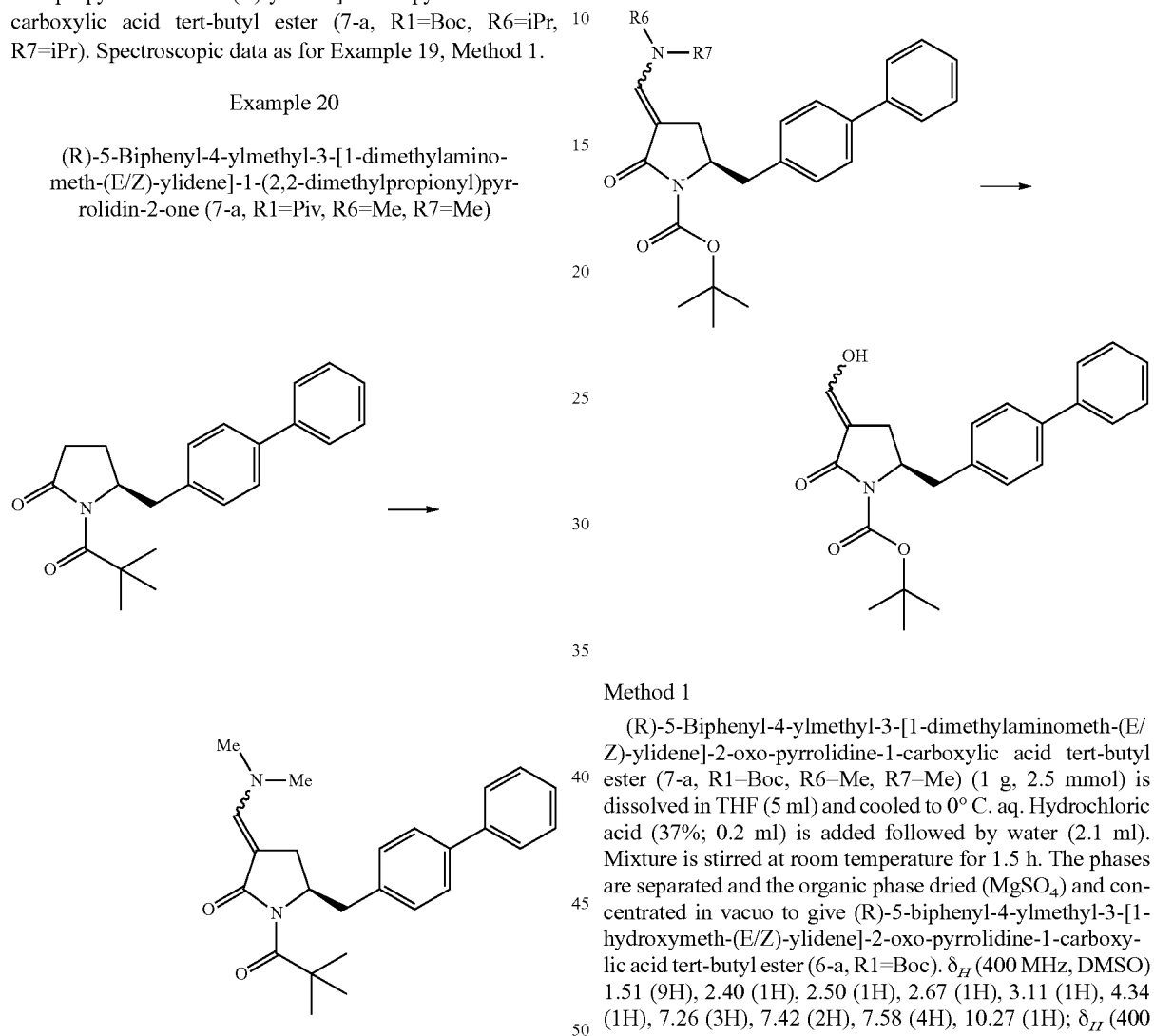

Method 1

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) (1 g, 2.5 mmol) is dissolved in THF (5 ml) and cooled to 0° C. aq. Hydrochloric acid (37%; 0.2 ml) is added followed by water (2.1 ml). Mixture is stirred at room temperature for 1.5 h. The phases are separated and the organic phase dried (MgSO$_4$) and concentrated in vacuo to give (R)-5-biphenyl-4-ylmethyl-3-[1-hydroxymeth-(E/Z)-ylidene]-2-oxo-pyrrolidine-1-carboxylic acid tert-butyl ester (6-a, R1=Boc). $\delta_H$ (400 MHz, DMSO) 1.51 (9H), 2.40 (1H), 2.50 (1H), 2.67 (1H), 3.11 (1H), 4.34 (1H), 7.26 (3H), 7.42 (2H), 7.58 (4H), 10.27 (1H); $\delta_H$ (400 MHz; CDCl$_3$) 1.53, 1.76-1.80, 1.88-1.96, 2.27-2.33, 2.35-2.43, 2.49-2.61, 2.80-2.86, 3.00-3.11, 3.16-3.21, 3.51-3.54, 3.65-3.70, 4.25-4.36, 7.15-7.20, 7.26-7.30, 7.34-7.39, 7.46-7.53, 9.74 (0.4H), 9.75 (0.2H), 10.86 (0.4H). m/z (+) 380 ([MH]+, 5%), 324 (100).

Method 2

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Et, R7=Et) (1 g) is dissolved in THF (6.9 ml) and cooled to 10-15° C. A solution of concentrated sulfuric acid (0.09 ml) in water (3 ml) is added. Mixture is stirred at room temperature for 1.5 h. The phases are separated and the aqueous phase is extracted with isopropyl acetate. The combined organic phases are dried (MgSO$_4$) and concentrated in vacuo to give (R)-5-biphenyl-4-ylmethyl-3-[1-hydroxymeth-(E/Z)-ylidene]-2-oxo-pyrrolidine-1-carboxylic acid tert-butyl ester (6-a, R1=Boc). $R_f$ 0.49 (ethyl acetate). Spectroscopic data as for Example 21, Method 1.

Method 3

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Et, R7=Et) (32.5 g) is dissolved in THF (190 ml) at 60° C. The mixture is then cooled to 10-15° C. An aqueous solution of 1 M sulfuric acid (96 ml) is added over a period of 30 min, giving a solution pH 2. Mixture is stirred at room temperature for 0.5 h. The phases are separated and the organic phase washed with 1 M potassium carbonate solution (50 ml). The phases are separated. The organic phase is dried (MgSO$_4$) and concentrated in vacuo to give (R)-5-biphenyl-4-ylmethyl-3-[1-hydroxymeth-(E/Z)-ylidene]-2-oxo-pyrrolidine-1-carboxylic acid tert-butyl ester (6-a, R1=Boc). $R_f$ 0.49 (ethyl acetate). Spectroscopic data as for Example 21, Method 1.

Example 22

Enol form: (R)-5-Biphenyl-4-ylmethyl-1-(2,2-dimethylpropionyl)-3-[1-hydroxymeth-(E,Z)-ylidene]pyrrolidin-2-one (6-a, R1=Piv)

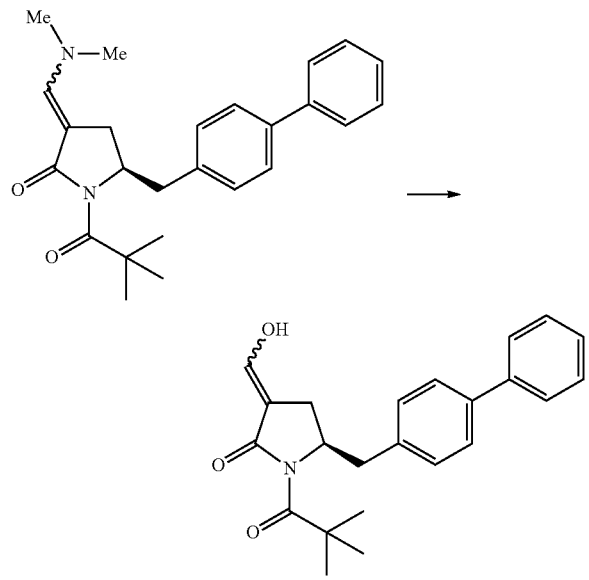

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Piv, R6=Me, R7=Me) (927 mg) is dissolved in THF (5 ml) and cooled to 10° C. Hydrochloric acid (1 M; 2.6 ml) is added followed by water (2.1 ml). Mixture is stirred at room temperature for 17 h. The mixture is diluted with ethyl acetate (5 ml) and the phases separated. The organic phase is washed with water, brine then dried (MgSO$_4$). Concentrated in vacuo to give (R)-5-biphenyl-4-ylmethyl-1-(2,2-dimethylpropionyl)-3-[1-hydroxymeth-(E,Z)-ylidene]pyrrolidin-2-one (6-a, R1=Piv). $\delta_H$ (400 MHz; DMSO) 1.31 (9H), 2.43 (1H), 2.50 (2H), 3.01 (1H), 4.53 (1H), 7.28 (2H), 7.35 (1H), 7.45 (2H), 7.61 (2H), 7.64 (2H); m/z (ES+) 364 ([MH]$^+$, 100%).

Example 23

(R)-5-Biphenyl-4-ylmethyl-3-methylene-2-oxo-pyrrolidine-1-carboxylic acid tert-butyl ester (4-a, R1=Boc)

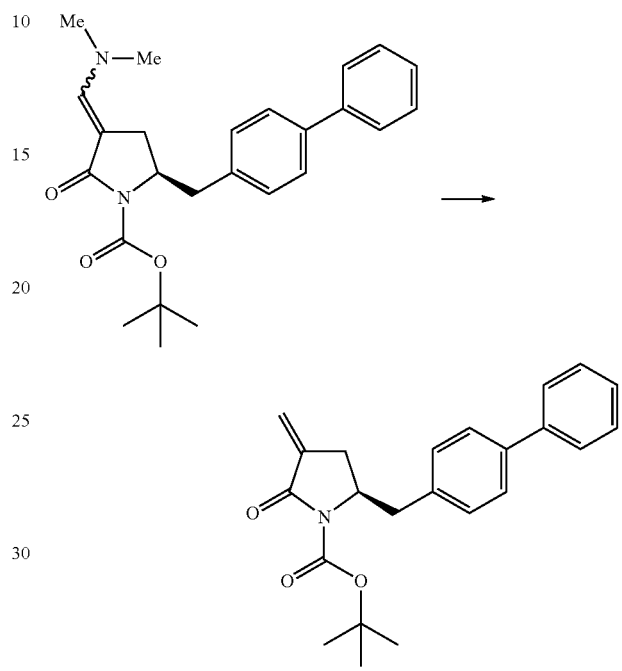

Method 1

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) (7 g) is added to THF (210 ml) and the resulting mixture cooled to −78° C. Diisobutylaluminium hydride (109 ml, 103 mmol; 0.95 M in THF) is added over 1.5 h. To the mixture is then added Rochelle's Salt (430 ml; 1.2 M in water) and the mixture stirred vigorously. Ethyl acetate (400 ml) is added and the phases are separated. The organic phase is concentrated in vacuo. The resulting residue is dissolved in ethyl acetate (20 ml) and washed with brine (20 ml). Phases are separated. The organic phase is then concentrated in vacuo. Diethyl ether (50 ml) is added, filtered and the filtrate concentrated to give (R)-5-biphenyl-4-ylmethyl-3-methylene-2-oxo-pyrrolidine-1-carboxylic acid tert-butyl ester (4-a, R1=Boc).

Crude (R)-5-biphenyl-4-ylmethyl-3-methylene-2-oxo-pyrrolidine-1-carboxylic acid tert-butyl ester (4-a, R1=Boc) can be optionally purified by column chromatography eluting with 3:1 heptane/ethyl acetate. 1H NMR: $\delta_H$ (400 MHz, CDCl$_3$) 1.62 (9H), 2.56 (1H), 2.60 (1H), 2.70 (1H), 3.26 (1H), 4.43 (1H), 5.45 (1H), 6.17 (1H), 7.26 (2H), 7.34 (1H), 7.44 (2H), 7.54 (2H), 7.57 (2H); m/z (+ESI) 381 ([MNa]$^+$, 7%), 364 ([MH]$^+$, 12), 308 (100), 264 (10).

(R)-5-Biphenyl-4-ylmethyl-3-methylene-2-oxo-pyrrolidine-1-carboxylic acid tert-butyl ester (4-a, R1=Boc) is a crystalline solid and can be characterised by single crystal X-ray analysis and X-ray powder patterns. Reflections in the X-ray diffraction pattern show the following interlattice plane intervals (average 2θ in [°] are indicated with error limit of ±0.2): 2θ in [°]: 4.7, 9.3, 10.5, 13.3, 13.9, 15.3, 16.9, 18.0, 18.6, 19.6, 20.9, 21.8, 22.9, 23.3, 27.5, 28.1, 30.7, 34.9. The most intensive reflections in the X-ray diffraction pattern show the following interlattice plane intervals (average 2θ in [°] are indicated with error limit of ±0.2): 2θ in [°]: 4.6, 10.5, 13.3, 13.9, 16.9, 18.6, 19.6, 20.9. Data taken using a Bruker D8 Advance diffractometer using Cu—Kα radiation.

The X-ray Structure of the obtained crystals is shown in FIG. 4. Single crystal for this determination is obtained from methanol/water as solvent.

Crystal Data [Recorded at 100(2) K]

| Empirical formula | $C_{23}H_{25}NO_3$ |
|---|---|
| Formula weight | 363.44 |
| Crystal system | Monoclinic |
| Space group | P21 |
| Cell parameters | a = 11.512(2) Å |
| | b = 9.197(2) Å |
| | c = 19.002(3) Å |
| | α = 90° |
| | β = 94.737(7)° |
| | γ = 90° |
| Volume of unit cell | 2005.0(6) Å³ |
| Z* | 4 |
| Calculated density | 1.204 mg m⁻³ |

*(number of asymmetric units in the unit cell)

Method 2

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) (100 mg, 0.25 mmol) is added to THF (0.5 ml) at 0° C. Sodium triacetoxyborohydride (111 mg, 0.50 mmol) is then added. The mixture is stirred for 1 h then stirred at room temperature overnight. Water (5 ml) is added and then extracted with toluene. Organic phase dried ($MgSO_4$) and concentrated in vacuo to give (R)-5-Biphenyl-4-ylmethyl-3-methylene-2-oxo-pyrrolidine-1-carboxylic acid tert-butyl ester (4-a, R1=Boc). Spectroscopic data as for Example 23, Method 1.

Example 24

(R)-5-Biphenyl-4-ylmethyl-3-methylene-2-oxo-pyrrolidine-1-carboxylic acid tert-butyl ester (4-a, R1=Boc)

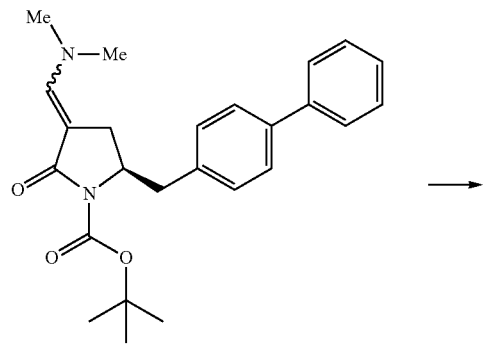

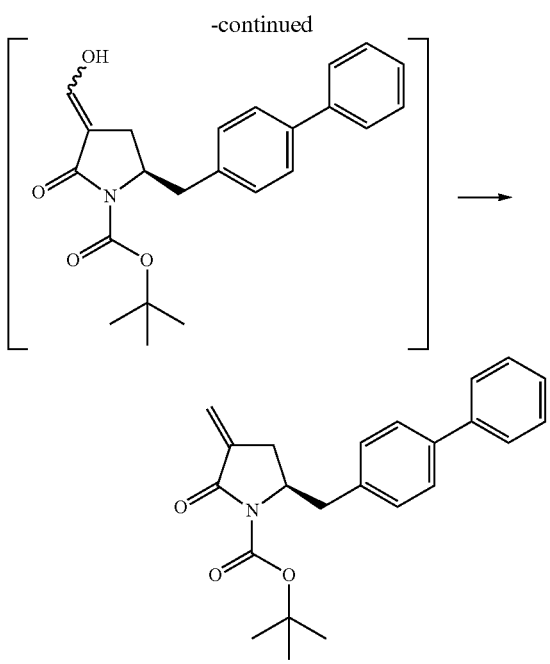

Method 1

Crude (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) (67.5 g) is dissolved in THF (340 ml) and cooled to 0° C. Hydrochloric acid (37%; 13.1 ml) is added followed by water (143.4 ml). Mixture is stirred at room temperature for 2 h. Phases are separated. To the organic phase is added formaldehyde solution (37% in water; 138 ml). Potassium carbonate (31.8 g) is added portionwise over 4 h. 1% Tetra-n-butylammoniumhydroxide solution (14.2 ml) is added followed by sodium hydroxide solution (30% in water) until pH 10.5. The mixture is stirred for 2 h. The phases are separated. The organic phase is washed with water (100 ml) and sodium bisulfite (20 g) added. Toluene (100 ml) and sodium chloride solution (20%; 50 ml). The phases are separated. The organic phase is extracted with a sodium chloride solution (20%; 50 ml), dried ($Na_2SO_4$) and concentrated in vacuo to give (R)-5-biphenyl-4-ylmethyl-3-methylene-2-oxo-pyrrolidine-1-carboxylic acid tert-butyl ester (4-a, R1=Boc) (63 g). The material can be recrystallised as follows: crude (R)-5-biphenyl-4-ylmethyl-3-methylene-2-oxo-pyrrolidine-1-carboxylic acid tert-butyl ester (4-a, R1=Boc) (58.4 g) is dissolved in methanol (525 ml) at 50° C. Water (175 ml) is added and the mixture is cooled to 0° C. The solid is collected by filtration and the cake washed with a mixture of methanol (53 ml) and water (18 ml). The solid is then dried in vacuo, giving (R)-5-biphenyl-4-ylmethyl-3-methylene-2-oxo-pyrrolidine-1-carboxylic acid tert-butyl ester (4-a, R1=Boc). Spectroscopic data as Example 23.

Method 2

Crude (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) (66.7 g) is dissolved in THF (340 ml) and cooled to 10° C. Sulphuric acid (96%; 6.9 ml) is added followed by water (152 ml). The mixture is stirred at room temperature for 0.5 h. Phases are separated. The organic phase is added to formaldehyde solution (37% in water; 138 ml). 1% Tetra-n-butylammoniumhydroxide solution (14.2 ml) is added. Potassium carbonate (27.8 g) is added portionwise over 0.5 h. Sodium hydroxide solution (15.1 g) is added over 3 h, maintaining pH 10.5. The phases are separated. The organic phase is washed with water (100 ml) followed by sodium bisulfite solution (21.4 g). Toluene (100 ml) and sodium chloride solution (50 ml) added. The phases are separated. The organic phase is extracted with sodium chloride solution (20%; 50 ml), dried (Na₂SO₄) and concentrated in vacuo to give (R)-5-Biphenyl-4-ylmethyl-3-methylene-2-oxo-pyrrolidine-1-carboxylic acid tert-butyl ester (4-a, R1=Boc) (63 g). Material can be recrystallised as follows: crude (R)-5-biphenyl-4-ylmethyl-3-methylene-2-oxo-pyrrolidine-1-carboxylic acid tert-butyl ester (4-a, R1=Boc) (58.4 g) is dissolved in methanol (525 ml) at 50° C. Water (175 ml) is added and the mixture is cooled to 0° C. The solid is collected by filtration and the cake washed with a mixture of methanol (53 ml) and water (18 ml). The solid is then dried in vacuo, giving (R)-5-biphenyl-4-ylmethyl-3-methylene-2-oxo-pyrrolidine-1-carboxylic acid tert-butyl ester (4-a, R1=Boc). Spectroscopic data as in Example 23.

HPLC Method (Example 24)

Column: X-BRIDGE C18; 150×3.0 mm; 3.5 μm. Mobile Phase A (0.1% NH₃ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min⁻¹. Wavelength: 210 or 254 nm. Temperature 60±2° C.

Retention Times:

6-a (R1=Boc): 2.62 min 7-a (R1=Boc; R6=Me; R7=Me): 11.0 min 4-a (R1=Boc): 12.0, min Example 25

(R)-5-Biphenyl-4-ylmethyl-3-methylene-2-oxo-pyrrolidine-1-carboxylic acid tert-butyl ester (4-a, R1=Boc) and (3R/S, 5S)-5-Biphenyl-4-ylmethyl-3-hydroxymethyl-2-oxo-pyrrolidine-1-carboxylic acid tert-butyl ester (5-a, R1=Boc)

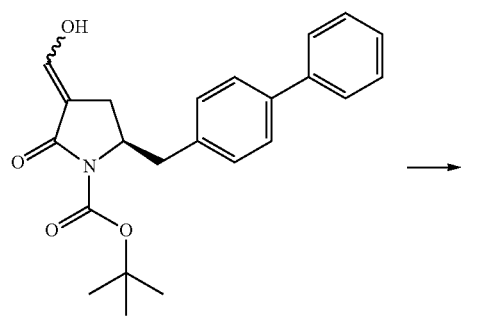

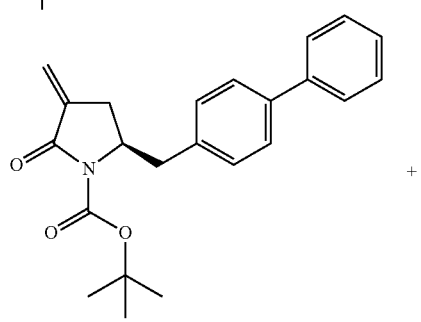

-continued

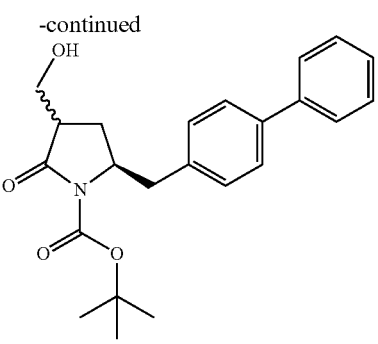

Method 1

2.0 g of crude (R)-5-biphenyl-4-ylmethyl-3-[1-hydroxymeth-(E/Z)-ylidene]-2-oxo-pyrrolidine-1-carboxylic acid tert-butyl ester (6-a, R1=Boc) in 10 ml THF is submitted to react with 5.0 g 37% aq. formaldehyde solution and 0.7 g sodium carbonate. After 1 h stirring at room temperature the aqueous phase is removed. The organic phase is diluted with toluene, washed with water and concentrated to dryness to yield an oily residue. The latter is then submitted to a silicagel chromatography (100 g silicagel Merck), eluting with a mixture 1:1 of ethyl and isopropyl acetate to separate (R)-5-biphenyl-4-ylmethyl-3-methylene-2-oxo-pyrrolidine-1-carboxylic acid tert-butyl ester (4-a, R1=Boc) and (3R/S, 5S)-5-biphenyl-4-ylmethyl-3-hydroxymethyl-2-oxo-pyrrolidine-1-carboxylic acid tert-butyl ester (5-a, R1=Boc).

Spectroscopic data for (R)-5-biphenyl-4-ylmethyl-3-methylene-2-oxo-pyrrolidine-1-carboxylic acid tert-butyl ester (4-a, R1=Boc) as in Example 23.

Spectroscopic data for (3R/S, 5S)-5-biphenyl-4-ylmethyl-3-hydroxymethyl-2-oxo-pyrrolidine-1-carboxylic acid tert-butyl ester (5-a, R1=Boc): $\delta_H$ (400 MHz, DMSO) 1.51 (9H), 1.89 (1H), 1.98 (1H), 2.55 (1H), 2.85 (1H), 3.50-2.62 (2H), 4.24-4.30 (1H), 4.45 (1H), 7.28-7.34 (3H), 7.41-7.45 (2H), 7.58-7.63 (4H); m/z (ES+) 382 ([MH]⁺, 9%), 326 (100), 282 (12).

Method 2

1 g (R)-5-biphenyl-4-ylmethyl-3-[1-hydroxymeth-(E/Z)-ylidene]-2-oxo-pyrrolidine-1-carboxylic acid tert-butyl ester (6-a, R1=Boc) is added to THF (2.5 ml) at room temperature. 37% Formaldehyde solution (1.3 ml) is then added. Potassium carbonate (0.28 g) is then added portionwise and the resulting mixture is then stirred for 72 h at room temperature. Water (1 ml) and sodium bisulfite solution (0.5 ml) are subsequently'added. The phases are separated and organic phase dried (MgSO₄). The mixture is concentrated in vacuo to give (R)-5-biphenyl-4-ylmethyl-3-methylene-2-oxo-pyrrolidine-1-carboxylic acid tert-butyl ester (4-a, R1=Boc) and 20% (5-a, R1=Boc) (by nmr). Spectroscopic data as for Example 25, Method 1.

Method 3

7.4 g (R)-5-biphenyl-4-ylmethyl-3-[1-hydroxymeth-(E/Z)-ylidene]-2-oxo-pyrrolidine-1-carboxylic acid tert-butyl ester (6-a, R1=Boc) dissolved in 50 ml THF are mixed together with 4.4 g 37% aq. formaldehyde solution, 0.13 g tetrabutylammonium hydroxide 40% solution and 40 ml potassium carbonate 1 M solution. After 1 h stirring at 40° C., the two phases are separated. The organic phase is diluted with 50 ml toluene and concentrated under vacuum to about 20 ml. The residue is again diluted with 85 ml toluene. 2.4-diazabicycloundecene is added followed with 0.42 g methanesulfonyl chloride. After 1 h at room temperature, 10 ml water were added and the mixture acidified with several drops of sulfuric acid. The aqueous phase is removed, the organic phase washed with 10 ml of water and concentrated under vacuum to dryness. The residue is dissolved in 100 ml methanol at 50° C. and saturated at the same temperature with 25 ml water. The suspension is afterwards cooled to 0° C., filtered, washed with 12 ml methanol/water 2:1 and dried under vacuum to yield (R)-5-biphenyl-4-ylmethyl-3-methylene-2-oxo-pyrrolidine-1-carboxylic acid tert-butyl ester (4-a, R1=Boc). Spectroscopic data as for Example 25, Method 1.

Method 4

A mixture of potassium carbonate solution in water (1 M, 2.3 ml), tetrabutylammonium hydroxide solution (40%, 0.01 ml) and formaldehyde solution (37% in water, 0.32 ml) is added to (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc). The resulting mixture is stirred rapidly and heated to 50° C. After 4 h, the mixture is cooled to room temperature and concentrated in vacuo. $R_f$ (ethyl acetate): 0.77 (4-a, R1=Boc); 0.44 (5-a, R1=Boc). Spectroscopic data as for Example 25, Method 1.

Method 5

To a solution of (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) in THF (3.8 g) (prepared according to Example 21, Method 3) is added potassium carbonate (2.8 g in 20 ml water), tetrabutylammonium hydroxide solution (40%, 0.03 g) and formaldehyde solution (37% in water, 2.2 ml) to give a solution of pH 11. The mixture is then stirred for 2 h at 45° C. The mixture is then cooled to room temperature and the phases are separated. The organic phase is diluted with toluene (20 ml) and washed with sodium bisulfite solution (20 ml, 40%) and then brine (20 ml). The organic phase is then dried ($MgSO_4$) and concentrated in vacuo to give (R)-5-biphenyl-4-ylmethyl-3-methylene-2-oxo-pyrrolidine-1-carboxylic acid tert-butyl ester (4-a, R1=Boc). Spectroscopic data as for Example 25, Method 1.

Method 6

To a solution of (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) in THF (3.8 g) (prepared according to Example 21, Method 3) is added potassium carbonate (2.8 g in 20 ml water), tetrabutylammonium hydroxide solution (40%, 0.03 g) and chloral (4.4 g) to give a solution of pH 11. The mixture is then stirred for 2 h at 45° C. The mixture is then cooled to room temperature and the phases are separated. The organic phase is diluted with toluene (20 ml) and washed with sodium bisulfite solution (20 ml, 40%) and then brine (20 ml). The organic phase is then dried ($MgSO_4$) and concentrated in vacuo to give (R)-5-biphenyl-4-ylmethyl-3-methylene-2-oxo-pyrrolidine-1-carboxylic acid tert-butyl ester (4-a, R1=Boc). Spectroscopic data as for Example 25, Method 1.

Method 7

To a solution of (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) in THF (3.8 g) (prepared according to Example 21, Method 3) is added aqueous potassium carbonate (0.2 ml, 1 M), tetrabutylammonium hydroxide solution (40%, 0.07 g) and formaldehyde solution (37% in water, 2.2 ml) to give a solution of pH 8. The mixture is then stirred for 2 h at 45° C. The mixture is then cooled to room temperature and the phases are separated. The organic phase is diluted with toluene (20 ml) and washed with sodium bisulfite solution (20 ml, 40%) and then brine (20 ml). The organic phase is then dried ($MgSO_4$) and concentrated in vacuo to give (R)-5-biphenyl-4-ylmethyl-3-methylene-2-oxo-pyrrolidine-1-carboxylic acid tert-butyl ester (4-a, R1=Boc). Spectroscopic data as for Example 25, Method 1.

Method 8

To a solution of (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) in THF (3.8 g) (prepared according to Example 21, Method 3) is added a 1 M aqueous sodium formate solution (20 ml), tetrabutylammonium hydroxide solution (40%, 0.07 g) and formaldehyde solution (37% in water, 2.2 ml) to give a solution of pH 7. The mixture is then stirred for 4 h at 45° C. The mixture is then cooled to room temperature and the phases are separated. The organic phase is diluted with toluene (20 ml) and washed with sodium bisulfite solution (20 ml, 40%) and then brine (20 ml). The organic phase is then dried ($MgSO_4$) and concentrated in vacuo to give (R)-5-biphenyl-4-ylmethyl-3-methylene-2-oxo-pyrrolidine-1-carboxylic acid tert-butyl ester (4-a, R1=Boc). Spectroscopic data as for Example 25, Method 1.

Method 9

To a solution of (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) in THF (3.8 g) (prepared according to Example 21, Method 3) is added a 1 M aqueous sodium acetate solution (20 ml), tetrabutylammonium hydroxide solution (40%, 0.07 g) and formaldehyde solution (37% in water, 2.2 ml) to give a solution of pH 8. The mixture is then stirred for 4 h at 45° C. The mixture is then cooled to room temperature and the phases are separated. The organic phase is diluted with toluene (20 ml) and washed with sodium bisulfite solution (20 ml, 40%) and then brine (20 ml). The organic phase is then dried ($MgSO_4$) and concentrated in vacuo to give (R)-5-biphenyl-4-ylmethyl-3-methylene-2-oxo-pyrrolidine-1-carboxylic acid tert-butyl ester (4-a, R1=Boc). Spectroscopic data as for Example 25, Method 1.

Method 10

To a mixture of 3.79 g (R)-5-biphenyl-4-ylmethyl-3-[1-hydroxymeth-(E/Z)-ylidene]-2-oxo-pyrrolidine-1-carboxylic acid tert-butyl ester (6-a, R1=Boc) in tetrahydrofuran (0.4 M solution) is added potassium carbonate (20 ml, 1 M solution in water) and tetrabutylammonium hydroxide (0.07 ml, 40% wt in water). Formaldehyde (2.2 ml, 37% wt in water) is then added to the mixture. The resulting mixture is stirred for 2 h at 45° C. The phases are separated. The organic phase is diluted with toluene (20 ml). The organic phase is then washed with sodium bisulfite solution (20 ml, 40% wt in water) and then with brine (5 ml). The separated organic phase is then dried ($MgSO_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 11

To a mixture of 3.79 g (R)-5-biphenyl-4-ylmethyl-3-[1-hydroxymeth-(E/Z)-ylidene]-2-oxo-pyrrolidine-1-carboxylic acid tert-butyl ester (6-a, R1=Boc) in tetrahydrofuran (0.4 M solution) is added potassium carbonate (20 ml, 1 M solution in water) and tetrabutylammonium hydroxide (0.07 ml, 40% wt in water). Formaldehyde (2.2 ml, 37% wt in water) is then added to the mixture. The pH of the mixture is adjusted to pH 14 by the addition of a sodium hydroxide solution (1 M in water). The resulting mixture is stirred for 2 h at 45° C. The phases are separated. The organic phase is diluted with toluene (20 ml). The organic phase is then washed with sodium bisulfite solution (20 ml, 40% wt in water) and then with brine (5 ml). The separated organic phase is then dried ($MgSO_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 12

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). Sodium hydrogen carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with brine (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 13

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). Cesium carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with brine (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 14

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). Sodium carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with brine (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 15

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). Potassium carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 16

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). Dimethylsulfoxide (1 ml) is then added. Potassium carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 17

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). 1-Methyl-2-pyrrolidinone (1 ml) is then added. Potassium carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 18

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). 1,3-Dimethyl-3,4,5,6-tetrahydro-2(1H)-pyrimidinone (1 ml) is then added. Potassium carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.

Method 19

To a mixture of 200 mg (R)-5-biphenyl-4-ylmethyl-3-[1-hydroxymeth-(E/Z)-ylidene]-2-oxo-pyrrolidine-1-carboxylic acid tert-butyl ester (6-a, R1=Boc) in tetrahydrofuran (2 ml) is added formaldehyde (0.12 ml, 37% wt in water) and tetrabutylammonium hydroxide (3.5 µl, 40% wt in water). The pH of the mixture is adjusted to pH 9 by the addition of a potassium carbonate solution (1 M in water). The resulting mixture is stirred for 2 h at 45° C. The phases are separated. The organic phase is diluted with toluene (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.
Method 20

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to acetonitrile (2 ml). Potassium carbonate (1.05 ml, 1 M solution in water) and tetrabutylammonium hydroxide (3.5 µl 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.
Method 21

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to acetone (2 ml). Potassium carbonate (1.05 ml, 1 M solution in water) and tetrabutylammonium hydroxide (3.5 µl 40% wt in water) are added to the mixture. Formaldehyde (0.12 ml, 37% wt in water) is then added to the mixture. The resulting mixture is stirred for 2 h at 45° C. The phases are separated. The organic phase is diluted with toluene (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.
Method 22

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tertiary-butanol (2 ml). Potassium carbonate (1.05 ml, 1 M solution in water) and tetrabutylammonium hydroxide (3.5 µl, 40% wt in water) are added to the mixture. Formaldehyde (0.12 ml, 37% wt in water) is then added to the mixture. The resulting mixture is stirred for 2 h at 45° C. The mixture is diluted with water (5 ml) and ethyl acetate (5 ml). The phases are separated. The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.
Method 23

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). Potassium carbonate (1.05 ml, 1 M solution in water) and tetrabutylammonium hydroxide (3.5 µl, 40% wt in water) are added to the mixture. Formaldehyde (0.10 ml, 37% wt in water) is then added to the mixture. The resulting mixture is stirred for 2 h at 45° C. The phases are separated. The organic phase is diluted with ethyl acetate (5 ml). The organic phase is then washed with sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.
Method 24

200 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to tetrahydrofuran (2 ml). Potassium carbonate (1.05 ml, 1 M solution in water) and tetrabutylammonium hydroxide (3.5 µl, 40% wt in water) are added to the mixture. Formaldehyde (0.16 ml, 37% wt in water) is then added to the mixture. The resulting mixture is stirred for 2 h at 45° C. The phases are separated. The organic phase is diluted with ethyl acetate (5 ml). The organic phase is then washed with a sodium bisulfite solution (5 ml, 40% wt in water) and then with water (5 ml). The separated organic phase is then dried (MgSO$_4$) and concentrated under reduced pressure to give (R)-5-biphenyl-4-ylmethyl-3-methylene-2-oxo-pyrrolidine-1-carboxylic acid tert-butyl ester (4-a, R1=Boc) as determined by hplc.
HPLC Method (Example 25, Methods 1-24)

Column: X-BRIDGE C18; 150×3.0 mm; 3.5 µm. Mobile Phase A (0.1% NH$_3$ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min$^{-1}$. Wavelength: 210 or 254 nm. Temperature 60±2° C.
Retention Times:
6-a (R1=Boc): 2.62 min
5-a (R1=Boc): 8.39 min
4-a (R1=Boc): 12.0 min Example 26

(R)-5-Biphenyl-4-ylmethyl-3-methylene-2-oxo-pyrrolidine-1-carboxylic acid tert-butyl ester (4-a, R1=Boc)

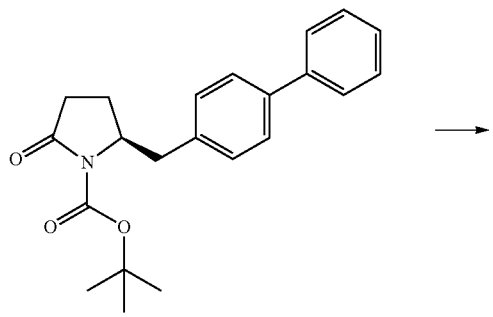

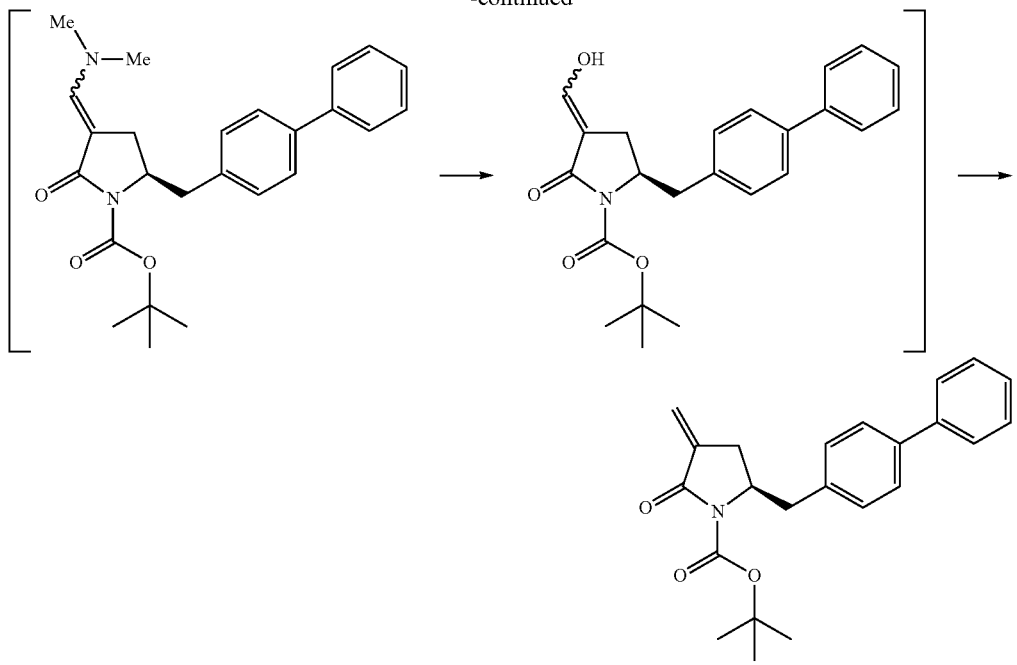

50 g (S)-2-Biphenyl-4-ylmethyl-5-oxo-pyrrolidine-1-carboxylic acid tert-butyl ester (8-a, R1=Boc) and 261 g Bredereck's reagent (14, R6=Me, R7=Me, R8=tBu) are stirred at 80° C. for 24 h and concentrated afterwards under vacuum to yield 67.5 g of a viscous residue. The later is dissolved in 340 ml THF and mixed with 13.1 ml hydrochloric acid 37% in 143 ml water. After 1 h stirring at room temperature, the lower aqueous phase is removed, and 150.2 g aqueous formaldehyde 37% is added followed with 30 g potassium carbonate added portions wise at 20-25° C. Again after 3 hour stirring, the aqueous phase is removed. The remaining organic phase is diluted with 100 ml toluene, washed with 50 ml brine and concentrated under vacuum to leave 58.4 g of a viscous residue. The latter is dissolved in 525 ml methanol at 50° C., and saturated at the same temperature with 175 ml water. The resulting suspension is cooled to 0° C., filtered to collect the crystals, washed with 60 ml methanol/water 2:1 and dried under vacuum to yield of white crystals of (R)-5-Biphenyl-4-ylmethyl-3-methylene-2-oxo-pyrrolidine-1-carboxylic acid tert-butyl ester (4-a, R1=Boc). Spectroscopic data as in Example 23.

HPLC Method (Example 26)

Column: X-BRIDGE C18; 150×3.0 mm; 3.5 μm. Mobile Phase A (0.1% $NH_3$ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min$^{-1}$. Wavelength: 210 or 254 nm. Temperature 60±2° C.

Retention Times:

6-a (R1=Boc): 2.62 min 8-a (R1=Boc): 10.4 min 7-a (R1=Boc; R6=Me; R7=Me): 11.0 min 4-a (R1=Boc): 12.0 min Example 27

(R)-5-Biphenyl-4-ylmethyl-1-(2,2-dimethylpropionyl)-3-methylenepyrrolidin-2-one (4-a, R1=Piv)

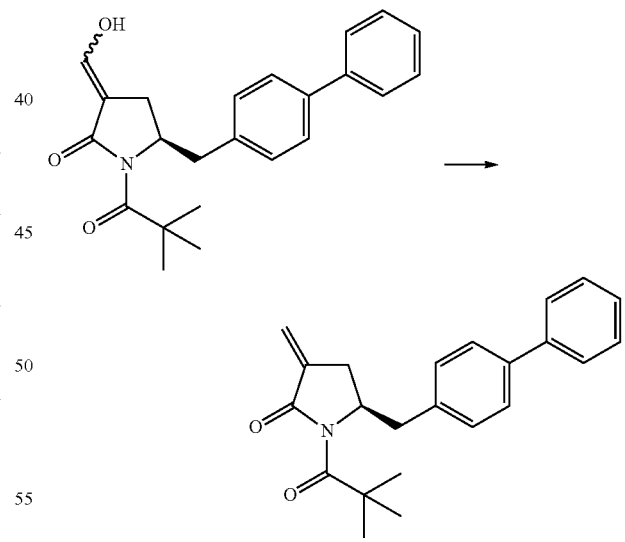

(R)-5-biphenyl-4-ylmethyl-3-[1-hydroxymeth-(E/Z)-ylidene]-2-oxo-pyrrolidine-1-carboxylic acid tert-butyl ester (6-a, R1=Piv) (680 mg) is dissolved in THF (3.5 ml) at room temperature. Formaldehyde solution (1.8 ml, 37% in water) is added followed by the portionwise addition of potassium carbonate (388 mg). The mixture is then stirred for 70 h. Water (1 ml) and sodium bisulfite solution (0.5 ml) are subsequently added. The phases are separated and organic phase dried (MgSO₄). The crude material is purified by chromatography (heptane/ethyl acetate, 10:1) to give (R)-5-biphenyl-4-ylmethyl-1-(2,2-dimethylpropionyl)-3-methylenepyrrolidin-2-one (4-a, R1=Piv). δ$_H$ (400 MHz, DMSO) 1.34 (9H), 2.55-2.64 (2H), 2.70 (1H), 3.26 (1H), 4.59 (1H), 5.55 (1H), 5.98 (1H), 7.26 (2H), 7.34 (1H), 7.44 (2H), 7.53-7.58 (4H). m/z (ES+) 348 ([MH]⁺, 100%).

Example 28

(R)-5-Biphenyl-4-ylmethyl-3-methylenepyrrolidin-2-one (4-a, R1=H)

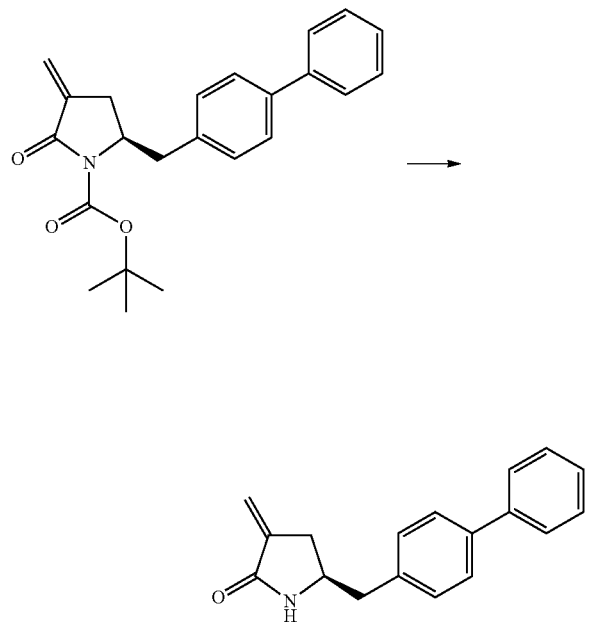

(R)-5-Biphenyl-4-ylmethyl-3-methylene-2-oxo-pyrrolidine-1-carboxylic acid tert-butyl ester (4-a, R1=Boc) (509 mg) is dissolved in dichloromethane (10 ml). Mixture is cooled to 0° C. and trifluoroacetic acid (0.5 ml) is added. The mixture is then stirred for 2 h then extracted with saturated sodium carbonate solution (20 ml). Phases are separated. The organic phase is dried (MgSO₄) and concentrated to give (R)-5-biphenyl-4-ylmethyl-3-methylenepyrrolidin-2-one (4-a, R1=H). δ$_H$ (400 MHz, DMSO) 2.47 (1H), 2.68 (1H), 2.74 (1H), 2.87 (1H), 3.87 (1H), 5.22 (1H), 5.64 (1H), 7.33 (3H), 7.45 (2H), 7.60 (2H), 7.65 (2H), 8.32 (1H); m/z (+) 264 ([MH]⁺, 100%); m/z (+ESI) 264 ([MH]⁺, 100%).

(R)-5-Biphenyl-4-ylmethyl-3-methylenepyrrolidin-2-one (4-a, R1=H) is a crystalline solid and can be characterised by an X-ray powder pattern. Reflections in the X-ray diffraction pattern show the following interlattice plane intervals (average 2θ in [°] are indicated with error limit of ±0.2): 2θ in [°]: 7.1, 13.3, 13.7, 14.5, 16.6, 17.7, 18.2, 19.4, 21.4, 22.5, 23.6, 24.0, 26.5, 27.6, 29.1, 29.9. Data taken using a Bruker D8 Advance diffractometer using Cu—Kα radiation.

HPLC Method (Example 28)
Column: X-BRIDGE C18; 150×3.0 mm; 3.5 μm. Mobile Phase A (0.1% NH₃ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min⁻¹. Wavelength: 210 or 254 nm. Temperature 60±2° C.
Retention Times:
4-a (R1=H): 5.70 min
4-a (R1=Boc): 12.0 min

Example 29

(3R/S,5S)-5-Biphenyl-4-ylmethyl-3-dimethoxymethyl-2-oxo-pyrrolidine-1-carboxylic acid tert-butyl ester (16-a, R1=Boc, R9=Me, R9=Me, Y=O)

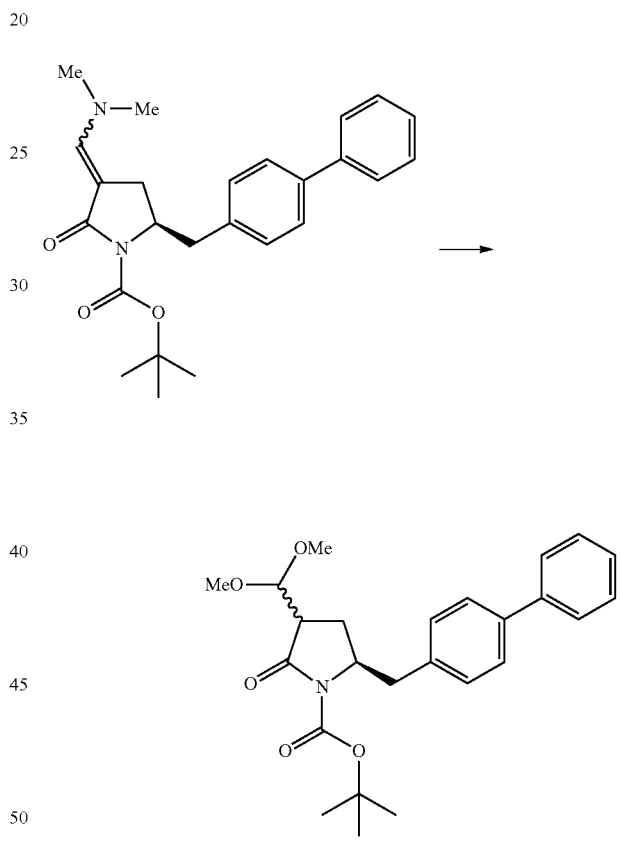

1.1 g (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is dissolved in 12 ml of methanol. HCl in methanol (prepared by feed pipe of gaseous HCl to methanol; determination of the HCl content is made by weight) is added until a pH of 2 is achieved. The resulting yellow solution is stirred for additional 4 hours, then quenched by addition of 10% aqueous sodium carbonate solution to give a pH above 7. After extraction with dichloromethane the combined organic phase are dried over sodium sulfate, filtered and evaporated to dryness. The resulting yellow oil is purified by column chromatography to give (3R/S, 5S)-5-biphenyl-4-ylmethyl-3-dimethoxymethyl-2-oxo-pyrrolidine-1-carboxylic acid tert-butyl ester (16-a, R1=Boc, R9=Me, R9=Me) as a 88:12 mixture of diastereomers [ratio of (3S):(3R) diastereomers, respectively]. 1H NMR (CDCl$_3$): Data for mixture of diastereomers: 1.62, 1.64, 1.89, 2.02, 2.26, 2.40, 2.69, 2.81, 2.92, 3.14, 3.20, 3.39, 3.44, 3.47, 3.52, 4.29, 4.40, 4.69, 7.27-7.39, 7.46, 7.56-7.62. Ratio of diastereomers determined by integration of the pairs of signals at 3.39 ppm and 3.44 ppm (major and minor diastereomer, respectively) or 3.47 ppm and 3.52 ppm (major and minor diastereomer, respectively).

(3R/S,5S)-5-biphenyl-4-ylmethyl-3-dimethoxymethyl-2-oxo-pyrrolidine-1-carboxylic acid tert-butyl ester (16-a, R1=Boc, R9=Me, R9=Me) as a 88:12 mixture of diastereomers [ratio of (3S):(3R) diastereomers, respectively] can be recrystallised from tert-butylmethylether to afford (3S,5S)-5-Biphenyl-4-ylmethyl-3-dimethoxymethyl-2-oxo-pyrrolidine-1-carboxylic acid tert-butyl ester (16-a, R1=Boc, R9=Me, R9=Me).

The X-ray Structure of the obtained crystals is shown in FIG. 5a.

Crystal Data [Recorded at 120(2) K]

|  |  |
| --- | --- |
| Empirical formula | C$_{25}$H$_{31}$NO$_5$ |
| Formula weight | 425.51 |
| Crystal system | Orthorhombic |
| Space group | P212121 |
| Cell parameters | a = 6.645(2) Å |
|  | b = 15.761(4) Å |
|  | c = 22.439(6) Å |
|  | α = 90° |
|  | β = 90° |
|  | γ = 90° |
| Volume of unit cell | 2350.1(11) Å$^3$ |
| Z* | 4 |
| Calculated density | 1.203 mg m$^{-3}$ |

*(number of asymmetric units in the unit cell)

(3R/S,5S)-5-biphenyl-4-ylmethyl-3-dimethoxymethyl-2-oxo-pyrrolidine-1-carboxylic acid tert-butyl ester (16-a, R1=Boc, R9=Me, R9=Me) as a 88:12 mixture of diastereomers [ratio of (3S):(3R) diastereomers, respectively] can be recrystallised from ethyl acetate/heptane to afford (3S,5S)-5-Biphenyl-4-ylmethyl-3-dimethoxymethyl-2-oxo-pyrrolidine-1-carboxylic acid tert-butyl ester (16-a, R1=Boc, R9=Me, R9=Me).

The X-ray Structure of the obtained crystals is shown in FIG. 5b.

Crystal Data [Recorded at 100(2) K]

|  |  |
| --- | --- |
| Empirical formula | C$_{25}$H$_{31}$NO$_5$ |
| Formula weight | 425.51 |
| Crystal system | Orthorhombic |
| Space group | P212121 |
| Cell parameters | a = 6.638(3) Å |
|  | b = 15.746(6) Å |
|  | c = 22.420(8) Å |
|  | α = 90° |
|  | β = 90° |
|  | γ = 90° |
| Volume of unit cell | 2343.4(16) Å$^3$ |
| Z* | 4 |
| Calculated density | 1.206 mg m$^{-3}$ |

*(number of asymmetric units in the unit cell)

Example 30

((3R/S,5S)-5-Biphenyl-4-ylmethyl-1-tert-butoxycarbonyl-2-oxo-pyrrolidin-3-ylmethyl)trimethylammonium iodide (10-a, R1=Boc, R6=Me, R7=Me, R10=Me)

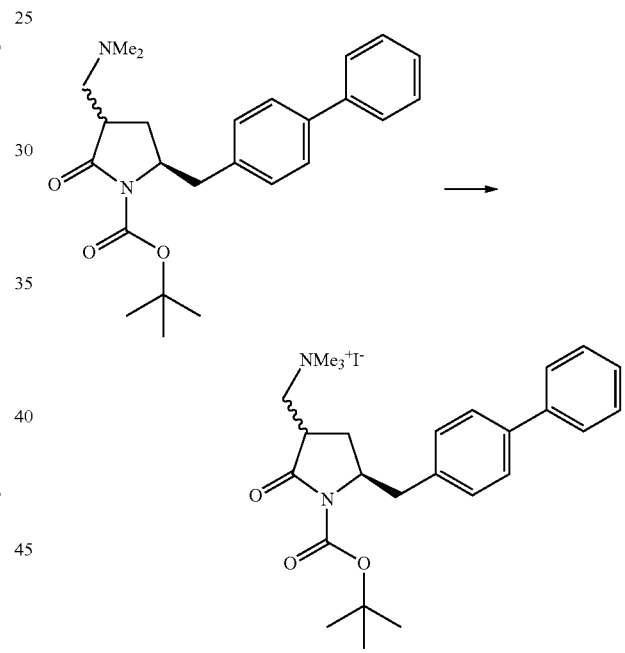

(3R/S,5S)-biphenyl-4-ylmethyl-3-dimethylaminomethyl-2-oxo-pyrrolidine-1-carboxylic acid tert-butyl ester (9-a, R1=Boc, R6=Me, R7=Me) (108 mg) (ratio of diastereomers (3S):(3R), 85:15 according to NMR analysis) is diluted with 4 ml methanol and 328 μl methyl iodide is then added. The reaction mixture is then stirred at room temperature for 17 h. The mixture is then concentrated to dryness to give ((3R/S,5S)-5-Biphenyl-4-ylmethyl-1-tert-butoxycarbonyl-2-oxo-pyrrolidin-3-ylmethyl)trimethylammonium iodide (10-a, R1=Boc, R6=Me, R7=Me, R10=Me). 1H NMR (DMSO): 1.51 (9H), 1.98 (1H), 2.18 (1H), 3.00 (1H), 3.08 (1H), 3.13 (9H), 3.38-3.43 (2H), 3.72 (1H), 4.25 (1H), 7.38 (1H), 7.42 (2H), 7.48 (2H), 7.67 (4H). m/z: 423 ([M]$^+$, 100%). IR (solution in CH$_2$Cl$_2$, v/cm$^{-1}$): 3040; 1781; 1742; 1724; 1487; 1371; 1298; 1277; 1150; 985. On the basis of NMR, the ratio of diastereomers (3S):(3R) is 85:15.

Example 31

(R)-5-Biphenyl-4-ylmethyl-3-methylene-2-oxo-pyrrolidine-1-carboxylic acid tert-butyl ester (4-a, R1=Boc)

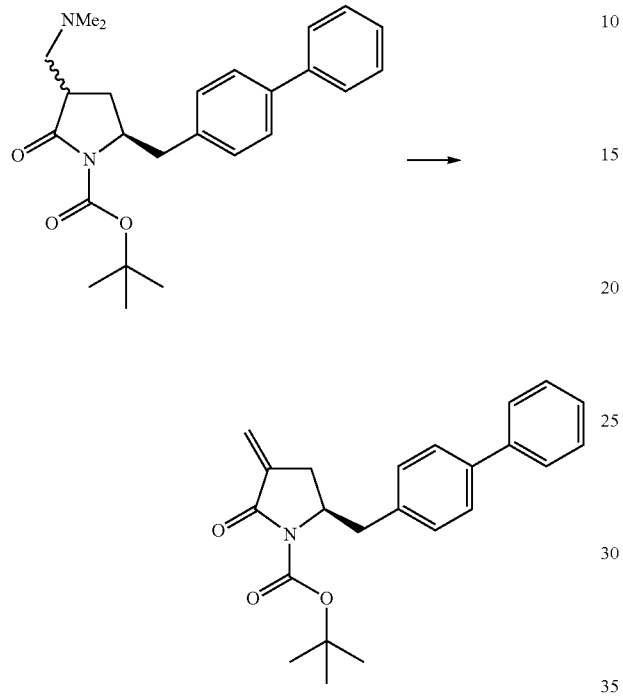

Crude (3R/S,5S)-biphenyl-4-ylmethyl-3-dimethylaminomethyl-2-oxo-pyrrolidine-1-carboxylic acid tert-butyl ester (9-a, R1=Boc, R6=Me, R7=Me) (13.8 g) is diluted with 40 ml methanol and 16.9 ml methyl iodide is then added. The reaction mixture is then stirred at room temperature overnight and is subsequently concentrated to dryness. 30 ml saturated NaHCO$_3$ solution and 15 ml dichloromethane are then added to the residue. The resulting emulsion is stirred at room temperature for 10 h. The organic layer is then separated, washed with water, dried over MgSO$_4$, filtered and concentrated in vacuo. The residue is purified using column chromatography (pentane/tert-butyl methyl ether=8:2 to 7:3) to give (R)-5-biphenyl-4-ylmethyl-3-methylene-2-oxo-pyrrolidine-1-carboxylic acid tert-butyl ester (4-a, R1=Boc). Spectroscopic data as in Example 23.

HPLC Method (Example 31)

Column: X-BRIDGE C18; 150×3.0 mm; 3.5 μm. Mobile Phase A (0.1% NH$_3$ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min$^{-1}$. Wavelength: 210 or 254 nm. Temperature 60±2° C.

Retention Times:

9-b (R1=Boc; R6=Me; R7=Me): 10.5 min
9-c (R1=Boc; R6=Me; R7=Me): 11.0 min
4-a (R1=Boc): 12.0 min

Example 32

(R)-5-Biphenyl-4-yl-4-tert-butoxycarbonylamino-2-methylenepentanoic acid (2-a, R1=Boc, R2=H, R3=CO$_2$H)

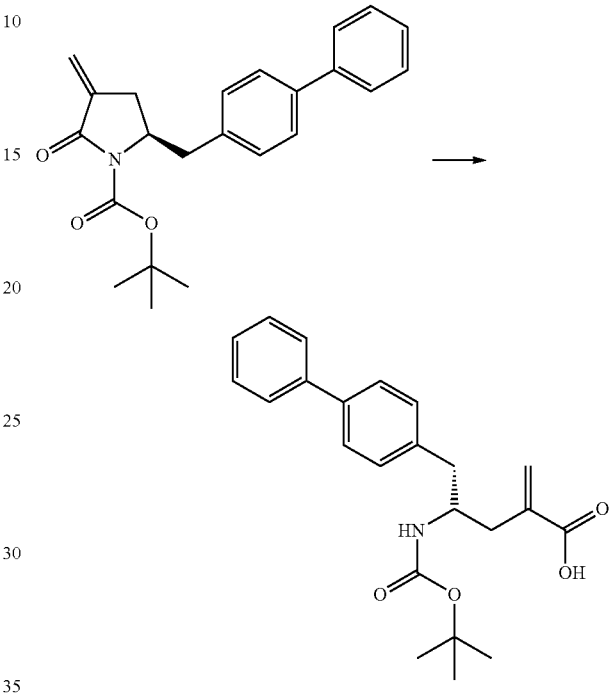

(R)-5-Biphenyl-4-ylmethyl-3-methylene-2-oxo-pyrrolidine-1-carboxylic acid tert-butyl ester (4-a, R1=Boc) (27.7 g) is dissolved in THF (270 ml) at room temperature. Tetrabutylammonium bromide (0.24 g) is added followed with water (10 ml). The mixture is then cooled to 10° C. A solution of lithium hydroxide (7.3 g) in water (92 ml) is added over 2 h. Phosphoric acid (37 g, 85%) is added until pH 3. Phases are then separated. The organic phase is diluted with toluene (100 ml) and washed with brine. Phases are separated. The organic phase is then concentrated in vacuo. The residue is dissolved in acetonitrile (350 ml) at 80° C. and azeotropically distilled. Further acetonitrile is added (150 ml) and the mixture cooled to 0° C. The solid is collected by filtration and dried, to afford (R)-5-biphenyl-4-yl-4-tert-butoxycarbonylamino-2-methylenepentanoic acid (2-a, R1=Boc, R2=H, R3=CO$_2$H) (25.7 g). δ$_H$ (400 MHz, DMSO) 1.30 (9H), 2.29 (1H), 2.50 (1H), 2.75 (2H), 3.91 (8H), 5.62 (1H), 6.09 (1H), 6.66 (1H), 7.28 (2H), 7.33 (1H), 7.44 (2H), 7.56 (2H), 7.63 (2H).

(R)-5-Biphenyl-4-yl-4-tert-butoxycarbonylamino-2-methylenepentanoic acid (2-a, R1=Boc, R2=H, R3=CO$_2$H) is a crystalline solid. Reflections in the X-ray diffraction pattern show the following interlattice plane intervals (average 2θ in [°] are indicated with error limit of ±0.2): 2θ in [°]: 4.4, 6.2, 8.6, 9.0, 9.9, 12.5, 13.4, 13.8, 14.1, 16.0, 17.8, 18.4, 19.3, 20.8, 21.7, 22.2, 23.1, 24.6, 25.0, 25.7, 27.6. The most intensive reflections in the X-ray diffraction pattern show the following interlattice plane intervals (average 2θ in [°] are indicated with error limit of ±0.2): 2θ in [°]: 4.3, 6.2, 8.6, 9.9, 12.5, 13.4, 16.0, 17.8, 18.4, 19.3. Data taken using a Bruker D8 Advance diffractometer using Cu—Kα radiation.

HPLC Method (Example 32)

Column: X-BRIDGE C18; 150×3.0 mm; 3.5 μm. Mobile Phase A (0.1% $NH_3$ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min$^{-1}$. Wavelength: 210 or 254 nm. Temperature 60±2° C.
Retention Times:
2-a (R1=Boc; R2=H; R3=$CO_2H$): 2.40 min
4-a (R1=Boc): 12.0 min Example 33

(R)-5-Biphenyl-4-yl-4-tert-butoxycarbonylamino-2-methylenepentanoic acid (2-a, R1=Boc, R2=H, R3=$CO_2H$)

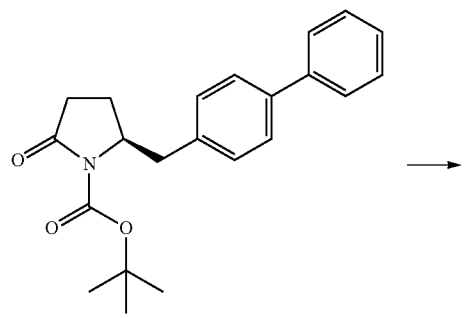

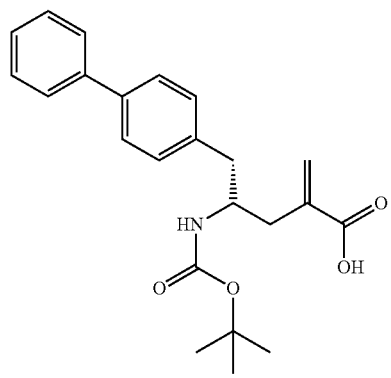

210 g (S)-2-Biphenyl-4-ylmethyl-5-oxo-pyrrolidine-1-carboxylic acid tert-butyl ester (8-a, R1=Boc) is added to 1285 g (2000 ml) of a mixture containing compounds of formula 13, 14, 15 (wherein R6=Me, R7=Me, R8=tBu) at room temperature. The solution is heated to 80-85° C. and stirred for about 15 h. The solution is concentrated under vacuum (90° C., 30 mbar) to yield a residue. (The collected distillate, containing compounds of formula 13, 14, 15 (wherein R6=Me, R7=Me, R8=tBu), may be optionally reused in subsequent reactions, where appropriate). The residue is dissolved in 1430 ml tetrahydrofuran. 37.8 g sulfuric acid diluted in 638 ml water is then added. The mixture is subsequently vigorously stirred at 10-15° C. During this time, the pH is maintained in the range pH 2-3 by the addition of further portions of sulfuric acid, as required. After 1 h the lower aqueous phase is removed, and the remaining organic phase washed with about 6 g saturated potassium carbonate solution. 1194 g Potassium carbonate solution (1M solution) is then added, followed by 3.94 g tetra butyl ammonium hydroxide solution (40%) and 133 g aqueous formaldehyde solution (37%). This mixture is heated to 40-45° C. and stirred heavily for about 2 hours. The aqueous phase is then removed. To the remaining organic phase, 300 ml water is added. 97 g Sodium sulfite solution (40%) is then added whilst maintaining the temperature below 40° C. Afterwards, the aqueous phase is removed and is replaced with 600 ml of fresh water. The THF is removed by distillation (jacket 50° C., 100-200 mbar) to provide a white suspension. 1500 ml toluene is added at 50° C. Again the lower aqueous phase is removed and the remaining organic phase is washed with about 200 ml water. The latter is partially concentrated under vacuum in order to remove any water by azeotrope distillation while the distillate is replaced with fresh toluene. Afterwards, 54 g diazabicycloundecene (DBU) is added as well as 17 g methansulfonylchloride, cautiously at 20-25° C. After one hour stirring, about 300 ml water is added followed by 1.4 g concentrated sulfuric acid in order to lower the pH to 6-7. The aqueous phase is removed and the remaining organic phase washed with 300 ml water. 600 ml Water is added and the solvent removed by distillation under reduced pressure to yield a white suspension. About 1500 ml THF is then added followed by 57 g lithium hydroxide dissolved in 300 ml water. The mixture is stirred heavily at 10-15° C. for about 2 hours. 100 g Phosphoric acid (58%) is then added cautiously in order to adjust the pH towards 3-4. About 300 ml toluene is then added, and the aqueous phase removed. The remaining organic phase is washed with 200 ml brine and concentrated to one half the original volume under vacuum. The residue is diluted with 300 ml THF and filtered. The THF is then replaced by acetonitrile by distillation, while maintaining the volume constant by distillation under vacuum. After removal of the majority of THF, the desired product crystallizes giving rise to a thick slurry. The later is cooled to 0° C., and the solid recovered by filtration. The later is dried under vacuum at 50° C. to yield (R)-5-Biphenyl-4-yl-4-tert-butoxycarbonylamino-2-methylenepentanoic acid (2-a, R1=Boc, R2=H, R3=$CO_2H$). Spectroscopic data as Example 32.

HPLC Method (Example 33)

Column: X-BRIDGE C18; 150×3.0 mm; 3.5 μm. Mobile Phase A (0.1% $NH_3$ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min$^{-1}$. Wavelength: 210 or 254 nm. Temperature 60±2° C.
Retention Times:
2-a (R1=Boc; R2=H; R3=$CO_2H$): 2.40 min
6-a (R1=Boc): 2.62 min
5-a (R1=Boc): 8.39 min
8-a (R1=Boc): 10.4 min
7-a (R1=Boc; R6=Me; R7=Me): 11.0 min
4-a (R1=Boc): 12.0 min

Example 34

(3R,5S)-5-Biphenyl-4-ylmethyl-3-methyl-2-oxo-pyrrolidine-1-carboxylic acid tert-butyl ester (3-a, R1=Boc) and (3S,5S)-5-Biphenyl-4-ylmethyl-3-methyl-2-oxo-pyrrolidine-1-carboxylic acid tert-butyl ester (3-b, R1=Boc)

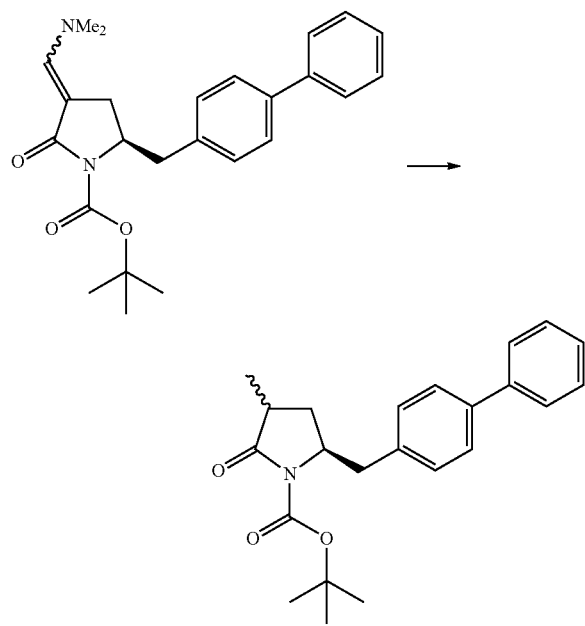

Method 1

1.3 g (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is dissolved in 40 ml of ethyl acetate. After addition of 0.3 g 10% Pd/C (Engelhard 4505) the system is flushed several times with hydrogen and subsequently stirred at 20° C. and 4 bar hydrogen for 5 days. The resulting reaction mixture is filtered through cellflock and concentrated to dryness yielding (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 33:67 (3-a, R1=Boc: 3-b, R1=Boc) as determined by hplc.

Method 2

(R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6,=Me, R7=Me) is added to tetrahydrofuran, to achieve a substrate concentration of 0.05 M. Triethylamine (1 equivalent) is added to the mixture. 5% Pd/C A102023 (25% w/w) is then added to the mixture. The mixture is then pressurised under a hydrogen atmosphere to 20 bar. The mixture is stirred at 40° C. for 3 h. The mixture is then filtered to remove the catalyst and concentrated under reduced pressure. The diastereomer ratio is 39:61 (3-a, R1=Boc: 3-b, R1=Boc) as determined by hplc.

General Procedure (Methods 3-8)

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is added to tetrahydrofuran, methanol or isopropyl acetate at ambient temperature, to achieve a substrate concentration of 0.05 M, 0.167 M or 0.25 M. A hetereogeneous catalyst (25 mas % with respect to 7-a) is then added to the mixture. The mixture is then pressurised under a hydrogen atmosphere to 20 bar. The mixture is stirred at 40° C., 45° C., 55° C. or 65° C. for 1.5 or 3 h. The mixture is then filtered to remove the catalyst and concentrated under reduced pressure.

Method 3

Catalyst: 5% Pd(S)/C A103038; Tetrahydrofuran; 0.05 M; 55° C.; 3 h. Diastereomer ratio 29:71 (3-a, R1=Boc: 3-b, R1=Boc) as determined by hplc.

Method 4

Catalyst: 5% Pd/C type 39; Methanol; 0.05 M; 55° C.; 3 h. Diastereomer ratio 42:58 (3-a, R1=Boc: 3-b, R1=Boc) as determined by hplc.

Method 5

Catalyst: 5% Pd(S)/C A103038; Tetrahydrofuran; 0.167 M; 40° C.; 1.5 h. Diastereomer ratio 14:86 (3-a, R1=Boc: 3-b, R1=Boc) as determined by hplc.

Method 6

Catalyst: 5% Pd(S)/C A103038; Tetrahydrofuran; 0.167 M; 40° C.; 3 h. Diastereomer ratio 21:79 (3-a, R1=Boc: 3-b, R1=Boc) as determined by hplc.

Method 7

Catalyst: 5% Pd/C type 37; Isopropyl acetate; 0.167 M; 65° C.; 3 h. Diastereomer ratio 34:66 (3-a, R1=Boc: 3-b, R1=Boc) as determined by hplc.

Method 8

Catalyst: 5% Pd/C type 39; Tetrahydrofuran; 0.25 M; 65° C.; 3 h. Diastereomer ratio 39:61 (3-a, R1=Boc: 3-b, R1=Boc) as determined by hplc.

Method 9

1.3 g (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is added to ethyl acetate (40 ml) at ambient temperature. 0.3 g of 10% Palladium on Carbon (Engelhard 4505) and water (0.3 ml) is added to the mixture. The mixture is then pressurised under a hydrogen atmosphere to 4 bar. The mixture is stirred at ambient temperature and 4 bar hydrogen pressure for 4 days. The mixture is then filtered to remove the catalyst and concentrated under reduced pressure. The residue is then purified by column chromatography (ethyl acetate/hexane, 70:30) to afford (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 67:33 (3-a, R1=Boc: 3-b, R1=Boc) as determined by hplc.

Method 10

1.3 g (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is added to ethyl acetate (40 ml) at ambient temperature. 0.3 g of Lindlar Catalyst (ex Aldrich) is added to the mixture. The mixture is then pressurised under a hydrogen atmosphere to 2 bar. The mixture is stirred at ambient temperature and 2 bar hydrogen pressure for 3 days. The mixture is then filtered to remove the catalyst and concentrated under reduced pressure. The residue is then purified by column chromatography (ethyl acetate/hexane, 70:30) to afford (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 99.2:0.8 (3-a, R1=Boc: 3-b, R1=Boc) as determined by hplc.

Method 11

1.3 g (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is added to ethyl acetate (40 ml) at ambient temperature. 0.3 g of 10% Palladium on Carbon (Engelhard 4505) is added to the mixture. The mixture is then pressurised under a hydrogen atmosphere to 2 bar. The mixture is stirred at ambient temperature and 2 bar hydrogen pressure for 3 days. The mixture is then filtered to remove the catalyst and concentrated under reduced pressure. The residue is then purified by column chromatography (ethyl acetate/hexane, 70:30) to afford (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 88.8:11.2 (3-a, R1=Boc: 3-b, R1=Boc) as determined by hplc.

Method 12

1.3 g (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is added to ethyl acetate (40 ml) at ambient temperature. 0.3 g of 10% Palladium on Carbon (Engelhard 4505) and one drop of aqueous sodium hydroxide solution are added to the mixture. The mixture is then pressurised under a hydrogen atmosphere to 4 bar. The mixture is stirred at ambient temperature and 4 bar hydrogen pressure for 4 days. The mixture is then filtered to remove the catalyst and concentrated under reduced pressure. The residue is then purified by column chromatography (ethyl acetate/hexane, 70:30) to afford (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 76:24 (3-a, R1=Boc: 3-b, R1=Boc) as determined by hplc.

HPLC Method 1 (Example 34, Methods 1, 9, 10, 11 and 12)

Column: X-BRIDGE C18; 150×3.0 mm; 3.5 µm. Mobile Phase A (0.1% $NH_3$ (32%) in water); Mobile Phase B (Acetonitrile). Gradient: 0 min (20% B); 3 min (40% B); 5 min (40% B); 10 min (70% B), 11 min (70% B), 13 min (80% B), 16 min (80% B), 16.1 min (20% B), 19 min 20% B). Flow rate: 1.4 ml $min^{-1}$. Wavelength: 210 or 254 nm. Temperature 55±2° C.

Retention Times:

7-a (R1=Boc; R6=Me; R7=Me): 9.6 min 3-a and 3-b (R1=Boc): 10.3 min

HPLC Method 2 (Example 34, Methods 1, 9, 10, 11 and 12)

Column: Chiralpak AD-RH, 150×2.6 mm, 5.0 µm. Mobile Phase A (Water); Mobile Phase B (Acetonitrile). Isocratic: 0 min (80% B); 15 min (80% B). Flow rate: 0.5 ml $min^{-1}$. Wavelength: 210 nm.

Retention Times:

3-a, R1=Boc: 6.3 min 3-b, R1=Boc: 6.9 min

HPLC Method 3 (Example 34, Methods 2-8)

Column: AD-RH Chiralpak; 150×4.6 mm. Mobile Phase A (water); Mobile Phase B (Acetonitrile). Isocratic: 0 min (20% B); 15 min (20% B). Flow rate: 0.5 ml $min^{-1}$. Wavelength 210 nm. Column temperature 40° C.

Retention Times:

(3-a, R1=Boc): 6.2 min (3-b, R1=Boc): 6.8 min

Example 35

Tris(dimethylamino)methane (13, R6=Me, R7=Me), Tert-Butoxy-bis(dimethylamino)methane (14, R6=Me, R7=Me, R8=tBu) and N,N-Dimethylformamide di-tert-butyl acetal (15, R6=Me, R7=Me, R8=tBu)

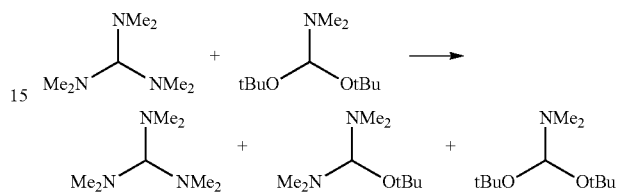

Method 1

A mixture of 1.01 g N,N-dimethylformamide di-tert-butyl acetal (15, R6=Me, R7=Me, R8=tBu) (Aldrich #358800) and 0.73 g tris(dimethylamino)methane (13, R6=Me, R7=Me) (Aldrich, #221058) are stirred at room temperature overnight. The resulting mixture is cooled to room temperature, affording a solution containing 13, 14 and 15 (R6=Me, R7=Me, R8=Me) as determined by nmr (spectroscopic data as in Example 14, Method 1).

Method 2

A mixture of 1.01 g N,N-dimethylformamide di-tert-butyl acetal (15, R6=Me, R7=Me, R8=tBu) (Aldrich #358800) and 0.73 g tris(dimethylamino)methane (13, R6=Me, R7=Me) (Aldrich, #221058) are heated at 45° C. for 4 h. The resulting mixture is cooled to room temperature, affording a solution containing 13, 14 and 15 (R6=Me, R7=Me, R8=Me) as determined by nmr (spectroscopic data as in Example 14, Method 1).

Method 3

A mixture of 1.01 g N,N-dimethylformamide di-tert-butyl acetal (15, R6=Me, R7=Me, R8=tBu) (Aldrich #358800) and 0.73 g tris(dimethylamino)methane (13, R6=Me, R7=Me) (Aldrich, #221058) are heated at 80° C. for 1 h. The resulting mixture is cooled to room temperature, affording a solution containing 13, 14 and 15 (R6=Me, R7=Me, R8=Me) as determined by nmr (spectroscopic data as in Example 14, Method 1).

Example 36

Tris(dimethylamino)methane (13, R6=Me, R7=Me), Tert-pentoxy-bis(dimethylamino)methane (14, R6=Me, R7=Me, R8=$CMe_2Et$) and N,N-Dimethylformamide di-tert-pentoxyacetal (15, R6=Me, R7=Me, R8=$CMe_2Et$)

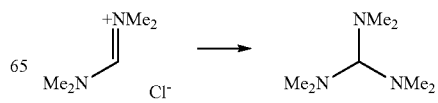

-continued

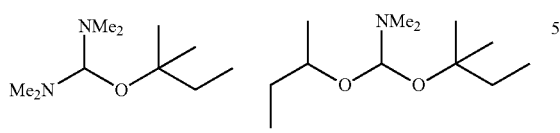

Method 1

57.5 g N,N,N,N-tetramethylformamidinium chloride is added to 93 g sodium amylate 40% solution in toluene. The resulting mixture is stirred at room temperature for 48 h. The mixture is then filtered and the cake washed with toluene (22 g) to afford a solution containing 13, 14 and 15 (R6=Me, R7=Me, R8=CMe$_2$Et). A sample of the filtrate is concentrated in vacuo. 1H NMR(C$_6$D$_6$): 0.81-0.84, 0.92-0.98, 1.02, 1.10, 1.20, 1.30-1.34, 1.47-1.62, 2.29, 2.33, 3.02, 4.06, 5.02. Relative amounts of 13 (R6=Me; R7=Me), 14 (R6=Me, R7=Me, R8=tBu), 15 (R6=Me, R7=Me, R8=Me) are determined by integration of signals at 3.02, 4.06 and 5.02 ppm, respectively.

Method 2

41 g N,N,N,N-tetramethylformamidinium chloride is added to 67 g sodium amylate 40% solution in toluene. The resulting mixture is stirred at room temperature for 48 h. The mixture is filtered and the cake washed with toluene (2×10 ml). The mixture is then diluted to a total volume of 100 ml to afford a solution containing 13, 14 and 15 (R6=Me, R7=Me, R8=CMe$_2$Et). Spectroscopic data as for Example 36, Method 1.

Example 37

(2R,4S)-5-biphenyl-4-yl-4-tert-butoxycarbonylamino-2-methylpentanoic acid diisopropylethylammonium salt (1-a, R1=Boc, R2=H, R3=CO$_2^-$[NHiPr$_2$Et]$^+$)

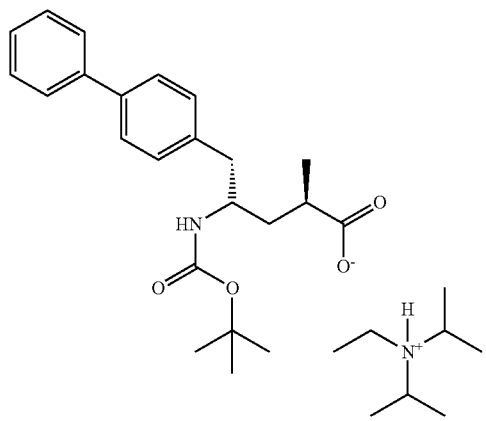

1 g (2R,4S)-5-Biphenyl-4-yl-4-tert-butoxycarbonylamino-2-methylpentanoic acid (1-a, R1=Boc, R2=H, R3=CO$_2$H) is added to ethanol (10 ml). Diisopropylethylamine (0.454 ml) is then added and the mixture is stirred at room temperature for 30 minutes. The mixture is then concentrated in vacuo to afford (2R,4S)-5-biphenyl-4-yl-4-tert-butoxycarbonylamino-2-methylpentanoic acid diisopropylethylammonium salt (1-a, R1=Boc, R2=H, R3=CO$_2^-$[NHiPr$_2$Et]$^+$). 1H NMR (DMSO-d6): 0.95-0.98 (15H), 1.04 (3H), 1.32 (9H), 1.36 (1H), 1.74 (1H), 2.38-2.49 (3H), 2.67 (2H), 2.99 (2H), 3.66 (1H), 6.29 and 6.70 (1H), 7.23-7.25 (2H), 7.33-7.37 (1H), 7.42-7.46 (2H), 7.55-7.57 (2H), 7.62-7.64 (2H).

Example 38

(2R,4S)-5-biphenyl-4-yl-4-tert-butoxycarbonylamino-2-methylpentanoic acid triethylammonium salt (1-a, R1=Boc, R2=H, R3=CO$_2^-$[NHEt$_3$]$^+$)

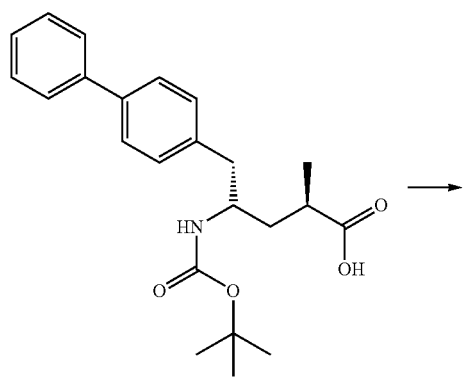

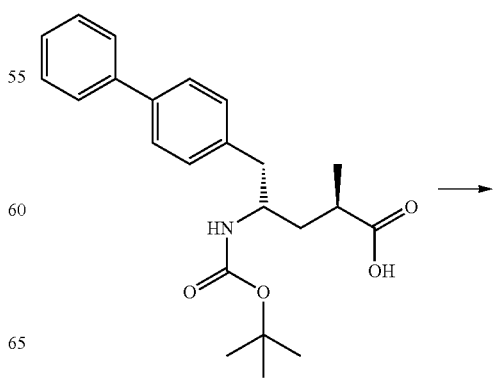

159
-continued

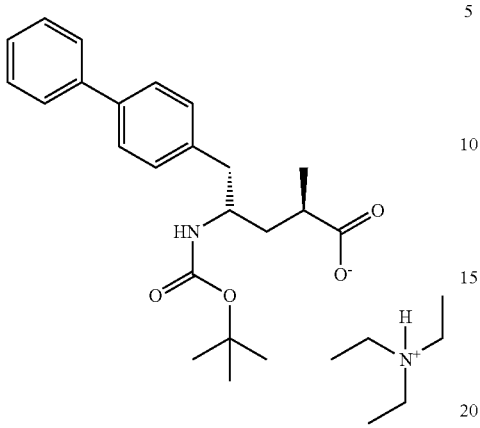

160
-continued

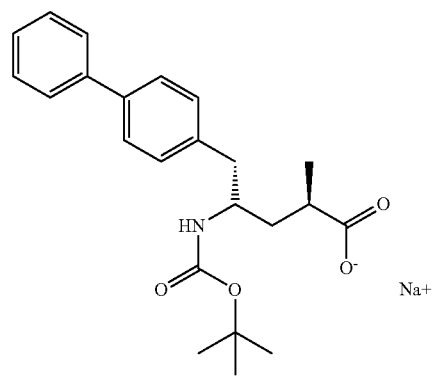

1 g (2R,4S)-5-Biphenyl-4-yl-4-tert-butoxycarbonylamino-2-methylpentanoic acid (1-a, R1=Boc, R2=H, R3=CO₂H) is added to ethanol (10 ml). Triethylamine (0.264 ml) is then added and the mixture is stirred at room temperature for 30 minutes. The mixture is then concentrated in vacuo to afford (2R,4S)-5-biphenyl-4-yl-4-tert-butoxycarbonylamino-2-methylpentanoic acid triethylammonium salt (1-a, R1=Boc, R2=H, R3=CO₂⁻[NHEt₃]⁺). 1H NMR (DMSO-d6): 0.95 (9H), 1.04 (3H), 1.32 (9H), 1.36 (1H), 1.74 (1H), 2.38-2.50 (7H), 2.67 (2H), 3.65 (1H), 6.29 and 6.70 (1H), 7.23-7.25 (2H), 7.33-7.37 (1H), 7.43-7.48 (2H), 7.55-7.57 (2H), 7.62-7.64 (2H).

Example 39

(2R,4S)-5-biphenyl-4-yl-4-tert-butoxycarbonylamino-2-methylpentanoic acid sodium salt (1-a, R1=Boc, R2=H, R3=CO₂⁻Na⁺)

1 g (2R,4S)-5-Biphenyl-4-yl-4-tert-butoxycarbonylamino-2-methylpentanoic acid (R1=Boc, R2=H, R3=CO₂H) is added to ethanol (10 ml). Sodium methoxide (141 mg) is then added and the mixture is stirred at room temperature for 30 minutes. The mixture is then concentrated in vacuo to afford (2R,4S)-5-biphenyl-4-yl-4-tert-butoxycarbonylamino-2-methylpentanoic acid sodium salt (1-a, R1=Boc, R2=H, R3=CO₂⁻Na⁺). 1H NMR (DMSO-d6): 0.91 (3H), 1.29 (1H), 1.34 (9H), 1.61 (1H), 2.12 (1H), 2.68-2.81 (2H), 3.60 (1H), 7.25-7.27 (2H), 7.32-7.36 (1H), 7.43-7.47 (2H), 7.55-7.57 (2H), 7.64-7.66 (2H), 7.76 (1H).

Example 40

(2R,4S)-5-biphenyl-4-yl-4-tert-butoxycarbonylamino-2-methylpentanoic acid (1-a, R1=Boc, R2=H, R3=CO₂H), (2S,4S)-5-biphenyl-4-yl-4-tert-butoxycarbonylamino-2-methylpentanoic acid (1-b, R1=Boc, R2=H, R3=CO₂H),

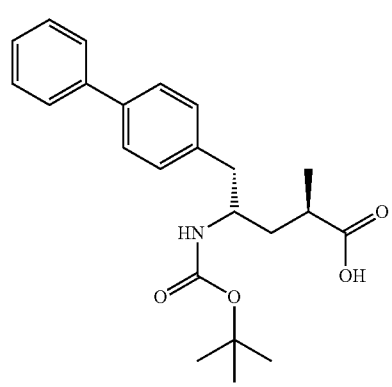

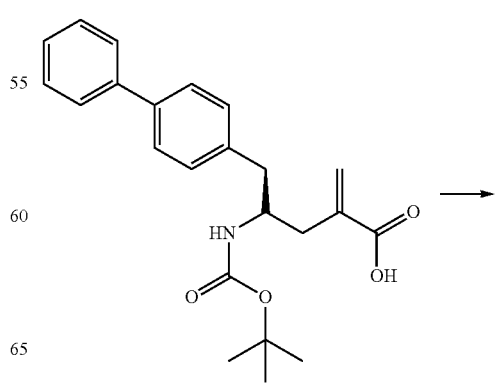

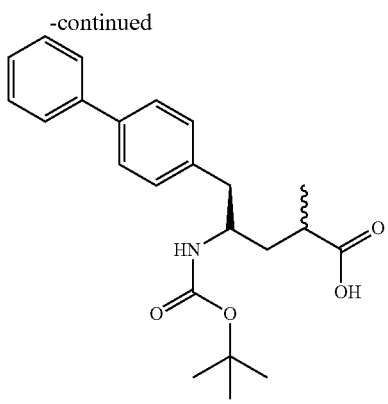

Method 1

20 mg (R)-5-Biphenyl-4-yl-4-tert-butoxycarbonylamino-2-methylenepentanoic acid (2-a, R1=Boc, R2=H, R3=CO$_2$H) is added to ethanol (400 μl). 10% Palladium on carbon (2 mg, 50% water wet, Degussa type E101 NE/W) is then added. Hydrogen gas at ambient pressure is applied to the mixture. The mixture is stirred at ambient temperature and pressure overnight. The mixture is then filtered over Celite and washed with ethanol (2×0.5 ml). The mixture is then concentrated in vacuo to give (2R,4S)-5-biphenyl-4-yl-4-tert-butoxycarbonylamino-2-methylpentanoic acid (1-a, R1=Boc, R2=H, R3=CO$_2$H) and (2S,4S)-5-biphenyl-4-yl-4-tert-butoxycarbonylamino-2-methylpentanoic acid (1-b, R1=Boc, R2=H, R3=CO$_2$H). 1H NMR (CDCl$_3$): 1.11-1.16, 1.21 and 1.33, 1.39-1.53, 1.70-1.92, 2.32-2.81, 3.72-3.97, 4.44-4.50, 6.41 and 6.56, 7.16-7.49, 10.84.

Method 2

20 mg (R)-5-Biphenyl-4-yl-4-tert-butoxycarbonylamino-2-methylenepentanoic acid (2-a, R1=Boc, R2=H, R3=CO$_2$H) is added to isopropyl acetate (400 μl). 10% Palladium on carbon (2 mg, 50% water wet, Degussa type E101 NE/W) is then added. Hydrogen gas at ambient pressure is applied to the mixture. The mixture is stirred at ambient temperature and pressure overnight. The mixture is then filtered over Celite and washed with isopropyl acetate (2×0.5 ml). The mixture is then concentrated in vacuo to give (2R,4S)-5-biphenyl-4-yl-4-tert-butoxycarbonylamino-2-methylpentanoic acid (1-a, R1=Boc, R2=H, R3=CO$_2$H) and (2S,4S)-5-biphenyl-4-yl-4-tert-butoxycarbonylamino-2-methylpentanoic acid (1-b, R1=Boc, R2=H, R3=CO$_2$H). Spectroscopic data as in Example 40, Method 1.

Method 3

20 mg (R)-5-Biphenyl-4-yl-4-tert-butoxycarbonylamino-2-methylenepentanoic acid (2-a, R1=Boc, R2=H, R3=CO$_2$H) is added to isopropyl acetate (400 μl). 10% Platinum on carbon (2 mg) is then added. Hydrogen gas at ambient pressure is applied to the mixture. The mixture is stirred at ambient temperature and pressure overnight. The mixture is then filtered over Celite and washed with isopropyl acetate (2×0.5 ml). The mixture is then concentrated in vacuo to give (2R,4S)-5-biphenyl-4-yl-4-tert-butoxycarbonylamino-2-methylpentanoic acid (1-a, R1=Boc, R2=H, R3=CO$_2$H) and (2S,4S)-5-biphenyl-4-yl-4-tert-butoxycarbonylamino-2-methylpentanoic acid (1-b, R1=Boc, R2=H, R3=CO$_2$H). Spectroscopic data as in Example 40, Method 1.

Method 4

20 mg (R)-5-Biphenyl-4-yl-4-tert-butoxycarbonylamino-2-methylenepentanoic acid (2-a, R1=Boc, R2=H, R3=CO$_2$H) is added to isopropyl acetate (400 μl). 5% Rhodium on carbon (2 mg) is then added. Hydrogen gas at ambient pressure is applied to the mixture. The mixture is stirred at ambient temperature and pressure overnight. The mixture is then filtered over Celite and washed with isopropyl acetate (2×0.5 ml). The mixture is then concentrated in vacuo to give (2R,4S)-5-biphenyl-4-yl-4-tert-butoxycarbonylamino-2-methylpentanoic acid (1-a, R1=Boc, R2=H, R3=CO$_2$H) and (2S,4S)-5-biphenyl-4-yl-4-tert-butoxycarbonylamino-2-methylpentanoic acid (1-b, R1=Boc, R2=H, R3=CO$_2$H). Spectroscopic data as in Example 40, Method 1.

Example 41

(R)-5-Biphenyl-4-yl-4-tert-butoxycarbonylamino-2-methylenepentanoic acid potassium salt (2-a, R1=Boc, R2=H, R3=CO$_2$K)

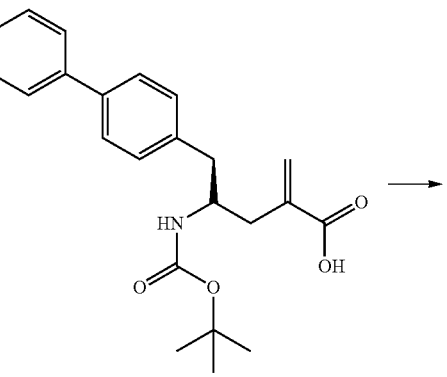

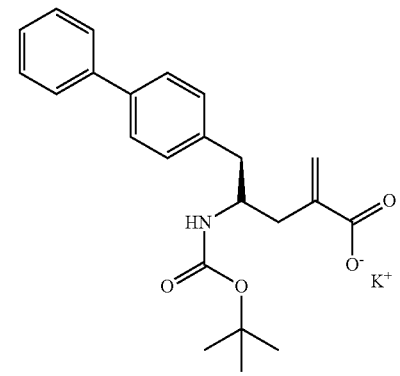

500 mg (R)-5-biphenyl-4-yl-4-tert-butoxycarbonylamino-2-methylenepentanoic acid (2-a, R1=Boc, R2=H, R3=CO$_2$H) is added to ethanol (5 ml) at room temperature. 2.6 ml of a 0.5 M Potassium hydroxide in ethanol solution is added to the mixture over a period of 5 minutes. The resulting mixture is stirred for 1 h at room temperature. The solvent is then removed under reduced pressure. Toluene (10 ml) is added to the mixture. The solvent is then removed under reduced pressure to give (R)-5-biphenyl-4-yl-4-tert-butoxycarbonylamino-2-methylenepentanoic acid potassium salt (2-a, R1=Boc, R2=H, R3=CO$_2$K). 1H NMR (DMSO): 1.35 (9H), 2.24-2.37 (2H), 2.67-2.84 (2H), 3.69-3.80 (1H), 5.04 (1H), 5.79 (1H), 7.12-7.17, 7.23-7.35, 7.42-7.46, 7.54-7.57, 7.62-7.67.

Example 42

(2R,4S)-5-Biphenyl-4-yl-4-tert-butoxycarbonylamino-2-methylpentanoic acid potassium salt (1-a, R1=Boc, R2=H, R3=CO$_2$K) and (2S,4S)-5-biphenyl-4-yl-4-tert-butoxycarbonylamino-2-methylpentanoic acid potassium salt (1-b, R1=Boc, R2=H, R3=CO$_2$K)

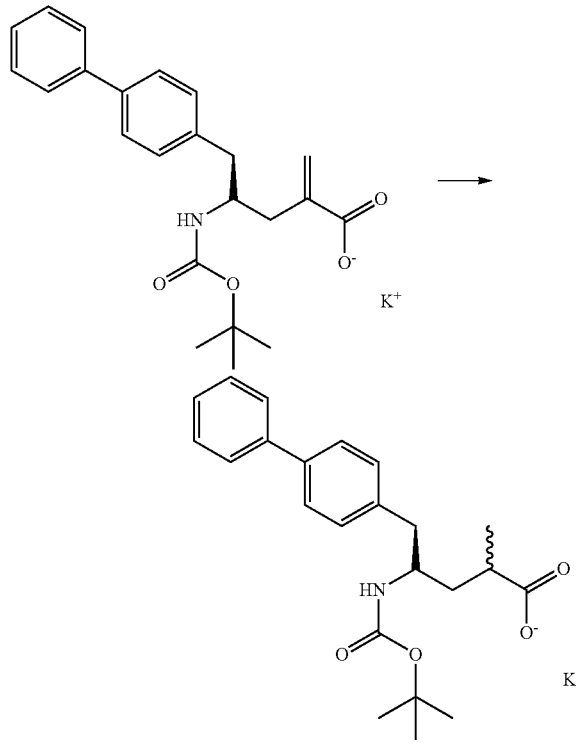

Method 1

100 mg (R)-5-Biphenyl-4-yl-4-tert-butoxycarbonylamino-2-methylenepentanoic acid potassium salt (2-a, R1=Boc, R2=H, R3=CO$_2$K) (prepared according to procedure in Example 42) is added to ethanol (1 ml). 10% Palladium on carbon (10 mg, 50% water wet, Degussa type E101 NE/W) is then added. Hydrogen gas at ambient pressure is applied to the mixture. The mixture is stirred at ambient temperature and pressure overnight. The mixture is then filtered over Celite and washed with ethanol (2×1 ml). The mixture is then concentrated in vacuo to give (2R,4S)-5-biphenyl-4-yl-4-tert-butoxycarbonylamino-2-methylpentanoic acid potassium salt (1-a, R1=Boc, R2=H, R3=CO$_2$K) and (2S,4S)-5-biphenyl-4-yl-4-tert-butoxycarbonylamino-2-methylpentanoic acid potassium salt (1-b, R1=Boc, R2=H, R3=CO$_2$K). 1H NMR (CDCl$_3$): 1.06-1.12, 1.31-1.36, 1.80-0.193, 2.25-2.49, 2.62-2.92, 3.74-4.08, 4.81 and 5.27, 6.20 and 6.54, 7.24-7.57.

Method 2

100 mg (R)-5-Biphenyl-4-yl-4-tert-butoxycarbonylamino-2-methylenepentanoic acid potassium salt (2-a, R1=Boc, R2=H, R3=CO$_2$K) (prepared according to procedure in Example 42) is added to isopropyl acetate (1 ml). 10% Palladium on carbon (10 mg, 50% water wet, Degussa type E101 NE/W) is then added. Hydrogen gas at ambient pressure is applied to the mixture. The mixture is stirred at ambient temperature and pressure overnight. The mixture is then filtered over Celite and washed with isopropyl acetate (2×1 ml). The mixture is then concentrated in vacuo to give (2R,4S)-5-biphenyl-4-yl-4-tert-butoxycarbonylamino-2-methylpentanoic acid potassium salt (1-a, R1=Boc, R2=H, R3=CO$_2$K) and (2S,4S)-5-biphenyl-4-yl-4-tert-butoxycarbonylamino-2-methylpentanoic acid potassium salt (1-b, R1=Boc, R2=H, R3=CO$_2$K). Spectroscopic data as in Example 42, Method 1.

Method 3

100 mg (R)-5-Biphenyl-4-yl-4-tert-butoxycarbonylamino-2-methylenepentanoic acid potassium salt (2-a, R1=Boc, R2=H, R3=CO$_2$K) (prepared according to procedure in Example 42) is added to isopropyl acetate (1 ml). 10% Platinum on carbon (10 mg) is then added. Hydrogen gas at ambient pressure is applied to the mixture. The mixture is stirred at ambient temperature and pressure overnight. The mixture is then filtered over Celite and washed with isopropyl acetate (2×1 ml). The mixture is then concentrated in vacuo to give (2R,4S)-5-biphenyl-4-yl-4-tert-butoxycarbonylamino-2-methylpentanoic acid potassium salt (1-a, R1=Boc, R2=H, R3=CO$_2$K) and (2S,4S)-5-biphenyl-4-yl-4-tert-butoxycarbonylamino-2-methylpentanoic acid potassium salt (1-b, R1=Boc, R2=H, R3=CO$_2$K). Spectroscopic data as in Example 42, Method 1.

Method 4

100 mg (R)-5-Biphenyl-4-yl-4-tert-butoxycarbonylamino-2-methylenepentanoic acid potassium salt (2-a, R1=Boc, R2=H, R3=CO$_2$K) (prepared according to procedure in Example 42) is added to isopropyl acetate (1 ml). 5% Rhodium on carbon (10 mg) is then added. Hydrogen gas at ambient pressure is applied to the mixture. The mixture is stirred at ambient temperature and pressure overnight. The mixture is then filtered over Celite and washed with isopropyl acetate (2×1 ml). The mixture is then concentrated in vacuo to give (2R,4S)-5-biphenyl-4-yl-4-tert-butoxycarbonylamino-2-methylpentanoic acid potassium salt (1-a, R1=Boc, R2=H, R3=CO$_2$K) and (2S,4S)-5-biphenyl-4-yl-4-tert-butoxycarbonylamino-2-methylpentanoic acid potassium salt (1-b, R1=Boc, R2=H, R3=CO$_2$K). Spectroscopic data as in Example 42, Method 1.

Example 43

(2R,4S)-5-Biphenyl-4-yl-4-tert-butoxycarbonylamino-2-methylpentanoic acid (1-a, R1=Boc, R2=H, R3=CO$_2$H), (2S,4S)-5-Biphenyl-4-yl-4-tert-butoxycarbonylamino-2-methylpentanoic acid (1-b, R1=Boc, R2=H, R3=CO$_2$H), (2R,4S)-5-Biphenyl-4-yl-4-tert-butoxycarbonylamino-2-methylpentanoic acid salt (1-a, R1=Boc, R2=H, R3=CO$_2^-$) or (2S,4S)-5-Biphenyl-4-yl-4-tert-butoxycarbonylamino-2-methylpentanoic acid salt (1-b, R1=Boc, R2=H, R3=CO$_2^-$)

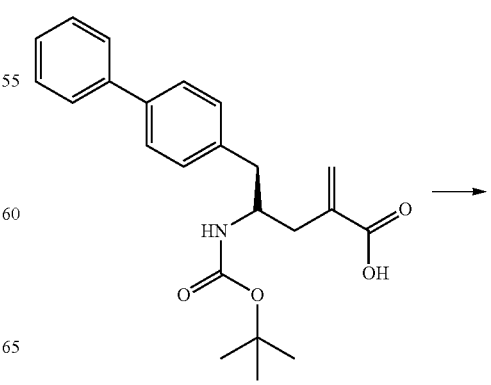

-continued

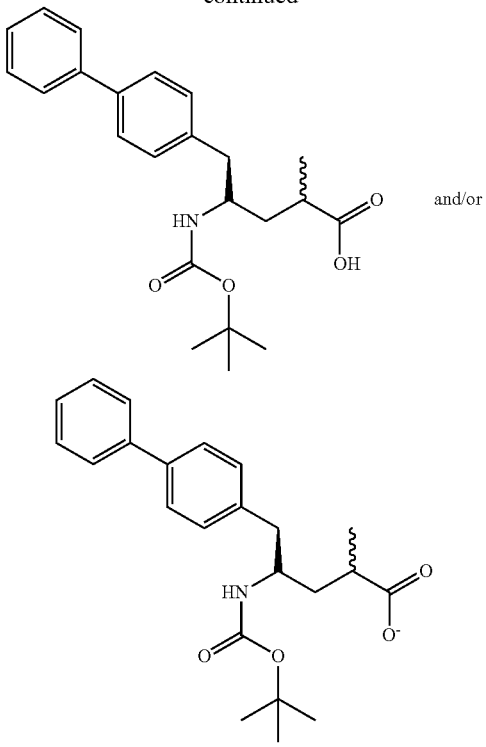

General Procedure 1

A mixture of Organometallic Catalyst (C) and (R)-5-biphenyl-4-yl-4-tert-butoxycarbonylamino-2-methylenepentanoic acid (2-a, R1=Boc, R2=H, R3=CO$_2$H) is added to the Solvent (S) (volume and identity of solvent given in the Table of Example 43) to achieve the concentration of 2-a (R1=Boc, R2=H, R3=CO$_2$H) given in the Table of Example 43 and an S/C ratio as given in the Table of Example 43.

Optionally and according to the Table of Example 43, an Additive (D) may be added at this stage. The identity and amount of the additive is given in the Table of Example 43. The amount of additive to be used is relative to the moles of (R)-5-biphenyl-4-yl-4-tert-butoxycarbonylamino-2-methylenepentanoic acid (2-a, R1=Boc, R2=H, R3=CO$_2$H) used.

Hydrogen has is then applied to the vessel containing the mixture (temperature, time and pressure are given in the Table of Example 43).

The volatiles are removed under reduced pressure and the resulting residue analysed by hplc to determine the ratio of (1-a, R1=Boc, R2=H, R3=CO$_2$H) or (1-a, R1=Boc, R2=H, R3=CO$_2$⁻) to (1-b, R1=Boc, R2=H, R3=CO$_2$H) or (1-b, R1=Boc, R2=H, R3=CO$_2$⁻).

General Procedure 2

Solvent (S) (volume and identity of solvent given in the Table of Example 43) is added to a mixture of the Organometallic Complex (A) and the Chiral Ligand (L). The mixture is stirred for 0.5 h at room temperature. (R)-5-Biphenyl-4-yl-4-tert-butoxycarbonylamino-2-methylenepentanoic acid (2-a, R1=Boc, R2=H, R3=CO$_2$H) in a solvent (volume and identity of solvent given in the Table of Example 43) is then added. The final concentration of 2-a (R1=Boc, R2=H, R3=CO$_2$H) is given in the Table of Example 43. The S/C ratio is given in the Table of Example 43. The ratio of Chiral Ligand per atom of metal within the Organometallic Complex is given in the Table of Example 43.

Hydrogen gas is then applied to the vessel containing the mixture (temperature, time and pressure is given in the Table of Example 43).

The volatiles are removed under reduced pressure and the resulting residue analysed by hplc to determine the ratio of (1-a, R1=Boc, R2=H, R3=CO$_2$H) or (1-a, R1=Boc, R2=H, R3=CO$_2$⁻) to (1-b, R1=Boc, R2=H, R3=CO$_2$H) or (1-b, R1=Boc, R2=H, R3=CO$_2$⁻).

General Procedure 3

(R)-5-Biphenyl-4-yl-4-tert-butoxycarbonylamino-2-methylenepentanoic acid (2-a, R1=Boc, R2=H, R3=CO$_2$H) in a Solvent (S) (0.244 ml, identity of solvent given in the Table of Example 43) is added to the vessel containing the Organometallic Catalyst (C). Further solvent (identity given in the Table of Example 43) is added to give a final concentration of 2-a ((R1=Boc, R2=H, R3=CO$_2$H) given in the Table of Example 43. The S/C ratio is given in the Table of Example 43.

Optionally and according to the Table of Example 43, an Additive (D) may be added at this stage. The identity and amount of the additive is given in the Table of Example 43. The amount of additive to be used is relative to the moles of (R)-5-biphenyl-4-yl-4-tert-butoxycarbonylamino-2-methylenepentanoic acid (2-a, R1=Boc, R2=H, R3=CO$_2$H) used.

The mixture is then stirred at the temperature and pressure given in the Table of Example 43 for a period of time also indicated in the Table of Example 43.

The crude reaction solutions are analysed by hplc to determine the ratio of (1-a, R1=Boc, R2=H, R3=CO$_2$H) or (1-a, R1=Boc, R2=H, R3=CO$_2$⁻) to (1-b, R1=Boc, R2=H, R3=CO$_2$H) or (1-b, R1=Boc, R2=H, R3=CO$_2$⁻).

General Procedure 4

The Organometallic Complex (A) and Chiral Ligand (L) are added to a mixture of ethanol (0.041 ml) and dichloroethane (0.135 ml). The mixture is stirred for 0.5 h. The solvent is then removed under reduced pressure. (R)-5-Biphenyl-4-yl-4-tert-butoxycarbonylamino-2-methylenepentanoic acid (2-a, R1=Boc, R2=H, R3=CO$_2$H) in a Solvent (S) (0.244 ml, identity of solvent given in the Table of Example 43) is added to the vessel containing the Organometallic Complex (A) and Chiral Ligand (L). Further solvent (identity given in the Table of Example 43) is added to give the final concentration of 2-a (R1=Boc, R2=H, R3=CO$_2$H) shown in the Table of Example 43. The S/C ratio is given in the Table of Example 43. The ratio of Chiral Ligand per atom of metal within the Organometallic Complex is given in the Table of Example 43.

Optionally and according to the Table of Example 43, an Additive (D) may be added at this stage. The identity and amount of the additive is given in the Table of Example 43. The amount of additive to be used is relative to the moles of (R)-5-biphenyl-4-yl-4-tert-butoxycarbonylamino-2-methylenepentanoic acid (2-a, R1=Boc, R2=H, R3=CO$_2$H) used.

Hydrogen gas is the applied to the vessel containing the mixture (temperature, time and pressure is given in the Table of Example 43).

The crude reaction solutions are analysed by hplc to determine the ratio of (1-a, R1=Boc, R2=H, R3=CO$_2$H) or (1-a, R1=Boc, R2=H, R3=CO$_2$⁻) to (1-b, R1=Boc, R2=H, R3=CO$_2$H) or (1-b, R1=Boc, R2=H, R3=CO$_2$⁻).

General Procedure 5

Solvent (S) (volume and identity of solvent given in the Table of Example 43) is added to a mixture of the Organometallic Complex (A) and the Chiral Ligand (L) in Vessel A. The mixture is stirred for 15 min at room temperature.

Solvent (S) (volume and identity of solvent given in the Table of Example 43) is added to (R)-5-biphenyl-4-yl-4-tert-butoxycarbonylamino-2-methylenepentanoic acid (2-a, R1=Boc, R2=H, R3=CO$_2$H) in Vessel B.

The contents of Vessel A and Vessel B are transferred to Vessel C (empty). The final concentration of 2-a (R1=Boc, R2=H, R3=CO$_2$H) is given in the Table of Example 43. The S/C ratio is given in the Table of Example 43. The ratio of Chiral Ligand per atom of metal within the Organometallic Complex is given in the Table of Example 43.

Hydrogen gas is then applied to Vessel C (temperature, time and pressure is given in the Table of Example 43).

The crude reaction solutions are analysed by hplc to determine the ratio of (1-a, R1=Boc, R2=H, R3=CO$_2$H) or (1-a, R1=Boc, R2=H, R3=CO$_2^-$) to (1-b, R1=Boc, R2=H, R3=CO$_2$H) or (1-b, R1=Boc, R2=H, R3=CO$_2^-$).

General Procedure 6

Solvent (S) (volume and identity of solvent given in the Table of Example 43) is added to a mixture of the Organometallic Complex (A) and the Chiral Ligand (L) in Vessel A. The mixture is stirred for 0.5 h at room temperature.

The mixture is transferred to Vessel B containing (R)-5-biphenyl-4-yl-4-tert-butoxycarbonylamino-2-methylenepentanoic acid (2-a, R1=Boc, R2=H, R3=CO$_2$H) and optionally (as indicated in the Table of Example 43),4-diazobicyclo[2.2.2]octane (amount given in the Table of Example 43). The amount of 1,4-diazobicyclo[2.2.2]octane used is relative to the moles of (R)-5-biphenyl-4-yl-4-tert-butoxycarbonylamino-2-methylenepentanoic acid (2-a, R1=Boc, R2=H, R3=CO$_2$H) used. The final concentration of 2-a (R1=Boc, R2=H, R3=CO$_2$H) is given in the Table of Example 43. The S/C ratio is given in the Table of Example 43. The ratio of Chiral Ligand per atom of metal within the Organometallic Complex is given in the Table of Example 43.

Optionally and according to the Table of Example 43, methanesulphonic acid may be added at this stage to Vessel B. The amount of methanesulphonic acid used is relative to the moles of (R)-5-biphenyl-4-yl-4-tert-butoxycarbonylamino-2-methylenepentanoic acid (2-a, R1=Boc, R2=H, R3=CO$_2$H) used and is given in the Table of Example 43.

Hydrogen gas is then applied to Vessel B and its contents at the temperature, time and pressure given in the Table of Example 43.

The crude reaction solutions are analysed by hplc to determine the ratio of (1-a, R1=Boc, R2=H, R3=CO$_2$H) or (1-a, R1=Boc, R2=H, R3=CO$_2^-$) to (1-b, R1=Boc, R2=H, R3=CO$_2$H) or (1-b, R1=Boc, R2=H, R3=CO$_2^-$).

General Procedure 7

Solvent (S) (volume and identity of solvent as given in the Table of Example 43) is added to a mixture of the Organometallic Complex (A) and the Chiral Ligand (L) in Vessel A. Hydrogen gas (1 bar) is applied to Vessel A and the mixture stirred for 5 min at ambient temperature.

Solvent (volume and identity of solvent given in the Table of Example 43) is added to (R)-5-biphenyl-4-yl-4-tert-butoxycarbonylamino-2-methylenepentanoic acid (2-a, R1=Boc, R2=H, R3=CO$_2$H) in Vessel B.

The contents of Vessel A and Vessel B are transferred to Vessel C (empty). The final concentration of 2-a (R1=Boc, R2=H, R3=CO$_2$H) is given in the Table of Example 43. The S/C ratio is given in the Table of Example 43. The ratio of Chiral Ligand per atom of metal within the Organometallic Complex is given in the Table of Example 43.

Hydrogen gas is then applied to Vessel C and its contents (temperature, time and pressure is given in the Table of Example 43.

The crude reaction solutions are analysed by hplc to determine the ratio of (1-a, R1=Boc, R2=H, R3=CO$_2$H) or (1-a, R1=Boc, R2=H, R3=CO$_2^-$) to (1-b, R1=Boc, R2=H, R3=CO$_2$H) or (1-b, R1=Boc, R2=H, R3=CO$_2^-$).

General Procedure 8

Solvent (S) (volume and identity of solvent given in the Table of Example 43) is added to a mixture of the Organometallic Complex (A) and the Chiral Ligand (L) in Vessel A. The mixture is stirred for 15 min at room temperature.

Solvent (volume and identity of solvent given in the Table of Example 43) is added to (R)-5-biphenyl-4-yl-4-tert-butoxycarbonylamino-2-methylenepentanoic acid (2-a, R1=Boc, R2=H, R3=CO$_2$H) in Vessel B. The mixture is heated at 70° C. for 0.5 h The contents of Vessel A and Vessel B are transferred to Vessel C (empty). The final concentration of 2-a (R1=Boc, R2=H, R3=CO$_2$H) is given in the Table of Example 43. The S/C ratio is given in the Table of Example 43. The ratio of Chiral Ligand per atom of metal within the Organometallic Complex is given in the Table of Example 43.

Hydrogen gas is then applied to Vessel C (temperature, time and pressure is given in the Table of Example 43.

The crude reaction solutions are analysed by hplc to determine the ratio of (1-a, R1=Boc, R2=H, R3=CO$_2$H) or (1-a, R1=Boc, R2=H, R3=CO$_2^-$) to (1-b, R1=Boc, R2=H, R3=CO$_2$H) or (1-b, R1=Boc, R2=H, R3=CO$_2^-$).

HPLC Method 1 (Reactions Performed According to Example 43, General Procedures 1 or 2).

Column: Chiralpak QD-AX; 150×4.6 mm; 5 µm. Mobile Phase A: Methanol, 0.05% AcOH (v/v), 0.01% NH$_4$OAc (m/v). Isocratic: 0 min (100%A); 15 min (100%A). Flow rate 0.8 ml min$^{-1}$. Wavelength: 254 nm. Column temperature: ambient (20-25° C.).

Retention Times:
(1-a, R1=Boc, R2=H, R3=CO$_2$H): 8.3 min
(1-b, R1=Boc, R2=H, R3=CO$_2$H): 5.0 min
(2-a, R1=Boc, R2=H, R3=CO$_2$H): 5.7 min HPLC Method 2 (Reactions Performed According to Example 43, General Procedures 3, 4, 5, 6, 7, or 8).

Column: Chiralpak QD-AX; 150×4.6 mm; 5 µm. Mobile Phase A: Methanol, 0.05% AcOH (v/v), 0.01% NH$_4$OAc (m/v). Isocratic: 0 min (100% A); 20 min (100% A). Flow rate: 0.8 ml min$^{-1}$. Wavelength: 220 nm. Column temperature: 25° C.

Retention Times:
(1-a, R1=Boc, R2=H, R3=CO$_2$H): 5.0 min
(1-b, R1=Boc, R2=H, R3=CO$_2$H): 5.8 min
(2-a, R1=Boc, R2=H, R3=CO$_2$H): 8.4 min Table of Example 43:

| Method | General Procedure | Transition Metal Catalyst Organometallic Catalyst (C) | Organometallic Complex (A) | Chiral Ligand (L) | Ratio of Ligand per atom of metal within the Organometallic Complex | Ratio 2-a (R1 = Boc, R2 = H, R3 = CO$_2$H) to Transition Metal Catalyst (S/C ratio) | Amount of 2-a (R1 = Boc, R2 = H, R3 = CO$_2$H) (mmol) | Solvent (S) | Solvent Volume (2-a, R1 = Boc, R2 = H, R3 = CO$_2$H) (ml) |
|---|---|---|---|---|---|---|---|---|---|
| 1 | 4 | — | A-2 | L-15 | 1.20 | 25 | 0.042 | S-3 | — |
| 2 | 3 | C-1 | — | — | — | 25 | 0.042 | S-5 | — |
| 3 | 1 | C-65 | — | — | — | 100 | 0.3 | S-1 | — |
| 4 | 3 | C-1 | — | — | — | 25 | 0.042 | S-1 | — |
| 5 | 6 | — | A-2 | L-48 | 1.05 | 500 | 0.66 | S-12 | 0 |

-continued

Table of Example 43:

| | | | | | | | | | |
|---|---|---|---|---|---|---|---|---|---|
| 6 | 4 | — | A-5 | L-36 | 1.20 | 100 | 0.042 | S-1 | — |
| 7 | 4 | — | A-4 | L-2 | 1.20 | 25 | 0.042 | S-1 | — |
| 8 | 1 | C-27 | — | — | — | 1000 | 0.6 | S-1 | — |
| 9 | 4 | — | A-2 | L-25 | 1.20 | 25 | 0.042 | S-1 | — |
| 10 | 1 | C-48 | — | — | — | 100 | 0.3 | S-1 | — |
| 11 | 6 | — | A-2 | L-48 | 1.05 | 2500 | 1.31 | S-1 | 0 |
| 12 | 1 | C-27 | — | — | — | 100 | 0.3 | S-1 | — |
| 13 | 1 | C-5 | — | — | — | 100 | 0.3 | S-1 | — |
| 14 | 5 | — | A-2 | L-28 | 1.05 | 2500 | 2.62 | S-1 | 16 |
| 15 | 4 | — | A-1 | L-16 | 1.20 | 25 | 0.042 | S-1 | — |
| 16 | 4 | — | A-2 | L-29 | 1.20 | 25 | 0.042 | S-5 | — |
| 17 | 1 | C-27 | — | — | — | 1000 | 0.6 | S-1 | — |
| 18 | 1 | C-27 | — | — | — | 1000 | 0.6 | S-1 | — |
| 19 | 4 | — | A-5 | L-48 | 1.20 | 25 | 0.042 | S-1 | — |
| 20 | 1 | C-27 | — | — | — | 100 | 0.3 | S-1 | — |
| 21 | 4 | — | A-3 | L-12 | 1.20 | 25 | 0.042 | S-1 | — |
| 22 | 1 | C-41 | — | — | — | 100 | 0.3 | S-1 | — |
| 23 | 4 | — | A-5 | L-17 | 1.20 | 25 | 0.042 | S-1 | — |
| 24 | 1 | C-17 | — | — | — | 100 | 0.3 | S-1 | — |
| 25 | 4 | — | A-2 | L-27 | 1.20 | 25 | 0.042 | S-1 | — |
| 26 | 4 | — | A-5 | L-14 | 1.20 | 25 | 0.042 | S-1 | — |
| 27 | 1 | C-38 | — | — | — | 100 | 0.3 | S-1 | — |
| 28 | 4 | — | A-2 | L-42 | 1.20 | 25 | 0.042 | S-1 | — |
| 29 | 1 | C-27 | — | — | — | 2500 | 0.79 | S-8 | — |
| 30 | 3 | C-3 | — | — | — | 25 | 0.042 | S-1 | — |
| 31 | 1 | C-19 | — | — | — | 100 | 0.3 | S-1 | — |
| 32 | 4 | — | A-5 | L-12 | 1.20 | 25 | 0.042 | S-1 | — |
| 33 | 4 | — | A-2 | L-21 | 1.20 | 25 | 0.042 | S-1 | — |
| 34 | 5 | — | A-5 | L-36 | 1.05 | 2500 | 1.31 | S-1 | 8 |
| 35 | 1 | C-24 | — | — | — | 100 | 0.3 | S-1 | — |
| 36 | 4 | — | A-1 | L-51 | 1.20 | 25 | 0.042 | S-1 | — |
| 37 | 1 | C-20 | — | — | — | 100 | 0.3 | S-1 | — |
| 38 | 1 | C-27 | — | — | — | 1000 | 0.6 | S-1 | — |
| 39 | 1 | C-10 | — | — | — | 100 | 0.3 | S-1 | — |
| 40 | 4 | — | A-2 | L-11 | 1.20 | 25 | 0.042 | S-1 | — |
| 41 | 4 | — | A-2 | L-26 | 1.20 | 25 | 0.042 | S-1 | — |
| 42 | 2 | — | A-7 | L-106 | 1.13 | 100 | 0.3 | S-1 | 2 |
| 43 | 4 | — | A-2 | L-6 | 1.20 | 25 | 0.042 | S-1 | — |
| 44 | 4 | — | A-2 | L-1 | 1.20 | 25 | 0.042 | S-1 | — |
| 45 | 4 | — | A-5 | L-11 | 1.20 | 25 | 0.042 | S-1 | — |
| 46 | 1 | C-39 | — | — | — | 100 | 0.3 | S-1 | — |
| 47 | 1 | C-27 | — | — | — | 1000 | 0.79 | S-1 | — |
| 48 | 6 | — | A-2 | L-48 | 1.05 | 500 | 0.66 | S-2 | 0 |
| 49 | 1 | C-27 | — | — | — | 500 | 0.79 | S-9 | — |
| 50 | 3 | C-1 | — | — | — | 25 | 0.042 | S-2 | — |
| 51 | 4 | — | A-2 | L-10 | 1.20 | 25 | 0.042 | S-1 | — |
| 52 | 4 | — | A-5 | L-6 | 1.20 | 25 | 0.042 | S-6 | — |
| 53 | 5 | — | A-2 | L-48 | 1.05 | 5000 | 2.62 | S-1 | 16 |
| 54 | 5 | — | A-5 | L-36 | 1.05 | 100 | 1.31 | S-1 | 8 |
| 55 | 4 | — | A-2 | L-3 | 1.20 | 25 | 0.042 | S-1 | — |
| 56 | 6 | — | A-5 | L-33 | 1.05 | 25 | 0.5 | S-1 | 0 |
| 57 | 4 | — | A-4 | L-48 | 1.20 | 25 | 0.042 | S-1 | — |
| 58 | 6 | — | A-2 | L-48 | 1.05 | 500 | 0.66 | S-8 | 0 |
| 59 | 4 | — | A-2 | L-27 | 1.20 | 25 | 0.042 | S-1 | — |
| 60 | 4 | — | A-2 | L-12 | 1.20 | 25 | 0.042 | S-1 | — |
| 61 | 4 | — | A-2 | L-16 | 1.20 | 25 | 0.042 | S-3 | — |
| 62 | 1 | C-64 | — | — | — | 100 | 0.3 | S-1 | — |
| 63 | 1 | C-27 | — | — | — | 2500 | 0.79 | S-1 | — |
| 64 | 6 | — | A-2 | L-48 | 1.10 | 500 | 2.62 | S-1 | 0 |
| 65 | 5 | — | A-2 | L-48 | 1.05 | 2500 | 2.62 | S-1 | 16 |
| 66 | 1 | C-44 | — | — | — | 100 | 0.3 | S-1 | — |
| 67 | 4 | — | A-2 | L-17 | 1.20 | 25 | 0.042 | S-1 | — |
| 68 | 5 | — | A-2 | L-48 | 1.05 | 2500 | 2.62 | S-1 | 16 |
| 69 | 1 | C-27 | — | — | — | 2500 | 0.79 | S-8 | — |
| 70 | 1 | C-43 | — | — | — | 500 | 0.3 | S-1 | — |
| 71 | 4 | — | A-5 | L-21 | 1.20 | 25 | 0.042 | S-1 | — |
| 72 | 4 | — | A-2 | L-50 | 1.20 | 25 | 0.042 | S-5 | — |
| 73 | 1 | C-13 | — | — | — | 100 | 0.3 | S-9 | — |
| 74 | 1 | C-44 | — | — | — | 100 | 0.3 | S-1 | — |
| 75 | 5 | — | A-2 | L-48 | 1.10 | 5000 | 21 | S-1 | 75 |
| 76 | 1 | C-40 | — | — | — | 1000 | 0.6 | S-1 | — |
| 77 | 6 | — | A-2 | L-48 | 1.05 | 500 | 0.66 | S-1 | 0 |
| 78 | 6 | — | A-2 | L-48 | 1.05 | 500 | 1.31 | S-1 | 0 |
| 79 | 5 | — | A-2 | L-28 | 1.05 | 2500 | 2.62 | S-1 | 16 |
| 80 | 4 | — | A-4 | L-19 | 1.20 | 25 | 0.042 | S-1 | — |
| 81 | 4 | — | A-5 | L-30 | 1.20 | 25 | 0.042 | S-1 | — |
| 82 | 1 | C-7 | — | — | — | 100 | 0.3 | S-9 | — |
| 83 | 4 | — | A-4 | L-25 | 1.20 | 25 | 0.042 | S-1 | — |

-continued

Table of Example 43:

| 84 | 1 | — | A-6 | — | — | 100 | 0.3 | S-9 | — |
| --- | --- | --- | --- | --- | --- | --- | --- | --- | --- |
| 85 | 3 | C-1 | — | — | — | 100 | 0.042 | S-1 | — |
| 86 | 4 | — | A-2 | L-16 | 1.20 | 25 | 0.042 | S-1 | — |
| 87 | 1 | C-14 | — | — | — | 100 | 0.3 | S-1 | — |
| 88 | 5 | — | A-2 | L-48 | 1.05 | 2500 | 2.62 | S-1 | 16 |
| 89 | 6 | — | A-2 | L-48 | 1.10 | 500 | 2.62 | S-1 | 0 |
| 90 | 1 | C-27 | — | — | — | 2500 | 2.1 | S-1 | — |
| 91 | 1 | C-65 | — | — | — | 100 | 0.3 | S-1 | — |
| 92 | 4 | — | A-2 | L-29 | 1.20 | 25 | 0.042 | S-3 | — |
| 93 | 1 | C-37 | — | — | — | 100 | 0.3 | S-1 | — |
| 94 | 4 | — | A-3 | L-42 | 1.20 | 25 | 0.042 | S-1 | — |
| 95 | 1 | C-28 | — | — | — | 100 | 0.3 | S-1 | — |
| 96 | 4 | — | A-3 | L-32 | 1.20 | 25 | 0.042 | S-1 | — |
| 97 | 1 | C-27 | — | — | — | 1000 | 0.79 | S-8 | — |
| 98 | 4 | — | A-2 | L-51 | 1.20 | 25 | 0.042 | S-1 | — |
| 99 | 1 | C-7 | — | — | — | 100 | 0.3 | S-1 | — |
| 100 | 1 | C-7 | — | — | — | 100 | 0.3 | S-9 | — |
| 101 | 3 | C-2 | — | — | — | 25 | 0.042 | S-3 | — |
| 102 | 1 | C-27 | — | — | — | 1000 | 0.79 | S-10 | — |
| 103 | 5 | — | A-2 | L-48 | 1.05 | 100 | 1.31 | S-1 | 8 |
| 104 | 4 | — | A-1 | L-27 | 1.20 | 25 | 0.042 | S-1 | — |
| 105 | 4 | — | A-5 | L-36 | 1.20 | 25 | 0.042 | S-3 | — |
| 106 | 4 | — | A-5 | L-43 | 1.20 | 25 | 0.042 | S-1 | — |
| 107 | 1 | C-43 | — | — | — | 100 | 0.3 | S-1 | — |
| 108 | 4 | — | A-2 | L-5 | 1.20 | 25 | 0.042 | S-1 | — |
| 109 | 4 | — | A-3 | L-31 | 1.20 | 25 | 0.042 | S-1 | — |
| 110 | 1 | C-45 | — | — | — | 100 | 0.3 | S-9 | — |
| 111 | 4 | — | A-5 | L-42 | 1.20 | 25 | 0.042 | S-1 | — |
| 112 | 4 | — | A-2 | L-52 | 1.20 | 25 | 0.042 | S-1 | — |
| 113 | 5 | — | A-2 | L-48 | 1.10 | 5000 | 21 | S-1 | 100 |
| 114 | 4 | — | A-4 | L-1 | 1.20 | 25 | 0.042 | S-1 | — |
| 115 | 4 | — | A-2 | L-36 | 1.20 | 25 | 0.042 | S-1 | — |
| 116 | 1 | C-18 | — | — | — | 100 | 0.3 | S-1 | — |
| 117 | 4 | — | A-2 | L-22 | 1.20 | 25 | 0.042 | S-4 | — |
| 118 | 4 | — | A-4 | L-42 | 1.20 | 25 | 0.042 | S-1 | — |
| 119 | 3 | C-2 | — | — | — | 25 | 0.042 | S-2 | — |
| 120 | 3 | C-4 | — | — | — | 25 | 0.042 | S-1 | — |
| 121 | 1 | C-8 | — | — | — | 100 | 0.3 | S-1 | — |
| 122 | 4 | — | A-5 | L-24 | 1.20 | 25 | 0.042 | S-1 | — |
| 123 | 1 | C-56 | — | — | — | 100 | 0.3 | S-1 | — |
| 124 | 1 | C-41 | — | — | — | 100 | 0.3 | S-1 | — |
| 125 | 4 | — | A-2 | L-31 | 1.20 | 25 | 0.042 | S-1 | — |
| 126 | 4 | — | A-5 | L-3 | 1.20 | 25 | 0.042 | S-1 | — |
| 127 | 4 | — | A-2 | L-37 | 1.20 | 25 | 0.042 | S-1 | — |
| 128 | 1 | C-27 | — | — | — | 2500 | 0.79 | S-1 | — |
| 129 | 4 | — | A-2 | L-16 | 1.20 | 25 | 0.042 | S-2 | — |
| 130 | 6 | — | A-2 | L-28 | 1.05 | 500 | 0.66 | S-1 | 0 |
| 131 | 1 | C-42 | — | — | — | 100 | 0.3 | S-1 | — |
| 132 | 4 | — | A-5 | L-6 | 1.20 | 100 | 0.042 | S-1 | — |
| 133 | 1 | C-21 | — | — | — | 100 | 0.3 | S-1 | — |
| 134 | 5 | — | A-2 | L-48 | 1.10 | 2500 | 21 | 5-1 | 60 |
| 135 | 4 | — | A-3 | L-19 | 1.20 | 25 | 0.042 | S-1 | — |
| 136 | 4 | — | A-5 | L-6 | 1.20 | 25 | 0.042 | S-2 | — |
| 137 | 4 | — | A-5 | L-48 | 1.20 | 25 | 0.042 | S-1 | — |
| 138 | 1 | C-40 | — | — | — | 100 | 0.3 | S-1 | — |
| 139 | 3 | C-2 | — | — | — | 25 | 0.042 | S-6 | — |
| 140 | 4 | — | A-2 | L-18 | 1.20 | 25 | 0.042 | S-1 | — |
| 141 | 4 | — | A-1 | L-12 | 1.20 | 25 | 0.042 | S-1 | — |
| 142 | 4 | — | A-2 | L-22 | 1.20 | 25 | 0.042 | S-3 | — |
| 143 | 1 | C-27 | — | — | — | 2500 | 2.1 | S-8 | — |
| 144 | 1 | C-56 | — | — | — | 100 | 0.3 | S-1 | — |
| 145 | 1 | C-27 | — | — | — | 500 | 0.79 | S-10 | — |
| 146 | 4 | — | A-5 | L-49 | 1.20 | 25 | 0.042 | S-1 | — |
| 147 | 3 | C-2 | — | — | — | 25 | 0.042 | S-1 | — |
| 148 | 4 | — | A-5 | L-35 | 1.20 | 25 | 0.042 | S-1 | — |
| 149 | 1 | C-12 | — | — | — | 100 | 0.3 | S-1 | — |
| 150 | 1 | C-55 | — | — | — | 100 | 0.3 | S-1 | — |
| 151 | 3 | C-2 | — | — | — | 25 | 0.042 | S-7 | — |
| 152 | 1 | C-50 | — | — | — | 100 | 0.3 | S-1 | — |
| 153 | 1 | C-49 | — | — | — | 100 | 0.3 | S-1 | — |
| 154 | 1 | C-47 | — | — | — | 100 | 0.3 | S-1 | — |
| 155 | 4 | — | A-2 | L-48 | 1.20 | 25 | 0.042 | S-1 | — |
| 156 | 4 | — | A-4 | L-5 | 1.20 | 25 | 0.042 | S-1 | — |
| 157 | 1 | C-18 | — | — | — | 100 | 0.3 | S-10 | — |
| 158 | 1 | C-7 | — | — | — | 100 | 0.3 | S-1 | — |
| 159 | 4 | — | A-3 | L-17 | 1.20 | 25 | 0.042 | S-1 | — |
| 160 | 1 | C-6 | — | — | — | 100 | 0.3 | S-1 | — |
| 161 | 1 | C-15 | — | — | — | 100 | 0.3 | S-1 | — |

-continued

Table of Example 43:

| | | | | | | | | | |
|---|---|---|---|---|---|---|---|---|---|
| 162 | 5 | — | A-2 | L-48 | 1.05 | 500 | 1.31 | S-1 | 8 |
| 163 | 5 | — | A-2 | L-48 | 1.10 | 2500 | 21 | S-1 | 70 |
| 164 | 5 | — | A-2 | L-48 | 1.10 | 2500 | 11.8 | S-1 | 60 |
| 165 | 4 | — | A-5 | L-34 | 1.20 | 25 | 0.042 | S-1 | — |
| 166 | 1 | C-27 | — | — | — | 1000 | 0.79 | S-1 | — |
| 167 | 4 | — | A-2 | L-48 | 1.20 | 100 | 0.042 | S-1 | — |
| 168 | 1 | C-33 | — | — | — | 100 | 0.3 | S-1 | — |
| 169 | 1 | C-27 | — | — | — | 2500 | 0.79 | S-1 | — |
| 170 | 3 | C-4 | — | — | — | 25 | 0.042 | S-1 | — |
| 171 | 1 | C-43 | — | — | — | 100 | 0.3 | S-1 | — |
| 172 | 1 | C-7 | — | — | — | 100 | 0.3 | S-11 | — |
| 173 | 4 | — | A-5 | L-18 | 1.20 | 25 | 0.042 | S-1 | — |
| 174 | 4 | — | A-2 | L-32 | 1.20 | 25 | 0.042 | S-1 | — |
| 175 | 5 | — | A-2 | L-48 | 1.05 | 5000 | 2.62 | S-1 | 16 |
| 176 | 1 | C-25 | — | — | — | 100 | 0.3 | S-1 | — |
| 177 | 4 | — | A-5 | L-9 | 1.20 | 25 | 0.042 | S-1 | — |
| 178 | 4 | — | A-4 | L-12 | 1.20 | 25 | 0.042 | S-1 | — |
| 179 | 3 | C-1 | — | — | — | 25 | 0.042 | S-7 | — |
| 180 | 1 | C-27 | — | — | — | 500 | 0.3 | S-1 | — |
| 181 | 5 | — | A-2 | L-28 | 1.05 | 500 | 1.31 | S-1 | 8 |
| 182 | 4 | — | A-5 | L-26 | 1.20 | 25 | 0.042 | S-1 | — |
| 183 | 1 | C-25 | — | — | — | 100 | 0.3 | S-1 | — |
| 184 | 1 | C-27 | — | — | — | 1000 | 0.79 | S-9 | — |
| 185 | 1 | C-40 | — | — | — | 1000 | 0.6 | S-1 | — |
| 186 | 1 | C-23 | — | — | — | 100 | 0.3 | S-1 | — |
| 187 | 5 | — | A-2 | L-48 | 1.05 | 100 | 1.31 | S-1 | 8 |
| 188 | 6 | — | A-2 | L-48 | 1.05 | 2500 | 1.31 | S-13 | 0 |
| 189 | 1 | C-18 | — | — | — | 100 | 0.3 | S-10 | — |
| 190 | 1 | C-40 | — | — | — | 500 | 0.3 | S-2 | — |
| 191 | 1 | C-63 | — | — | — | 100 | 0.3 | S-1 | — |
| 192 | 5 | — | A-5 | L-36 | 1.05 | 500 | 1.31 | S-1 | 8 |
| 193 | 1 | C-43 | — | — | — | 100 | 0.3 | S-1 | — |
| 194 | 5 | — | A-2 | L-28 | 1.05 | 100 | 1.31 | S-1 | 8 |
| 195 | 1 | C-7 | — | — | — | 100 | 0.3 | S-11 | — |
| 196 | 1 | C-27 | — | — | — | 1000 | 0.6 | S-1 | — |
| 197 | 1 | C-27 | — | — | — | 1000 | 0.79 | S-8 | — |
| 198 | 4 | — | A-2 | L-44 | 1.20 | 25 | 0.042 | S-1 | — |
| 199 | 4 | — | A-4 | L-15 | 1.20 | 25 | 0.042 | S-1 | — |
| 200 | 4 | — | A-2 | L-34 | 1.20 | 25 | 0.042 | S-1 | — |
| 201 | 5 | — | A-5 | L-36 | 1.05 | 100 | 1.31 | S-1 | 8 |
| 202 | 1 | C-40 | — | — | — | 1000 | 0.6 | S-1 | — |
| 203 | 5 | — | A-2 | L-28 | 1.05 | 2500 | 2.62 | S-1 | 8 |
| 204 | 1 | C-7 | — | — | — | 100 | 0.3 | S-10 | — |
| 205 | 1 | C-45 | — | — | — | 100 | 0.3 | S-1 | — |
| 206 | 4 | — | A-2 | L-16 | 1.20 | 25 | 0.042 | S-4 | — |
| 207 | 4 | — | A-2 | L-13 | 1.20 | 25 | 0.042 | S-1 | — |
| 208 | 1 | C-43 | — | — | — | 100 | 0.3 | S-1 | — |
| 209 | 4 | — | A-5 | L-13 | 1.20 | 25 | 0.042 | S-1 | — |
| 210 | 4 | — | A-5 | L-45 | 1.20 | 25 | 0.042 | S-1 | — |
| 211 | 4 | — | A-3 | L-25 | 1.20 | 25 | 0.042 | S-1 | — |
| 212 | 2 | — | A-7 | L-54 | 1.13 | 100 | 0.3 | S-1 | 2 |
| 213 | 5 | — | A-2 | L-48 | 1.05 | 2500 | 2.62 | S-1 | 16 |
| 214 | 2 | — | A-7 | L-56 | 1.13 | 100 | 0.3 | S-1 | 2 |
| 215 | 4 | — | A-2 | L-22 | 1.20 | 25 | 0.042 | S-2 | — |
| 216 | 1 | C-29 | — | — | — | 100 | 0.3 | S-1 | — |
| 217 | 4 | — | A-2 | L-29 | 1.20 | 25 | 0.042 | S-1 | — |
| 218 | 1 | C-27 | — | — | — | 2500 | 0.79 | S-1 | — |
| 219 | 4 | — | A-2 | L-50 | 1.20 | 25 | 0.042 | S-6 | — |
| 220 | 1 | C-18 | — | — | — | 100 | 0.3 | S-11 | — |
| 221 | 4 | — | A-2 | L-22 | 1.20 | 25 | 0.042 | S-1 | — |
| 222 | 4 | — | A-2 | L-4 | 1.20 | 25 | 0.042 | S-1 | — |
| 223 | 1 | C-27 | — | — | — | 500 | 0.3 | S-8 | — |
| 224 | 4 | — | A-2 | L-15 | 1.20 | 100 | 0.042 | S-1 | — |
| 225 | 4 | — | A-5 | L-7 | 1.20 | 25 | 0.042 | S-1 | — |
| 226 | 4 | — | A-2 | L-48 | 1.20 | 25 | 0.042 | S-1 | — |
| 227 | 1 | C-18 | — | — | — | 100 | 0.3 | S-9 | — |
| 228 | 1 | C-40 | — | — | — | 1000 | 0.6 | S-1 | — |
| 229 | 2 | — | A-7 | L-105 | 1.13 | 100 | 0.3 | S-1 | 2 |
| 230 | 1 | C-25 | — | — | — | 500 | 0.3 | S-8 | — |
| 231 | 4 | — | A-5 | L-36 | 1.20 | 25 | 0.042 | S-2 | — |
| 232 | 5 | — | A-2 | L-48 | 1.10 | 2500 | 2.62 | S-1 | 16 |
| 233 | 4 | — | A-4 | L-17 | 1.20 | 25 | 0.042 | S-1 | — |
| 234 | 4 | — | A-5 | L-6 | 1.20 | 25 | 0.042 | S-1 | — |
| 235 | 1 | C-7 | — | — | — | 100 | 0.3 | S-10 | — |
| 236 | 4 | — | A-2 | L-39 | 1.20 | 25 | 0.042 | S-1 | — |
| 237 | 4 | — | A-5 | L-27 | 1.20 | 25 | 0.042 | S-1 | — |
| 238 | 1 | C-9 | — | — | — | 100 | 0.3 | S-1 | — |
| 239 | 4 | — | A-2 | L-39 | 1.20 | 25 | 0.042 | S-5 | — |

-continued

Table of Example 43:

| 240 | 1 | C-41 | — | — | — | 100 | 0.3 | S-1 | — |
|---|---|---|---|---|---|---|---|---|---|
| 241 | 5 | — | A-2 | L-48 | 1.05 | 100 | 1.31 | S-1 | 8 |
| 242 | 5 | — | A-2 | L-48 | 1.05 | 2500 | 2.62 | S-1 | 17 |
| 243 | 4 | — | A-5 | L-7 | 1.20 | 25 | 0.042 | S-3 | — |
| 244 | 1 | C-52 | — | — | — | 100 | 0.3 | S-1 | — |
| 245 | 4 | — | A-5 | L-36 | 1.20 | 25 | 0.042 | S-1 | — |
| 246 | 5 | — | A-5 | L-36 | 1.05 | 2500 | 1.31 | S-1 | 8 |
| 247 | 4 | — | A-2 | L-43 | 1.20 | 25 | 0.042 | S-1 | — |
| 248 | 4 | — | A-5 | L-23 | 1.20 | 25 | 0.042 | S-1 | — |
| 249 | 4 | — | A-3 | L-1 | 1.20 | 25 | 0.042 | S-1 | — |
| 250 | 4 | — | A-5 | L-33 | 1.20 | 25 | 0.042 | S-1 | — |
| 251 | 4 | — | A-2 | L-15 | 1.20 | 25 | 0.042 | S-2 | — |
| 252 | 6 | — | A-2 | L-48 | 1.05 | 25 | 0.5 | S-1 | 0 |
| 253 | 2 | — | A-7 | L-59 | 1.13 | 100 | 0.3 | S-1 | 2 |
| 254 | 1 | C-42 | — | — | — | 100 | 0.3 | S-1 | — |
| 255 | 1 | C-18 | — | — | — | 100 | 0.3 | S-9 | — |
| 256 | 1 | C-9 | — | — | — | 100 | 0.3 | S-1 | — |
| 257 | 4 | — | A-2 | L-24 | 1.20 | 25 | 0.042 | S-1 | — |
| 258 | 5 | — | A-2 | L-48 | 1.05 | 2500 | 2.62 | S-1 | 16 |
| 259 | 4 | — | A-3 | L-33 | 1.20 | 25 | 0.042 | S-1 | — |
| 260 | 4 | — | A-2 | L-53 | 1.20 | 25 | 0.042 | S-1 | — |
| 261 | 1 | C-43 | — | — | — | 1000 | 0.6 | S-1 | — |
| 262 | 1 | C-27 | — | — | — | 2500 | 0.79 | S-8 | — |
| 263 | 4 | — | A-1 | L-50 | 1.20 | 25 | 0.042 | S-1 | — |
| 264 | 4 | — | A-2 | L-29 | 1.20 | 25 | 0.042 | S-2 | — |
| 265 | 1 | C-55 | — | — | — | 100 | 0.3 | S-1 | — |
| 266 | 6 | — | A-5 | L-36 | 1.10 | 100 | 1.31 | S-1 | 0 |
| 267 | 4 | — | A-3 | L-2 | 1.20 | 25 | 0.042 | S-1 | — |
| 268 | 3 | C-2 | — | — | — | 100 | 0.042 | S-1 | — |
| 269 | 1 | C-54 | — | — | — | 100 | 0.3 | S-1 | — |
| 270 | 4 | — | A-2 | L-50 | 1.20 | 25 | 0.042 | S-1 | — |
| 271 | 1 | C-22 | — | — | — | 100 | 0.3 | S-1 | — |
| 272 | 4 | — | A-5 | L-47 | 1.20 | 25 | 0.042 | S-1 | — |
| 273 | 1 | C-66 | — | — | — | 100 | 0.3 | S-1 | — |
| 274 | 1 | C-27 | — | — | — | 2500 | 0.79 | S-8 | — |
| 275 | 1 | C-25 | — | — | — | 1000 | 0.6 | S-1 | — |
| 276 | 1 | C-57 | — | — | — | 100 | 0.3 | S-1 | — |
| 277 | 1 | C-31 | — | — | — | 100 | 0.3 | S-1 | — |
| 278 | 1 | C-40 | — | — | — | 500 | 0.3 | S-1 | — |
| 279 | 5 | — | A-2 | L-28 | 1.05 | 500 | 1.31 | S-1 | 8 |
| 280 | 6 | — | A-2 | L-48 | 1.05 | 100 | 1.31 | S-1 | 0 |
| 281 | 5 | — | A-2 | L-48 | 1.10 | 2500 | 11.8 | S-1 | 60 |
| 282 | 4 | — | A-2 | L-50 | 1.20 | 25 | 0.042 | S-2 | — |
| 283 | 1 | C-32 | — | — | — | 100 | 0.3 | S-1 | — |
| 284 | 4 | — | A-2 | L-36 | 1.20 | 25 | 0.042 | S-1 | — |
| 285 | 1 | C-43 | — | — | — | 500 | 0.3 | S-2 | — |
| 286 | 4 | — | A-5 | L-19 | 1.20 | 25 | 0.042 | S-1 | — |
| 287 | 1 | C-27 | — | — | — | 2500 | 0.79 | S-1 | — |
| 288 | 1 | C-36 | — | — | — | 100 | 0.3 | S-1 | — |
| 289 | 1 | C-27 | — | — | — | 1000 | 0.79 | S-8 | — |
| 290 | 3 | C-1 | — | — | — | 25 | 0.042 | S-3 | — |
| 291 | 4 | — | A-2 | L-46 | 1.20 | 25 | 0.042 | S-1 | — |
| 292 | 1 | C-27 | — | — | — | 1000 | 0.6 | S-1 | — |
| 293 | 1 | C-27 | — | — | — | 1000 | 0.6 | S-1 | — |
| 294 | 1 | C-30 | — | — | — | 100 | 0.3 | S-1 | — |
| 295 | 1 | C-55 | — | — | — | 100 | 0.3 | S-9 | — |
| 296 | 1 | C-40 | — | — | — | 1000 | 0.6 | S-1 | — |
| 297 | 1 | C-53 | — | — | — | 100 | 0.3 | S-1 | — |
| 298 | 1 | C-27 | — | — | — | 1000 | 0.6 | S-1 | — |
| 299 | 4 | — | A-2 | L-48 | 1.20 | 25 | 0.042 | S-2 | — |
| 300 | 1 | C-48 | — | — | — | 100 | 0.3 | S-1 | — |
| 301 | 1 | C-27 | — | — | — | 1000 | 0.79 | S-1 | — |
| 302 | 4 | — | A-2 | L-49 | 1.20 | 25 | 0.042 | S-1 | — |
| 303 | 4 | — | A-5 | L-31 | 1.20 | 25 | 0.042 | S-1 | — |
| 304 | 1 | C-25 | — | — | — | 500 | 0.3 | S-1 | — |
| 305 | 1 | C-57 | — | — | — | 100 | 0.3 | S-1 | — |
| 306 | 1 | C-46 | — | — | — | 100 | 0.3 | S-1 | — |
| 307 | 1 | C-27 | — | — | — | 1000 | 0.6 | S-1 | — |
| 308 | 4 | — | A-2 | L-15 | 1.20 | 25 | 0.042 | S-1 | — |
| 309 | 1 | C-27 | — | — | — | 500 | 0.3 | S-2 | — |
| 310 | 2 | — | A-7 | L-55 | 1.13 | 100 | 0.3 | S-1 | 2 |
| 311 | 1 | C-25 | — | — | — | 100 | 0.3 | S-1 | — |
| 312 | 1 | C-45 | — | — | — | 100 | 0.3 | S-1 | — |
| 313 | 4 | — | A-5 | L-9 | 1.20 | 25 | 0.042 | S-3 | — |
| 314 | 1 | C-64 | — | — | — | 100 | 0.3 | S-1 | — |
| 315 | 4 | — | A-2 | L-20 | 1.20 | 25 | 0.042 | S-1 | — |
| 316 | 5 | — | A-2 | L-48 | 1.10 | 100 | 2.62 | S-1 | 140 |
| 317 | 1 | C-54 | — | — | — | 100 | 0.3 | S-9 | — |

-continued

Table of Example 43:

| | | | | | | | | | |
|---|---|---|---|---|---|---|---|---|---|
| 318 | 4 | — | A-5 | L-2 | 1.20 | 25 | 0.042 | S-1 | — |
| 319 | 1 | C-30 | — | — | — | 100 | 0.3 | S-1 | — |
| 320 | 1 | C-50 | — | — | — | 100 | 0.3 | S-9 | — |
| 321 | 4 | — | A-2 | L-30 | 1.20 | 25 | 0.042 | S-1 | — |
| 322 | 1 | C-20 | — | — | — | 100 | 0.3 | S-1 | — |
| 323 | 6 | — | A-2 | L-48 | 1.10 | 2500 | 1.31 | S-1 | 0 |
| 324 | 4 | — | A-5 | L-29 | 1.20 | 25 | 0.042 | S-1 | — |
| 325 | 4 | — | A-5 | L-5 | 1.20 | 25 | 0.042 | S-1 | — |
| 326 | 1 | C-58 | — | — | — | 100 | 0.3 | S-1 | — |
| 327 | 1 | C-26 | — | — | — | 100 | 0.3 | S-1 | — |
| 328 | 4 | — | A-2 | L-50 | 1.20 | 25 | 0.042 | S-3 | — |
| 329 | 5 | — | A-2 | L-48 | 1.05 | 100 | 1.31 | S-1 | 8 |
| 330 | 1 | C-41 | — | — | — | 100 | 0.3 | S-1 | — |
| 331 | 1 | C-27 | — | — | — | 1000 | 0.79 | S-1 | — |
| 332 | 1 | C-21 | — | — | — | 100 | 0.3 | S-1 | — |
| 333 | 1 | C-62 | — | — | — | 100 | 0.3 | S-1 | — |
| 334 | 1 | C-13 | — | — | — | 100 | 0.3 | S-1 | — |
| 335 | 5 | — | A-2 | L-28 | 1.05 | 500 | 1.31 | S-1 | 8 |
| 336 | 1 | C-40 | — | — | — | 1000 | 0.6 | S-1 | — |
| 337 | 1 | C-27 | — | — | — | 1000 | 0.79 | S-1 | — |
| 338 | 1 | C-34 | — | — | — | 100 | 0.3 | S-1 | — |
| 339 | 1 | — | A-6 | — | — | 100 | 0.3 | S-1 | — |
| 340 | 1 | C-43 | — | — | — | 500 | 0.3 | S-8 | — |
| 341 | 1 | C-27 | — | — | — | 1000 | 0.6 | S-1 | — |
| 342 | 4 | — | A-3 | L-15 | 1.20 | 25 | 0.042 | S-1 | — |
| 343 | 4 | — | A-2 | L-33 | 1.20 | 25 | 0.042 | S-1 | — |
| 344 | 5 | — | A-2 | L-48 | 1.05 | 500 | 1.31 | S-1 | 8 |
| 345 | 1 | C-27 | — | — | — | 100 | 0.3 | S-1 | — |
| 346 | 4 | — | A-5 | L-12 | 1.20 | 25 | 0.042 | S-1 | — |
| 347 | 1 | C-31 | — | — | — | 100 | 0.3 | S-1 | — |
| 348 | 5 | — | A-2 | L-48 | 1.05 | 2500 | 2.62 | S-1 | 16 |
| 349 | 4 | — | A-3 | L-5 | 1.20 | 25 | 0.042 | S-1 | — |
| 350 | 1 | C-60 | — | — | — | 100 | 0.3 | S-1 | — |
| 351 | 1 | C-27 | — | — | — | 1000 | 2.1 | S-8 | — |
| 352 | 1 | C-35 | — | — | — | 100 | 0.3 | S-1 | — |
| 353 | 4 | — | A-5 | L-37 | 1.20 | 25 | 0.042 | S-1 | — |
| 354 | 4 | — | A-5 | L-11 | 1.20 | 25 | 0.042 | S-1 | — |
| 355 | 4 | — | A-5 | L-1 | 1.20 | 25 | 0.042 | S-1 | — |
| 356 | 4 | — | A-2 | L-14 | 1.20 | 25 | 0.042 | S-1 | — |
| 357 | 4 | — | A-2 | L-19 | 1.20 | 25 | 0.042 | S-1 | — |
| 358 | 1 | C-51 | — | — | — | 100 | 0.3 | S-1 | — |
| 359 | 5 | — | A-2 | L-48 | 1.10 | 5000 | 21 | S-1 | 100 |
| 360 | 4 | — | A-5 | L-8 | 1.20 | 25 | 0.042 | S-1 | — |
| 361 | 4 | — | A-5 | L-44 | 1.20 | 25 | 0.042 | S-1 | — |
| 362 | 4 | — | A-2 | L-6 | 1.20 | 25 | 0.042 | S-3 | — |
| 363 | 4 | — | A-2 | L-35 | 1.20 | 25 | 0.042 | S-1 | — |
| 364 | 4 | — | A-5 | L-6 | 1.20 | 25 | 0.042 | S-1 | — |
| 365 | 1 | C-61 | — | — | — | 100 | 0.3 | S-1 | — |
| 366 | 5 | — | A-2 | L-48 | 1.10 | 100 | 1.31 | S-1 | 100 |
| 367 | 5 | — | A-2 | L-48 | 1.05 | 100 | 1.31 | S-1 | 8 |
| 368 | 1 | C-40 | — | — | — | 500 | 0.3 | S-8 | — |
| 369 | 1 | C-25 | — | — | — | 500 | 0.3 | S-2 | — |
| 370 | 1 | C-18 | — | — | — | 100 | 0.3 | S-11 | — |
| 371 | 4 | — | A-2 | L-6 | 1.20 | 25 | 0.042 | S-1 | — |
| 372 | 1 | C-47 | — | — | — | 100 | 0.3 | S-1 | — |
| 373 | 6 | — | A-2 | L-48 | 1.05 | 2500 | 1.31 | S-13 | 0 |
| 374 | 4 | — | A-2 | L-15 | 1.20 | 25 | 0.042 | S-1 | — |
| 375 | 4 | — | A-5 | L-4 | 1.20 | 25 | 0.042 | S-1 | — |
| 376 | 1 | C-27 | — | — | — | 1000 | 0.6 | S-1 | — |
| 377 | 4 | — | A-5 | L-36 | 1.20 | 25 | 0.042 | S-1 | — |
| 378 | 4 | — | A-1 | L-53 | 1.20 | 25 | 0.042 | S-1 | — |
| 379 | 1 | C-11 | — | — | — | 100 | 0.3 | S-1 | — |
| 380 | 3 | C-3 | — | — | — | 25 | 0.042 | S-1 | — |
| 381 | 5 | — | A-2 | L-48 | 1.05 | 5000 | 2.62 | S-1 | 16 |
| 382 | 4 | — | A-2 | L-23 | 1.20 | 25 | 0.042 | S-1 | — |
| 383 | 1 | C-59 | — | — | — | 100 | 0.3 | S-1 | — |
| 384 | 4 | — | A-4 | L-27 | 1.20 | 25 | 0.042 | S-1 | — |
| 385 | 4 | — | A-2 | L-11 | 1.20 | 25 | 0.042 | S-1 | — |
| 386 | 4 | — | A-2 | L-22 | 1.20 | 25 | 0.042 | S-3 | — |
| 387 | 3 | C-4 | — | — | — | 25 | 0.042 | S-1 | — |
| 388 | 1 | C-44 | — | — | — | 100 | 0.3 | S-9 | — |
| 389 | 4 | — | A-3 | L-27 | 1.20 | 25 | 0.042 | S-1 | — |
| 390 | 7 | — | A-2 | L-48 | 1.05 | 100 | 1.31 | S-1 | 12 |
| 391 | 4 | — | A-3 | L-48 | 1.20 | 25 | 0.042 | S-1 | — |
| 392 | 4 | — | A-2 | L-45 | 1.20 | 25 | 0.042 | S-1 | — |
| 393 | 4 | — | A-2 | L-2 | 1.20 | 25 | 0.042 | S-1 | — |
| 394 | 4 | — | A-5 | L-25 | 1.20 | 25 | 0.042 | S-1 | — |
| 395 | 6 | — | A-2 | L-48 | 1.05 | 500 | 0.66 | S-1 | 0 |

-continued

Table of Example 43:

| | | | | | | | | | | |
|---|---|---|---|---|---|---|---|---|---|---|
| 396 | 3 | C-3 | — | — | — | 25 | 0.042 | S-1 | — |
| 397 | 4 | — | A-4 | L-33 | 1.20 | 25 | 0.042 | S-1 | — |
| 398 | 4 | — | A-2 | L-15 | 1.20 | 25 | 0.042 | S-3 | — |
| 399 | 1 | C-27 | — | — | — | 100 | 0.3 | S-1 | — |
| 400 | 1 | C-27 | — | — | — | 2500 | 2.1 | S-8 | — |
| 401 | 2 | — | A-7 | L-58 | 1.13 | 100 | 0.3 | S-1 | 2 |
| 402 | 4 | — | A-2 | L-29 | 1.20 | 25 | 0.042 | S-4 | — |
| 403 | 4 | — | A-2 | L-48 | 1.20 | 25 | 0.042 | S-3 | — |
| 404 | 1 | C-43 | — | — | — | 1000 | 0.6 | S-1 | — |
| 405 | 4 | — | A-2 | L-12 | 1.20 | 25 | 0.042 | S-1 | — |
| 406 | 1 | C-25 | — | — | — | 100 | 0.3 | S-1 | — |
| 407 | 1 | C-67 | — | — | — | 100 | 0.3 | S-1 | — |
| 408 | 4 | — | A-4 | L-32 | 1.20 | 25 | 0.042 | S-1 | — |
| 409 | 1 | C-16 | — | — | — | 100 | 0.3 | S-1 | — |
| 410 | 4 | — | A-2 | L-48 | 1.20 | 25 | 0.042 | S-4 | — |
| 411 | 4 | — | A-5 | L-36 | 1.20 | 25 | 0.042 | S-7 | — |
| 412 | 6 | — | A-2 | L-48 | 1.10 | 1500 | 6.53 | S-1 | 0 |
| 413 | 1 | C-66 | — | — | — | 100 | 0.3 | S-1 | — |
| 414 | 4 | — | A-2 | L-47 | 1.20 | 25 | 0.042 | S-1 | — |
| 415 | 6 | — | A-2 | L-48 | 1.05 | 500 | 0.66 | S-1 | 0 |
| 416 | 4 | — | A-4 | L-31 | 1.20 | 25 | 0.042 | S-1 | — |
| 417 | 4 | — | A-5 | L-15 | 1.20 | 25 | 0.042 | S-1 | — |
| 418 | 1 | C-27 | — | — | — | 2500 | 0.79 | S-1 | — |
| 419 | 4 | — | A-2 | L-16 | 1.20 | 25 | 0.042 | S-3 | — |
| 420 | 5 | — | A-2 | L-48 | 1.05 | 2500 | 2.62 | S-1 | 8 |
| 421 | 8 | — | A-2 | L-48 | 1.05 | 2500 | 1.31 | S-1 | 8 |
| 422 | 1 | C-27 | — | — | — | 1000 | 0.6 | S-1 | — |
| 423 | 2 | — | A-7 | L-57 | 1.13 | 100 | 0.3 | S-1 | 2 |
| 424 | 5 | — | A-2 | L-48 | 1.10 | 2500 | 21 | S-1 | 60 |

| Method | Solvent Volume (Transition Metal Catalyst) (ml) | Solvent Volume (Total reaction volume) (ml) | Concentration of 2-a (R1 = Boc, R2 = H, R3 = CO$_2$H) (mM) | Additive (D) | Equivalents of Additive | Temperature (° C.) | Pressure (bar) | Reaction Time (hours) | Diastereo-selectivity 1-a (R1 = Boc, R2 = H, R3 = CO$_2$H or CO$_2^-$) (area % hplc) | 1-b (R1 = Boc, R2 = H, R3 = CO$_2$H or CO$_2^-$) (area % hplc) |
|---|---|---|---|---|---|---|---|---|---|---|
| 1 | — | 0.5 | 84.0 | D-3 | 0.5 | rt | 7 | 16 | 88.8 | 11.2 |
| 2 | — | 0.5 | 84.0 | D-3 | 0.5 | rt | 7 | 16 | 93.9 | 6.1 |
| 3 | — | 3 | 100.0 | — | — | 60 | 20 | 16 | 52.5 | 47.5 |
| 4 | — | 0.5 | 84.0 | — | — | rt | 7 | 16 | 63.1 | 36.9 |
| 5 | 5 | 5 | 132.0 | — | — | rt | 7 | 16 | 49.2 | 50.8 |
| 6 | — | 0.5 | 84.0 | — | — | rt | 7 | 16 | 90.8 | 9.2 |
| 7 | — | 0.5 | 84.0 | — | — | rt | 20 | 16 | 60.7 | 39.3 |
| 8 | — | 3 | 200.0 | D-6 | 0.5 | 25 | 20 | 16 | 95.5 | 4.5 |
| 9 | — | 0.5 | 84.0 | — | — | rt | 20 | 16 | 48.2 | 51.8 |
| 10 | — | 3 | 100.0 | D-4 | 1 | 30 | 5 | 16 | 82.0 | 18.0 |
| 11 | 10 | 10 | 131.0 | — | — | rt | 7 | 16 | 92.1 | 7.9 |
| 12 | — | 3 | 100.0 | D-4 | 1 | 50 | 20 | 16 | 92.5 | 7.5 |
| 13 | — | 3 | 100.0 | — | — | 50 | 20 | 16 | 46.5 | 53.5 |
| 14 | 4 | 20 | 131.0 | — | — | rt | 7 | 16 | 90.8 | 9.2 |
| 15 | — | 0.5 | 84.0 | — | — | rt | 7 | 16 | 34.6 | 65.4 |
| 16 | — | 0.5 | 84.0 | D-3 | 0.5 | rt | 7 | 16 | 91.5 | 8.5 |
| 17 | — | 3 | 200.0 | D-7 | 1 | 25 | 20 | 16 | 93.0 | 7.0 |
| 18 | — | 3 | 200.0 | D-6 | 0.5 | 25 | 20 | 16 | 95.5 | 4.5 |
| 19 | — | 0.5 | 84.0 | — | — | rt | 7 | 16 | 50.9 | 49.1 |
| 20 | — | 3 | 100.0 | D-4 | 1 | 30 | 5 | 16 | 93.5 | 6.5 |
| 21 | — | 0.5 | 84.0 | D-1 | 0.08 | rt | 20 | 16 | 74.9 | 25.1 |
| 22 | — | 3 | 100.0 | D-4 | 1 | 30 | 20 | 16 | 84.0 | 16.0 |
| 23 | — | 0.5 | 84.0 | — | — | rt | 20 | 16 | 28.1 | 71.9 |
| 24 | — | 3 | 100.0 | D-4 | 1 | 50 | 20 | 16 | 63.0 | 37.0 |
| 25 | — | 0.5 | 84.0 | — | — | rt | 7 | 16 | 9.0 | 91.0 |
| 26 | — | 0.5 | 84.0 | — | — | rt | 20 | 16 | 61.8 | 38.2 |
| 27 | — | 3 | 100.0 | — | — | 50 | 20 | 16 | 52.5 | 47.5 |
| 28 | — | 0.5 | 84.0 | — | — | rt | 20 | 16 | 44.9 | 55.1 |
| 29 | — | 3 | 263.3 | D-6 | 0.5 | 25 | 20 | 16 | 50.0 | 50.0 |
| 30 | — | 0.5 | 84.0 | — | — | rt | 20 | 16 | 92.9 | 7.1 |
| 31 | — | 3 | 100.0 | D-4 | 1 | 50 | 20 | 16 | 62.0 | 38.0 |
| 32 | — | 0.5 | 84.0 | — | — | rt | 20 | 16 | 78.9 | 21.1 |
| 33 | — | 0.5 | 84.0 | — | — | rt | 7 | 16 | 52.0 | 48.0 |
| 34 | 2 | 10 | 131.0 | — | — | rt | 15 | 16 | 92.2 | 7.8 |
| 35 | — | 3 | 100.0 | — | — | 50 | 20 | 16 | 62.5 | 37.5 |
| 36 | — | 0.5 | 84.0 | — | — | rt | 7 | 16 | 35.2 | 64.8 |
| 37 | — | 3 | 100.0 | — | — | 60 | 20 | 16 | 61.0 | 39.0 |
| 38 | — | 3 | 200.0 | D-6 | 0.25 | 25 | 20 | 16 | 95.5 | 4.5 |
| 39 | — | 3 | 100.0 | D-4 | 1 | 60 | 20 | 16 | 73.5 | 26.5 |
| 40 | — | 0.5 | 84.0 | — | — | rt | 20 | 16 | 74.7 | 25.3 |

-continued

Table of Example 43:

| | | | | | | | | | | |
|---|---|---|---|---|---|---|---|---|---|---|
| 41 | — | 0.5 | 84.0 | — | — | rt | 7 | 16 | 9.8 | 90.2 |
| 42 | 1 | 3 | 100.0 | — | — | 50 | 20 | 16 | 52.5 | 47.5 |
| 43 | — | 0.5 | 84.0 | — | — | rt | 7 | 16 | 75.1 | 24.9 |
| 44 | — | 0.5 | 84.0 | — | — | rt | 20 | 16 | 40.4 | 59.6 |
| 45 | — | 0.5 | 84.0 | — | — | rt | 20 | 16 | 77.7 | 22.3 |
| 46 | — | 3 | 100.0 | D-4 | 1 | 50 | 20 | 16 | 41.5 | 58.5 |
| 47 | — | 3 | 263.3 | D-6 | 0.9 | 25 | 20 | 16 | 95.5 | 4.5 |
| 48 | 5 | 5 | 132.0 | — | — | rt | 7 | 16 | 81.9 | 18.1 |
| 49 | — | 3 | 263.3 | D-6 | 0.5 | 25 | 20 | 16 | 96.0 | 4.0 |
| 50 | — | 0.5 | 84.0 | — | — | rt | 7 | 16 | 70.1 | 29.9 |
| 51 | — | 0.5 | 84.0 | — | — | rt | 7 | 16 | 79.5 | 20.5 |
| 52 | — | 0.5 | 84.0 | — | — | rt | 7 | 16 | 59.1 | 40.9 |
| 53 | 4 | 20 | 131.0 | — | — | rt | 7 | 16 | 95.2 | 4.8 |
| 54 | 2 | 10 | 131.0 | — | — | 65 | 7 | 16 | 87.6 | 12.4 |
| 55 | — | 0.5 | 84.0 | — | — | rt | 20 | 16 | 61.6 | 38.4 |
| 56 | 15 | 15 | 33.3 | — | — | rt | 15 | 16 | 74.0 | 26.0 |
| 57 | — | 0.5 | 84.0 | — | — | rt | 20 | 16 | 45.2 | 54.8 |
| 58 | 5 | 5 | 132.0 | — | — | rt | 7 | 16 | 79.5 | 20.5 |
| 59 | — | 0.5 | 84.0 | — | — | rt | 20 | 16 | 10.5 | 89.5 |
| 60 | — | 0.5 | 84.0 | — | — | rt | 20 | 16 | 80.7 | 19.3 |
| 61 | — | 0.5 | 84.0 | — | — | rt | 7 | 16 | 26.8 | 73.2 |
| 62 | — | 3 | 100.0 | — | — | 60 | 20 | 16 | 44.0 | 56.0 |
| 63 | — | 3 | 263.3 | D-6 | 0.9 | 30 | 20 | 16 | 95.0 | 5.0 |
| 64 | 20 | 20 | 131.0 | — | — | rt | 7 | 16 | 94.0 | 6.0 |
| 65 | 4 | 20 | 131.0 | — | — | rt | 20 | 16 | 93.2 | 6.8 |
| 66 | — | 3 | 100.0 | — | — | 60 | 20 | 16 | 68.0 | 32.0 |
| 67 | — | 0.5 | 84.0 | — | — | rt | 20 | 16 | 31.9 | 68.1 |
| 68 | 4 | 20 | 131.0 | — | — | rt | 7 | 16 | 77.5 | 22.5 |
| 69 | — | 3 | 263.3 | D-6 | 0.9 | 30 | 20 | 16 | 96.5 | 3.5 |
| 70 | — | 3 | 100.0 | D-4 | 1 | 50 | 20 | 16 | 78.5 | 21.5 |
| 71 | — | 0.5 | 84.0 | — | — | rt | 7 | 16 | 67.2 | 32.8 |
| 72 | — | 0.5 | 84.0 | D-3 | 0.5 | rt | 7 | 16 | 88.1 | 11.9 |
| 73 | — | 3 | 100.0 | — | — | 50 | 20 | 16 | 62.0 | 38.0 |
| 74 | — | 3 | 100.0 | D-4 | 1 | 60 | 20 | 16 | 70.0 | 30.0 |
| 75 | 10 | 85 | 262.5 | — | — | rt | 20 | 17 | 95.9 | 4.1 |
| 76 | — | 3 | 200.0 | D-4 | 0.5 | 25 | 20 | 16 | 93.5 | 6.5 |
| 77 | 5 | 5 | 132.0 | D-3 | 0.1 | rt | 7 | 16 | 90.3 | 9.7 |
| 78 | 5 | 5 | 262.0 | — | — | rt | 7 | 16 | 85.3 | 14.7 |
| 79 | 4 | 20 | 131.0 | — | — | rt | 7 | 16 | 83.8 | 16.2 |
| 80 | — | 0.5 | 84.0 | — | — | rt | 20 | 16 | 57.2 | 42.8 |
| 81 | — | 0.5 | 84.0 | — | — | rt | 7 | 16 | 73.6 | 26.4 |
| 82 | — | 3 | 100.0 | — | — | 60 | 20 | 16 | 73.5 | 26.5 |
| 83 | — | 0.5 | 84.0 | — | — | rt | 20 | 16 | 53.4 | 46.6 |
| 84 | — | 3 | 100.0 | — | — | 50 | 20 | 16 | 41.0 | 59.0 |
| 85 | — | 0.5 | 84.0 | — | — | rt | 7 | 16 | 82.9 | 17.1 |
| 86 | — | 0.5 | 84.0 | — | — | rt | 7 | 16 | 26.0 | 74.0 |
| 87 | — | 3 | 100.0 | D-4 | 1 | 50 | 20 | 16 | 52.5 | 47.5 |
| 88 | 4 | 20 | 131.0 | — | — | 65 | 7 | 16 | 92.7 | 7.3 |
| 89 | 20 | 20 | 131.0 | — | — | rt | 7 | 16 | 93.9 | 6.1 |
| 90 | — | 8 | 262.5 | D-8 | 0.9 | 25 | 20 | 18 | 94.0 | 6.0 |
| 91 | — | 3 | 100.0 | D-4 | 1 | 60 | 20 | 16 | 57.0 | 43.0 |
| 92 | — | 0.5 | 84.0 | — | — | rt | 7 | 16 | 76.4 | 23.6 |
| 93 | — | 3 | 100.0 | — | — | 50 | 20 | 16 | 56.5 | 43.5 |
| 94 | — | 0.5 | 84.0 | D-1 | 0.08 | rt | 20 | 16 | 61.5 | 38.5 |
| 95 | — | 3 | 100.0 | — | — | 50 | 20 | 16 | 52.5 | 47.5 |
| 96 | — | 0.5 | 84.0 | D-1 | 0.08 | rt | 20 | 16 | 56.3 | 43.7 |
| 97 | — | 3 | 263.3 | D-8 | 0.5 | 25 | 20 | 16 | 97.0 | 3.0 |
| 98 | — | 0.5 | 84.0 | — | — | rt | 7 | 16 | 84.1 | 15.9 |
| 99 | — | 3 | 100.0 | D-4 | 1 | 60 | 20 | 16 | 82.5 | 17.5 |
| 100 | — | 3 | 100.0 | D-4 | 1 | 60 | 20 | 16 | 69.5 | 30.5 |
| 101 | — | 0.5 | 84.0 | — | — | rt | 7 | 16 | 27.4 | 72.6 |
| 102 | — | 3 | 263.3 | D-6 | 0.5 | 25 | 20 | 16 | 50.0 | 50.0 |
| 103 | 2 | 10 | 131.0 | — | — | rt | 7 | 16 | 94.6 | 5.4 |
| 104 | — | 0.5 | 84.0 | — | — | rt | 7 | 16 | 50.7 | 49.3 |
| 105 | — | 0.5 | 84.0 | D-3 | 0.5 | rt | 7 | 16 | 90.4 | 9.6 |
| 106 | — | 0.5 | 84.0 | — | — | rt | 20 | 16 | 71.3 | 28.7 |
| 107 | — | 3 | 100.0 | D-4 | 1 | 30 | 5 | 16 | 84.0 | 16.0 |
| 108 | — | 0.5 | 84.0 | — | — | rt | 20 | 16 | 43.5 | 56.5 |
| 109 | — | 0.5 | 84.0 | D-1 | 0.08 | rt | 20 | 16 | 57.6 | 42.4 |
| 110 | — | 3 | 100.0 | — | — | 60 | 20 | 16 | 34.0 | 66.0 |
| 111 | — | 0.5 | 84.0 | — | — | rt | 20 | 16 | 62.5 | 37.5 |
| 112 | — | 0.5 | 84.0 | — | — | rt | 7 | 16 | 82.8 | 17.2 |
| 113 | 60 | 160 | 131.3 | — | — | rt | 7 | 16 | 95.8 | 4.2 |
| 114 | — | 0.5 | 84.0 | — | — | rt | 20 | 16 | 80.9 | 19.1 |
| 115 | — | 0.5 | 84.0 | — | — | rt | 7 | 16 | 65.9 | 34.1 |
| 116 | — | 3 | 100.0 | D-4 | 1 | 60 | 20 | 16 | 76.0 | 24.0 |
| 117 | — | 0.5 | 84.0 | D-2 | 0.1 | rt | 7 | 16 | 12.8 | 87.2 |
| 118 | — | 0.5 | 84.0 | — | — | rt | 20 | 16 | 64.6 | 35.4 |

-continued

Table of Example 43:

| | | | | | | | | | | |
|---|---|---|---|---|---|---|---|---|---|---|
| 119 | — | 0.5 | 84.0 | — | — | rt | 7 | 16 | 65.4 | 34.6 |
| 120 | — | 0.5 | 84.0 | — | — | rt | 20 | 16 | 41.4 | 58.6 |
| 121 | — | 3 | 100.0 | — | — | 60 | 20 | 16 | 39.0 | 61.0 |
| 122 | — | 0.5 | 84.0 | — | — | rt | 7 | 16 | 65.7 | 34.3 |
| 123 | — | 3 | 100.0 | D-4 | 1 | 60 | 20 | 16 | 61.0 | 39.0 |
| 124 | — | 3 | 100.0 | D-4 | 1 | 50 | 20 | 16 | 83.0 | 17.0 |
| 125 | — | 0.5 | 84.0 | — | — | rt | 20 | 16 | 61.5 | 38.5 |
| 126 | — | 0.5 | 84.0 | — | — | rt | 20 | 16 | 55.7 | 44.3 |
| 127 | — | 0.5 | 84.0 | — | — | rt | 20 | 16 | 40.7 | 59.3 |
| 128 | — | 3 | 263.3 | D-6 | 0.5 | 25 | 20 | 16 | 96.0 | 4.0 |
| 129 | — | 0.5 | 84.0 | — | — | rt | 7 | 16 | 27.0 | 73.0 |
| 130 | 5 | 5 | 132.0 | — | — | rt | 7 | 16 | 96.4 | 3.6 |
| 131 | — | 3 | 100.0 | — | — | 50 | 20 | 16 | 26.0 | 74.0 |
| 132 | — | 0.5 | 84.0 | — | — | rt | 7 | 16 | 89.5 | 10.5 |
| 133 | — | 3 | 100.0 | — | — | 60 | 20 | 16 | 52.5 | 47.5 |
| 134 | 20 | 80 | 262.5 | — | — | rt | 7 | 16 | 93.1 | 6.9 |
| 135 | — | 0.5 | 84.0 | D-1 | 0.08 | rt | 20 | 16 | 62.5 | 37.5 |
| 136 | — | 0.5 | 84.0 | — | — | rt | 7 | 16 | 84.2 | 15.8 |
| 137 | — | 0.5 | 84.0 | — | — | rt | 20 | 16 | 50.3 | 49.7 |
| 138 | — | 3 | 100.0 | D-4 | 1 | 50 | 20 | 16 | 87.5 | 12.5 |
| 139 | — | 0.5 | 84.0 | — | — | rt | 7 | 16 | 42.7 | 57.3 |
| 140 | — | 0.5 | 84.0 | — | — | rt | 20 | 16 | 40.8 | 59.2 |
| 141 | — | 0.5 | 84.0 | — | — | rt | 7 | 16 | 60.7 | 39.3 |
| 142 | — | 0.5 | 84.0 | — | — | rt | 7 | 16 | 34.6 | 65.4 |
| 143 | — | 8 | 262.5 | D-6 | 0.9 | 35 | 20 | 18 | 96.0 | 4.0 |
| 144 | — | 3 | 100.0 | — | — | 60 | 20 | 16 | 52.5 | 47.5 |
| 145 | — | 3 | 263.3 | D-6 | 0.5 | 25 | 20 | 16 | 50.0 | 50.0 |
| 146 | — | 0.5 | 84.0 | — | — | rt | 20 | 16 | 63.0 | 37.0 |
| 147 | — | 0.5 | 84.0 | — | — | rt | 7 | 16 | 30.4 | 69.6 |
| 148 | — | 0.5 | 84.0 | — | — | rt | 20 | 16 | 67.7 | 32.3 |
| 149 | — | 3 | 100.0 | — | — | 50 | 20 | 16 | 34.0 | 66.0 |
| 150 | — | 3 | 100.0 | D-4 | 1 | 60 | 20 | 16 | 52.5 | 47.5 |
| 151 | — | 0.5 | 84.0 | D-2 | 0.1 | rt | 7 | 16 | 34.4 | 65.6 |
| 152 | — | 3 | 100.0 | — | — | 50 | 20 | 16 | 37.5 | 62.5 |
| 153 | — | 3 | 100.0 | D-4 | 1 | 30 | 20 | 16 | 79.0 | 21.0 |
| 154 | — | 3 | 100.0 | D-4 | 1 | 30 | 20 | 16 | 83.0 | 17.0 |
| 155 | — | 0.5 | 84.0 | — | — | rt | 7 | 16 | 93.1 | 6.9 |
| 156 | — | 0.5 | 84.0 | — | — | rt | 20 | 16 | 63.1 | 36.9 |
| 157 | — | 3 | 100.0 | — | — | 60 | 20 | 16 | 42.5 | 57.5 |
| 158 | — | 3 | 100.0 | — | — | 60 | 20 | 16 | 75.0 | 25.0 |
| 159 | — | 0.5 | 84.0 | D-1 | 0.08 | rt | 20 | 16 | 71.6 | 28.4 |
| 160 | — | 3 | 100.0 | — | — | 60 | 20 | 16 | 65.0 | 35.0 |
| 161 | — | 3 | 100.0 | D-4 | 1 | 50 | 20 | 16 | 62.0 | 38.0 |
| 162 | 2 | 10 | 131.0 | — | — | 65 | 7 | 16 | 94.3 | 5.7 |
| 163 | 10 | 80 | 262.5 | — | — | rt | 20 | 16 | 92.1 | 7.9 |
| 164 | 30 | 90 | 131.1 | — | — | rt | 7 | 16 | 95.4 | 4.6 |
| 165 | — | 0.5 | 84.0 | — | — | rt | 20 | 16 | 48.2 | 51.8 |
| 166 | — | 3 | 263.3 | D-6 | 0.5 | 25 | 20 | 16 | 96.0 | 4.0 |
| 167 | — | 0.5 | 84.0 | — | — | rt | 7 | 16 | 94.8 | 5.2 |
| 168 | — | 3 | 100.0 | D-4 | 1 | 50 | 20 | 16 | 57.0 | 43.0 |
| 169 | — | 3 | 263.3 | D-8 | 0.5 | 25 | 20 | 16 | 96.5 | 3.5 |
| 170 | — | 0.5 | 84.0 | — | — | rt | 20 | 16 | 39.9 | 60.1 |
| 171 | — | 3 | 100.0 | D-4 | 1 | 50 | 20 | 16 | 85.0 | 15.0 |
| 172 | — | 3 | 100.0 | — | — | 60 | 20 | 16 | 81.0 | 19.0 |
| 173 | — | 0.5 | 84.0 | — | — | rt | 20 | 16 | 47.9 | 52.1 |
| 174 | — | 0.5 | 84.0 | — | — | rt | 20 | 16 | 73.8 | 26.2 |
| 175 | 4 | 20 | 131.0 | — | — | rt | 14 | 16 | 81.5 | 18.5 |
| 176 | — | 3 | 100.0 | D-4 | 1 | 30 | 20 | 16 | 90.0 | 10.0 |
| 177 | — | 0.5 | 84.0 | — | — | rt | 7 | 16 | 79.1 | 20.9 |
| 178 | — | 0.5 | 84.0 | — | — | rt | 20 | 16 | 20.1 | 79.9 |
| 179 | — | 0.5 | 84.0 | D-2 | 0.1 | rt | 7 | 16 | 36.4 | 63.6 |
| 180 | — | 3 | 100.0 | D-4 | 1 | 50 | 20 | 16 | 91.5 | 8.5 |
| 181 | 2 | 10 | 131.0 | — | — | 65 | 7 | 16 | 93.4 | 6.6 |
| 182 | — | 0.5 | 84.0 | — | — | rt | 7 | 16 | 37.8 | 62.2 |
| 183 | — | 3 | 100.0 | — | — | 50 | 20 | 16 | 83.0 | 17.0 |
| 184 | — | 3 | 263.3 | D-6 | 0.5 | 25 | 20 | 16 | 96.0 | 4.0 |
| 185 | — | 3 | 200.0 | D-7 | 1 | 25 | 20 | 16 | 86.5 | 13.5 |
| 186 | 2 | 3 | 100.0 | D-4 | 1 | 50 | 20 | 16 | 54.0 | 46.0 |
| 187 | 2 | 10 | 131.0 | — | — | rt | 7 | 16 | 91.4 | 8.6 |
| 188 | 7 | 7 | 187.1 | — | — | rt | 7 | 16 | 87.9 | 12.1 |
| 189 | — | 3 | 100.0 | D-4 | 1 | 60 | 20 | 16 | 44.0 | 56.0 |
| 190 | — | 3 | 100.0 | D-4 | 1 | 50 | 20 | 16 | 92.5 | 7.5 |
| 191 | — | 3 | 100.0 | D-4 | 1 | 50 | 20 | 16 | 57.0 | 43.0 |
| 192 | 2 | 10 | 131.0 | — | — | 65 | 15 | 16 | 87.0 | 13.0 |
| 193 | — | 3 | 100.0 | D-4 | 1 | 30 | 20 | 16 | 84.5 | 15.5 |
| 194 | 2 | 10 | 131.0 | — | — | rt | 7 | 16 | 87.8 | 12.2 |
| 195 | — | 3 | 100.0 | D-4 | 1 | 60 | 20 | 16 | 82.5 | 17.5 |
| 196 | — | 3 | 200.0 | D-6 | 0.75 | 25 | 20 | 16 | 95.5 | 4.5 |

-continued

Table of Example 43:

| | | | | | | | | | | |
|---|---|---|---|---|---|---|---|---|---|---|
| 197 | — | 3 | 263.3 | D-6 | 0.9 | 25 | 20 | 16 | 97.0 | 3.0 |
| 198 | — | 0.5 | 84.0 | — | — | rt | 20 | 16 | 49.3 | 50.7 |
| 199 | — | 0.5 | 84.0 | — | — | rt | 20 | 16 | 71.1 | 28.9 |
| 200 | — | 0.5 | 84.0 | — | — | rt | 20 | 16 | 28.2 | 71.8 |
| 201 | 2 | 10 | 131.0 | — | — | rt | 50 | 16 | 91.5 | 8.5 |
| 202 | — | 3 | 200.0 | D-7 | 0.5 | 25 | 20 | 16 | 92.5 | 7.5 |
| 203 | 2 | 10 | 262.0 | — | — | rt | 7 | 16 | 96.7 | 3.3 |
| 204 | — | 3 | 100.0 | — | — | 60 | 20 | 16 | 81.0 | 19.0 |
| 205 | — | 3 | 100.0 | — | — | 60 | 20 | 16 | 47.0 | 53.0 |
| 206 | — | 0.5 | 84.0 | D-2 | 0.1 | rt | 7 | 16 | 28.4 | 71.6 |
| 207 | — | 0.5 | 84.0 | — | — | rt | 20 | 16 | 63.9 | 36.1 |
| 208 | — | 3 | 100.0 | — | — | 50 | 20 | 16 | 73.0 | 27.0 |
| 209 | — | 0.5 | 84.0 | — | — | rt | 20 | 16 | 52.6 | 47.4 |
| 210 | — | 0.5 | 84.0 | — | — | rt | 20 | 16 | 43.5 | 56.5 |
| 211 | — | 0.5 | 84.0 | D-1 | 0.08 | rt | 20 | 16 | 53.0 | 47.0 |
| 212 | 1 | 3 | 100.0 | — | — | 50 | 20 | 16 | 52.5 | 47.5 |
| 213 | 4 | 20 | 131.0 | — | — | rt | 7 | 16 | 89.6 | 10.4 |
| 214 | 1 | 3 | 100.0 | — | — | 50 | 20 | 16 | 52.5 | 47.5 |
| 215 | — | 0.5 | 84.0 | — | — | rt | 7 | 16 | 33.5 | 66.5 |
| 216 | — | 3 | 100.0 | D-4 | 1 | 50 | 20 | 16 | 84.5 | 15.5 |
| 217 | — | 0.5 | 84.0 | — | — | rt | 7 | 16 | 83.9 | 16.1 |
| 218 | — | 3 | 263.3 | D-6 | 0.9 | 25 | 20 | 16 | 95.5 | 4.5 |
| 219 | — | 0.5 | 84.0 | — | — | rt | 7 | 16 | 9.9 | 90.1 |
| 220 | — | 3 | 100.0 | D-4 | 1 | 60 | 20 | 16 | 52.5 | 47.5 |
| 221 | — | 0.5 | 84.0 | — | — | rt | 7 | 16 | 33.2 | 66.8 |
| 222 | — | 0.5 | 84.0 | — | — | rt | 20 | 16 | 78.5 | 21.5 |
| 223 | — | 3 | 100.0 | D-4 | 1 | 50 | 20 | 16 | 94.0 | 6.0 |
| 224 | — | 0.5 | 84.0 | — | — | rt | 7 | 16 | 89.9 | 10.1 |
| 225 | — | 0.5 | 84.0 | — | — | rt | 7 | 16 | 74.4 | 25.6 |
| 226 | — | 0.5 | 84.0 | — | — | rt | 20 | 16 | 94.1 | 5.9 |
| 227 | — | 3 | 100.0 | D-4 | 1 | 60 | 20 | 16 | 60.5 | 39.5 |
| 228 | — | 3 | 200.0 | D-6 | 1 | 25 | 20 | 16 | 94.0 | 6.0 |
| 229 | 1 | 3 | 100.0 | — | — | 50 | 20 | 16 | 44.5 | 55.5 |
| 230 | — | 3 | 100.0 | D-4 | 1 | 50 | 20 | 16 | 83.5 | 16.5 |
| 231 | — | 0.5 | 84.0 | — | — | rt | 7 | 16 | 86.1 | 13.9 |
| 232 | 4 | 20 | 131.0 | — | — | rt | 1 | 16 | 94.9 | 5.1 |
| 233 | — | 0.5 | 84.0 | — | — | rt | 20 | 16 | 61.5 | 38.5 |
| 234 | — | 0.5 | 84.0 | — | — | rt | 7 | 16 | 91.6 | 8.4 |
| 235 | — | 3 | 100.0 | D-4 | 1 | 60 | 20 | 16 | 85.0 | 15.0 |
| 236 | — | 0.5 | 84.0 | — | — | rt | 7 | 16 | 80.3 | 19.7 |
| 237 | — | 0.5 | 84.0 | — | — | rt | 20 | 16 | 51.6 | 48.4 |
| 238 | — | 3 | 100.0 | — | — | 60 | 20 | 16 | 59.0 | 41.0 |
| 239 | — | 0.5 | 84.0 | D-3 | 0.5 | rt | 7 | 16 | 91.8 | 8.2 |
| 240 | — | 3 | 100.0 | D-4 | 1 | 30 | 5 | 16 | 83.5 | 16.5 |
| 241 | 2 | 10 | 131.0 | — | — | 65 | 3 | 16 | 94.4 | 5.6 |
| 242 | 3 | 20 | 131.0 | — | — | rt | 7 | 16 | 95.5 | 4.5 |
| 243 | — | 0.5 | 84.0 | D-3 | 0.5 | rt | 7 | 16 | 88.7 | 11.3 |
| 244 | — | 3 | 100.0 | — | — | 50 | 20 | 16 | 50.0 | 50.0 |
| 245 | — | 0.5 | 84.0 | — | — | rt | 7 | 16 | 90.5 | 9.5 |
| 246 | 0.4 | 8.4 | 156.0 | — | — | 65 | 15 | 16 | 87.0 | 13.0 |
| 247 | — | 0.5 | 84.0 | — | — | rt | 20 | 16 | 70.3 | 29.7 |
| 248 | — | 0.5 | 84.0 | — | — | rt | 7 | 16 | 64.8 | 35.2 |
| 249 | — | 0.5 | 84.0 | D-1 | 0.08 | rt | 20 | 16 | 83.0 | 17.0 |
| 250 | — | 0.5 | 84.0 | — | — | rt | 20 | 16 | 65.9 | 34.1 |
| 251 | — | 0.5 | 84.0 | — | — | rt | 7 | 16 | 87.4 | 12.6 |
| 252 | 15 | 15 | 33.3 | — | — | rt | 15 | 16 | 92.0 | 8.0 |
| 253 | 1 | 3 | 100.0 | — | — | 50 | 20 | 16 | 62.0 | 38.0 |
| 254 | — | 3 | 100.0 | D-4 | 1 | 50 | 20 | 16 | 24.0 | 76.0 |
| 255 | — | 3 | 100.0 | — | — | 60 | 20 | 16 | 58.5 | 41.5 |
| 256 | — | 3 | 100.0 | D-4 | 1 | 60 | 20 | 16 | 64.5 | 35.5 |
| 257 | — | 0.5 | 84.0 | — | — | rt | 7 | 16 | 24.2 | 75.8 |
| 258 | 4 | 20 | 131.0 | — | — | rt | 7 | 16 | 85.1 | 14.9 |
| 259 | — | 0.5 | 84.0 | D-1 | 0.08 | rt | 20 | 16 | 63.9 | 36.1 |
| 260 | — | 0.5 | 84.0 | — | — | rt | 7 | 16 | 68.2 | 31.8 |
| 261 | — | 3 | 200.0 | D-5 | 0.8 | 25 | 20 | 16 | 83.5 | 16.5 |
| 262 | — | 3 | 263.3 | D-6 | 0.9 | 25 | 20 | 16 | 96.5 | 3.5 |
| 263 | — | 0.5 | 84.0 | — | — | rt | 7 | 16 | 32.3 | 67.7 |
| 264 | — | 0.5 | 84.0 | — | — | rt | 7 | 16 | 76.5 | 23.5 |
| 265 | — | 3 | 100.0 | — | — | 60 | 20 | 16 | 52.5 | 47.5 |
| 266 | 8 | 8 | 163.8 | — | — | rt | 7 | 16 | 88.5 | 11.5 |
| 267 | — | 0.5 | 84.0 | D-1 | 0.08 | rt | 20 | 16 | 47.0 | 53.0 |
| 268 | — | 0.5 | 84.0 | — | — | rt | 7 | 16 | 44.6 | 55.4 |
| 269 | — | 3 | 100.0 | — | — | 60 | 20 | 16 | 56.0 | 44.0 |
| 270 | — | 0.5 | 84.0 | — | — | rt | 7 | 16 | 13.4 | 86.6 |
| 271 | — | 3 | 100.0 | — | — | 50 | 20 | 16 | 52.5 | 47.5 |
| 272 | — | 0.5 | 84.0 | — | — | rt | 20 | 16 | 68.8 | 31.2 |
| 273 | — | 3 | 100.0 | D-4 | 1 | 50 | 20 | 16 | 81.0 | 19.0 |
| 274 | — | 3 | 263.3 | D-6 | 0.9 | 40 | 20 | 16 | 94.5 | 5.5 |

-continued

Table of Example 43:

| | | | | | | | | | | |
|---|---|---|---|---|---|---|---|---|---|---|
| 275 | — | 3 | 200.0 | D-5 | 0.8 | 25 | 20 | 16 | 84.0 | 16.0 |
| 276 | — | 3 | 100.0 | D-4 | 1 | 60 | 20 | 16 | 61.5 | 38.5 |
| 277 | — | 3 | 100.0 | D-4 | 1 | 50 | 20 | 16 | 50.0 | 50.0 |
| 278 | — | 3 | 100.0 | D-4 | 1 | 50 | 20 | 16 | 92.0 | 8.0 |
| 279 | 2 | 10 | 131.0 | — | — | 65 | 20 | 16 | 93.3 | 6.7 |
| 280 | 8 | 8 | 163.8 | — | — | rt | 7 | 16 | 94.6 | 5.4 |
| 281 | 30 | 90 | 131.1 | — | — | rt | 7 | 16 | 95.3 | 4.7 |
| 282 | — | 0.5 | 84.0 | — | — | rt | 7 | 16 | 25.7 | 74.3 |
| 283 | — | 3 | 100.0 | D-4 | 1 | 50 | 20 | 16 | 70.5 | 29.5 |
| 284 | — | 0.5 | 84.0 | — | — | rt | 20 | 16 | 70.4 | 29.6 |
| 285 | — | 3 | 100.0 | D-4 | 1 | 50 | 20 | 16 | 81.0 | 19.0 |
| 286 | — | 0.5 | 84.0 | — | — | rt | 20 | 16 | 35.4 | 64.6 |
| 287 | — | 3 | 263.3 | D-6 | 0.9 | 40 | 20 | 16 | 93.5 | 6.5 |
| 288 | — | 3 | 100.0 | D-4 | 1 | 50 | 20 | 16 | 87.0 | 13.0 |
| 289 | — | 3 | 263.3 | D-6 | 0.5 | 25 | 20 | 16 | 97.0 | 3.0 |
| 290 | — | 0.5 | 84.0 | — | — | rt | 7 | 16 | 64.4 | 35.6 |
| 291 | — | 0.5 | 84.0 | — | — | rt | 7 | 16 | 85.1 | 14.9 |
| 292 | — | 3 | 200.0 | D-6 | 1 | 25 | 20 | 16 | 95.0 | 5.0 |
| 293 | — | 3 | 200.0 | D-6 | 0.1 | 25 | 20 | 16 | 95.5 | 4.5 |
| 294 | — | 3 | 100.0 | — | — | 50 | 20 | 16 | 45.5 | 54.5 |
| 295 | — | 3 | 100.0 | — | — | 60 | 20 | 16 | 30.0 | 70.0 |
| 296 | — | 3 | 200.0 | D-6 | 0.5 | 25 | 20 | 16 | 93.5 | 6.5 |
| 297 | — | 3 | 100.0 | — | — | 50 | 20 | 16 | 47.5 | 52.5 |
| 298 | — | 3 | 200.0 | D-7 | 0.5 | 25 | 20 | 16 | 95.0 | 5.0 |
| 299 | — | 0.5 | 84.0 | — | — | rt | 7 | 16 | 89.7 | 10.3 |
| 300 | — | 3 | 100.0 | D-4 | 1 | 30 | 20 | 16 | 78.0 | 22.0 |
| 301 | — | 3 | 263.3 | D-8 | 0.5 | 25 | 20 | 16 | 96.5 | 3.5 |
| 302 | — | 0.5 | 84.0 | — | — | rt | 20 | 16 | 11.8 | 88.2 |
| 303 | — | 0.5 | 84.0 | — | — | rt | 20 | 16 | 56.6 | 43.4 |
| 304 | — | 3 | 100.0 | D-4 | 1 | 50 | 20 | 16 | 85.5 | 14.5 |
| 305 | — | 3 | 100.0 | — | — | 60 | 20 | 16 | 59.0 | 41.0 |
| 306 | — | 3 | 100.0 | D-4 | 1 | 60 | 20 | 16 | 66.5 | 33.5 |
| 307 | — | 3 | 200.0 | D-4 | 1 | 50 | 20 | 16 | 91.5 | 8.5 |
| 308 | — | 0.5 | 84.0 | — | — | rt | 7 | 16 | 89.6 | 10.4 |
| 309 | — | 3 | 100.0 | D-4 | 1 | 50 | 20 | 16 | 89.0 | 11.0 |
| 310 | 1 | 3 | 100.0 | — | — | 50 | 20 | 16 | 52.5 | 47.5 |
| 311 | — | 3 | 100.0 | D-4 | 1 | 30 | 5 | 16 | 91.0 | 9.0 |
| 312 | — | 3 | 100.0 | D-4 | 1 | 60 | 20 | 16 | 52.5 | 47.5 |
| 313 | — | 0.5 | 84.0 | D-3 | 0.5 | rt | 7 | 16 | 88.3 | 11.7 |
| 314 | — | 3 | 100.0 | D-4 | 1 | 60 | 20 | 16 | 46.0 | 54.0 |
| 315 | — | 0.5 | 84.0 | — | — | rt | 7 | 16 | 50.8 | 49.2 |
| 316 | 60 | 200 | 13.1 | — | — | rt | 7 | 16 | 95.1 | 4.9 |
| 317 | — | 3 | 100.0 | — | — | 60 | 20 | 16 | 52.5 | 47.5 |
| 318 | — | 0.5 | 84.0 | — | — | rt | 20 | 16 | 38.7 | 61.3 |
| 319 | — | 3 | 100.0 | D-4 | 1 | 50 | 20 | 16 | 37.5 | 62.5 |
| 320 | — | 3 | 100.0 | — | — | 50 | 20 | 16 | 29.0 | 71.0 |
| 321 | — | 0.5 | 84.0 | — | — | rt | 7 | 16 | 28.8 | 71.2 |
| 322 | — | 3 | 100.0 | D-4 | 1 | 60 | 20 | 16 | 68.5 | 31.5 |
| 323 | 10 | 10 | 131.0 | — | — | rt | 7 | 16 | 93.9 | 6.1 |
| 324 | — | 0.5 | 84.0 | — | — | rt | 7 | 16 | 54.4 | 45.6 |
| 325 | — | 0.5 | 84.0 | — | — | rt | 20 | 16 | 62.0 | 38.0 |
| 326 | — | 3 | 100.0 | — | — | 60 | 20 | 16 | 69.5 | 30.5 |
| 327 | — | 3 | 100.0 | — | — | 50 | 20 | 16 | 52.5 | 47.5 |
| 328 | — | 0.5 | 84.0 | — | — | rt | 7 | 16 | 11.9 | 88.1 |
| 329 | 2 | 10 | 131.0 | — | — | 65 | 1 | 16 | 94.7 | 5.3 |
| 330 | — | 3 | 100.0 | — | — | 50 | 20 | 16 | 60.0 | 40.0 |
| 331 | — | 3 | 263.3 | D-8 | 0.9 | 25 | 20 | 16 | 96.5 | 3.5 |
| 332 | — | 3 | 100.0 | D-4 | 1 | 60 | 20 | 16 | 63.5 | 36.5 |
| 333 | — | 3 | 100.0 | — | — | 50 | 20 | 16 | 42.5 | 57.5 |
| 334 | — | 3 | 100.0 | — | — | 50 | 20 | 16 | 63.0 | 37.0 |
| 335 | 2 | 10 | 131.0 | — | — | rt | 20 | 16 | 87.3 | 12.7 |
| 336 | — | 3 | 200.0 | D-4 | 1 | 25 | 20 | 16 | 94.0 | 6.0 |
| 337 | — | 3 | 263.3 | D-8 | 0.5 | 25 | 20 | 16 | 96.0 | 4.0 |
| 338 | — | 3 | 100.0 | — | — | 50 | 20 | 16 | 51.5 | 48.5 |
| 339 | — | 3 | 100.0 | — | — | 50 | 20 | 16 | 40.5 | 59.5 |
| 340 | — | 3 | 100.0 | D-4 | 1 | 50 | 20 | 16 | 75.0 | 25.0 |
| 341 | — | 3 | 200.0 | D-4 | 0.5 | 25 | 20 | 16 | 95.0 | 5.0 |
| 342 | — | 0.5 | 84.0 | D-1 | 0.08 | rt | 20 | 16 | 67.8 | 32.2 |
| 343 | — | 0.5 | 84.0 | — | — | rt | 20 | 16 | 73.2 | 26.8 |
| 344 | 2 | 10 | 131.0 | — | — | rt | 1 | 16 | 94.7 | 5.3 |
| 345 | — | 3 | 100.0 | D-4 | 1 | 30 | 20 | 16 | 94.0 | 6.0 |
| 346 | — | 0.5 | 84.0 | — | — | rt | 7 | 16 | 72.0 | 28.0 |
| 347 | — | 3 | 100.0 | — | — | 50 | 20 | 16 | 62.0 | 38.0 |
| 348 | 4 | 20 | 131.0 | — | — | rt | 14 | 16 | 81.5 | 18.5 |
| 349 | — | 0.5 | 84.0 | D-1 | 0.08 | rt | 20 | 16 | 54.0 | 46.0 |
| 350 | — | 3 | 100.0 | D-4 | 1 | 60 | 20 | 16 | 73.5 | 26.5 |
| 351 | — | 8 | 262.5 | D-6 | 0.9 | 25 | 20 | 18 | 97.0 | 3.0 |
| 352 | — | 3 | 100.0 | D-4 | 1 | 50 | 20 | 16 | 58.0 | 42.0 |

-continued

Table of Example 43:

| | | | | | | | | | | |
|---|---|---|---|---|---|---|---|---|---|---|
| 353 | — | 0.5 | 84.0 | — | — | rt | 20 | 16 | 46.3 | 53.7 |
| 354 | — | 0.5 | 84.0 | — | — | rt | 20 | 16 | 77.5 | 22.5 |
| 355 | — | 0.5 | 84.0 | — | — | rt | 20 | 16 | 82.6 | 17.4 |
| 356 | — | 0.5 | 84.0 | — | — | rt | 20 | 16 | 75.2 | 24.8 |
| 357 | — | 0.5 | 84.0 | — | — | rt | 20 | 16 | 31.3 | 68.7 |
| 358 | — | 3 | 100.0 | — | — | 50 | 20 | 16 | 86.5 | 13.5 |
| 359 | 60 | 160 | 131.3 | — | — | rt | 7 | 16 | 93.9 | 6.1 |
| 360 | — | 0.5 | 84.0 | — | — | rt | 7 | 16 | 77.5 | 22.5 |
| 361 | — | 0.5 | 84.0 | — | — | rt | 20 | 16 | 54.6 | 45.4 |
| 362 | — | 0.5 | 84.0 | D-3 | 0.5 | rt | 7 | 16 | 76.2 | 23.8 |
| 363 | — | 0.5 | 84.0 | — | — | rt | 20 | 16 | 69.3 | 30.7 |
| 364 | — | 0.5 | 84.0 | — | — | rt | 20 | 16 | 93.3 | 6.7 |
| 365 | — | 3 | 100.0 | — | — | 50 | 20 | 16 | 39.5 | 60.5 |
| 366 | 60 | 160 | 8.2 | — | — | rt | 7 | 16 | 95.2 | 4.8 |
| 367 | 2 | 10 | 131.0 | — | — | 65 | 7 | 16 | 93.2 | 6.8 |
| 368 | — | 3 | 100.0 | D-4 | 1 | 50 | 20 | 16 | 89.0 | 11.0 |
| 369 | — | 3 | 100.0 | D-4 | 1 | 50 | 20 | 16 | 86.5 | 13.5 |
| 370 | — | 3 | 100.0 | — | — | 60 | 20 | 16 | 40.0 | 60.0 |
| 371 | — | 0.5 | 84.0 | — | — | rt | 20 | 16 | 76.6 | 23.4 |
| 372 | — | 3 | 100.0 | D-4 | 1 | 50 | 20 | 16 | 82.5 | 17.5 |
| 373 | 10 | 10 | 131.0 | — | — | rt | 7 | 16 | 87.9 | 12.1 |
| 374 | — | 0.5 | 84.0 | — | — | rt | 20 | 16 | 90.9 | 9.1 |
| 375 | — | 0.5 | 84.0 | — | — | rt | 20 | 16 | 70.6 | 29.4 |
| 376 | — | 3 | 200.0 | D-4 | 1 | 25 | 20 | 16 | 94.5 | 5.5 |
| 377 | — | 0.5 | 84.0 | — | — | rt | 20 | 16 | 92.0 | 8.0 |
| 378 | — | 0.5 | 84.0 | — | — | rt | 7 | 16 | 75.0 | 25.0 |
| 379 | — | 3 | 100.0 | D-4 | 1 | 60 | 20 | 16 | 66.5 | 33.5 |
| 380 | — | 0.5 | 84.0 | — | — | rt | 20 | 16 | 92.2 | 7.8 |
| 381 | 4 | 20 | 131.0 | — | — | 45 | 7 | 16 | 83.1 | 16.9 |
| 382 | — | 0.5 | 84.0 | — | — | rt | 7 | 16 | 32.3 | 67.7 |
| 383 | — | 3 | 100.0 | — | — | 60 | 20 | 16 | 67.5 | 32.5 |
| 384 | — | 0.5 | 84.0 | — | — | rt | 20 | 16 | 53.2 | 46.8 |
| 385 | — | 0.5 | 84.0 | — | — | rt | 20 | 16 | 74.5 | 25.5 |
| 386 | — | 0.5 | 84.0 | D-3 | 0.5 | rt | 7 | 16 | 40.7 | 59.3 |
| 387 | — | 0.5 | 84.0 | — | — | rt | 20 | 16 | 41.2 | 58.8 |
| 388 | — | 3 | 100.0 | — | — | 60 | 20 | 16 | 68.0 | 32.0 |
| 389 | — | 0.5 | 84.0 | D-1 | 0.08 | rt | 20 | 16 | 54.3 | 45.7 |
| 390 | 3 | 15 | 87.3 | — | — | rt | 1 | 16 | 94.5 | 5.5 |
| 391 | — | 0.5 | 84.0 | D-1 | 0.08 | rt | 20 | 16 | 50.6 | 49.4 |
| 392 | — | 0.5 | 84.0 | — | — | rt | 20 | 16 | 62.6 | 37.4 |
| 393 | — | 0.5 | 84.0 | — | — | rt | 20 | 16 | 52.7 | 47.3 |
| 394 | — | 0.5 | 84.0 | — | — | rt | 20 | 16 | 60.3 | 39.7 |
| 395 | 5 | 5 | 132.0 | D-3 | 0.5 | rt | 7 | 16 | 84.9 | 15.1 |
| 396 | — | 0.5 | 84.0 | — | — | rt | 20 | 16 | 93.7 | 6.3 |
| 397 | — | 0.5 | 84.0 | — | — | rt | 20 | 16 | 66.4 | 33.6 |
| 398 | — | 0.5 | 84.0 | — | — | rt | 7 | 16 | 89.2 | 10.8 |
| 399 | — | 3 | 100.0 | — | — | 50 | 20 | 16 | 70.5 | 29.5 |
| 400 | — | 8 | 262.5 | D-6 | 0.9 | 40 | 20 | 18 | 94.5 | 5.5 |
| 401 | 1 | 3 | 100.0 | — | — | 50 | 20 | 16 | 52.5 | 47.5 |
| 402 | — | 0.5 | 84.0 | D-2 | 0.1 | rt | 7 | 16 | 73.2 | 26.8 |
| 403 | — | 0.5 | 84.0 | — | — | rt | 7 | 16 | 94.8 | 5.2 |
| 404 | — | 3 | 200.0 | D-4 | 1 | 50 | 20 | 16 | 78.0 | 22.0 |
| 405 | — | 0.5 | 84.0 | — | — | rt | 7 | 16 | 79.7 | 20.3 |
| 406 | — | 3 | 100.0 | D-4 | 1 | 50 | 20 | 16 | 87.5 | 12.5 |
| 407 | — | 3 | 100.0 | — | — | 50 | 20 | 16 | 46.0 | 54.0 |
| 408 | — | 0.5 | 84.0 | — | — | rt | 20 | 16 | 28.6 | 71.4 |
| 409 | — | 3 | 100.0 | D-4 | 1 | 50 | 20 | 16 | 47.5 | 52.5 |
| 410 | — | 0.5 | 84.0 | D-2 | 0.1 | rt | 7 | 16 | 62.1 | 37.9 |
| 411 | — | 0.5 | 84.0 | D-2 | 0.1 | rt | 7 | 16 | 72.3 | 27.7 |
| 412 | 25 | 25 | 261.2 | — | — | rt | 7 | 16 | 94.7 | 5.3 |
| 413 | — | 3 | 100.0 | — | — | 50 | 20 | 16 | 67.0 | 33.0 |
| 414 | — | 0.5 | 84.0 | — | — | rt | 20 | 16 | 88.8 | 11.2 |
| 415 | 5 | 5 | 132.0 | D-2 | 0.5 | rt | 7 | 16 | 39.2 | 60.8 |
| 416 | — | 0.5 | 84.0 | — | — | rt | 20 | 16 | 55.7 | 44.3 |
| 417 | — | 0.5 | 84.0 | — | — | rt | 20 | 16 | 71.3 | 28.7 |
| 418 | — | 3 | 263.3 | D-8 | 0.9 | 25 | 20 | 16 | 96.5 | 3.5 |
| 419 | — | 0.5 | 84.0 | D-3 | 0.5 | rt | 7 | 16 | 26.0 | 74.0 |
| 420 | 2 | 10 | 262.0 | — | — | rt | 7 | 16 | 94.6 | 5.4 |
| 421 | 2 | 10 | 131.0 | — | — | rt | 7 | 16 | 91.5 | 8.5 |
| 422 | — | 3 | 200.0 | D-5 | 0.8 | 25 | 20 | 16 | 91.5 | 8.5 |
| 423 | 1 | 3 | 100.0 | — | — | 50 | 20 | 16 | 56.5 | 43.5 |
| 424 | 20 | 80 | 262.5 | — | — | rt | 20 | 16 | 95.5 | 4.5 |

For the purpose of Example 43, the following abbreviations apply:

Organometallic Catalyst (C)
C-1=[Rh(COD)(SL-P005-1)]BF$_4$=[Rh(COD)(L-38)]BF$_4$
C-2=[Rh(COD)(SL-P102-1)]O$_3$SCF$_3$=[Rh(COD)(L-40)]O$_3$SCF$_3$
C-3=[Rh(COD)(SL-P102-1)]BF$_4$=[Rh(COD)(L-40)]BF$_4$
C-4=[Rh(COD)(SL-P104-2)]O$_3$SCF$_3$=[Rh(COD)(L-41)]O$_3$SCF$_3$
C-5=[(S)MeBoPhoz Rh(COD)]BF$_4$=[(L-55)Rh(COD)]BF$_4$
C-6=[(R)4-F—C6H4-MeBoPhoz Ru(benzene)Cl]Cl=[(L-60)Ru(benzene)Cl]Cl
C-7=[(R)Phenethyl-(R)-MeBoPhoz Ru(benzene)Cl]Cl=[(L-61)Ru(benzene)Cl]Cl
C-8=(R)BINOL-(R)-MeBoPhoz Ru(benzene)Cl]Cl=[(L-62)Ru(benzene)Cl]Cl
C-9=[(S)BINOL-(R)-MeBoPhoz Ru(benzene)Cl]Cl=[(L-63)Ru(benzene)Cl]Cl
C-10=[(R)MeBoPhoz RuCl(Benzene)]Cl=[(L-54)RuCl(Benzene)]Cl
C-11=[(R)p-F-MeBoPhoz RuCl(Benzene)]Cl=[(L-64)RuCl(Benzene)]Cl
C-12=[(S)MeBoPhoz Ir(COD)]Cl=[(L-55)Ir(COD)]Cl
C-13=[(R)MeBoPhoz Ir(COD)]Cl=[(L-54)Ir(COD)]Cl
C-14=[(R,R)BDPP Rh(COD)]BF$_4$=[(L-65)Rh(COD)]BF$_4$
C-15=[(S,S)BDPP Rh(COD)]BF$_4$=[(L-66)Rh(COD)]BF$_4$
C-16=[(R)Binam-P Rh(COD)]BF$_4$=[(L-67)Rh(COD)]BF$_4$
C-17=[(S)Binam-P Rh(COD)]BF$_4$=[(L-68)Rh(COD)]BF$_4$
C-18=[(R)Tol-BINAP RuCl(benzene)]Cl=[(L-69)RuCl(benzene)]Cl
C-19=[(S)Tol-Binap Rh(COD)]BF$_4$=[(L-70)Rh(COD)]BF$_4$
C-20=[(R)Binap RuCl(benzene)]Cl=[(L-71)(benzene)]Cl
C-21=[(S)Binap RuCl(benzene)]Cl=[(L-72)(benzene)]Cl
C-22=[(S)BINAP Rh(COD)]BF$_4$=[(L-72)Rh(COD)]BF$_4$
C-23=[(R)Binaphane Rh(COD)]BF$_4$=[(L-73)Rh(COD)]BF$_4$
C-24=[(S,S)Me-BPE Rh(COD)]BF$_4$=[(L-74)Rh(COD)]BF$_4$
C-25=[(S,S)Ph-BPE Rh(COD)]BF$_4$=[(L-75)Rh(COD)]BF$_4$
C-26=[(R)CatASium D Rh(COD)]BF$_4$=[(L-76)Rh(COD)]BF$_4$
C-27=[(R)CatASium M Rh(COD)]BF$_4$=[(L-77)Rh(COD)]BF$_4$
C-28=[(R)CatASium MN Rh(COD)]BF$_4$=[(L-78)MN Rh(COD)]BF$_4$
C-29=[(R)CatASium MNN Rh(COD)]BF$_4$=[(L-79)MNN Rh(COD)]BF$_4$
C-30=[(S)CatASium M Rh(COD)]BF$_4$=[(L-80)M Rh(COD)]BF$_4$
C-31=[(S)CatASium MN Rh(COD)]BF$_4$=[(L-81)Rh(COD)]BF$_4$
C-32=[(S,S)ChiraPhos Rh(COD)]BF$_4$=[(L-82)Rh(COD)]BF$_4$
C-33=[(R,R)DIOP Rh(COD)]BF$_4$=[(L-83)Rh(COD)]BF$_4$
C-34=[(S,S)DIOP Rh(COD)]BF$_4$=[(L-84)Rh(COD)]BF$_4$
C-35=[(R,R)DIPAMP Rh(COD)]BF$_4$=[(L-85)Rh(COD)]BF$_4$
C-36=[(R,R)DuanPhos Rh(COD)]BF$_4$=[(L-86)Rh(COD)]BF$_4$
C-37=[(R)MeDuPhos Rh(COD)]BF$_4$=[(L-87)Rh(COD)]BF$_4$
C-38=[(S,S)Et-Ferrotane Rh(COD)]BF$_4$=[(L-88)Rh(COD)]BF$_4$
C-39=[(R,R)NorPhos Rh(COD)]BF$_4$=[(L-89)Rh(COD)]BF$_4$
C-40=[(S,S)NorPhos Rh(COD)]BF$_4$=[(L-90)Rh(COD)]BF$_4$
C-41=[(R)PhanePhos Rh(COD)]BF$_4$=[(L-91)Rh(COD)]BF$_4$
C-42=[(S)PhanePhos Rh(COD)]BF$_4$=[(L-92)Rh(COD)]BF$_4$
C-43=[(R)Xyl-PhanePhos Rh(COD)]BF$_4$=[(L-92)Rh(COD)]BF$_4$
C-44=[(R)Xyl-PhanePhos RuCl$_2$(dmf)$_2$]=[(L-93)RuCl$_2$(dmf)$_2$]
C-45=[(S)Xyl-PhanePhos RuCl$_2$(dmf)$_2$]=[(L-94)RuCl$_2$(dmf)$_2$]
C-46=[(R)PhanePhos RuCl$_2$(dmf)$_2$]=[(L-91)RuCl$_2$(dmf)$_2$]
C-47=[(R)An-PhanePhos Rh(COD)]BF$_4$=[(L-96)Rh(COD)]BF$_4$
C-48=[(R)MeO-Xyl-PhanePhos Rh(COD)]BF$_4$=[(L-97)Rh(COD)]BF$_4$
C-49=[(R)Tol-PhanePhos Rh(COD)]BF$_4$=[(L-95)Rh(COD)]BF$_4$
C-50=[(S)iPr-PHOX Ir(COD)]BArF=[(L-98)Ir(COD)]BArF
C-51=[(S)Cy-tBu-SIMPLEPHOX Ir(COD)]BArF=[(L-99)Ir(COD)]BArF
C-52=[(R)P-Phos Rh(COD)]BF$_4$=[(L-100)Rh(COD)]BF$_4$
C-53=[(S)P-Phos Rh(COD)]BF$_4$=[(L-101)Rh(COD)]BF$_4$
C-54=[(R)Xyl-P-Phos RuCl$_2$(dmf)$_2$]=[(L-102)RuCl$_2$(dmf)$_2$]
C-55=[(S)Xyl-P-Phos RuCl$_2$(dmf)$_2$]=[(L-103)RuCl$_2$(dmf)$_2$]
C-56=[(S)P-Phos RuCl(benzene)]Cl=[(L-101)RuCl(benzene)]Cl
C-57=[(R)P-Phos RuCl(benzene)]Cl=[(L-100)RuCl(benzene)]Cl
C-58=[(R)P-Phos Ru(acac)$_2$]=[(L-100)Ru(acac)$_2$]
C-59=[(R)Xyl-P-Phos Ru(acac)$_2$]=[(L-102)Ru(acac)$_2$]
C-60=[(R)Xyl-P-Phos RuCl(benzene)]Cl=[(L-102)RuCl(benzene)]Cl
C-61=[(S)P-Phos Ir(COD)]Cl=[(L-101)Ir(COD)]Cl
C-62=[(S)Xyl-P-Phos Ir(COD)]Cl=[(L-103)Ir(COD)]Cl
C-63=[(R)ProPhos Rh(COD)]BF$_4$=[(L-104)Rh(COD)]BF$_4$
C-64=[(R$_a$,S$_c$)1Np-QUINAPHOS RuCl$_2$(dmf)$_2$]=[(L-105)RuCl$_2$(dmf)$_2$]
C-65=[(S$_a$,R$_c$)1Np-QUINAPHOS RuCl$_2$(dmf)$_2$]=[(L-106)RuCl$_2$(dmf)$_2$]
C-66=[(S,S,R,R)TangPhos Rh(COD)]BF$_4$=[(L-107)Rh(COD)]BF$_4$
C-67=[(R)-JafaPhos Rh(COD)]BF$_4$=[(L-108)Rh(COD)]BF$_4$ Organometallic Complex (A)
A-1=[Ir(COD)Cl]$_2$
A-2=[Rh(NBD)$_2$]BF$_4$
A-3=[Ru(COD)(2-metallyl)$_2$]
A-4=[Ru(COD)(OOCCF$_3$)$_2$]
A-5=[RuI$_2$(p-cymene)]$_2$
A-6=[(Cy$_3$P)Ir(pyr)]Cl
A-7=[Rh(COD)$_2$]BF$_4$ Chiral Ligand (L)
L-1=Atropisomer SL-A101-1
L-2=Atropisomer SL-A109-2
L-3=Atropisomer SL-A116-2
L-4=Atropisomer SL-A118-1
L-5=Atropisomer SL-A132-2
L-6=Fenphos SL-F131-1

L-7=Fenphos SL-F132-1
L-8=Fenphos SL-F133-1
L-9=Fenphos SL-F134-1
L-10=Fenphos SL-F135-1
L-11=Fenphos SL-F355-1
L-12=Fenphos SL-F356-1
L-13=Fenphos SL-F365-1
L-14=Josiphos SL-J005-2
L-15=Josiphos SL-J008-1
L-16=Josiphos SL-J009-1
L-17=Josiphos SL-J013-1
L-18=Josiphos SL-J211-1
L-19=Josiphos SL-J301-1
L-20=Josiphos SL-J403-1
L-21=Josiphos SL-J408-1
L-22=Josiphos SL-J412-1
L-23=Josiphos SL-J430-1
L-24=Josiphos SL-J431-1
L-25=Josiphos SL-J501-1
L-26=Josiphos SL-J503-1
L-27=Josiphos SL-J504-1
L-28=Josiphos SL-J504-2
L-29=Josiphos SL-J505-2
L-30=Josiphos SL-J506-1
L-31=Mandyphos SL-M002-1
L-32=Mandyphos SL-M003-1
L-33=Mandyphos SL-M004-1
L-34=Mandyphos SL-M004-2
L-35=Mandyphos SL-M009-1
L-36=Mandyphos SL-M010-1
L-37=Mandyphos SL-M012-1
L-38=Phospholane SL-P005-1
L-39=Phospholane SL-P051-1
L-40=Phospholane SL-P102-1
L-41=Phospholane SL-P104-2
L-42=Taniaphos SL-T001-1
L-43=Taniaphos SL-T001-2
L-44=Taniaphos. SL-T003-1
L-45=Taniaphos SL-T021-2
L-46=Walphos SL-W001-1
L-47=Walphos SL-W005-1
L-48=Walphos SL-W008-1
L-49=Walphos SL-W008-2
L-50=Walphos SL-W009-1
L-51=Walphos SL-W012-1
L-52=Walphos SL-W021-1
L-53=Walphos SL-W024-1
L-54=(R)-MeBophoz
L-55=(S)-MeBoPhoz
L-56=(R)-3,5-F2C6H3-BnBoPhoz
L-57=(R)-Cy-MeBoPhoz
L-58=(R)-Phenethyl-(R)-BoPhoz
L-59=(R)-Phenethyl-(S)-BoPhoz
L-60=(R)-4-F—C6H4-MeBoPhoz
L-61=(R)-Phenethyl-(R)-MeBoPhoz
L-62=(R)-BINOL-(R)-MeBoPhoz
L-63=(S)-BINOL-(R)-MeBoPhoz
L-64=(R)-p-F-MeBoPhoz
L-65=(R,R)-BDPP
L-66=(S,S)-BDPP
L-67=(R)BINAM-P
L-68=(S)-BINAM-P
L-69=(R)-Tol-BINAP
L-70=(S)-Tol-BINAP
L-71=(R)-BINAP
L-72=(S)-BINAP
L-73=(R)-Binaphane
L-74=(S,S)-Me-BPE
L-75=(S,S)-Ph-BPE
L-76=(R)-CatASium D
L-77=(R)-CatASium M
L-78=(R)-CatASium MN
L-79=(R)-CatASium MNN
L-80=(S)-CatASium M
L-81=(S)-CatASium MN
L-82=(S,S)-ChiraPhos
L-83=(R,R)-DIOP
L-84=(S,S)-DIOP
L-85=(R,R)-DIPAMP
L-86=(R,R)-DuanPhos
L-87=(R)-MeDuPhos
L-88=(S,S)-Et-Ferrotane
L-89=(R,R)-NorPhos
L-90=(S,S)-NorPhos
L-91=(R)-PhanePhos
L-92=(S)-PhanePhos
L-93=(R)-Xyl-PhanePhos
L-94=(S)-Xyl-PhanePhos
L-95=(R)-Tol-PhanePhos
L-96=(R)-An-PhanePhos
L-97=(R)-MeO-Xyl-PhanePhos
L-98=(S)-iPr-PHOX
L-99=(S)-Cy-tBu-SIMPLEPHOX
L-100=(R)—P-Phos
L-101=(S)—P-Phos
L-102=(R)-Xyl-P-Phos
L-103=(S)-Xyl-P-Phos
L-104=(R)-ProPhos
L-105=($R_a,S_c$)-1Np-QUINAPHOS
L-106=($S_a,R_c$)-1Np-QUINAPHOS
L-107=(S,S,R,R)TangPhos
L-108=(R)-JafaPhos (=(R)-(+)-1,1'-Bis(diphenylphosphino)-2,2'-bis(N,N-diisopropylamido)ferrocene)
Solvent (S)
S-1: Ethanol
S-2: Methanol
S-3: Ethanol/Isopropanol (1:1)
S-4: Ethanol/Trifluoroethanol/2-Methyltetrahydrofuran (48:47:5)
S-5: Ethanol/Isopropanol (18:1)
S-6: Trifluoroethanol/Ethanol (1:1)
S-7: 2-Methyltetrahydrofuran/Ethanol (5:95)
S-8: Isopropanol
S-9: Dichloroethane
S-10: Ethyl acetate
S-11: Tetrahydrofuran
S-12: 2-Methyltetrahydrofuran
S-13: Ethanol/Water (7:3)
Additive (D)
D-1: Tetrafluoroboric acid etherate
D-2: Methanesulphonic acid
D-3: 1,4-Diazobicyclo[2.2.2]octane
D-4: Triethylamine
D-5: Potassium ethoxide
D-6: Diisopropylethylamine
D-7: 1,1,3,3-Tetramethylguanidine
D-8: Sodium methoxide

Example 44

(2R,4S)-5-Biphenyl-4-yl-4-tert-butoxycarbonylamino-2-methylpentanoic acid (1-a, R1=Boc, R2=H, R3=CO$_2$H)

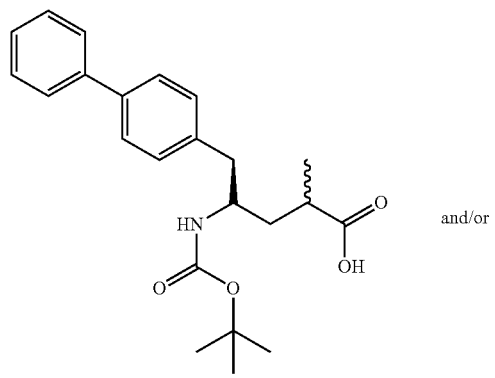

and/or

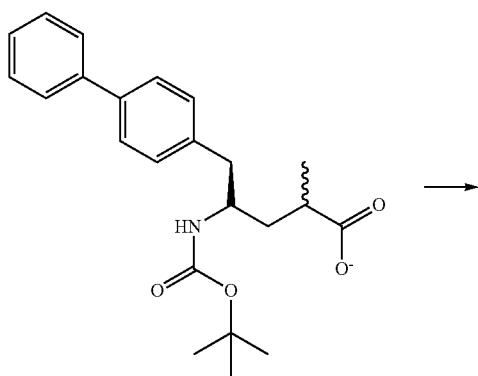

→

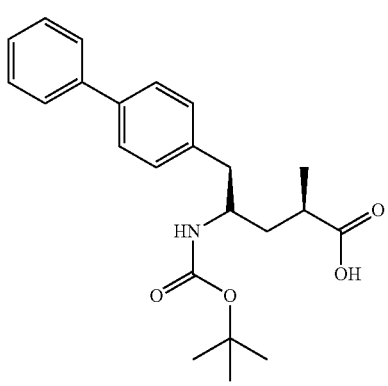

For a given reaction, after the reaction time indicated in the table shown in Example 43, the solvent may be optionally removed, for example, under reduced pressure. The residue may then be used in subsequent transformations.

Method 1

Ethanol (1.2 ml) is added to the reaction concentrate obtained from Example 43, Method 351 (240 mg). The mixture is heated to reflux. Water (0.6 ml) and acetic acid (43 µl) are added. The mixture is cooled to 0° C. and stirred at this temperature for 1 h. The solid is collected by filtration and washed with an ethanol-water mixture (2 ml, 2:1). The solid is then dried under vacuum to give (2R,4S)-5-biphenyl-4-yl-4-tert-butoxycarbonylamino-2-methylpentanoic acid (1-a, R1=Boc, R2=H, R3=CO$_2$H). Ratio of diastereomers 99.8:0.2 (1-a, R1=Boc, R2=H, R3=CO$_2$H:1-a, R1=Boc, R2=H, R3=CO$_2$H) from hplc.

Method 2

Isopropyl acetate (1.5 ml) is added to the reaction concentrate obtained from Example 43, Method 351 (240 mg). Citric acid (145 mg) dissolved in water (1.3 ml) is added. The phases are separated. The organic phase is washed with water (1.5 ml). The phases are then separated. The organic phase is then concentrated in vacuo to give (2R,4S)-5-biphenyl-4-yl-4-tert-butoxycarbonylamino-2-methylpentanoic acid (1-a, R1=Boc, R2=H, R3=CO$_2$H) and (2S,4S)-5-biphenyl-4-yl-4-tert-butoxycarbonylamino-2-methylpentanoic acid (1-b, R1=Boc, R2=H, R3=CO$_2$H). Ratio of diastereomers 97.7:2.3 (1-a, R1=Boc, R2=H, R3=CO$_2$H:1-a, R1=Boc, R2=H, R3=CO$_2$H) from hplc.

Optionally, the material obtained from General Procedures 1 and 2 can be subsequently and repeatedly recrystallised, for example, by following General Procedure 3.

Method 3

A mixture of 174 mg (2R,4S)-5-biphenyl-4-yl-4-tert-butoxycarbonylamino-2-methylpentanoic acid (1-a, R1=Boc, R2=H, R3=CO$_2$H) obtained from Example 44, Method 2 in isopropyl acetate (350 µl) is heated to give a solution. Heptane (700 µl) is added. The mixture is cooled to 0° C. and stirred at this temperature for 1 h. The solid is collected by filtration and washed with an isopropyl acetate: heptane mixture (1 ml, 1:2). The solid is then dried under vacuum to give (2R,4S)-5-biphenyl-4-yl-4-tert-butoxycarbonylamino-2-methylpentanoic acid (1-a, R1=Boc, R2H, R3=CO$_2$H). Ratio of diastereomers 99.9:0.1 (1-a, R1=Boc, R2=H, R3=CO$_2$H: 1-a, R1=Boc, R2=H, R3=CO$_2$H) from hplc.

Performing of reactions in accordance with Methods 1, 2 or 3 is independent of whether an additive, for example, a base, is used during the reaction given in Example 41. Reactions performed in the absence of a base may also be subsequently processed according to methods given in Methods 1, 2 or 3. Alternatively, they may be processed according to methods described in WO2008/031567, for example, Examples 2 or 3

HPLC Method (Reactions Performed According to Example 44, Methods 1, 2 or 3)

Column: Daicel QN-AX; 150×4.6 mm; 5 µm. Mobile Phase A: Methanol-Ethanol (1:1), 0.1% AcOH (v/v), 0.1% NH$_4$OAc (m/v). Isocratic: 0 min (100% A); 20 min (100% A). Flow rate: 0.5 ml min$^{-1}$. Wavelength: 254 nm. Column temperature: 10° C.

Retention Times:

(1-a, R1=Boc, R2=H, R3=CO$_2$H):7.8 min
(1-b, R1=Boc, R2=H, R3=CO$_2$H):10.3 min
(2-a, R1=Boc, R2=H, R3=CO$_2$H):14.3 min

Example 45

(3R,5S)-5-Biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc)

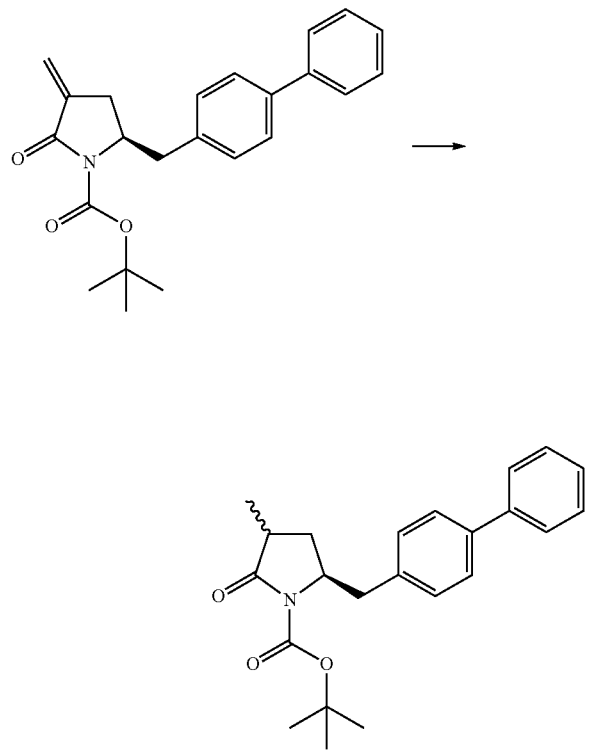 [SMILES: CC(C)(C)OC(=O)N1C(=O)CC[C@H]1Cc1ccc(-c2ccccc2)cc1 ; CC(C)(C)OC(=O)N1C(=O)C(=CN2CCCC2)C[C@H]1Cc1ccc(-c2ccccc2)cc1]

Method 1

Ethanol (1 ml) is added to a mixture of 100 mg (R)-5-biphenyl-4-ylmethyl-3-methylene-2-oxo-pyrrolidine-1-carboxylic acid tert-butyl ester (4-a, R1=Boc) and 10% palladium on carbon (10 mg, 50% water wet, Degussa type E101 NE/W). Hydrogen gas is applied to the mixture. The mixture is stirred at ambient temperature and pressure for 24 h. The mixture is then filtered over Celites and washed with ethanol (2×0.5 ml). The mixture is then concentrated in vacuo to give (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 20:80 (3-a, R1=Boc: 3-b, R1=Boc) as determined by hplc. Spectroscopic data in described in WO/2008/083967, for example, Examples 14 and 18.

Method 2

Isopropyl acetate (1 ml) is added to a mixture of 100 mg (R)-5-biphenyl-4-ylmethyl-3-methylene-2-oxo-pyrrolidine-1-carboxylic acid tert-butyl ester (4-a, R1=Boc) and 10% palladium on carbon (10 mg, 50% water wet, Degussa type E101 NE/W). Hydrogen gas is applied to the mixture. The mixture is stirred at ambient temperature and pressure for 24 h. The mixture is then filtered over Celite and washed with isopropyl acetate (2×0.5 ml). The mixture is then concentrated in vacuo to give (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 15:85 (3-a, R1=Boc): 3-b, R1=Boc) as determined by hplc. Spectroscopic data in described in WO/2008/083967, for example, Examples 14 and 18.

Method 3

Isopropyl acetate (1 ml) is added to a mixture of 100 mg (R)-5-biphenyl-4-ylmethyl-3-methylene-2-oxo-pyrrolidine-1-carboxylic acid tert-butyl ester (4-a, R1=Boc) and 10% platinium on carbon (10 mg). Hydrogen gas (ambient pressure) is applied to the mixture. The mixture is stirred at ambient temperature and pressure for 4 h. The mixture is then filtered over Celites and washed with isopropyl acetate (2×0.5 ml). The mixture is then concentrated in vacuo to give (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 33:67 (3-a, R1=Boc: 3-b, R1=Boc) as determined by hplc. Spectroscopic data in described in WO/2008/083967, for example, Examples 14 and 18.

Method 4

Isopropyl acetate (1 ml) is added to a mixture of 100 mg (R)-5-biphenyl-4-ylmethyl-3-methylene-2-oxo-pyrrolidine-1-carboxylic acid tert-butyl ester (4-a, R1=Boc) and 10% rhodium on carbon (10 mg). Hydrogen gas (ambient pressure) is applied to the mixture. The mixture is stirred at ambient temperature and pressure for 50 h. The mixture is then filtered over Celites and washed with isopropyl acetate (2×0.5 ml). The mixture is then concentrated in vacuo to give (3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc). Diastereomer ratio 21:79 (3-a, R1=Boc: 3-b, R1=Boc) as determined by hplc. Spectroscopic data in described in WO/2008/083967, for example, Examples 14 and 18.

HPLC Method 1 (Methods 1-4)

Column: AD-RH Chiralpak; 150×4.6 mm. Mobile Phase A (water); Mobile Phase B (Acetonitrile). Isocratic: 0 min (20% B); 15 min (20% B). Flow rate: 0.5 ml min$^{-1}$. Wavelength 210 nm. Column temperature: 40° C.

Retention Times:

(3-a, R1=Boc): 6.2 min (3-b, R1=Boc): 6.8 min

HPLC Method 2 (Methods 1-4)

Column: Zorbax SB-C18; 150×3.0 mm; 3.5 μm. Mobile Phase A (0.01 M $KH_2PO_4$ in water); Mobile Phase B (Acetonitrile). Gradient: 0 min (30% B); 10 min (80% B); 15 min (80% B); 15.1 min (30% B); 18 min (30% B). Flow rate: 1.0 ml min$^{-1}$. Wavelength: 210 nm. Temperature 50° C.

Retention Times:

(4-a, R1=Boc): 9.8 min (3-a, R1=Boc; 3-b, R1=Boc): 10.1 min

Example 46

(3R,5S)-5-biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc)

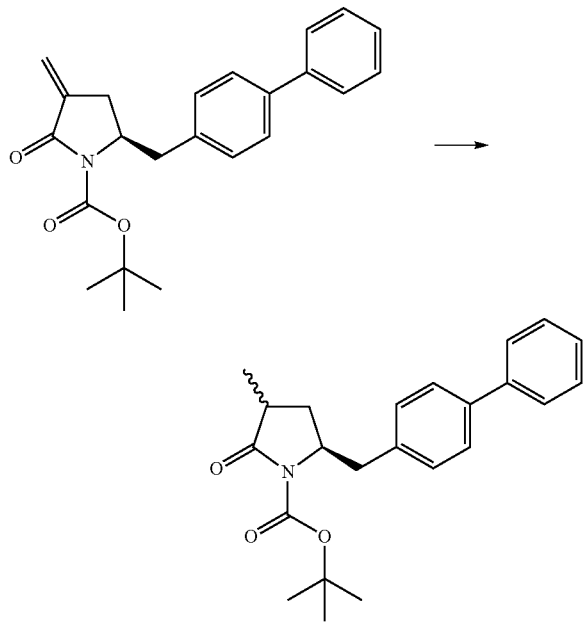 [SMILES: C=C1C[C@@H](Cc2ccc(-c3ccccc3)cc2)N(C(=O)OC(C)(C)C)C1=O ; CC1C[C@@H](Cc2ccc(-c3ccccc3)cc2)N(C(=O)OC(C)(C)C)C1=O]

General Procedure for Methods 1-7

To a mixture of 0.5 mmol (R)-5-Biphenyl-4-ylmethyl-3-methylene-2-oxo-pyrrolidine-1-carboxylic acid tert-butyl ester (4-a, R1=Boc) in methanol or ethanol (5 ml) at ambient temperature, a solution of Organometallic Complex (S/C ratio of 50 or 100) and Chiral Ligand (1.1 eq per metal atom within the organometallic complex) is added in methanol or ethanol (5 ml). A hydrogen pressure of 20 bar is applied for 20 h at ambient temperature. The solvent is then removed in vacuo to provide the corresponding product. The samples are analysed by hplc to determine the ratio of (3R,5S)-5-biphenyl-4-ylmethyl-3-methyl-2-oxo-pyrrolidine-1-carboxylic acid tert-butyl ester (3-a, R1=Boc) to (3S,5S)-5-biphenyl-4-ylmethyl-3-methyl-2-oxo-pyrrolidine-1-carboxylic acid tert-butyl ester (3-b, R1=Boc). Spectroscopic data in described in WO/2008/083967, for example, Examples 14 and 18.

Method 1

Chiral Ligand {(S)-(−)-(6,6'-Dimethoxybiphenyl-2,2'-diyl)-bis(diphenylphosphine)=(S)-Ph-MeOBIPHEP=SL-A101-2}; Organometallic Complex {dichloro(p-cymene)ruthenium(II)dimer}; Ethanol. Diastereomer ratio 82:18 (3-a, R1=Boc: 3-b, R1=Boc) as determined by hplc.

Method 2

Chiral Ligand {(αS,αS)-2,2'-Bis(α-N,N-dimethylaminophenylmethyl)-(R,R)-1,1'-bis[di(3,5-dimethyl-4-methoxyphenyl)phosphino]ferrocene=(S)—(R)—NMe$_2$-P(3,5-Me-4-MeOPh)-2-Mandyphos=SL-M004-2}; Organometallic Complex {dichloro(p-cymene)ruthenium(II)dimer}; Ethanol. Diastereomer ratio 82:18 (3-a, R1=Boc: 3-b, R1=Boc) as determined by hplc.

Method 3

Chiral Ligand {(R)-1-[(S)-2-Di-cyclohexylphosphino)ferrocenyl]ethyldi-(2-methylphenyl)phosphine=(R)—(S)-Cy$_2$PF—P°Tol$_2$=SL-J504-1}; Organometallic Complex {dichloro(p-cymene)ruthenium(II)dimer}; Methanol. Diastereomer ratio 53:47 (3-a, R1=Boc: 3-b, R1=Boc) as determined by hplc.

Method 4

Chiral Ligand {(R,R)-2,2''-Bis[(S)-1-(diarylphosphino)ethyl]-1,1''-biferrocene=SL-F115-1}; Organometallic Complex {bis(norbornadiene)rhodium(I)tetrafluoroborate}; Methanol. Diastereomer ratio 71:29 (3-a, R1=Boc: 3-b, R1=Boc) as determined by hplc.

Method 5

Chiral Ligand {(S-1-[(R)-2-Diphenylphosphinoferrocenyl]ethyldi-tert.-butylphosphine=(S)—(R)—PPF—PtBu$_2$=SL-J002-2}; Organometallic Complex {bis(trifluoroacetoxy)(1,5-cyclooctadiene)ruthenium(II)}; Methanol. Diastereomer ratio 56:44 (3-a, R1=Boc: 3-b, R1=Boc) as determined by hplc.

Method 6

Chiral Ligand {(R)-1-[(R)-2-(2'-Dicyclohexylphosphinophenyl)ferrocenyl]ethyldi(bis-(3,5-trifluoromethyl)phenyl)phosphine=(R)—(R)-cy$_2$PPhFCHCH$_3$P(3,5-CF$_3$Ph)$_2$=SL-W008-1-1}; Organometallic Complex {bis(norbornadiene)rhodium(1)tetrafluoroborate}; Methanol. Diastereomer ratio 27:73 (3-a, R1=Boc: 3-b, R1=Boc) as determined by hplc.

Method 7

Chiral Ligand {(S-1-[(R)-2-Diphenylphosphinoferrocenyl]ethyldi-tert.-butylphosphine=(S)—(R)—PPF—PtBu$_2$=SL-J002-2}; Organometallic Complex {dichloro(p-cymene)ruthenium(II)dimer}; Methanol. Diastereomer ratio 61:39 (3-a, R1=Boc: 3-b, R1=Boc) as determined by hplc.

HPLC Method (Methods 1-7)

Column: Gemini C6 Phenyl; 150×3.0 mm; 3.0 µm. Mobile Phase A (0.01 M KH$_2$PO$_4$ in water); Mobile Phase B (Methanol). Gradient: 0 min (40% B); 5 min (70% B); 12 min (70% B); 13 min (80% B); 21 min (80% B); 21.1 min (40% B); 25 min (40% B). Flow rate: 0.7 ml min$^-$. Wavelength: 210 nm. Temperature 50° C.

Retention Times:

(4-a, R1=Boc): 12.3 min
(3-a, R1=Boc): 12.9 min
(3-b, R1=Boc): 13.2 min

Example 47

(3R/S,5S)-biphenyl-4-ylmethyl-3-dimethylaminomethyl-2-oxo-pyrrolidine-1-carboxylic acid tert-butyl ester (9-a, R1=Boc, R6=Me, R7=Me)

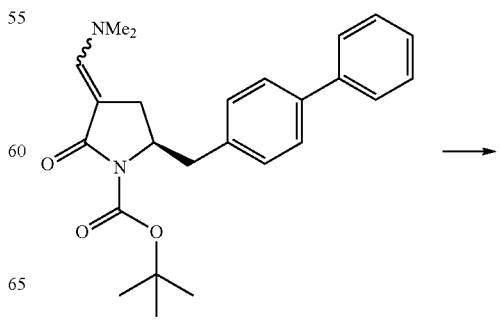

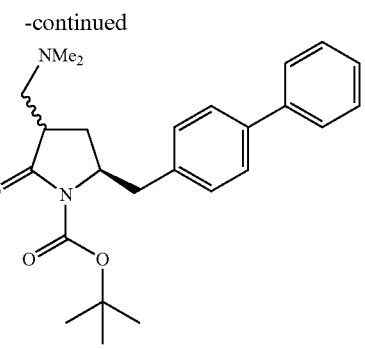

General Procedure for Methods 1-178

Solvent is added to a vessel containing (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) to achieve a final concentration as indicated in the Table of Example 47 (Methods 1-178).

Optionally and according to the table, an additive may be added at this stage. The identity and amount of the additive is given in the Table of Example 47 (Methods 1-178). The amount of additive to be used is relative to the moles of (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) used.

The catalyst is then added. The type and amount of catalyst used is given in the Table of Example 47 (Methods 1-178).

Hydrogen gas is applied to the vessel containing the mixture at the pressure given in the Table of Example 47 (Methods 1-178). The mixture is then stirred at the temperature and pressure given in the Table of Example 47 (Methods 1-178) for a period of time also indicated in the Table of Example 47 (Methods 1-178).

Spectrocopic data: 1H NMR (DMSO). 9-b (R1=Boc, R6=Me, R7=Me): 7.66 (m, 4H), 7.47 (t, J=7.8, 2H); 7.39-7.26 (m, 3H); 4.25 (m, 1H); 3.04 (dd, J=3.7, 13.1, 1H); 2.91 (m, 1H); 2.6 (m, 1H); 2.46 (dd, J=4.1, 12.2, 1H); 2.27 (m, 1H); 2.08 (s, 6H); 1.95 (m, 1H); 1.78 (m, 1H); 1.51 (s, 9H). 9-c (R1=Boc, R6=Me, R7=Me) separable signals at 1.51, 1.62, 2.08, 2.17, 3.28 ppm.

Table of Example 47 (Methods 1-178):

| Method | Hetereogeneous Catalyst | Amount of Catalyst (% w/w) | Solvent | Initial Concentration of 7-a (R1 = Boc) (mol dm$^{-3}$) | Additive | Eqivalents of Additive | Temperature (°C.) | Pressure (bar) | Time (h) | 9-b (R1 = Boc, R6 = R7 = Me):9-c (R1 = Boc, R6 = R7 = Me) |
|---|---|---|---|---|---|---|---|---|---|---|
| 1 | 5% Pd/C type 37 | 25 | THF | 0.05 | — | — | 45 | 5 | 3 | 63:37 |
| 2 | 5% Pd(S)/C A103038 | 25 | THF | 0.167 | — | — | 40 | 20 | 6 | 51:49 |
| 3 | 5% Pd(S)/C A103038 | 25 | THF | 0.167 | — | — | 40 | 20 | 1.5 | 53:47 |
| 4 | 5% Pd/C A401102 | 25 | EtOAc | 0.05 | — | — | 40 | 10 | 16 | 53:47 |
| 5 | 5% Pt/C B104032 | 25 | THF | 0.05 | — | — | 40 | 10 | 16 | 65:35 |
| 6 | 5% Pd/C A401102 | 25 | THF | 0.05 | — | — | 40 | 20 | 16 | 55:45 |
| 7 | 5% Pd/C type 37 | 25 | MeOH | 0.05 | — | — | 45 | 5 | 3 | 67:33 |
| 8 | 5% Pd/Al$_2$O$_3$ A302084-5 | 50 | THF | 0.05 | Cs$_2$CO$_3$ | 1 | 40 | 3 | 2 | 36:64 |
| 9 | 5% Pd/C A109047 | 50 | EtOAc | 0.05 | — | — | 25 | 3 | 4 | 67:33 |
| 10 | 5% Pd/C A401102 | 25 | THF | 0.05 | — | — | 55 | 3 | 16 | 55:45 |
| 11 | 5% Pd/C A401102 | 25 | THF | 0.05 | — | 1 | 55 | 10 | 16 | 48:52 |
| 12 | 5% Pd/C type 37 | 10 | THF | 0.25 | — | — | 70 | 20 | 3 | 57:43 |
| 13 | 5% Pd/C A401102 | 25 | THF | 0.05 | — | — | 40 | 3 | 16 | 57:43 |
| 14 | 5% Pd/C type 37 | 10 | THF | 0.25 | — | — | 70 | 20 | 3 | 58:42 |
| 15 | 5% Pd/C A109047 | 50 | iPrOH | 0.05 | — | — | 25 | 3 | 4 | 75:25 |
| 16 | 5% Pd/C type 37 | 25 | THF | 0.167 | — | — | 60 | 20 | 1.5 | 61:39 |
| 17 | 5% Pd(S)/C A103038 | 25 | THF | 0.05 | — | — | 40 | 20 | 3 | 54:46 |
| 18 | 5% Pd/C type 37 | 25 | THF | 0.25 | — | — | 75 | 20 | 1.3 | 58:42 |
| 19 | 5% Pd/C A401102 | 10 | EtOH | 0.05 | — | — | 40 | 10 | 16 | 53:47 |
| 20 | 5% Pd/C A401102 | 25 | THF | 0.05 | K$_2$CO$_3$ | 2 | 40 | 10 | 16 | 62:38 |
| 21 | 5% Pd/C A109047 | 50 | EtOH | 0.05 | — | — | 25 | 3 | 4 | 60:40 |
| 22 | 5% Pd/C type 37 | 25 | THF | 0.05 | — | — | 45 | 20 | 3 | 64:36 |

Table of Example 47 (Methods 1-178):

| Method | Hetereogeneous Catalyst | Amount of Catalyst (% w/w) | Solvent | Initial Concentration of 7-a (R1 = Boc) (mol dm$^{-3}$) | Additive | Eqivalents of Additive | Temperature (° C.) | Pressure (bar) | Time (h) | 9-b (R1 = Boc, R6 = R7 = Me):9-c (R1 = Boc, R6 = R7 = Me) |
|---|---|---|---|---|---|---|---|---|---|---|
| 23 | 5% Pd/Al$_2$O$_3$ A302084-5 | 50 | EtOH | 0.05 | — | — | 25 | 3 | 4 | 75:25 |
| 24 | 5% Pt/C B103018 | 25 | THF | 0.05 | — | — | 40 | 10 | 16 | 67:33 |
| 25 | 5% Pd/C type 37 | 25 | i-PrOAc | 0.25 | — | — | 65 | 20 | 3 | 50:50 |
| 26 | 5% Pd/C A401102 | 25 | THF | 0.05 | — | — | 40 | 10 | 16 | 52:48 |
| 27 | 5% Pd/C type 39 | 25 | THF | 0.05 | — | — | 45 | 5 | 3 | 64:36 |
| 28 | 5% Pt/C B501018 | 25 | THF | 0.05 | — | — | 45 | 5 | 3 | 60:40 |
| 29 | 5% Pt/C B 501032 | 25 | THF | 0.05 | — | — | 40 | 10 | 16 | 66:34 |
| 30 | 5% Pd/C type 37 | 40 | THF | 0.25 | — | — | 75 | 20 | 1.3 | 64:36 |
| 31 | 5% Pd/C type 37 | 10 | THF | 0.05 | — | — | 40 | 10 | 16 | 62:38 |
| 32 | 5% Pd/C A401102 | 25 | EtOH | 0.05 | — | — | 40 | 10 | 16 | 59:41 |
| 33 | 5% Pt/C B501018 | 25 | MeOH | 0.05 | — | — | 45 | 5 | 3 | 67:33 |
| 34 | 5% Pd/C type 37 | 25 | THF | 0.05 | — | — | 75 | 5 | 3 | 67:33 |
| 35 | 5% Pd/C type 39 | 25 | THF | 0.25 | — | — | 65 | 20 | 3 | 62:38 |
| 36 | 5% Pd/C type 398 | 10 | THF | 0.05 | — | — | 40 | 10 | 16 | 49:51 |
| 37 | 5% Pd/SiO$_2$/Al$_2$O$_3$ C7079 | 25 | THF | 0.05 | — | — | 40 | 10 | 16 | 44:56 |
| 38 | 5% Pd/C type 37 | 25 | THF | 0.05 | — | — | 60 | 20 | 3 | 61:39 |
| 39 | 5% Pd/C type 37 | 25 | Me-THF | 0.25 | — | — | 75 | 20 | 1.5 | 57:43 |
| 40 | 5% Pd/CaCO$_3$ type 405 | 10 | THF | 0.05 | — | — | 40 | 10 | 16 | 50:50 |
| 41 | 5% Pd/C type 37 | 25 | THF | 0.25 | — | — | 65 | 20 | 4.5 | 73:27 |
| 42 | 5% Pd/CaCO$_3$ A303060 | 25 | THF | 0.05 | — | — | 40 | 10 | 16 | 55:45 |
| 43 | 5% Pd/C type 39 | 25 | THF | 0.05 | — | — | 45 | 20 | 3 | 64:36 |
| 44 | 5% Pd/C type 37 | 27 | THF | 0.25 | — | — | 75 | 20 | 2 | 61:39 |
| 45 | 5% Pd/C A401102 | 25 | THF | 0.05 | — | — | 40 | 10 | 16 | 53:47 |
| 46 | 5% Pd/C A401102 | 25 | EtOH | 0.05 | — | — | 25 | 10 | 16 | 54:46 |
| 47 | 5% Pd/C A401102 | 25 | THF | 0.05 | — | — | 25 | 3 | 16 | 53:47 |
| 48 | 5% Pd(S)/C A103038 | 10 | THF | 0.05 | — | — | 40 | 10 | 16 | 52:48 |
| 49 | 5% Pd/C type 37 | 25 | THF | 0.25 | — | — | 65 | 20 | 1.5 | 63:37 |
| 50 | 5% Pd/C A401102 | 25 | THF | 0.05 | Cs$_2$CO$_3$ | 1 | 40 | 10 | 16 | 45:55 |
| 51 | 5% Pd/C A109047 | 50 | THF | 0.05 | — | — | 25 | 3 | 4 | 67:33 |
| 52 | 5% Pd/C type 37 | 25 | THF | 0.25 | — | — | 65 | 20 | 3 | 63:37 |
| 53 | 5% Pd/C A102023 | 10 | THF | 0.05 | — | — | 40 | 10 | 16 | 50:50 |
| 54 | 5% Pd/Al$_2$O$_3$ A302084-5 | 50 | THF | 0.05 | — | — | 25 | 3 | 4 | 60:40 |
| 55 | 5% Pd/C A405032 | 10 | THF | 0.05 | — | — | 40 | 10 | 16 | 48:52 |
| 56 | 5% Pt/C B501018 | 25 | THF | 0.05 | — | — | 40 | 10 | 16 | 61:39 |
| 57 | 5% Pt/C B501018 | 25 | THF | 0.05 | Et$_3$N | 1 | 40 | 20 | 3 | 50:50 |

-continued

Table of Example 47 (Methods 1-178):

| Method | Hetereogeneous Catalyst | Amount of Catalyst (% w/w) | Solvent | Initial Concentration of 7-a (R1 = Boc) (mol dm$^{-3}$) | Additive | Eqivalents of Additive | Temperature (° C.) | Pressure (bar) | Time (h) | 9-b (R1 = Boc, R6 = R7 = Me):9-c (R1 = Boc, R6 = R7 = Me) |
|---|---|---|---|---|---|---|---|---|---|---|
| 58 | 5% Pd/C type 37 | 25 | i-PrOAc | 0.25 | — | — | 65 | 20 | 3 | 52:48 |
| 59 | 5% Pd/C type 37 | 25 | i-PrOAc | 0.25 | — | — | 65 | 20 | 3 | 58:42 |
| 60 | 5% Pd/C type 37 | 25 | Me-THF | 0.25 | — | — | 65 | 20 | 3 | 66:34 |
| 61 | 5% Pd/Al$_2$O$_3$ A302011 | 25 | THF | 0.05 | — | — | 40 | 10 | 16 | 38:62 |
| 62 | 5% Pd/C type 37 | 25 | THF | 0.05 | — | — | 75 | 20 | 3 | 65:35 |
| 63 | 5% Pd/C A401102 | 25 | THF | 0.05 | — | — | 55 | 20 | 16 | 53:47 |
| 64 | 5% Pd/C A405028 | 25 | THF | 0.05 | — | — | 40 | 10 | 16 | 52:48 |
| 65 | 5% Pd/C type 39 | 25 | THF | 0.05 | — | — | 60 | 20 | 3 | 63:38 |
| 66 | 5% Pd/C type 37 | 10 | THF | 0.05 | — | — | 75 | 20 | 3 | 57:43 |
| 67 | 5% Pd/C A102023 | 25 | THF | 0.05 | — | — | 40 | 10 | 16 | 52:48 |
| 68 | 5% Pd/C type 37 | 27 | THF | 0.25 | — | — | 75 | 20 | 2.5 | 64:36 |
| 69 | 5% Pd/Al$_2$O$_3$ A302084-5 | 50 | THF/H$_2$O (9:1) | 0.05 | — | — | 25 | 3 | 4 | 60:40 |
| 70 | 5% Pd/C type 37 | 25 | THF | 0.167 | — | — | 60 | 20 | 3 | 61:39 |
| 71 | 5% Pd/C A405028 | 50 | EtOH | 0.05 | — | — | 25 | 3 | 4 | 82:18 |
| 72 | 5% Pd/C type 37 | 25 | THF | 0.167 | — | — | 45 | 20 | 3 | 59:41 |
| 73 | 5% Pd/C type 37 | 25 | THF | 0.167 | — | — | 45 | 20 | 1.5 | 61:39 |
| 74 | 5% Pd(S)/C A103038 | 25 | THF | 0.05 | Et$_3$N | 1 | 40 | 20 | 3 | 48:52 |
| 75 | 5% Pd/C type 394 | 10 | THF | 0.05 | — | — | 40 | 10 | 16 | 57:43 |
| 76 | 5% Pd/C A102023 | 25 | THF | 0.05 | Et$_3$N | 1 | 40 | 20 | 3 | 45:55 |
| 77 | 5% Pd/C A503038 | 10 | HF | 0.05 | — | — | 40 | 10 | 16 | 51:49 |
| 78 | 5% Pd/C type 39 | 25 | Me-THF | 0.25 | — | — | 65 | 20 | 3 | 63:37 |
| 79 | 5% Pd/C type 37 | 25 | THF | 0.25 | — | — | 65 | 20 | 1.5 | 56:44 |
| 80 | 5% Pd/C type 37 | 25 | THF | 0.167 | — | — | 45 | 20 | 6 | 60:40 |
| 81 | 5% Pd/C type 37 | 15 | THF | 0.25 | — | — | 65 | 20 | 4 | 60:40 |
| 82 | 5% Pd/C type 37 | 15 | THF | 0.25 | — | — | 65 | 20 | 1.5 | 60:40 |
| 83 | 5% Pd/C type 37 | 25 | THF | 0.05 | — | — | 60 | 20 | 3 | 61:39 |
| 84 | 5% Pd/C type 37 | 15 | THF | 0.25 | — | — | 75 | 20 | 1.3 | 57:43 |
| 85 | 5% Pd/C A405038 | 25 | THF | 0.05 | — | — | 40 | 10 | 16 | 52:48 |
| 86 | 5% Pd/C A102038 | 25 | THF | 0.05 | — | — | 40 | 10 | 16 | 45:55 |
| 87 | 5% Pd/C type 37 | 15 | THF | 0.25 | — | — | 75 | 20 | 1.3 | 56:44 |
| 88 | 5% Pd/C A405032 | 25 | THF | 0.05 | — | — | 40 | 10 | 16 | 48:52 |
| 89 | 5% Pd/C type 37 | 27 | THF | 0.25 | — | — | 75 | 20 | 1.3 | 58:42 |
| 90 | 5% Pd(Pb)/CaCO$_3$ A 305060 | 25 | THF | 0.05 | — | — | 40 | 10 | 16 | 50:50 |
| 91 | 5% Pd(S)/C A103038 | 25 | THF | 0.167 | — | — | 40 | 20 | 7.5 | 51:49 |
| 92 | 5% Pd(S)/C A103038 | 25 | THF | 0.167 | — | — | 40 | 20 | 72 | 80:20 |

Table of Example 47 (Methods 1-178):

| Method | Heterogeneous Catalyst | Amount of Catalyst (% w/w) | Solvent | Initial Concentration of 7-a (R1 = Boc) (mol dm$^{-3}$) | Additive | Eqivalents of Additive | Temperature (° C.) | Pressure (bar) | Time (h) | 9-b (R1 = Boc, R6 = R7 = Me):9-c (R1 = Boc, R6 = R7 = Me) |
|---|---|---|---|---|---|---|---|---|---|---|
| 93 | 5% Pd/C type 487 | 10 | THF | 0.05 | — | — | 40 | 10 | 16 | 45:55 |
| 94 | 5% Pd/C type 37 | 25 | THF | 0.05 | — | — | 60 | 20 | 3 | 62:38 |
| 95 | 5% Pd/C type 39 | 25 | THF | 0.25 | — | — | 65 | 20 | 3 | 59:41 |
| 96 | 5% Pd(S)/C A103038 | 25 | THF | 0.05 | — | — | 55 | 20 | 3 | 45:55 |
| 97 | 5% Pd/C type 37 | 25 | THF | 0.25 | — | — | 65 | 20 | 4.5 | 72:28 |
| 98 | 5% Pd/C A503038 | 25 | THF | 0.05 | — | — | 40 | 10 | 16 | 53:47 |
| 99 | 10% Pd/C type 394 | 10 | THF | 0.05 | — | — | 40 | 10 | 16 | 58:42 |
| 100 | 5% Pd/SiO$_2$/Al$_2$O$_3$ C7078 | 25 | THF | 0.05 | — | — | 40 | 10 | 16 | 46:54 |
| 101 | 5% Pd/C type 37 | 25 | EtOAc | 0.25 | — | — | 65 | 20 | 3 | 61:39 |
| 102 | 5% Pd/C type 37 | 25 | THF | 0.05 | — | — | 75 | 20 | 3 | 63:37 |
| 103 | 5% Pd/C A401102 | 25 | iPrOH | 0.05 | — | — | 40 | 10 | 16 | 60:40 |
| 104 | 5% Pt/C B501018 | 25 | THF | 0.05 | — | — | 30 | 20 | 3 | 60:40 |
| 105 | 5% Pd/C type 37 | 15 | THF | 0.25 | — | — | 75 | 20 | 1.3 | 58:42 |
| 106 | 5% Pd/C A401102 | 25 | THF | 0.05 | — | — | 55 | 10 | 16 | 56:44 |
| 107 | 5% Pd/C type 37 | 25 | THF | 0.25 | — | — | 65 | 20 | 1.5 | 56:44 |
| 108 | 5% Pd/C A405038 | 10 | THF | 0.05 | — | — | 40 | 10 | 16 | 48:52 |
| 109 | 5% Pd/C A401102 | 10 | THF | 0.05 | — | — | 40 | 10 | 16 | 50:50 |
| 110 | 5% Pd/C A401102 | 15 | THF | 0.05 | — | — | 40 | 10 | 16 | 53:47 |
| 111 | 5% Pt/C B501018 | 25 | MeOH | 0.05 | — | — | 45 | 20 | 3 | 71:29 |
| 112 | 5% Pd/C type 37 | 25 | THF | 0.05 | — | — | 60 | 30 | 3 | 61:39 |
| 113 | 5% Pd/C type 37 | 15 | THF | 0.167 | — | — | 30 | 20 | 16 | 62:38 |
| 114 | 5% Pd/C type 39 | 25 | MeOH | 0.05 | — | — | 45 | 5 | 3 | 63:37 |
| 115 | 5% Pd/C type 37 | 25 | THF | 0.25 | — | — | 75 | 20 | 1.3 | 57:43 |
| 116 | 5% Pd//TiO$_2$ C6944 | 25 | THF | 0.05 | — | — | 40 | 10 | 16 | 49:51 |
| 117 | 5% Pd/Al$_2$O$_3$ A302084-5 | 50 | THF | 0.05 | — | — | 40 | 3 | 2 | 44:56 |
| 118 | 5% Pd/C A109047 | 10 | THF | 0.05 | — | — | 40 | 10 | 16 | 47:53 |
| 119 | 5% Pt/C B103014 | 25 | THF | 0.05 | — | — | 40 | 10 | 16 | 68:32 |
| 120 | 5% Pd/C A401102 | 25 | iPrOH | 0.05 | K$_2$CO$_3$ | 1 | 40 | 10 | 16 | 54:46 |
| 121 | 5% Pd/C type 37 | 25 | THF | 0.05 | — | — | 40 | 10 | 16 | 62:38 |
| 122 | 5% Pt/C B103032 | 25 | THF | 0.05 | — | — | 40 | 10 | 16 | 66:34 |
| 123 | 5% Pt/C B109032 | 25 | THF | 0.05 | — | — | 40 | 10 | 16 | 63:37 |
| 124 | 5% Pd/C type 37 | 25 | THF | 0.167 | — | — | 30 | 20 | 72 | 69:31 |
| 125 | 5% Pd/C A401102-5 | 50 | THF | 0.05 | — | — | 40 | 3 | 2 | 57:43 |
| 126 | 5% Pd(S)/C A103038 | 25 | THF | 0.05 | — | — | 40 | 10 | 16 | 50:50 |
| 127 | 5% Pd/C A405028 | 50 | EtOAc | 0.05 | — | — | 25 | 3 | 4 | 69:31 |

-continued

Table of Example 47 (Methods 1-178):

| Method | Hetereogeneous Catalyst | Amount of Catalyst (% w/w) | Solvent | Initial Concentration of 7-a (R1 = Boc) (mol dm$^{-3}$) | Additive | Eqivalents of Additive | Temperature (° C.) | Pressure (bar) | Time (h) | 9-b (R1 = Boc, R6 = R7 = Me):9-c (R1 = Boc, R6 = R7 = Me) |
|---|---|---|---|---|---|---|---|---|---|---|
| 128 | 5% Pd/BaSO$_4$ A308053 | 25 | THF | 0.05 | — | — | 40 | 10 | 16 | 54:46 |
| 129 | 5% Pd/ZrO$_2$ C7140 | 25 | THF | 0.05 | — | — | 40 | 10 | 16 | 54:46 |
| 130 | 5% Pd(S)/C A103038 | 25 | THF | 0.05 | — | — | 40 | 20 | 3 | 53:47 |
| 131 | 5% Pd/C A405028 | 50 | iPrOH | 0.05 | — | — | 25 | 3 | 4 | 64:36 |
| 132 | 5% Pd/C A102023 | 25 | THF | 0.05 | — | — | 40 | 10 | 16 | 53:47 |
| 133 | 5% Pd/C A405028 | 10 | THF | 0.05 | — | — | 40 | 10 | 16 | 50:50 |
| 134 | 5% Pd/C type 37 | 25 | MeOH | 0.05 | — | — | 45 | 20 | 3 | 65:35 |
| 135 | 5% Pd/C A401102 | 10 | THF | 0.05 | — | — | 40 | 10 | 16 | 55:45 |
| 136 | 5% Pd(S)/C A103038 | 25 | THF | 0.167 | — | — | 40 | 20 | 3 | 53:47 |
| 137 | 5% Pd/C type 37 | 15 | THF | 0.25 | — | — | 75 | 20 | 1.3 | 58:42 |
| 138 | 5% Pd/C A503032 | 25 | THF | 0.05 | — | — | 40 | 10 | 16 | 50:50 |
| 139 | 5% Pd/C type 39 | 10 | THF | 0.05 | — | — | 40 | 10 | 16 | 62:38 |
| 140 | 5% Pd/C type 5R394 | 25 | THF | 0.05 | — | — | 40 | 10 | 16 | 57:43 |
| 141 | 5% Pd/C type 37 | 25 | THF | 0.167 | — | — | 60 | 20 | 4.5 | 62:38 |
| 142 | 5% Pd/C A405028 | 50 | THF | 0.05 | — | — | 25 | 3 | 4 | 67:33 |
| 143 | 3% Pd/C type 39 | 10 | THF | 0.05 | — | — | 40 | 10 | 16 | 75:25 |
| 144 | 5% Pd/C type 39 | 25 | THF | 0.05 | — | — | 40 | 10 | 16 | 60:40 |
| 145 | 5% Pd/C type 374 | 10 | THF | 0.05 | — | — | 40 | 10 | 16 | 44:56 |
| 146 | 5% Pd/C A401102 | 25 | THF | 0.05 | Cs$_2$CO$_3$ | 1 | 40 | 10 | 16 | 54:46 |
| 147 | 5% Pd/C A401102 | 25 | THF | 0.05 | — | — | 25 | 10 | 16 | 42:58 |
| 148 | 5% Pt(S)/C B106032 | 25 | THF | 0.05 | — | — | 40 | 10 | 16 | 64:36 |
| 149 | 5% Pd/C type 37 | 10 | THF | 0.25 | — | — | 70 | 20 | 1 | 57:43 |
| 150 | 5% Pd/C type 37 | 25 | THF | 0.05 | — | — | 60 | 5 | 3 | 60:40 |
| 151 | 5% Pd/C A102023 | 25 | THF | 0.05 | — | — | 40 | 20 | 3 | 50:50 |
| 152 | 5% Pt/C B501018 | 25 | THF | 0.05 | — | — | 45 | 20 | 3 | 61:39 |
| 153 | 5% Pd/C type 5R338 | 25 | THF | 0.05 | — | — | 40 | 10 | 16 | 59:41 |
| 154 | 5% Pd/C type 37 | 10 | THF | 0.25 | — | — | 70 | 20 | 1 | 60:40 |
| 155 | 5% Pd/C A401102 | 25 | THF | 0.05 | — | — | 25 | 20 | 16 | 58:42 |
| 156 | 1% Pd/C type 39 | 10 | THF | 0.05 | — | — | 40 | 10 | 16 | 74:26 |
| 157 | 5% Pd/C A503023 | 10 | THF | 0.05 | — | — | 40 | 10 | 16 | 49:51 |
| 158 | 5% Pd/C type 39 | 25 | THF | 0.05 | — | — | 60 | 5 | 3 | 62:38 |
| 159 | 5% Pd/C type 37 | 25 | THF | 0.167 | — | — | 45 | 20 | 4.5 | 59:41 |
| 160 | 5% Pd(S)/C A103038 | 25 | THF | 0.05 | Et$_3$N | 1 | 40 | 20 | 3 | 53:47 |
| 161 | 5% Pd/C A401102 | 25 | EtOH | 0.05 | — | — | 40 | 3 | 16 | 57:43 |
| 162 | 5% Pd/C type 87L | 10 | THF | 0.05 | — | — | 40 | 10 | 16 | 44:56 |
| 163 | 5% Pd/C type 39 | 25 | MeOH | 0.05 | — | — | 45 | 20 | 3 | 62:38 |

-continued

Table of Example 47 (Methods 1-178):

| Method | Hetereogeneous Catalyst | Amount of Catalyst (% w/w) | Solvent | Initial Concentration of 7-a (R1 = Boc) (mol dm$^{-3}$) | Additive | Eqivalents of Additive | Temperature (° C.) | Pressure (bar) | Time (h) | 9-b (R1 = Boc, R6 = R7 = Me):9-c (R1 = Boc, R6 = R7 = Me) |
|---|---|---|---|---|---|---|---|---|---|---|
| 164 | 5% Pd/C type 37 | 15 | THF | 0.25 | — | — | 65 | 20 | 3 | 60:40 |
| 165 | 5% Pd/C A401102 | 25 | THF | 0.05 | K$_2$CO$_3$ | 1 | 40 | 10 | 16 | 58:42 |
| 166 | 5% Pd/C A405028 | 50 | Toluene | 0.05 | — | — | 25 | 3 | 4 | 73:27 |
| 167 | 10% Pd/C type 37 | 7.5 | THF | 0.25 | — | — | 75 | 20 | 1.3 | 55:45 |
| 168 | 5% Pd/Al$_2$O$_3$ A302084-5 | 50 | iPrOH | 0.05 | — | — | 25 | 3 | 4 | 63:38 |
| 169 | 5% Pd/C type 37 | 25 | THF | 0.25 | — | — | 65 | 20 | 1.5 | 62:38 |
| 170 | 5% Pd/C type 37 | 25 | THF | 0.25 | — | — | 65 | 20 | 3 | 64:36 |
| 171 | 5% Pt/C B501018 | 25 | THF | 0.05 | — | — | 40 | 20 | 3 | 61:39 |
| 172 | 5% Pd/Al$_2$O$_3$ A302084-5 | 50 | EtOH | 0.05 | — | — | 40 | 3 | 2 | 33:67 |
| 173 | 5% Pd/C type 37 | 25 | THF | 0.25 | — | — | 75 | 20 | 0.5 | 58:42 |
| 174 | 5% Pd/C A401102 | 25 | EtOH | 0.05 | — | — | 25 | 3 | 16 | 50:50 |
| 175 | 5% Pd/C A503023 | 25 | THF | 0.05 | — | — | 40 | 10 | 16 | 52:48 |
| 176 | 5% Pd(S)/C A103038 | 25 | THF | 0.05 | — | — | 40 | 10 | 16 | 51:49 |
| 177 | 5% Pd/C A109047 | 25 | THF | 0.05 | — | — | 40 | 10 | 16 | 46:54 |
| 178 | 5% Pd/C A503032 | 10 | THF | 0.05 | — | — | 40 | 10 | 16 | 50:50 |

HPLC Method (Example 47, Methods 1-178)

Column: X-BRIDGE; 75×4.6 mm; 3.5 μm. Mobile Phase A (0.1% NH$_3$ (32%) in water); Mobile Phase B (Acetonitrile). Gradient: 0 min (40% B); 1 min (40% B); 15 min (70% B); 18 min (70% B); 19 min (40% B); 20 min (40% B). Flow rate: 1 ml min$^{-1}$. Wavelength: 254 nm. Column temperature: 10° C.
Retention Times
9-b (R1=Boc, R6=Me, R7=Me): 9.4 min
9-c (R1=Boc, R6=Me, R7=Me): 10.4 min
7-a (R1=Boc): 11.5 min
4-a (R1=Boc): 14.1 min
3-a (R1=Boc) and 3-b (R1=Boc): 14.9 min Example 48

(3R/S, 5S)-5-Biphenyl-4-ylmethyl-3-hydroxymethyl-2-oxo-pyrrolidine-1-carboxylic acid tert-butyl ester (5-a, R1=Boc)

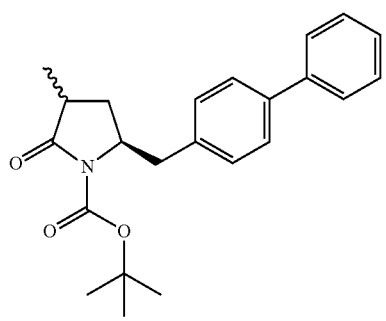

+

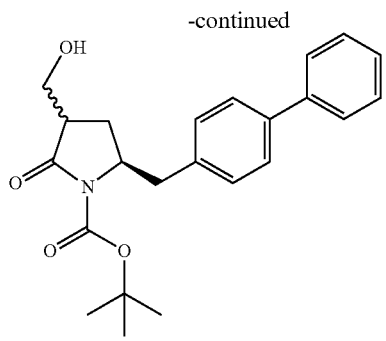

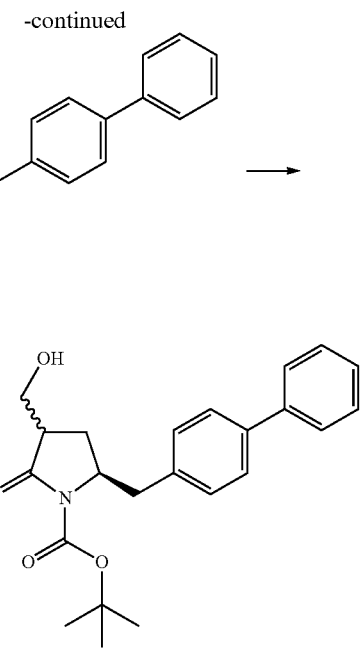

The residue obtained from Example 69 containing (3R, 5S)-5-biphenyl-4-ylmethyl-3-methyl-2-oxo-pyrrolidine-1-carboxylic acid tert-butyl ester (3-a, R1=Boc), (3S,5S)-5-biphenyl-4-ylmethyl-3-methyl-2-oxo-pyrrolidine-1-carboxylic acid tert-butyl ester (3-b, R1=Boc) and (3R/S, 5S)-5-biphenyl-4-ylmethyl-3-hydroxymethyl-2-oxo-pyrrolidine-1-carboxylic acid tert-butyl ester (5-a, R1=Boc) is purified by column chromatography, eluting with ethyl acetate-heptane (1:1) to give (3R/S, 5S)-5-biphenyl-4-ylmethyl-3-hydroxymethyl-2-oxo-pyrrolidine-1-carboxylic acid tert-butyl ester (5-a, R1=Boc) as a 62:38 mixture of (3S,5S): (3R,5S) diastereoisomers, respectively, as determined by NMR. 1H NMR (DMSO): 1.49-1.51, 1.67-1.72, 1.81-1.85, 1.93-2.04, 2.56-2.63, 2.72-2.77, 2.81-2.85, 3.03-3.06, 3.28-3.32, 3.46-3.52, 3.57-3.63, 4.17-4.27, 4.72-4.74, 4.94-4.96, 7.30-7.36, 7.43-7.46, 7.62-7.66.

Example 49

(3R/S,5S)-5-Biphenyl-4-ylmethyl-2-oxo-3-(toluene-4-sulfonyloxymethyl)-pyrrolidine-1-carboxylic acid tert-butyl ester (11-a, R1=Boc, R4=Tosyl)

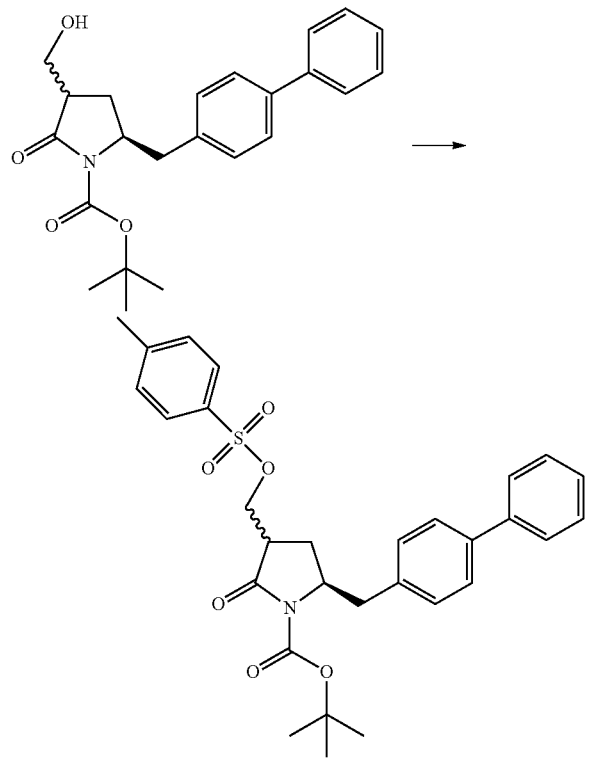

Method 1

20 mg (3R/S, 5S)-5-Biphenyl-4-ylmethyl-3-hydroxymethyl-2-oxo-pyrrolidine-1-carboxylic acid tert-butyl ester (5-a, R1=Boc) (prepared according to Example 48) is added to chloroform (5 ml) at room temperature. Triethylamine (11 μl) is added to the mixture. 4-Toluenesulphonic acid anhydride (20.5 mg) is then added to the mixture. The mixture is then stirred for 20 h at room temperature. The volatiles are removed under reduced pressure and the resulting crude material is purified by column chromatography, eluting with heptane-ethyl acetate (2:1) to afford (3R/S,5S)-5-biphenyl-4-ylmethyl-2-oxo-3-(toluene-4-sulfonyloxymethyl)-pyrrolidine-1-carboxylic acid tert-butyl ester (11-a, R1=Boc, R4=Tosyl) as a 69:31 mixture of diastereoisomers as determined by NMR. 1H NMR (CDCl$_3$): 1.51-1.53, 1.67-1.80, 2.08-2.17, 2.36, 2.64-2.79, 3.01 and 3.33, 3.89-4.16, 4.20-4.36, 7.15-7.69.

Method 2

100 mg (3R/S, 5S)-5-Biphenyl-4-ylmethyl-3-hydroxymethyl-2-oxo-pyrrolidine-1-carboxylic acid tert-butyl ester (5-a, R1=Boc) (prepared according to Example 48) is added to chloroform (3 ml) at room temperature. Triethylamine (110 μl) is added to the mixture. 4-Toluenesulphonic acid anhydride (128 mg) is then added to the mixture. The mixture is then stirred for 20 h at room temperature. Ethyl acetate (2 ml) is added to the mixture.

The mixture is washed with saturated sodium hydrogen carbonate solution (2×1 ml). The organic phase is dried (MgSO$_4$) and concentrated under reduced pressure. Purification by column chromatography, eluting with heptane-ethyl acetate (2:1) affords (3R/S,5S)-5-biphenyl-4-ylmethyl-2-oxo-3-(toluene-4-sulfonyloxymethyl)-pyrrolidine-1-carboxylic acid tert-butyl ester (11-a, R1=Boc, R4=Tosyl). LC-MS (+ES): 480 ([MH—C$_4$H$_8$]$^+$, 100%), 553 ([MNH$_4$]$^+$, 55), 1088 ([2M+NH$_4$]$^+$, 20).

Example 50

Potassium[(R)-5-biphenyl-4-ylmethyl-3-[1-dimethylaminometh-(E/Z)-ylidene]-2-oxo-pyrrolidine-1-carboxylic acid tert-butyl ester]hexafluorophosphate (7-a, R1=Boc, R6=Me, R7=Me)

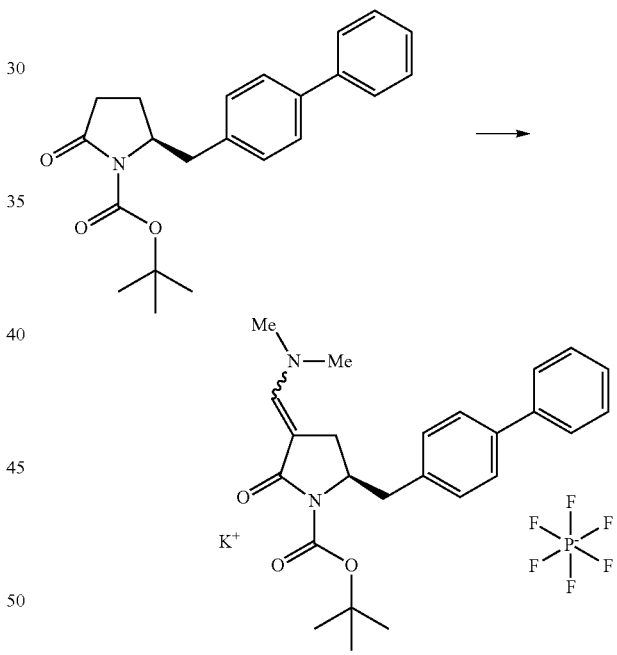

Potassium tert-butoxide solution (16 ml, 0.5 M in tetrahydrofuran) is added to 2.46 g N,N,N',N'-tetramethylformamidinium hexafluorophosphate (18, R6=Me, R7=Me) (prepared according to Example 3). The resulting mixture is heated to 60° C. and stirred at this temperature for 1 h. The resulting mixture is cooled to ambient temperature. 1 g (S)-2-Biphenyl-4-ylmethyl-5-oxo-pyrrolidine-1-carboxylic acid tert-butyl ester (8-a, R1=Boc) is added to the mixture. The resulting mixture is stirred for 20 h at ambient temperature. The mixture is then diluted with water (20 ml) and toluene (20 ml). The phases are then separated. The organic phase is washed with saturated sodium carbonate solution (2×20 ml) and then with brine (20 ml). The organic phase is dried (MgSO$_4$) and concentrated under reduced pressure. The residue is purified by column chromatography, eluting with 40% ethyl acetate in hexane. Diethyl ether is added to the residue after concentration and the resulting solid is collected by filtration and dried. 1H NMR (CDCl$_3$): 1.57-1.59, 2.57-2.63, 2.68-2.71, 2.79-2.84, 3.00, 3.24-3.28, 4.30-4.34, 7.17, 7.30-7.60. 19F NMR (CDCl$_3$): −74.9 ppm.

The X-ray Structure of the obtained crystals is shown in FIG. 6. Single crystal for this determination is obtained from tert-butylmethylether as solvent.

Crystal Data [Recorded at 120(2) K]

| | |
|---|---|
| Empirical formula | $C_{27.5}H_{36}F_3K_{0.5}N_2O_{3.5}P_{0.5}$ |
| Formula weight | 542.62 |
| Crystal system | Triclinic |
| Space group | P1 |
| Cell parameters | a = 15.089(9) Å |
| | b = 17.068(10) Å |
| | c = 18.798(12) Å |
| | α = 88.79(4)° |
| | β = 67.67(3)° |
| | γ = 72.63(4)° |
| Volume of unit cell | 4251(4) Å$^3$ |
| Z* | 6 |
| Calculated density | 1.272 mg m$^{-3}$ |

*(number of asymmetric units in the unit cell)

Example 51

(R)-5-Biphenyl-4-ylmethyl-3-[1-dimethylami-nometh-(E/Z)-ylidene]-2-oxo-pyrrolidine-1-carboxylic acid tert-butyl ester (7-a, R1=Boc, R6=Me, R7=Me)

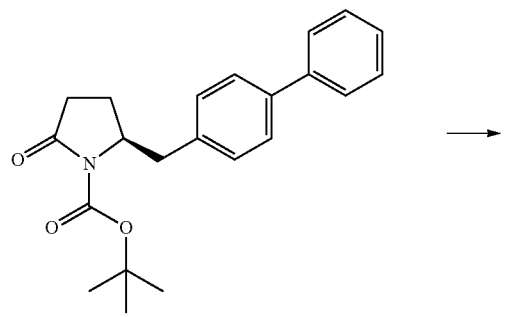

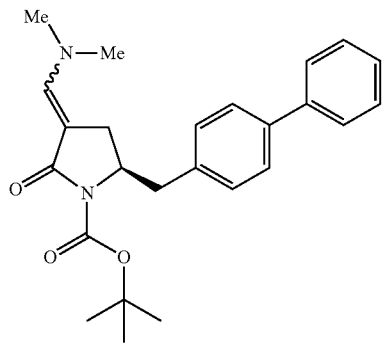

General Procedure for Methods 1-35

(S)-2-Biphenyl-4-ylmethyl-5-oxo-pyrrolidine-1-carboxylic acid tert-butyl ester (8-a, R1=Boc) (amount in mmol given in the Table of Example 51 (Methods 1-35)) is added to an ionic salt (identity and amount given in the Table of Example 51 (Methods 1-35)). Optionally, a solvent (volume and identity given in the Table of Example 51 (Methods 1-35)) is added. Bredereck's reagent [Tris(dimethylamino)methane (13, R6=Me, R7=Me), Tert-Butoxy-bis(dimethylamino) methane (14, R6=Me, R7=Me, R8=tBu) and N,N-Dimethylformamide di-tert-butyl acetal (15, R6=Me, R7=Me, R8=tBu)] (volume given in the Table of Example 51 (Methods 1-35)). The mixture is then stirred at ambient temperature for 3 h to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). $R_F$ 0.21 (salt of 7-a, R1=Boc, R6=Me, R7=Me); $R_F$ 0.27 (7-a, R1=Boc, R6=Me, R7=Me); $R_F$ 0.68 (8-a, R1=Boc).

Table of Example 51 (Methods 1-35):

| Method | 8-a (R1 = Boc) (mmol) | Total Volume [13, 14 and 15 (R6 = Me, R7 = Me, R8 = tBu)] (ml) | Ionic Salt | Equivalents of ionic salt | Solvent | Volume of solvent (ml) |
|---|---|---|---|---|---|---|
| 1 | 2 | 4 | KPF$_6$ | 1 | — | |
| 2 | 2 | 4 | NH$_4$PF$_6$ | 1 | — | |
| 3 | 2 | 4 | 1-Butyl-3-methyl imidazolium PF$_5$ | 1 | — | |
| 4 | 2 | 4 | 1-Butyl-3-methyl imidazolium BF$_4$ | 1 | — | |
| 5 | 2 | 4 | NaCl | 1 | — | |
| 6 | 2 | 4 | KCl | 1 | — | |
| 7 | 2 | 4 | KClO$_4$ | 1 | — | |
| 8 | 2 | 4 | NaPF$_6$ | 1 | — | |
| 9 | 2 | 4 | LiPF$_6$ | 1 | — | |
| 10 | 2 | 4 | LiCl | 1 | — | |
| 11 | 2 | 4 | LiBr | 1 | — | |
| 12 | 2 | 4 | Na$_2$SiF$_6$ | 1 | — | |
| 13 | 1 | 2 | LiNH$_2$ | 1 | — | |

Table of Example 51 (Methods 1-35):

| Method | 8-a (R1 = Boc) (mmol) | Total Volume [13, 14 and 15 (R6 = Me, R7 = Me, R8 = tBu)] (ml) | Ionic Salt | Equivalents of ionic salt | Solvent | Volume of solvent (ml) |
|---|---|---|---|---|---|---|
| 14 | 1 | 2 | Li$_2$CO$_3$ | 1 | — | |
| 15 | 1 | 2 | KPF$_6$ | 1 | — | |
| 16 | 1 | 1 | KPF$_6$ | 1 | THF | 1 |
| 17 | 1 | 2 | KPF$_6$ | 0.5 | — | |
| 18 | 1 | 2 | KPF$_6$ | 0.1 | — | |
| 19 | 1 | 2 | LiPF$_6$ | 1 | — | |
| 20 | 1 | 1 | LiPF$_6$ | 1 | THF | 1 |
| 21 | 1 | 0.6 | LiPF$_6$ | 1 | THF | 1.4 |
| 22 | 1 | 0.4 | LiPF$_6$ | 1 | THF | 1.6 |
| 23 | 1 | 0.3 | LiPF$_6$ | 1 | THF | 1.7 |
| 24 | 1 | 1 | LiPF$_6$ | 0.2 | THF | 1 |
| 25 | 1 | 0.6 | LiPF$_6$ | 0.2 | THF | 1.4 |
| 26 | 1 | 0.3 | LiPF$_6$ | 0.2 | THF | 1.7 |
| 27 | 1 | 2 | LiCl | 1 | — | |
| 28 | 1 | 2 | LiCl | 1 | — | |
| 29 | 1 | 1 | LiCl | 1 | THF | 1 |
| 30 | 1 | 0.6 | LiCl | 1 | THF | 1.4 |
| 31 | 1 | 0.4 | LiCl | 1 | THF | 1.6 |
| 32 | 1 | 2 | LiCl | 0.2 | — | |
| 33 | 1 | 1 | LiCl | 0.2 | THF | 1 |
| 34 | 1 | 0.6 | LiCl | 0.2 | THF | 1.4 |
| 35 | 1 | 0.4 | LiCl | 0.2 | THF | 1.6 |

Method 36

(S)-2-Biphenyl-4-ylmethyl-5-oxo-pyrrolidine-1-carboxylic acid tert-butyl ester (8-a, R1=Boc) (2 mmol) is added to potassium hexafluorophosphate (1 eq) and 18-crown-6 (1 eq). Bredereck's reagent [Tris(dimethylamino)methane (13, R6=Me, R7=Me), Tert-Butoxy-bis(dimethylamino)methane (14, R6=Me, R7=Me, R8=tBu) and N,N-Dimethylformamide di-tert-butyl acetal (15, R6=Me, R7=Me, R8=tBu)] (4 ml) is added. The mixture is then stirred at ambient temperature for 3 h to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). R$_F$ 0.21 (salt of 7-a, R1=Boc, R6=Me, R7=Me); R$_F$ 0.27 (7-a, R1=Boc, R6=Me, R7=Me); R$_F$ 0.68 (8-a, R1=Boc).

Example 52

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me)

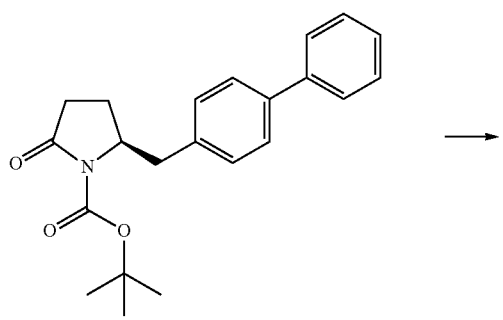

-continued

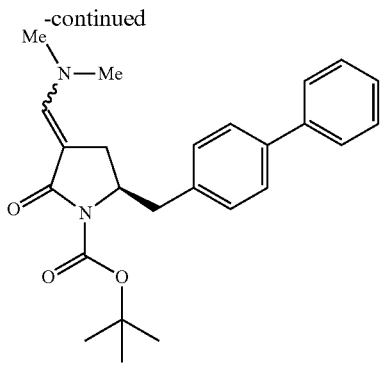

Method 1

A mixture of lithium tert-butoxide (2.8 eq, 2.8 mmol, 1 M solution in THF) and N,N,N'N'-tetramethylformamidinium hexafluorophosphate (18, R6=Me, R7=Me) (3 eq, 3 mmol) is stirred at 60° C. for 1 h. The mixture is then cooled to room temperature. The mixture is then diluted with tetrahydrofuran to a total volume of 5 ml. (S)-2-Biphenyl-4-ylmethyl-5-oxo-pyrrolidine-1-carboxylic acid tert-butyl ester (8-a, R1=Boc) (1 eq, 1 mmol) is then added to the mixture. The mixture is then stirred at room temperature for 3 h. The volatiles are removed under reduced pressure. Ethyl acetate (20 ml) is added to the mixture. The phases are separated and the organic phase washed with saturated sodium carbonate solution (2×20 ml) and brine (20 ml). The organic phase is dried (Na$_2$SO$_4$) and concentrated under reduced pressure to afford (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). R$_F$ 0.21 (salt of 7-a, R1=Boc, R6=Me, R7=Me); R$_F$ 0.27 (7-a, R1=Boc, R6=Me, R7=Me); R$_F$ 0.68 (8-a, R1=Boc).

Method 2

A mixture of lithium tert-butoxide (2.8 eq, 2.8 mmol, 1 M solution in THF) and N,N,N'N'-tetramethylformamidinium chloride (18, R6=Me, R7=Me) (3 eq, 3 mmol) are stirred at 60° C. for 1 h. The mixture is then cooled to room temperature. The mixture is then diluted with tetrahydrofuran to a total volume of 5 ml. (S)-2-Biphenyl-4-ylmethyl-5-oxo-pyrrolidine-1-carboxylic acid tert-butyl ester (8-a, R1=Boc) (1 eq, 1 mmol) is then added to the mixture. The mixture is then stirred at room temperature for 3 h. The volatiles are removed under reduced pressure. Ethyl acetate (20 ml) is added to the mixture. The phases are separated and the organic phase is washed with saturated sodium carbonate solution (2×20 ml) and brine (20 ml). The organic phase is dried ($Na_2SO_4$) and concentrated under reduced pressure to afford (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). $R_F$ 0.21 (salt of 7-a, R1=Boc, R6=Me, R7=Me); $R_F$ 0.27 (7-a, R1=Boc, R6=Me, R7=Me); $R_F$ 0.68 (8-a, R1=Boc).

Method 3

A mixture of potassium tert-butoxide (2.8 eq, 2.8 mmol, 1 M solution in THF) and N,N,N'N'-tetramethylformamidinium chloride (18, R6=Me, R7=Me) (3 eq, 3 mmol) are stirred at 60° C. for 1 h. The mixture is then cooled to room temperature. The mixture is then diluted with tetrahydrofuran to a total volume of 5 ml. (S)-2-Biphenyl-4-ylmethyl-5-oxo-pyrrolidine-1-carboxylic acid tert-butyl ester (8-a, R1=Boc) (1 eq, 1 mmol) and lithium chloride (1 eq, 1 mmol) is then added to the mixture. The mixture is then stirred at room temperature for 3 h. The volatiles are removed under reduced pressure. Ethyl acetate (20 ml) is added to the mixture. The phases are separated and the organic phase washed with saturated sodium carbonate solution (2×20 ml) and brine (20 ml). The organic phase is dried ($Na_2SO_4$) and concentrated under reduced pressure to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). $R_F$ 0.21 (salt of 7-a, R1=Boc, R6=Me, R7=Me); $R_F$ 0.27 (7-a, R1=Boc, R6=Me, R7=Me); $R_F$ 0.68 (8-a, R1=Boc).

Example 53

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me)

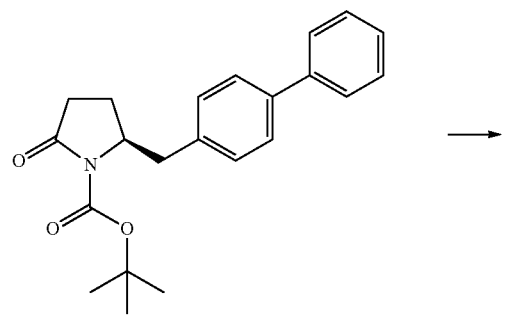

→

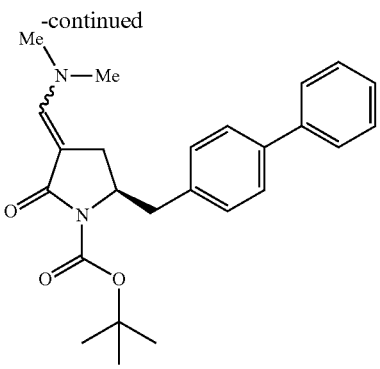

Method 1

351 mg (S)-2-Biphenyl-4-ylmethyl-5-oxo-pyrrolidine-1-carboxylic acid tert-butyl ester (8-a, R1=Boc) (1 eq, 1 mmol) and lithium hexafluorophosphate (1 eq) is added to tetrahydrofuran (10 ml). N,N-Dimethylformamide di-tert-butyl acetal (15, R6=Me, R7=Me, R8=tBu) (3 eq) and dimethylamine (0.5 eq) are added to the mixture. The mixture is stirred at room temperature for 3 h. The volatiles are removed under reduced pressure. Ethyl acetate (20 ml) is then added. The mixture is washed with saturated sodium carbonate solution (2×20 ml) and then with brine (20 ml). The organic layer is dried ($Na_2SO_4$) and concentrated under reduced pressure to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). $R_F$ 0.21 (salt of 7-a, R1=Boc, R6=Me, R7=Me); $R_F$ 0.27 (7-a, R1=Boc, R6=Me, R7=Me); $R_F$ 0.68 (8-a, R1=Boc).

General Procedure for Methods 2-6

351 mg (S)-2-Biphenyl-4-ylmethyl-5-oxo-pyrrolidine-1-carboxylic acid tert-butyl ester (8-a, R1=Boc) (1 eq, 1 mmol) and lithium hexafluorophosphate (1 eq) is added to tetrahydrofuran (10 ml). Tris(dimethylamino)methane (13, R6=Me, R7=Me) (1.5 eq, 2 eq or 3 eq) and N,N-Dimethylformamide di-tert-butyl acetal (15, R6=Me, R7=Me, R8=tBu), diisopropylamine or diphenylamine (1 eq, 1.5 eq, 3 eq or 4 eq) are added to the mixture. The mixture is stirred at room temperature for 3 h. The volatiles are removed under reduced pressure. Ethyl acetate (20 ml) is then added. The mixture is washed with saturated sodium carbonate solution (2×20 ml) and then with brine (20 ml). The organic layer is dried ($Na_2SO_4$) and concentrated under reduced pressure to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). $R_F$ 0.21 (salt of 7-a, R1=Boc, R6=Me, R7=Me); $R_F$ 0.27 (7-a, R1=Boc, R6=Me, R7=Me); $R_F$ 0.68 (8-a, R1=Boc).

Method 2

Tris(dimethylamino)methane (13, R6=Me, R7=Me) (1.5 eq); N,N-Dimethylformamide di-tert-butyl acetal (15, R6=Me, R7=Me, R8=tBu) (1.5 eq)

Method 3

Tris(dimethylamino)methane (13, R6=Me, R7=Me) (3 eq); diisopropylamine (3 eq)

Method 4

Tris(dimethylamino)methane (13, R6=Me, R7=Me) (3 eq); Diphenylamine (3 eq)

Method 5

Tris(dimethylamino)methane (13, R6=Me, R7=Me) (2 eq); Diphenylamine (4 eq)

Method 6
  Tris(dimethylamino)methane (13, R6=Me, R7=Me) (3 eq); Diphenylamine (1 eq)

Example 54

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me)

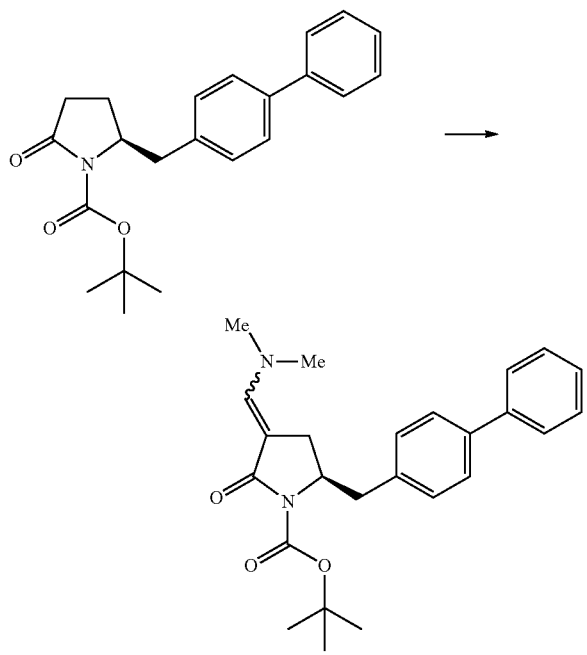

General Procedure for Methods 1-8

351 mg (S)-2-Biphenyl-4-ylmethyl-5-oxo-pyrrolidine-1-carboxylic acid tert-butyl ester (8-a, R1=Boc) and N,N,N'N'-tetramethylformamidinium hexafluorophosphate (18, R6=Me, R7=Me) (0.1 or 1 eq) are dissolved in 10 ml of a solvent (tetrahydrofuran, 1 dioxane in tetrahydrofuran, 5% dioxane in tetrahydrofuran, 20% dioxane in tetrahydrofuran, dioxane or tetrahydrofuran containing 50 mol % N,N,N'N'-tetramethylethylenediamine). 520 µl Tris(dimethylamino)methane (13, R6=Me, R7=Me) is added to the mixture. Tertiary butanol (1 eq or 3 eq) is then added to the mixture. The resulting mixture is stirred at ambient temperature for 3 h. The volatiles are then removed under reduced pressure. Ethyl acetate (20 ml) is added to the mixture. The mixture is then washed with saturated sodium carbonate solution (2×20 ml) and then with brine. The organic phase is dried (Na$_2$SO$_4$) and concentrated under reduced pressure to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). R$_F$ 0.21 (salt of 7-a, R1=Boc, R6=Me, R7=Me); R$_F$ 0.27 (7-a, R1=Boc, R6=Me, R7=Me); R$_F$ 0.68 (8-a, R1=Boc).

Method 1
  N,N,N'N'-tetramethylformamidinium hexafluorophosphate (18, R6=Me, R7=Me): 1 eq; Tertiary butanol (3 eq); Solvent: Tetrahydrofuran Method 2
  N,N,N'N'-tetramethylformamidinium hexafluorophosphate (18, R6=Me, R7=Me): 1 eq; Tertiary butanol (1 eq); Solvent: Tetrahydrofuran Method 3
  N,N,N'N'-tetramethylformamidinium hexafluorophosphate (18, R6=Me, R7=Me): 0.1 eq; tertiary butanol (1 eq); Solvent: 1 Dioxane in Tetrahydrofuran Method 4
  N,N,N'N'-tetramethylformamidinium hexafluorophosphate (18, R6=Me, R7=Me): 0.1 eq; tertiary butanol (1 eq); Solvent: 5% Dioxane in Tetrahydrofuran Method 5
  N,N,N'N'-tetramethylformamidinium hexafluorophosphate (18, R6=Me, R7=Me): 0.1 eq; tertiary butanol (1 eq); Solvent: 10% Dioxane in Tetrahydrofuran Method 6
  N,N,N'N'-tetramethylformamidinium hexafluorophosphate (18, R6=Me, R7=Me): 0.1 eq; tertiary butanol (1 eq); Solvent: 20% Dioxane in Tetrahydrofuran Method 7
  N,N,N'N'-tetramethylformamidinium hexafluorophosphate (18, R6=Me, R7=Me): 0.1 eq; tertiary butanol (1 eq); Solvent: Dioxane Method 8
  N,N,N'N'-tetramethylformamidinium hexafluorophosphate (18, R6=Me, R7=Me): 0.1 eq; tertiary butanol (3 eq); Solvent: Tetrahydrofuran containing 50 mol % N,N,N'N'-tetramethylethylenediamine

Example 55

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me)

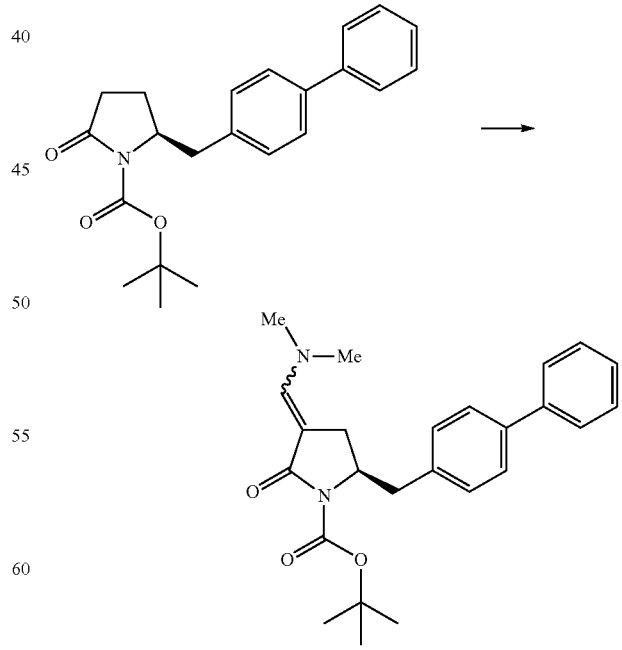

General Procedure for Methods 1-3
  351 mg (1 mmol) (S)-2-Biphenyl-4-ylmethyl-5-oxo-pyrrolidine-1-carboxylic acid tert-butyl ester (8-a, R1=Boc) and magnesium chloride (0.1, 1 or 2 eq) are added to tetrahydrofuran (10 ml). The mixture is stirred at room temperature. Tris(dimethylamino)methane (13, R6=Me, R7=Me) (3 eq) and tertiary butanol (3 eq) are added. The mixture is stirred at room temperature for 3 h. The volatiles are removed under reduced pressure. Ethyl acetate (2×20 ml) is added. The mixture is washed with saturated sodium carbonate solution (2×20 ml) and brine (20 ml). The organic phase is dried (Na$_2$SO$_4$) and concentrated under reduced pressure to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). R$_F$ 0.21 (salt of 7-a, R1=Boc, R6=Me, R7=Me); R$_F$ 0.27 (7-a, R1=Boc, R6=Me, R7=Me); R$_F$ 0.68 (8-a, R1=Boc).

Method 1
  Magnesium chloride (0.1 eq)
Method 2
  Magnesium chloride (1 eq)
Method 3
  Magnesium chloride (2 eq)

Example 56

(R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me)

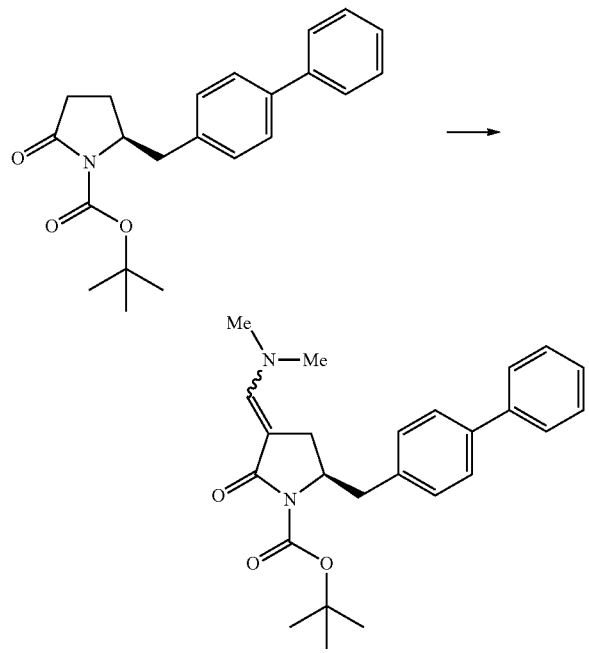

LHMDS (1 M solution in THF, 2 ml, 2 mmol) is added to a mixture of diphenylamine (340 mg, 2 mmol) and N,N,N',N'-tetramethylformamidinium hexafluorophosphate (492 mg, 2 mmol) in tetrahydrofuran (2 ml). The mixture is then stirred at room temperature for 0.5 h. The mixture is diluted by addition of tetrahydrofuran (5 ml). (S)-2-Biphenyl-4-ylmethyl-5-oxo-pyrrolidine-1-carboxylic acid tert-butyl ester (8-a, R1=Boc) (351 mg, 1 mmol) is then added to the mixture. The mixture is stirred for 15 min at room temperature. The volatiles are removed under reduced pressure. Ethyl acetate (20 ml) is added to the mixture. The mixture is washed with saturated sodium carbonate solution (2×20 ml) and brine (20 ml). The organic phase is dried (Na$_2$CO$_3$) and concentrated under reduced pressure to afford (R)-5-biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) or a salt thereof. The solutions are analysed by TLC (50% ethyl acetate in hexane). R$_F$ 0.21 (salt of 7-a, R1=Boc, R6=Me, R7=Me); R$_F$ 0.27 (7-a, R1=Boc, R6=Me, R7=Me); R$_F$ 0.68 (8-a, R1=Boc).

Example 57

(S)-1-benzyl-5-biphenyl-4-ylmethyl-pyrrolidin-2-one (8-a, R1=Benzyl)

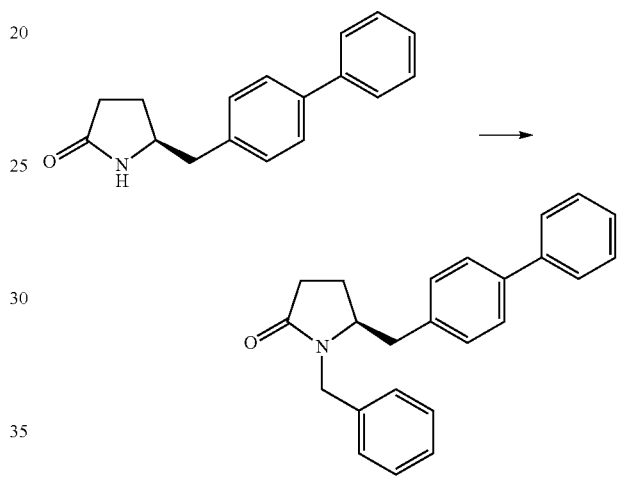

2.51 g S)-5-Biphenyl-4-ylmethyl-pyrrolidin-2-one (8-a, R1=H) and sodium hydride (312 mg, 13 mmol) are added to tetrahydrofuran, with stirring. Benzyl bromide (1.43 ml) is added and the resulting mixture stirred for 4 h. The volatiles are removed under reduced pressure. Ethyl acetate (50 ml) is added to the mixture. The organic phase is washed with saturated sodium carbonate solution (2×40 ml) and brine (40 ml). The organic phase is dried (Na$_2$SO$_4$) and concentrated under reduced pressure. The residue is purified by column chromatography (60% ethyl acetate in hexane) to afford (S)-1-benzyl-5-biphenyl-4-ylmethyl-pyrrolidin-2-one (8-a, R1=Benzyl). 1H NMR (DMSO): 1.6-1.9 (2H), 2.1 (2H), 2.6 (1H), 3.0 (1H), 3.5-3.7 (1H), 4.2 (1H), 4.8 (1H), 7.1-7.7 (14H).

Example 58

Tris(dimethylamino)methane (13, R6=Me, R7=Me), Tert-Butoxy-bis(dimethylamino)methane (14, R6=Me, R7=Me, R8=tBu) and N,N-Dimethylformamide di-tert-butyl acetal (15, R6=Me, R7=Me, R8=tBu)

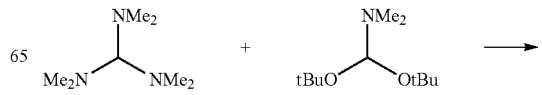

-continued

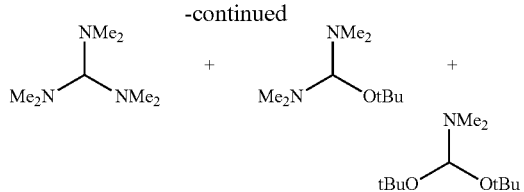

General Procedure for Methods 1-39

Tris(dimethylamino)methane (13, R6=Me, R7=Me) (0.1 eq or 0.25 eq or 0.5 eq or 0.75 eq or 0.9 eq) is added to N,N-Dimethylformamide di-tert-butyl acetal (15, R6=Me, R7=Me, R8=tBu) (0.1 eq or 0.25 eq or 0.5 eq or 0.75 eq or 0.9 eq) at room temperature. Optionally, potassium hexafluorophosphate (0 eq or 0.2 eq or 1 eq) is added to the mixture. Optionally, lithium chloride (0 eq or 1 eq) is added to the mixture. The resulting mixture is then stirred at room temperature or at elevated temperature (45° C. or 60° C. or 80° C.) for a given time (1 h or 2 h or 4 h or 16 h or 18 h or 21 h) to afford a mixture of tris(dimethylamino)methane (13, R6=Me, R7=Me), tert-butoxy-bis(dimethylimino)methane (14, R6=Me, R7=Me, R8=tBu) and N,N-dimethylformamide di-tert-butyl acetal (15, R6=Me, R7=Me, R8=tBu). Spectroscopic data as in Example 14, Method 1.

Example 59

(2R,4S)-5-Biphenyl-4-yl-4-tert-butoxycarbonylamino-2-methylpentanoic acid methyl ester (1-a, R1=Boc, R2=H, R3=CO$_2$Me)

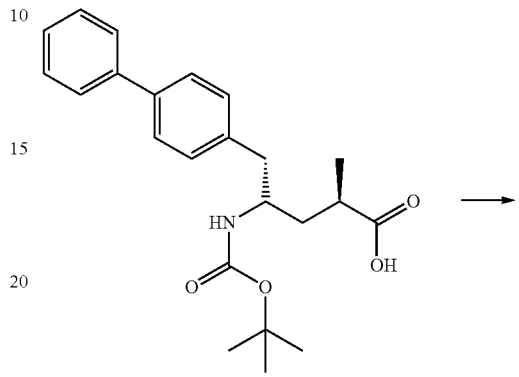

| Method | Equivalents of 13 (R6 = Me, R7 = Me) | Equivalents of 15 (R6 = Me, R7 = Me) | Equivalents of potassium hexafluorophosphate | Equivalents of lithium chloride | Temperature (° C.) | Reaction Time (hours) |
|---|---|---|---|---|---|---|
| 1 | 0.5 | 0.5 | 0 | 0 | rt | 16 |
| 2 | 0.5 | 0.5 | 1 | 0 | rt | 2 |
| 3 | 0.9 | 0.1 | 0 | 0 | 45 | 16 |
| 4 | 0.9 | 0.1 | 0 | 0 | 45 | 4 |
| 5 | 0.25 | 0.75 | 0 | 0 | 45 | 1 |
| 6 | 0.75 | 0.25 | 0 | 0 | 45 | 16 |
| 7 | 0.5 | 0.5 | 0 | 0 | 80 | 4 |
| 8 | 0.9 | 0.1 | 0 | 0 | 80 | 16 |
| 9 | 0.1 | 0.9 | 0 | 0 | 80 | 4 |
| 10 | 0.25 | 0.75 | 0 | 0 | 80 | 1 |
| 11 | 0.5 | 0.5 | 0 | 0 | 80 | 1 |
| 12 | 0.25 | 0.75 | 0 | 0 | 80 | 4 |
| 13 | 0.5 | 0.5 | 0 | 0 | 80 | 16 |
| 14 | 0.9 | 0.1 | 0 | 0 | 80 | 1 |
| 15 | 0.9 | 0.1 | 0 | 0 | 45 | 1 |
| 16 | 0.1 | 0.9 | 0 | 0 | 45 | 16 |
| 17 | 0.75 | 0.25 | 0 | 0 | 45 | 1 |
| 18 | 0.5 | 0.5 | 0 | 0 | rt | 1 |
| 19 | 0.5 | 0.5 | 1 | 0 | rt | 21 |
| 20 | 0.5 | 0.5 | 0 | 0 | 45 | 16 |
| 21 | 0.5 | 0.5 | 0 | 0 | 45 | 4 |
| 22 | 0.75 | 0.25 | 0 | 0 | 80 | 4 |
| 23 | 0.75 | 0.25 | 0 | 0 | 80 | 16 |
| 24 | 0.1 | 0.9 | 0 | 0 | 80 | 16 |
| 25 | 0.1 | 0.9 | 0 | 0 | 45 | 4 |
| 26 | 0.25 | 0.75 | 0 | 0 | 45 | 4 |
| 27 | 0.25 | 0.75 | 0 | 0 | 80 | 16 |
| 28 | 0.1 | 0.9 | 0 | 0 | 45 | 1 |
| 29 | 0.5 | 0.5 | 1 | 0 | rt | 18 |
| 30 | 0.75 | 0.25 | 0 | 0 | 80 | 1 |
| 31 | 0.5 | 0.5 | 0 | 0 | rt | 4 |
| 32 | 0.75 | 0.25 | 0 | 0 | 45 | 4 |
| 33 | 0.9 | 0.1 | 0 | 0 | 80 | 4 |
| 34 | 0.5 | 0.5 | 0 | 1 | 60 | 2 |
| 35 | 0.5 | 0.5 | 1 | 0 | 60 | 2 |
| 36 | 0.1 | 0.9 | 0 | 0 | 80 | 1 |
| 37 | 0.5 | 0.5 | 0.2 | 0 | 60 | 2 |
| 38 | 0.5 | 0.5 | 0 | 0 | 45 | 1 |
| 39 | 0.25 | 0.75 | 0 | 0 | 45 | 16 |

-continued

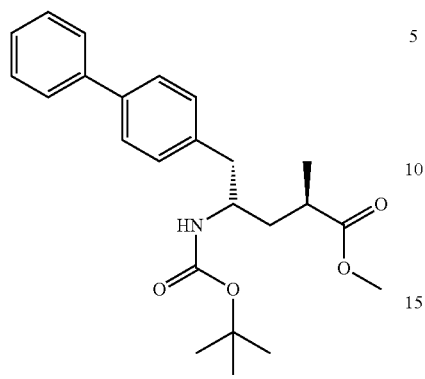

2 g (2R,4S)-5-Biphenyl-4-yl-4-tert-butoxycarbony-lamino-2-methylpentanoic acid (1-a, R1=Boc, R2=H, R3=CO$_2$H) prepared according to Example 2 in WO/2008/031567 is added to 2.55 g caesium carbonate. Dimethylformamide (4 ml) is then added. Methyl iodide (0.55 ml) is then added and the mixture is stirred for 16 h at room temperature. Water (10 ml) and isopropyl acetate (10 ml) are added. The phases are separated. The aqueous phase is washed with isopropyl acetate (2×10 ml). The combined organic phases are washed with 20% aqueous sodium chloride solution (15 ml) and then dried (MgSO$_4$). The mixture is concentrated under reduced pressure to afford (2R,4S)-5-biphenyl-4-yl-4-tert-butoxycarbonylamino-2-methylpentanoic acid methyl ester (1-a, R1=Boc, R2=H, R3=CO$_2$Me). 1H NMR (CDCl$_3$): 1.18 (3H), 1.41 (9H), 1.51 (1H), 1.95 (1H), 2.66 (1H), 2.85 (2H), 3.70 (3H), 3.94 (1H), 4.36 (1H), 7.25 (2H), 7.35 (1H), 7.45 (2H), 7.53 (2H), 7.59 (2H).

Example 60

(2R,4S)-5-Biphenyl-4-yl-4-tert-butoxycarbony-lamino-2-methylpentanoic acid methyl ester (1-a, R1=Boc, R2=H, R3=CO$_2$Me) and (2S,4S)-5-biphe-nyl-4-yl-4-tert-butoxycarbonylamino-2-methylpen-tanoic acid methyl ester (1-b, R1=Boc, R2=H, R3=CO$_2$Me)

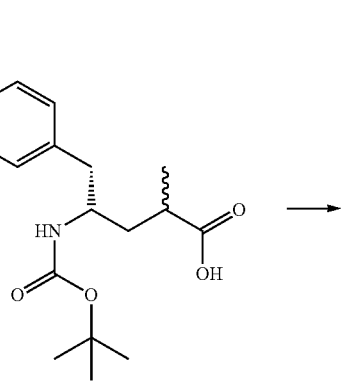

-continued

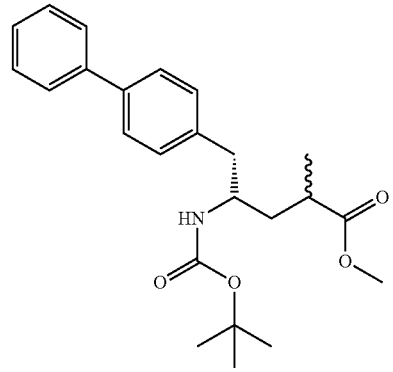

2 g (2R,4S)-5-Biphenyl-4-yl-4-tert-butoxycarbony-lamino-2-methylpentanoic acid (1-a, R1=Boc, R2=H, R3=CO$_2$H) and (2S,4S)-5-Biphenyl-4-yl-4-tert-butoxycar-bonylamino-2-methylpentanoic acid (1-a, R1=Boc, R2=H, R3=CO$_2$H), ratio of diastereomers of 80:20 ratio, respectively, prepared according to Example 3 in WO/2008/031567, is added to 2.55 g caesium carbonate. Dimethylformamide (4 ml) is then added. Methyl iodide (0.55 ml) is then added and the mixture is stirred for 16 h at room temperature. Water (10 ml) and isopropyl acetate (10 ml) are added. The phases are separated. The aqueous phase is washed with isopropyl acetate (2×10 ml). The combined organic phases are washed with 20% aqueous sodium chloride solution (15 ml) and then dried (MgSO$_4$). The mixture is concentrated under reduced pressure to afford (2R,4S)-5-biphenyl-4-yl-4-tert-butoxycar-bonylamino-2-methylpentanoic acid methyl ester (1-a, R1=Boc, R2=H, R3=CO$_2$Me) and (2S,4S)-5-biphenyl-4-yl-4-tert-butoxycarbonylamino-2-methylpentanoic acid methyl ester (1-a, R1=Boc, R2=H, R3=CO$_2$Me) as an 80:20 mixture of diastereomers, respectively. 1H NMR (CDCl$_3$): 1.17-1.20, 1.25-1.26, 1.41, 1.46-1.63, 1.76-1.85, 1.92-1.99, 2.51-2.59, 2.61-2.71, 2.76-2.85, 3.70, 3.83-3.99, 4.09-4.40, 7.25-7.28, 7.33-7.37, 7.43-7.47, 7.53-7.55, 7.59-7.61. Ratio of diastereomers 80:20 (1-a, R1=Boc, R2=H, R3=CO$_2$Me: 1-b, R1=Boc, R2=H, R3=CO$_2$Me) by integration of signals at 1.76-1.85 (1-b, R1=Boc, R2=H, R3=CO$_2$Me) and 1.92-1.99 (1-a, R1=Boc, R2=H, R3=CO$_2$Me).

Example 61

(R)-5-Biphenyl-4-yl-4-tert-butoxycarbonylamino-2-methylenepentanoic acid methyl ester (2-a, R1=Boc, R2=H, R3=CO$_2$Me)

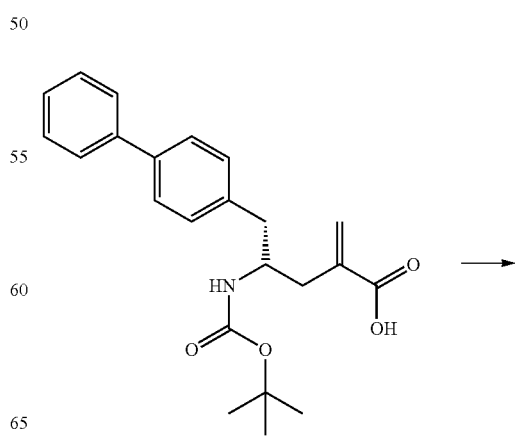

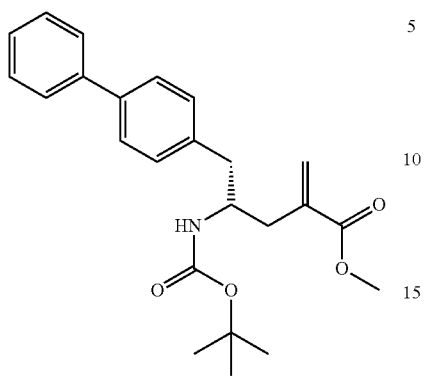

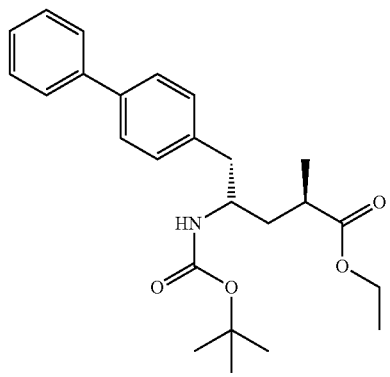

30 g (R)-5-Biphenyl-4-yl-4-tert-butoxycarbonylamino-2-methylenepentanoic acid (2-a, R1=Boc, R2=H, R3=CO₂H), prepared according to Example 33 is added to 38.4 g caesium carbonate. Dimethylformamide (50 ml) is then added. Methyl iodide (8.26 ml) is then added and the mixture is stirred for 16 h at room temperature. Water (1200 ml) and isopropyl acetate (120 ml) are added. The phases are separated. The aqueous phase is washed with isopropyl acetate (2×120 ml). The combined organic phases are washed with 20% aqueous sodium chloride solution (180 ml) and then dried (MgSO₄). The mixture is concentrated under reduced pressure to afford (R)-5-biphenyl-4-yl-4-tert-butoxycarbonylamino-2-methylenepentanoic acid methyl ester (2-a, R1=Boc, R2=H, R3=CO₂Me). 1H NMR (CDCl₃): 1.40 (9H), 2.38 (1H), 2.61 (1H), 2.86 (1H), 2.91 (1H), 3.78 (3H), 4.07 (1H), 4.52 (1H), 5.64 (1H), 6.25 (1H), 7.29 (2H), 7.35 (1H), 7.45 (2H), 7.55 (2H), 7.59 (2H).

2 g (2R,4S)-5-Biphenyl-4-yl-4-tert-butoxycarbonylamino-2-methylpentanoic acid (1-a, R1=Boc, R2=H, R3=CO₂H) prepared according to Example 2 in WO/2008/031567 is added to 2.55 g caesium carbonate. Dimethylformamide (4 ml) is then added. Ethyl iodide (0.55 ml) is then added and the mixture is stirred for 16 h at room temperature. Water (10 ml) and isopropyl acetate (10 ml) are added. The phases are separated. The aqueous phase is washed with isopropyl acetate (2×10 ml). The combined organic phases are washed with 20% aqueous sodium chloride solution (15 ml) and then dried (MgSO₄). The mixture is concentrated under reduced pressure to afford (2R,4S)-5-biphenyl-4-yl-4-tert-butoxycarbonylamino-2-methylpentanoic acid ethyl ester (1-a, R1=Boc, R2=H, R3=CO₂Et). 1H NMR (CDCl₃): 1.18 (3H), 1.27 (3H), 1.42 (9H), 1.49 (1H), 1.95 (1H), 2.62 (1H), 2.85 (2H), 3.94 (1H), 4.16 (2H), 4.36 (1H), 7.26 (2H), 7.35 (1H), 7.45 (2H), 7.55 (2H), 7.59 (2H).

Example 62

(2R,4S)-5-biphenyl-4-yl-4-tert-butoxycarbonylamino-2-methylpentanoic acid ethyl ester (1-a, R1=Boc, R2=H, R3=CO₂Et)

Example 63

(2R,4S)-5-biphenyl-4-yl-4-tert-butoxycarbonylamino-2-methylpentanoic acid ethyl ester (1-a, R1=Boc, R2=H, R3=CO₂Et) and (2S,4S)-5-biphenyl-4-yl-4-tert-butoxycarbonylamino-2-methylpentanoic acid ethyl ester (1-b, R1=Boc, R2=H, R3=CO₂Et)

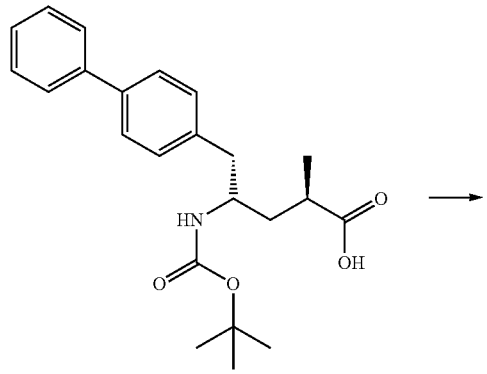

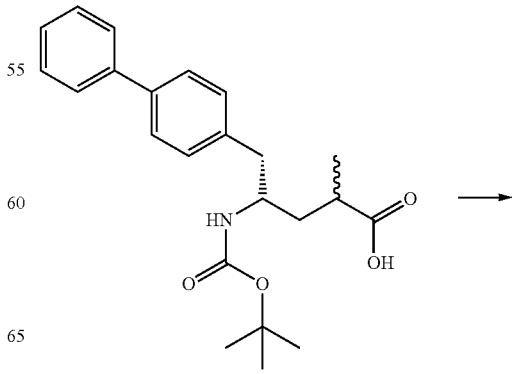

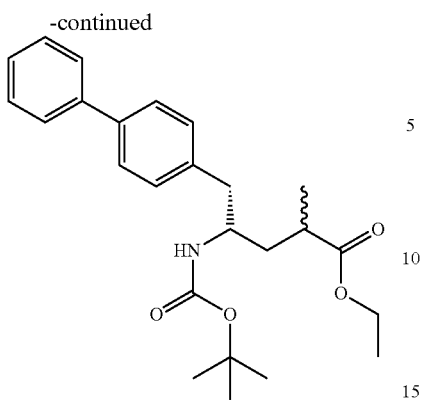

2 g (2R,4S)-5-Biphenyl-4-yl-4-tert-butoxycarbonylamino-2-methylpentanoic acid (1-a, R1=Boc, R2=H, R3=CO₂H) and (2S,4S)-5-Biphenyl-4-yl-4-tert-butoxycarbonylamino-2-methylpentanoic acid (1-a, R1=Boc, R2=H, R3=CO₂H), ratio of diastereomers of 80:20 ratio, respectively, prepared according to Example 3 in WO/2008/031567, is added to 2.55 g caesium carbonate. Dimethylformamide (4 ml) is then added. Ethyl iodide (0.55 ml) is then added and the mixture is stirred for 16 h at room temperature. Water (10 ml) and isopropyl acetate (10 ml) are added. The phases are separated. The aqueous phase is washed with isopropyl acetate (2×10 ml). The combined organic phases are washed with 20% aqueous sodium chloride solution (15 ml) and then dried (MgSO₄). The mixture is concentrated under reduced pressure to afford (2R,4S)-5-biphenyl-4-yl-4-tert-butoxycarbonylamino-2-methylpentanoic acid ethyl ester (1-a, R1=Boc, R2=H, R3=CO₂Et) and (2S,4S)-5-biphenyl-4-yl-4-tert-butoxycarbonylamino-2-methylpentanoic acid ethyl ester (1-a, R1=Boc, R2=H, R3=CO₂Et) as an 80:20 mixture of diastereomers, respectively. 1H NMR (CDCl₃): 1.16-1.20, 1.25-1.29, 1.42, 1.47-1.52, 1.56-1.62, 1.76-1.84, 1.92-1.98, 2.48-2.57, 2.58-2.67, 2.77-2.88, 3.77-4.01, 4.10-4.18, 4.32-4.41, 7.26-7.28, 7.33-7.37, 7.43-7.47, 7.53-7.55, 7.59-7.60. Ratio of diastereomers 80:20 (1-a, R1=Boc, R2=H, R3=CO₂Et: 1-b, R1=Boc, R2=H, R3=CO₂Et) by integration of signals at 1.76-1.84 (1-b, R1=Boc, R2=H, R3=CO₂Et) and 1.92-1.98 (1-a, R1=Boc, R2=H, R3=CO₂Et).

Example 64

(R)-5-Biphenyl-4-yl-4-tert-butoxycarbonylamino-2-methylenepentanoic acid ethyl ester (2-a, R1=Boc, R2=H, R3=CO₂Et)

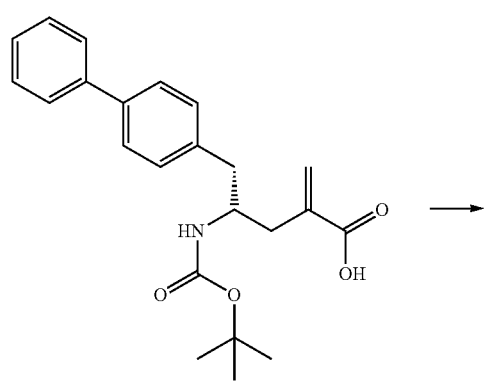

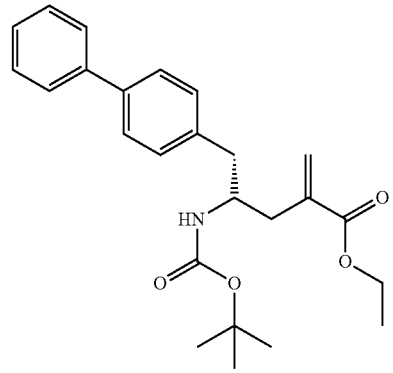

30 g (R)-5-Biphenyl-4-yl-4-tert-butoxycarbonylamino-2-methylenepentanoic acid (2-a, R1=Boc, R2=H, R3=CO₂H), prepared according to Example 33 is added to 38.4 g caseium carbonate. Dimethylformamide (50 ml) is then added. Ethyl iodide (8.26 ml) is then added and the mixture is stirred for 16 h at room temperature. Water (1200 ml) and isopropyl acetate (120 ml) are added. The phases are separated. The aqueous phase is washed with isopropyl acetate (2×120 ml). The combined organic phases are washed with 20% aqueous sodium chloride solution (180 ml) and then dried (MgSO₄). The mixture is concentrated under reduced pressure to afford (R)-5-biphenyl-4-yl-4-tert-butoxycarbonylamino-2-methylenepentanoic acid, ethyl ester (2-a, R1=Boc, R2=H, R3=CO₂Et). 1H NMR (CDCl₃): 1.31 (3H), 1.40 (9H), 2.37 (1H), 2.59 (1H), 2.84 (1H), 2.93 (1H), 4.06 (1H), 4.24 (2H), 4.56 (1H), 5.62 (1H), 6.25 (1H), 7.29 (2H), 7.35 (1H), 7.45 (2H), 7.54 (2H), 7.59 (2H).

Example 65

(2R,4S)-5-biphenyl-4-yl-4-tert-butoxycarbonylamino-2-methylpentanoic acid ethyl ester (1-a, R1=Boc, R2=H, R3=CO₂Et) and (2S,4S)-5-biphenyl-4-yl-4-tert-butoxycarbonylamino-2-methylpentanoic acid ethyl ester (1-b, R1=Boc, R2=H, R3=CO₂Et)

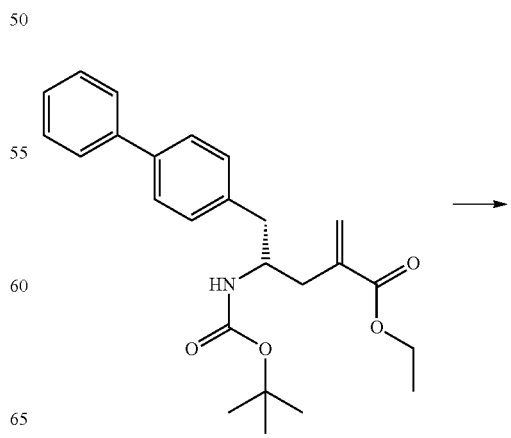

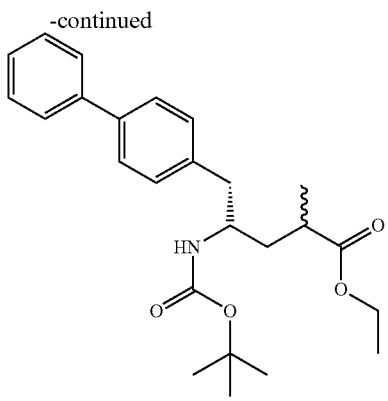

Method 1

409 mg (R)-5-Biphenyl-4-yl-4-tert-butoxycarbonylamino-2-methylenepentanoic acid ethyl ester (2-a, R1=Boc, R2=H, R3=CO₂Et) is added to ethanol (9 ml) in Vessel A. 14.9 mg [Rh(NBD)₂]BF₄ and 39.6 mg (R)-1-[(R)-2-(2'-dicyclohexylphosphinophenyl)-ferrocenyl]ethyldi(bis-(3,5-trifluoromethyl)phenyl)-phosphine (=Walphos SL-W008-1) are added to ethanol (3 ml) in Vessel B. The contents of Vessel B are stirred for 0.5 h at room temperature. The contents of Vessel A and Vessel B are then transferred to Vessel C. Vessel C is purged with hydrogen (20 bar) and then pressurised under a hydrogen atmosphere at 20 bar. The mixture is stirred for 16 h. The volatiles are removed under reduced pressure. The residue is analysed by hplc to determine the ratio of (2R,4S)-5-biphenyl-4-yl-4-tert-butoxycarbonylamino-2-methylpentanoic acid ethyl ester (1-a, R1=Boc, R2=H, R3=CO₂Et) to (2S,4S)-5-biphenyl-4-yl-4-tert-butoxycarbonylamino-2-methylpentanoic acid ethyl ester (1-b, R1=Boc, R2=H, R3=CO₂Et). Diastereomer ratio 50.2:49.8 (1-a, R1=Boc, R2=H, R3=COEt: 1-b, R1=Boc, R2=H, R3=COEt) as determined by hplc.

Method 2

409 mg (R)-5-Biphenyl-4-yl-4-tert-butoxycarbonylamino-2-methylenepentanoic acid ethyl ester (2-a, R1=Boc, R2=H, R3=CO₂Et) is added to ethanol (9 ml) in Vessel A. 17.4 mg [Ru(COD)(CF₃CO₂)₂] and 44.2 mg (αR,αR)-2,2'-bis(α-N,N-dimethylaminophenylmethyl)-(S,S)-1,1'-bis[di(3,5-dimethyl-4-methoxyphenyl]phosphino]ferrocene (=Mandyphos SL-M004-1) are added to dichloroethane (3 ml) in Vessel B. The contents of Vessel B are stirred for 0.5 h at 50° C. The volatiles are removed from the mixture in Vessel B under reduced pressure. Ethanol (3 ml) is then added to Vessel B. The contents of Vessel A and Vessel B are then transferred to Vessel C. Vessel C is purged with hydrogen (20 bar) and then pressurised under a hydrogen atmosphere at 20 bar. The mixture is stirred for 16 h. The volatiles are removed under reduced pressure. The residue is analysed by hplc to determine the ratio of (2R,4S)-5-biphenyl-4-yl-4-tert-butoxycarbonylamino-2-methylpentanoic acid ethyl ester (1-a, R1=Boc, R2=H, R3=CO₂Et) to (2S,4S)-5-biphenyl-4-yl-4-tert-butoxycarbonylamino-2-methylpentanoic acid ethyl ester (1-b, R1=Boc, R2=H, R3=CO₂Et). Diastereomer ratio 25.5:74.5 (1-a, R1=Boc, R2=H, R3=COEt: 1-b, R1=Boc, R2=H, R3=COEt) as determined by hplc.

General Procedure (Example 65, Methods 3-12)

The Organometallic Complex (A) and Chiral Ligand (L) are added to a mixture of ethanol (0.041 ml) and dichloroethane (0.135 ml). The ratio of Chiral Ligand per atom of metal within the Organometallic Complex used is 1.20:1. The S/C ratio is 25. The mixture is stirred for 0.5 h. The solvent is then removed. (R)-5-Biphenyl-4-yl-4-tert-butoxycarbonylamino-2-methylenepentanoic acid (2-a, R1=Boc, R2=H, R3=CO₂Et) in ethanol or dichloroethane (0.244 ml) is added to the vessel containing the Organometallic Complex (A) and Chiral Ligand (L). Further solvent is added to give the final concentration of 2-a (R1=Boc, R2=H, R3=CO₂H) of 84 mM.

Hydrogen gas at 20 bar is the applied to the vessel containing the mixture. The mixture is stirred at 20 bar hydrogen pressure and at room temperature for 16 hours.

The reaction solutions are analysed by hplc to determine the ratio of (1-a, R1=Boc, R2=H, R3=CO₂Et) and (1-b, R1=Boc, R2=H, R3=CO₂Et).

Method 3

Chiral Ligand {(2S,4S)-2,4-Bis(diphenylphosphino)pentane=(S,S)-BDPP}; Organometallic Complex {bis(trifluoroacetoxy)(1,5-cyclooctadiene)ruthenium(II)}; Solvent: Ethanol. Diastereomer ratio 85:15 ((1-a, R1=Boc, R2=H, R3=CO₂Et):(1-b, R1=Boc, R2=H, R3=CO₂Et) as determined by hplc.

Method 4

Chiral Ligand {(R)-1-[(S)-2-Di-tert.-butylphosphino)ferrocenyl]ethyldicyclohexylphosphine=SL-J505-1}; Organometallic Complex {bis(trifluoroacetoxy)(1,5-cyclooctadiene)ruthenium(II)}; Solvent: Ethanol. Diastereomer ratio 71:29 ((1-a, R1=Boc, R2=H, R3=CO₂Et): (1-b, R1=Boc, R2=H, R3=CO₂Et) as determined by hplc.

Method 5

Chiral Ligand {(1S)-Diphenylphosphino-2-[(R)-α-(N,N-dimethylamino)-o-diphenylphosphinophenyl)-methyl]ferrocene=SL-T001-1}; Organometallic Complex {bis(trifluoroacetoxy)(1,5-cyclooctadiene)ruthenium(II)}; Solvent: Ethanol. Diastereomer ratio 70:30 ((1-a, R1=Boc, R2=H, R3=CO₂Et): (1-b, R1=Boc, R2=H, R3=CO₂Et) as determined by hplc.

Method 6

Chiral Ligand {(R)-1-[(S)-2-(Diphenylphosphino)ferrocenyl]ethyldi(3,5-xylyl)phosphine=SL-J005-1}; Organometallic Complex {bis(trifluoroacetoxy)(1,5-cyclooctadiene)ruthenium(II)}; Solvent: Ethanol. Diastereomer ratio 67:33 ((1-a, R1=Boc, R2=H, R3=CO₂Et): (1-b, R1=Boc, R2=H, R3=CO₂Et) as determined by hplc.

Method 7

Chiral Ligand {(S)-(−)-(6,6'-Dimethoxybiphenyl-2,2'-diyl)-bis(diphenylphosphine)=(S)-Ph-MeOBIPHEP=SL-A101-2}; Organometallic Complex {[Ir(COD)₂]BArF}; Solvent: Dichloroethane. Diastereomer ratio 63:37 ((1-a, R1=Boc, R2=H, R3=CO₂Et): (1-b, R1=Boc, R2=H, R3=CO₂Et) as determined by hplc.

Method 8

Chiral Ligand {(S)-1-[(R)-2-(Diphenylphosphino)ferrocenyl]ethyldi(3,5-xylyl)phosphine=SL-J005-2}; Organometallic Complex {bis(norbornadiene)rhodium(I)tetrafluoroborate}; Solvent: Ethanol. Diastereomer ratio 58:42 ((1-a, R1=Boc, R2=H, R3=CO₂Et): (1-b, R1=Boc, R2=H, R3=CO₂Et) as determined by hplc.

Method 9

Chiral Ligand {(R)-1-[(R)-2-(2.-Diphenylphosphinophenyl)ferrocenyl]ethyldi(bis-3,5-trifluoromethylphenyl)phosphine=SL-W001-1}; Organometallic Complex {bis(norbornadiene)rhodium(I)tetrafluoroborate}; Solvent: Ethanol. Diastereomer ratio 31:69 ((1-a, R1=Boc, R2=H, R3=CO₂Et): (1-b, R1=Boc, R2=H, R3=CO₂Et) as determined by hplc.

Method 10

Chiral Ligand {(S)-1-[(S)-2-(2'-Dicyclohexylphosphinophenyl)ferrocenyl]ethyldi(bis-(3,5-trifluoromethyl)phenyl)-phosphine=SL-W008-2}; Organometallic Complex {bis(norbornadiene)rhodium(I)tetrafluoroborate}; Solvent: Ethanol. Diastereomer ratio 16:84 ((1-a, R1=Boc, R2=H, R3=CO₂Et):(1-b, R1=Boc, R2=H, R3=CO₂Et) as determined by hplc.

Method 11

Chiral Ligand {(R)-1-[(S)-2-Diphenylphosphino)ferrocenyl]ethyldi-tert.-butylphosphine=SL-J002-1}; Organometallic Complex {bis(norbornadiene)rhodium(I)tetrafluoroborate}; Solvent: Ethanol. Diastereomer ratio 2:98 ((1-a, R1=Boc, R2=H, R3=CO₂Et): (1-b, R1=Boc, R2=H, R3=CO₂Et) as determined by hplc.

Method 12

Chiral Ligand {(R)-1-[(S)-2-diethylphosphino)ferrocenyl]ethyl di(tert-butyl)-phosphine=SL-J301-1}; Organometallic Complex {bis(norbornadiene)rhodium(I)tetrafluoroborate}; Solvent: Ethanol. Diastereomer ratio 5:95 ((1-a, R1=Boc, R2=H, R3=CO₂Et):(1-b, R1=Boc, R2=H, R3=CO₂Et) as determined by hplc.

HPLC Method (Example 65, Methods 1-12)

Column: Chiralcel OJ-RH; 150×4.6 mm; 5 μm. Mobile Phase A (water); Mobile Phase B (Acetonitrile). Isocratic: 0 min (60% B); 15 min (60% B). Flow rate: 0.8 ml min⁻¹. Wavelength 254 nm. Column temperature: 10° C.

Retention Times:
1-b (R1=Boc, R2=H, R3=CO₂Et):9.8 min
1-a (R1=Boc, R2=H, R3=CO₂Et):10.8 min
2-a (R1=Boc, R2=H, R3=CO₂Et):15.2 min Example 66

(R)-5-Biphenyl-4-ylmethyl-3-[1-hydroxymeth-(E/Z)-ylidene]-2-oxo-pyrrolidine-1-carboxylic acid tert-butyl ester (6-a, R1=Boc)

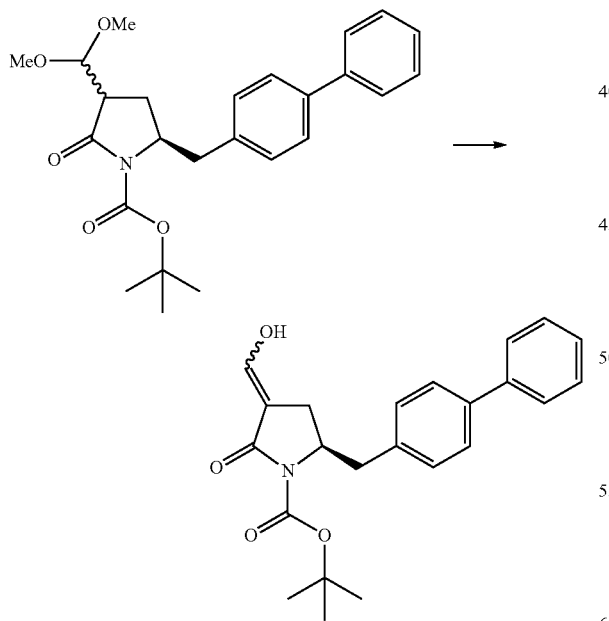

0.05 g of (3R/S,5S)-5-Biphenyl-4-ylmethyl-3-dimethoxymethyl-2-oxo-pyrrolidine-1-carboxylic acid tert-butyl ester (16-a, R1=Boc, R9=Me, R9=Me, Y═O) are dissolved in 1 ml of acetone under argon. Then 15 mg of water and 40 mg of amberlyst 15 are added. The mixture is stirred for 3 days, then filtered and concentrated in vacuo to afford (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) as determined by hplc.

HPLC Method

Column: X-BRIDGE C18; 150×3.0 mm; 3.5 μm. Mobile Phase A (0.1% NH₃ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min⁻¹. Wavelength: 210 or 254 nm. Temperature 60° C.

Retention Times
2-a (R1=Boc, R2=H, R3=CO₂H): 2.3 min
6-a (R1=Boc): 2.5 min
4-a (R1=H): 5.6 min
5-a (R1=Boc): 8.3 min
8-a (R1=Boc): 10.3 min
9-b (R1=Boc, R6=Me, R7=Me): 10.4 min
9-c (R1=Boc, R6=Me, R7=Me): 10.9 min
4-a (R1=Boc): 11.9 min Example 67

(3R/S,5S)-5-Biphenyl-4-ylmethyl-3-(bis-butylsulfanyl-methyl)-2-oxo-pyrrolidine-1-carboxylic acid tert-butyl ester (16-a, R1=Boc, R9=nBu, R9=nBu, Y═S)

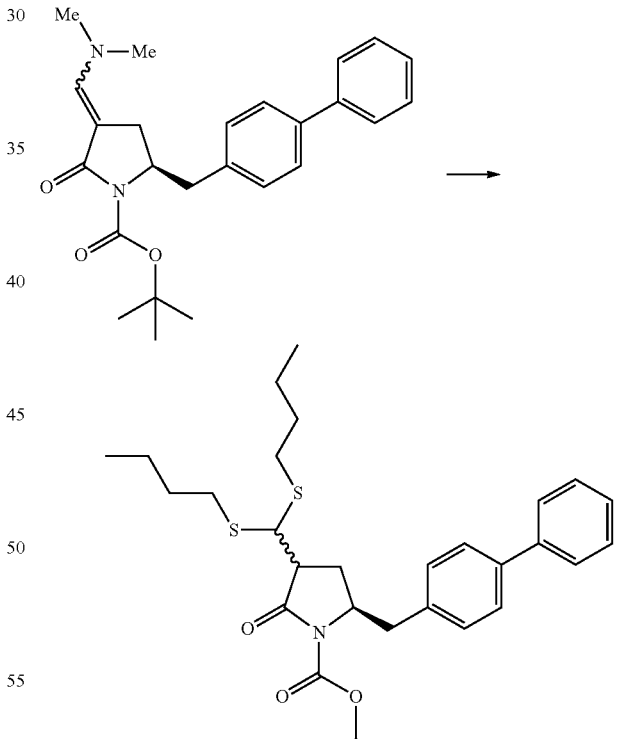

0.5 g of 5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) are added to 5 ml of n-butane-1-thiol. After the addition of 0.2 g of p-toluenesulfonic acid the mixture is stirred for 6 days at 25° C., then heated to 60° C. for 16 hours. The mixture is then quenched by addition of 5 ml of an 8% aqueous bicarbonate solution and any remaining n-butane-1-thiol distilled off under reduced pressure at 40° C. The aqueous phase is extracted 3 times with 5 ml ethyl acetate each and the combined organic phase evaporated to dryness at 40° C. under reduced pressure. The residue is purified by column chromatography (heptane: ethyl acetate 75:25) to afford (3R/S,5S)-5-biphenyl-4-ylmethyl-3-(bis-butylsulfanyl-methyl)-2-oxo-pyrrolidine-1-carboxylic acid tert-butyl ester (16-a, R1=Boc, R9=nBu, R9=nBu, Y=S). Ratio of C-3 diastereomers determined as 70:30 ((3S,5S):(3R,5S) diastereomers, respectively). 1H NMR (CDCl₃): Data for mixture of diastereomers: 0.86-0.96 (6H), 1.32-1.47 (4H), 1.50-1.68 (4H), 1.62 (9H), 1.94-2.30 (2H), 2.48-2.74 (4H), 2.80-2.89 (2H), 3.10-3.16 (1H), 3.55-3.59 (1H, minor stereoisomer), 4.23-4.31 (1H, minor stereoisomer), 4.30 (1H), 4.38 (1H, minor stereoisomer), 4.43-4.47 (1H), 7.27-7.30 (2H), 7.32-7.40 (1H), 7.44-7.50 (2H), 7.56-7.65 (4H).

Example 68

(R)-5-Biphenyl-4-ylmethyl-3-[1-hydroxymeth-(E/Z)-ylidene]-2-oxo-pyrrolidine-1-carboxylic acid tert-butyl ester (6-a, R1=Boc)

0.101 g (0.19 mmol) of (3R/S,5S)-5-Biphenyl-4-ylmethyl-3-(bis-butylsulfanyl-methyl)-2-oxo-pyrrolidine-1-carboxylic acid tert-butyl ester (16-a, R1=Boc, R9=nBu, R9=nBu, Y=S) are dissolved in a mixture of 1.6 ml acetonitrile and 0.4 ml water. After addition of 0.115 g HgCl₂ and 0.048 g calcium carbonate, the suspension is stirred over night. Diethyl ether (10 ml) and 18% aq. ammonium chloride solution (5 ml) are added to the mixture. The mixture is then filtered and the phases are separated. The organic phase is washed with water and brine and then concentrated under reduced pressure to give (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc). Material analysed by hplc (hplc method for Example 66)

Example 69

(3R,5S)-5-Biphenyl-4-ylmethyl-3-methyl-2-oxo-pyrrolidine-1-carboxylic acid tert-butyl ester (3-a, R1=Boc) and (3S,5S)-5-biphenyl-4-ylmethyl-3-methyl-2-oxo-pyrrolidine-1-carboxylic acid tert-butyl ester (3-b, R1=Boc)

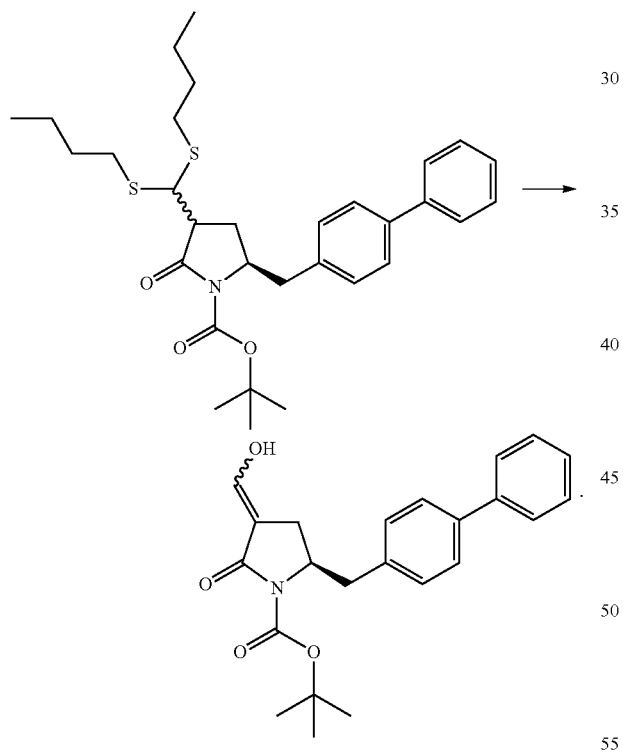

0.24 g (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to a mixture of ethyl acetate (10.8 ml) and methanol (1.2 ml) at 22° C. 0.1 g of 10% Palladium on carbon (Engelhard 4505) is added to the mixture along with water (0.3 ml). The mixture is flushed with hydrogen and subsequently is stirred at 22° C. and 4 bar hydrogen pressure for five days. The mixture is then filtered through Cellflock and concentrated under reduced pressure to afford (3R,5S)-5-biphenyl-4-ylmethyl-3-methyl-2-oxo-pyrrolidine-1-carboxylic acid tert-butyl ester (3-a, R1=Boc), (3S,5S)-5-biphenyl-4-ylmethyl-3-methyl-2-oxo-pyrrolidine-1-carboxylic acid tert-butyl ester (3-b, R1=Boc) and (3R/S, 5S)-5-Biphenyl-4-ylmethyl-3-hydroxymethyl-2-oxopyrrolidine-1-carboxylic acid tert-butyl ester (5-a, R1=Boc) as determined by hplc. HPLC Conditions as given in Example 66 and Example 71.

Example 70

(3R/S, 5S)-5-Biphenyl-4-ylmethyl-3-hydroxymethyl-2-oxo-pyrrolidine-1-carboxylic acid tert-butyl ester (5-a, R1=Boc)

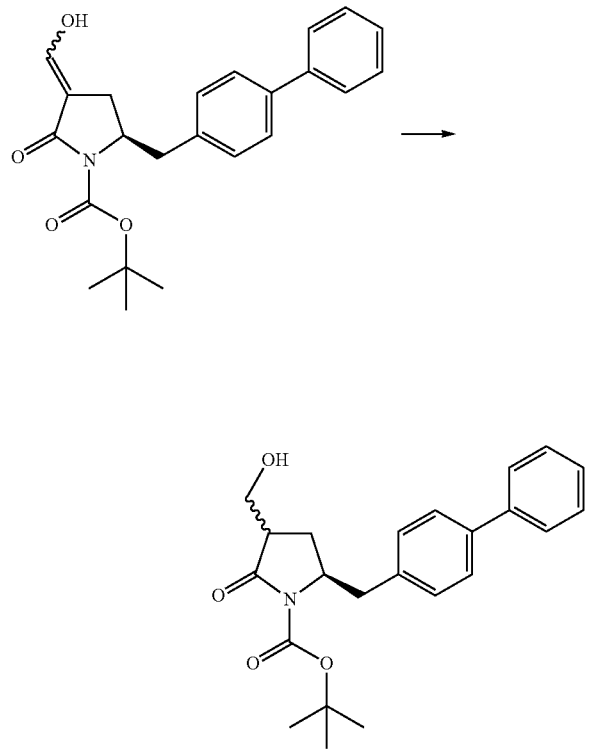

99 mg (R)-5-Biphenyl-4-ylmethyl-3-[1-hydroxymeth-(E/Z)-ylidene]-2-oxo-pyrrolidine-1-carboxylic acid tert-butyl ester (6-a, R1=Boc) is added to a mixture of toluene (0.25 ml) and water (0.25 ml) at room temperature. Tetrabutylammonium bromide (19.7 mg) is then added. The mixture is then cooled to 0° C. Sodium borohydride (20.8 mg) is then added and the resulting mixture is stirred at 0° C. for 1 h. The mixture is then warmed to room temperature and stirred overnight. Water (10 ml) and toluene (10 ml) are then added to the mixture. The phases are separated. The organic phase is washed with water (10 ml), dried (MgSO$_4$) and concentrated in vacuo to afford (3R/S, 5S)-5-biphenyl-4-ylmethyl-3-hydroxymethyl-2-oxo-pyrrolidine-1-carboxylic acid tert-butyl ester (5-a, R1=Boc) as detected by LC-MS. m/z(+ESI): 266 (10%), 282 (2), 310 (20), 326 (100), 366 (15), 382 ([MH$^+$], 8). 1H NMR (DMSO): 1.22-1.52, 1.59-1.65, 1.80-1.87, 1.94-2.03, 2.10-2.18, 2.57-2.89, 3.02-3.11, 3.15-3.30, 3.34-3.44, 3.46-3.66, 3.67-3.79, 3.82-3.93, 4.16-4.38, 4.63-4.69, 4.72-4.77, 4.93-5.00, 5.14-5.27, 5.40-5.63, 5.66-5.78, 6.23-6.29, 6.63-6.29, 6.63-6.67, 7.12-7.20, 7.23-7.37, 7.43-7.47, 7.55-7.68.

Example 71

(R)-5-Biphenyl-4-ylmethyl-3-[1-hydroxymeth-(E/Z)-ylidene]-2-oxo-pyrrolidine-1-carboxylic acid tert-butyl ster (6-a, R1=Boc)

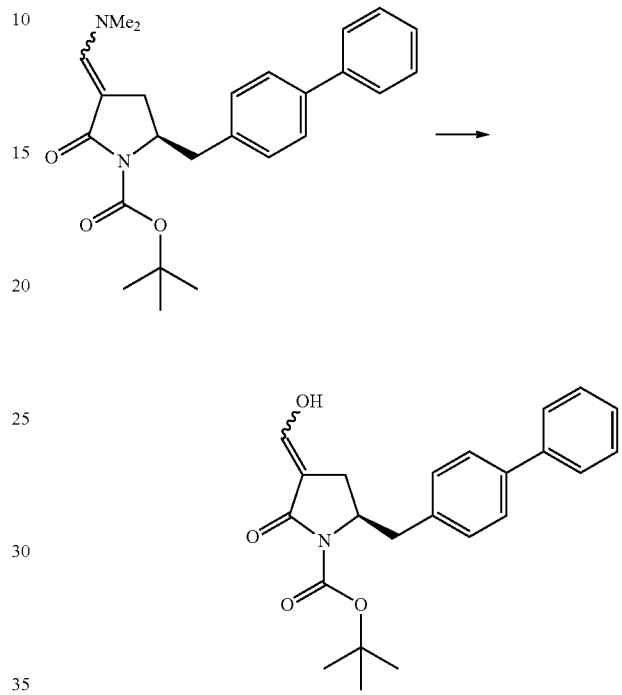

Method 1

100 mg (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is added to ethanol (0.5 ml). 160 mg Cesium carbonate is added to the mixture. 30 mg Palladium on Carbon (10% loading, 50% water wet, Degussa E101 NE/W) is added to the mixture. Hydrogen gas is applied to the mixture. The mixture is then stirred at ambient temperature and pressure overnight. The catalyst is then filtered and the mixture concentrated under reduced pressure. The residue is analysed by hplc to identify (R)-5-biphenyl-4-ylmethyl-3-[1-hydroxymeth-(E/Z)-ylidene]-2-oxo-pyrrolidine-1-carboxylic acid tert-butyl ester (6-a, R1=Boc).

Method 2

189 mg (R)-5-Biphenyl-4-ylmethyl-3-[1-dimethylaminometh-(E/Z)-ylidene]-2-oxo-pyrrolidine-1-carboxylic acid tert-butyl ester (7-a, R1=Boc, R6=Me, R7=Me) is added to ethanol (0.5 ml). 108 µl 2,6-Lutidine are added to the mixture. 57 mg Palladium on Carbon (10% loading, 50% water wet, Johnson Matthey type 39) is added to the mixture. Hydrogen gas is applied to the mixture. The mixture is then stirred at ambient temperature and pressure overnight. The catalyst is then filtered and the mixture concentrated under reduced pressure. The residue is analysed by hplc to identify (R)-5-biphenyl-4-ylmethyl-3-[1-hydroxymeth-(E/Z)-ylidene]-2-oxo-pyrrolidine-1-carboxylic acid tert-butyl ester (6-a, R1=Boc).

HPLC Method 1 (Example 71)

Column: Zorbax Extend C18; 150×4.6 mm; 3.5 µm. Mobile Phase A (0.1% NH$_3$ (32%) in water); Mobile Phase B (Acetonitrile); Mobile Phase C (Methanol). Gradient: 0 min (5% B; 50% C); 1 min (5% B; 50% C); 5 min (5% B; 75% C); 15 min (5% B; 75% C); 15.1 min (5% B; 50% C); 18 min (5% B; 50% C). Flow rate: 1.2 ml min$^{-1}$. Wavelength: 254 nm. Column temperature: 10° C.

Retention Times:

6-a (R1=Boc): 4.1 min 9-b (R1=Boc, R6=Me, R7=Me): 9.9 min 9-c (R1=Boc, R6=Me, R7=Me): 10.5 min 4-a (R1=Boc): 11.2 min 7-a (R1=Boc): 11.5 min 3-a (R1=Boc): 12.1 min 3-b (R1=Boc): 12.5 min HPLC Method 2 (Example 71)

Column: X-BRIDGE; 150×3.0 mm; 3.5 µm. Mobile Phase A (0.1% NH$_3$ (32%) in water); Mobile Phase B (Acetonitrile). Gradient: 0 min (20% B); 3 min (40% B); 5 min (40% B); 7 min (50% B); 11 min (50% B); 13 min (80% B); 16 min (80% B); 16.1 min (20% B); 20 min (20% B). Flow rate: 1.4 ml min$^{-1}$. Wavelength: 254 nm. Column temperature: 60° C.

Retention Times 6-a (R1=Boc): 2.6 min 9-b (R1=Boc, R6=Me, R7=Me): 10.7 min 9-c (R1=Boc, R6=Me, R7=Me): 11.2 min 4-a (R1=Boc): 12.2 min 3-a (R1=Boc) and 3-b (R1=Boc): 12.8 min

Example 72

(2R,4S)-5-Biphenyl-4-yl-4-tert-butoxycarbonylamino-2-methylpentanoic acid ethyl ester (1-a, R1=Boc, R2=H, R3=CO$_2$Et) and (2S,4S)-5-biphenyl-4-yl-4-tert-butoxycarbonylamino-2-methylpentanoic acid ethyl ester (1-b, R1=Boc, R2=H, R3=CO$_2$Et)

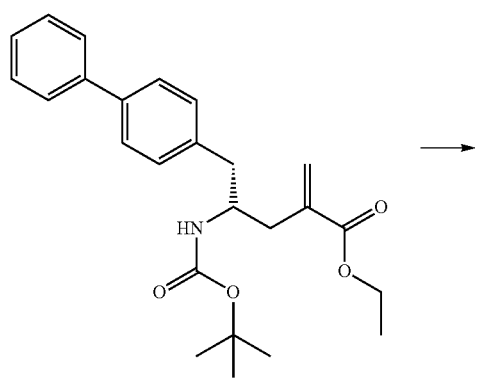

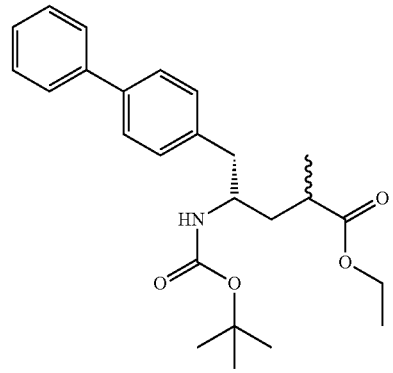

500 mg (R)-5-Biphenyl-4-yl-4-tert-butoxycarbonylamino-2-methylenepentanoic acid ethyl ester (2-a, R1=Boc, R2=H, R3=CO$_2$Et) is added to ethanol (5 ml) at ambient temperature. Triethylamine (170 µl) is then added to the mixture. 50 mg Palladium on carbon (10%, 50% water-wet, Degussa E101 NE/W) is then added. Hydrogen gas at ambient pressure is applied to the mixture. The mixture is then stirred overnight at ambient temperature and pressure. The mixture is then filtered and concentrated under reduced pressure to afford 2R,4S)-5-Biphenyl-4-yl-4-tert-butoxycarbonylamino-2-methylpentanoic acid ethyl ester (1-a, R1=Boc, R2=H, R3=CO$_2$Et) and (2S,4S)-5-biphenyl-4-yl-4-tert-butoxycarbonylamino-2-methylpentanoic acid ethyl ester (1-b, R1=Boc, R2=H, R3=CO$_2$Et). Spectroscopic data as in Example 63. Ratio of diastereomers 70:30 (1-a, R1=Boc, R2=H, R3=CO$_2$Et: 1-b, R1=Boc, R2=H, R3=CO$_2$Et) as determined by hplc (hplc method as in Example 65)

Example 73

(2R,4S)-5-Biphenyl-4-yl-4-tert-butoxycarbonylamino-2-methylpentanoic acid methyl ester (1-a, R1=Boc, R2=H, R3=CO$_2$Me) and (2S,4S)-5-Biphenyl-4-yl-4-tert-butoxycarbonylamino-2-methylpentanoic acid methyl ester (1-b, R1=Boc, R2=H, R3=CO$_2$Me)

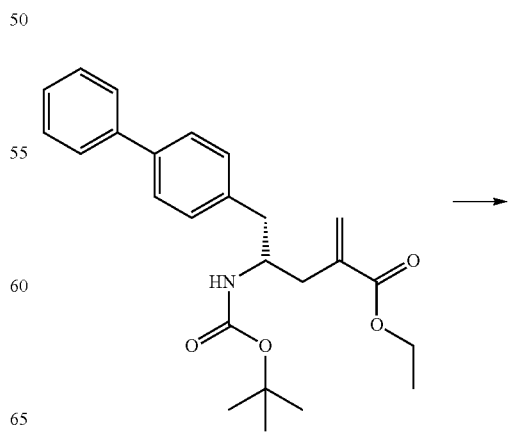

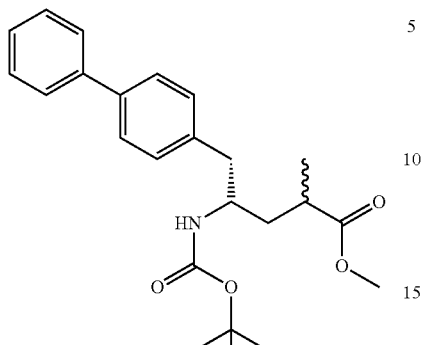

500 mg (R)-5-Biphenyl-4-yl-4-tert-butoxycarbonylamino-2-methylenepentanoic acid methyl ester (2-a, R1=Boc, R2=H, R3=CO₂Me) is added to ethanol (5 ml) at ambient temperature. Triethylamine (176 μl) is then added to the mixture. 50 mg Palladium on carbon (10%, 50% water-wet, Degussa E101 NE/W) is then added. Hydrogen gas at ambient pressure is applied to the mixture. The mixture is then stirred overnight at ambient temperature and pressure. The mixture is then filtered and concentrated under reduced pressure to afford 2R,4S)-5-Biphenyl-4-yl-4-tert-butoxycarbonylamino-2-methylpentanoic acid methyl ester (1-a, R1=Boc, R2=H, R3=CO₂Me) and (2S,4S)-5-biphenyl-4-yl-4-tert-butoxycarbonylamino-2-methylpentanoic acid methyl ester (1-b, R1=Boc, R2=H, R3=CO₂Me). Spectroscopic data as in Example 60. Ratio of diastereomers 66:34 (1-a, R1=Boc, R2=H, R3=CO₂Me: 1-b, R1=Boc, R2=H, R3=CO₂Me) by integration of signals at 1.76-1.85 (1-b, R1=Boc, R2=H, R3=CO₂Me) and 1.92-1.99 (1-a, R1=Boc, R2=H, R3=CO₂Me).

Example 74

(3R/S,5S)-5-Biphenyl-4-ylmethyl-2-oxo-3-(toluene-4-sulfonyloxymethyl)-pyrrolidine-1-carboxylic acid tert-butyl ester (11-a, R1=Boc, R4=Tosyl) and (R)-5-Biphenyl-4-ylmethyl-3-methylene-2-oxo-pyrrolidine-1-carboxylic acid tert-butyl ester (4-a, R1=Boc)

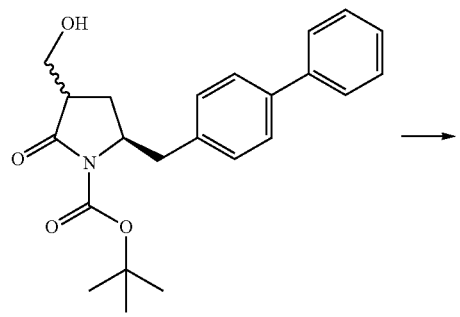

→

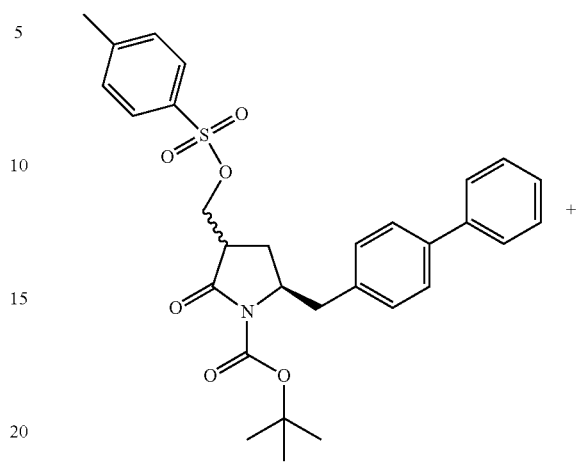

20 mg (3R/S, 5S)-5-Biphenyl-4-ylmethyl-3-hydroxymethyl-2-oxo-pyrrolidine-1-carboxylic acid tert-butyl ester (5-a, R1=Boc) (prepared according to Example 48) is added to chloroform (5 ml) at room temperature. Triethylamine (11 μl) is added to the mixture. 4-Toluenesulphonic acid anhydride (20.5 mg) is then added to the mixture. The mixture is then stirred for 20 h at reflux. Ethyl acetate (1 ml) and water (1 ml) are added. The phases are separated. The organic phase is concentrated under reduced pressure. The residue is then purified by column chromatography, eluting with heptane-ethyl acetate (1:1) to afford (3R/S,5S)-5-biphenyl-4-ylmethyl-2-oxo-3-(toluene-4-sulfonyloxymethyl)-pyrrolidine-1-carboxylic acid tert-butyl ester (11-a, R1=Boc, R4=Tosyl) and (R)-5-biphenyl-4-ylmethyl-3-methylene-2-oxo-pyrrolidine-1-carboxylic acid tert-butyl ester (4-a, R1=Boc). Spectroscopic data for (3R/S,5S)-5-biphenyl-4-ylmethyl-2-oxo-3-(toluene-4-sulfonyloxymethyl)-pyrrolidine-1-carboxylic acid tert-butyl ester (11-a, R1=Boc, R4=Tosyl) as for Example 49, Method 1. Spectroscopic data for (R)-5-biphenyl-4-ylmethyl-3-methylene-2-oxo-pyrrolidine-1-carboxylic acid tert-butyl ester (4-a, R1=Boc) as for Example 23, Method 1.

Example 75

(3R/S,5S)-5-Biphenyl-4-ylmethyl-3-iodomethyl-pyrrolidin-2-one (12-a, R1=H, R5=I)

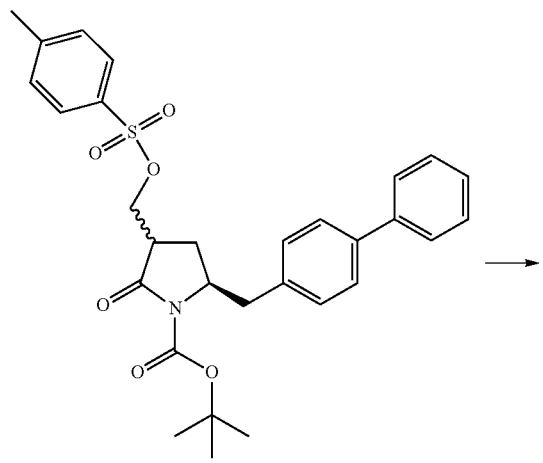

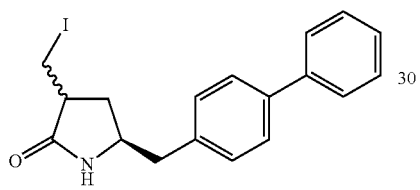

122 mg (3R/S,5S)-5-Biphenyl-4-ylmethyl-2-oxo-3-(toluene-4-sulfonyloxymethyl)-pyrrolidine-1-carboxylic acid tert-butyl ester (11-a, R1=Boc, R4=Tosyl) prepared according to Example 49, Method 2 is added to acetonitrile (3 ml). Sodium iodide (105 mg) is then added to the mixture. The resulting mixture is heated at reflux overnight. The mixture is then concentrated under reduced pressure. Purification by column chromatography, eluting with ethyl acetate-heptane (1:1) gives (3R/S,5S)-5-biphenyl-4-ylmethyl-3-iodomethyl-pyrrolidin-2-one (12-a, R1=H, R5=I). 1H NMR (CDCl$_3$): 2.13 (2H), 2.69 (2H), 2.82 (1H), 3.28 (1H), 3.35 (1H), 3.85 (1H), 5.84 (1H), 7.17 (2H), 7.28 (1H), 7.37 (2H), 7.49 (4H).

Example 76

(R)-5-Biphenyl-4-ylmethyl-3-methylene-2-oxo-pyrrolidine-1-carboxylic acid tert-butyl ester (4-a, R1=Boc)

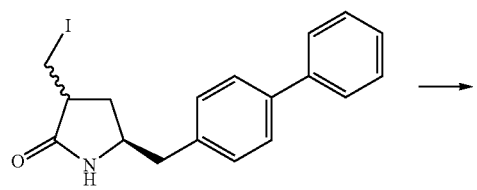

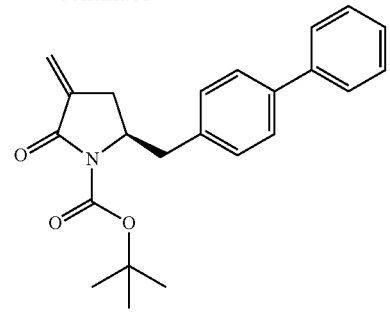

5 mg (3R/S,5S)-5-Biphenyl-4-ylmethyl-3-iodomethyl-pyrrolidin-2-one (12-a, R1=H, R5=I) is added to toluene (1 ml). 4-(Dimethylamino)pyridine (0.1 mg) and triethylamine (1 µl) are then added to the mixture. The mixture is heated to 70° C. Di-tert-butyl dicarbonate (2 mg) is then added to the mixture. The mixture is stirred for 1 h at 70° C. The mixture is concentrated under reduced pressure. Ethyl acetate (1 ml) and water (1 ml) are added. The phases are separated. The organic phase is concentrated under reduced pressure to give (R)-5-Biphenyl-4-ylmethyl-3-methylene-2-oxo-pyrrolidine-1-carboxylic acid tert-butyl ester (4-a, R1=Boc). Spectroscopic data as for Example 23, Method 1.

Example 77

(3R,5S)-5-Biphenyl-4-ylmethyl-3-methylpyrrolidin-2-one (3-a, R1=H) and (3S,5S)-5-Biphenyl-4-ylmethyl-3-methylpyrrolidin-2-one (3-b, R1=H)

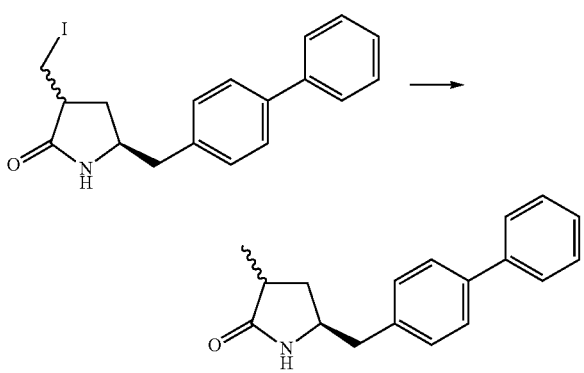

4 mg (3R/S,5S)-5-Biphenyl-4-ylmethyl-3-iodomethyl-pyrrolidin-2-one (12-a, R1=H, R5=I) is added to ethanol (1 ml) at ambient temperature. Triethylamine (5 µl) is then added to the mixture. 0.4 mg Palladium on carbon (10%, 50% water-wet, Degussa E101 NE/W) is then added. Hydrogen gas at ambient pressure is applied to the mixture. The mixture is then stirred overnight at ambient temperature and pressure. The mixture is then filtered and concentrated under reduced pressure to afford (3R,5S)-5-biphenyl-4-ylmethyl-3-methylpyrrolidin-2-one (3-a, R1=H) and (3S,5S)-5-biphenyl-4-ylmethyl-3-methylpyrrolidin-2-one (3-b, R1=H. Ratio of diastereomers 22:88 (3-a, R1=H to 3-b, R1=H) as determined by nmr. Spectroscopic data for 3-a (R1=H) as for Example 6 in WO/2008/083967. Spectroscopic data for 3-b (R1=H) as for Example 47 in WO/2008/083967.

The invention claimed is:

1. A compound of formula (4)

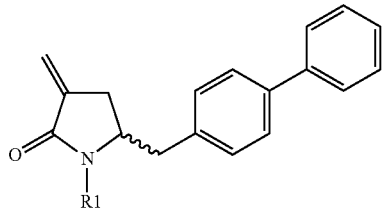
(4)

or a salt thereof,
wherein R1 is hydrogen or a nitrogen protecting group, having a configuration according to formula (4-a),

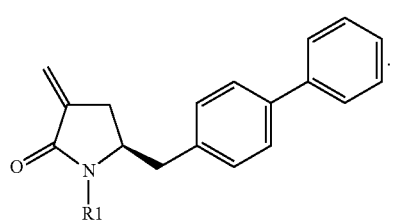
(4-a)

2. A compound of formula (5), or a salt thereof,

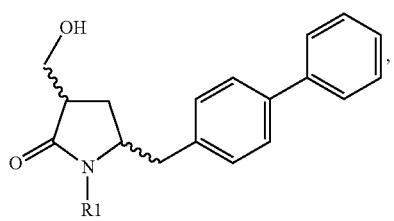
(5)

wherein R1 is hydrogen or a nitrogen protecting group, of formulae (5-a), (5-b) or (5-c),

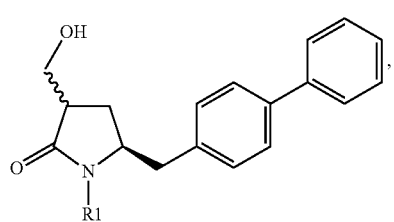
(5-a)

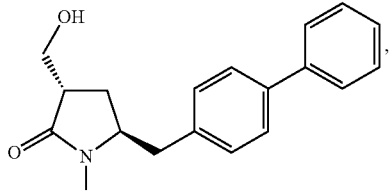
(5-b)

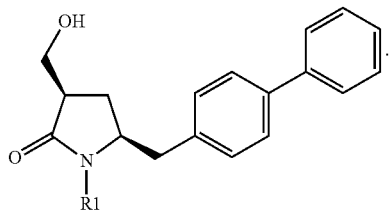
(5-c)

3. A compound of formula (6), or a tautomer thereof,

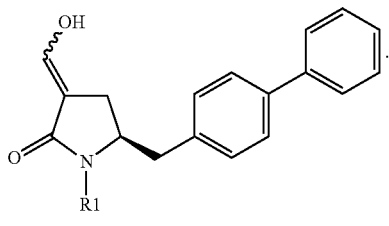
(6)

or a salt thereof,
wherein R1 is hydrogen or a nitrogen protecting group, having a configuration according to formula (6-a), (6-a)

4. A compound of formula (7), or a salt thereof,

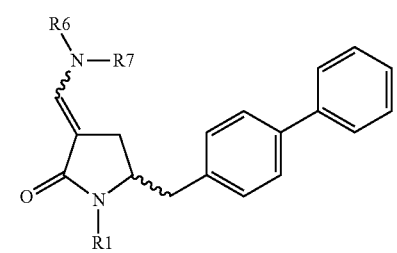
(7)

wherein R1 is hydrogen or a nitrogen protecting group and, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, including nitrogen, oxygen or sulphur, whereby the cycle contains 3 to 8, ring atoms, having a configuration according to formula (7-a), (7-b) or (7-c),

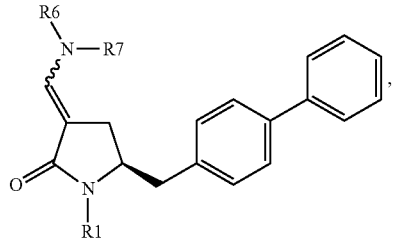
(7-a)

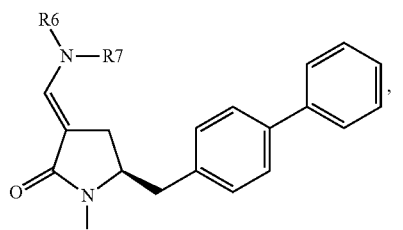
(7-b)

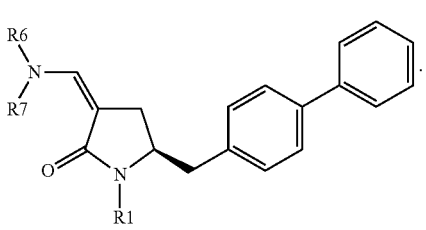
(7-c)

5. A compound of formula (9-a), or a salt thereof,

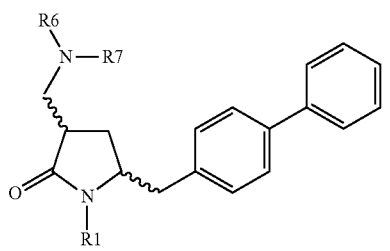
(9)

wherein R1 is hydrogen or a nitrogen protecting group and, R6 and R7 are, independently, an alkyl group or together are an alkylene group, having a configuration according to formula (9-a) (9-b) or (9-c),

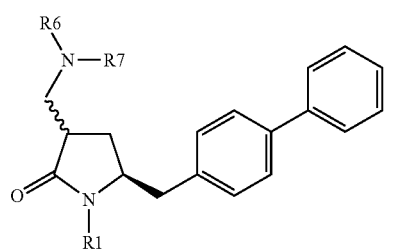
(9-a)

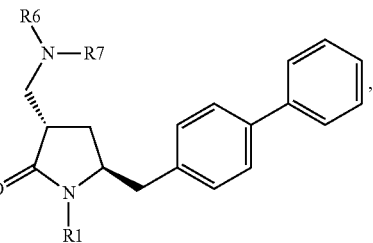
(9-b)

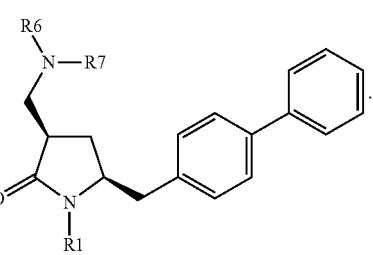
(9-c)

6. A compound of formula (10), or a salt thereof,

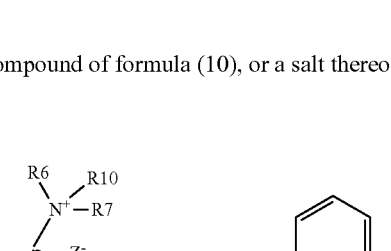
(10)

wherein R1 is hydrogen or a nitrogen protecting group, R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, including nitrogen, oxygen or sulphur, whereby the cycle contains 3 to 8, ring atoms, Z⁻ is a halide, an alkyl sulphate or a sulfonyl ester and R10 is hydrogen, alkyl or aryl; having a configuration according to formula (10-a), (10-b) or (10-c),

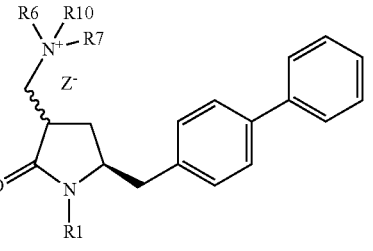
(10-a)

-continued

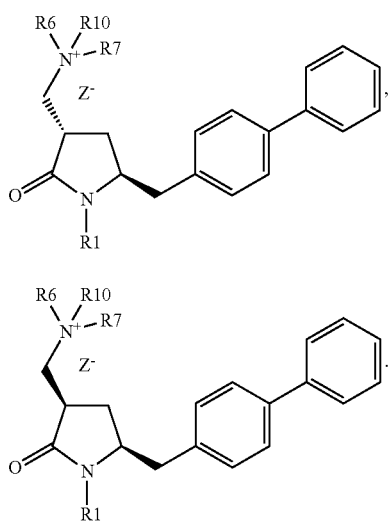

7. A compound of formula (11)

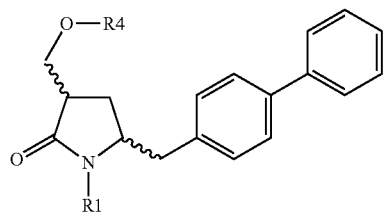

or a salt thereof, wherein R1 is hydrogen or a nitrogen protecting group and R4 is an OH-activating group, having a configuration according to formula (11-a), (11-b) or (11-c),

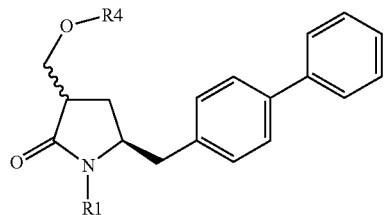

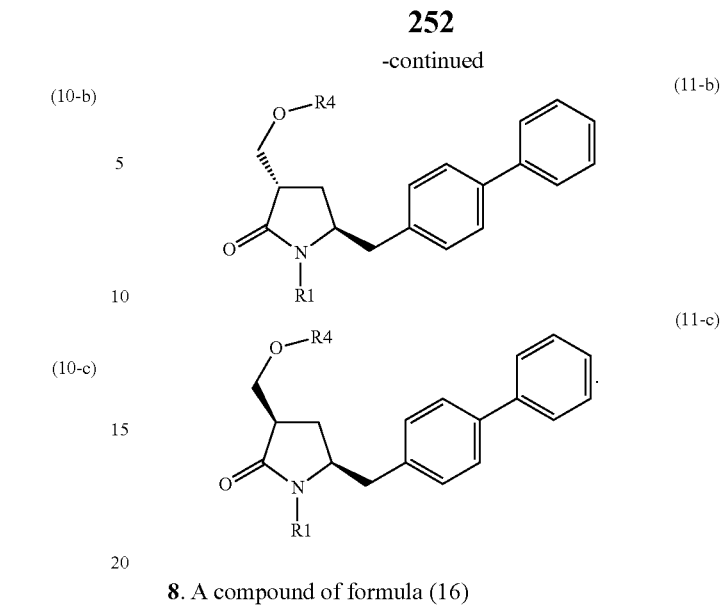

8. A compound of formula (16)

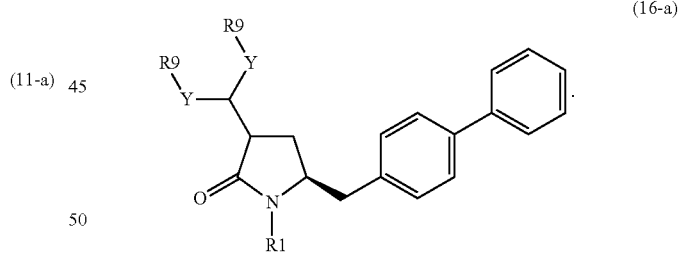

or a salt thereof,
wherein R1 is hydrogen or a nitrogen protecting group, Y is O or S and each R9, is, independently, alkyl, aryl, arylalkyl or acetyl
having a configuration according to formula (16-a),

* * * * *

UNITED STATES PATENT AND TRADEMARK OFFICE
CERTIFICATE OF CORRECTION

| | | |
|---|---|---|
| PATENT NO. | : 8,580,974 B2 | Page 1 of 1 |
| APPLICATION NO. | : 12/863213 | |
| DATED | : November 12, 2013 | |
| INVENTOR(S) | : Hook et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this
Twenty-sixth Day of May, 2015

Michelle K. Lee
*Director of the United States Patent and Trademark Office*